United States Patent
O'Connor et al.

(10) Patent No.: US 12,410,438 B2
(45) Date of Patent: Sep. 9, 2025

(54) METHODS FOR CONTROLLING MERISTEM SIZE FOR CROP IMPROVEMENT

(71) Applicant: Pairwise Plants Services, Inc., Durham, NC (US)

(72) Inventors: Devin O'Connor, Hillsborough, NC (US); Nathaniel Graham, Durham, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 0 days.

(21) Appl. No.: 17/335,264

(22) Filed: Jun. 1, 2021

(65) Prior Publication Data

US 2021/0371873 A1    Dec. 2, 2021

Related U.S. Application Data

(60) Provisional application No. 63/033,273, filed on Jun. 2, 2020.

(51) Int. Cl.
| | | |
|---|---|---|
| *C12N 15/82* | (2006.01) | |
| *C12N 9/22* | (2006.01) | |
| *C12N 15/11* | (2006.01) | |

(52) U.S. Cl.
CPC .......... *C12N 15/8262* (2013.01); *C12N 9/22* (2013.01); *C12N 15/11* (2013.01); *C12N 15/8213* (2013.01); *C12N 2310/20* (2017.05); *C12N 2800/80* (2013.01)

(58) Field of Classification Search
CPC ...... C12N 15/11; C12N 9/22; C12N 2310/20; C12N 2800/80
See application file for complete search history.

(56) References Cited

U.S. PATENT DOCUMENTS

| | | |
|---|---|---|
| 10,876,129 B2 | 12/2020 | Pennell et al. |
| 2019/0032071 A1 | 1/2019 | Pennell et al. |
| 2020/0377900 A1 | 12/2020 | Cargill et al. |

FOREIGN PATENT DOCUMENTS

| | | |
|---|---|---|
| CN | 103088054 A | 5/2013 |
| CN | 108192912 A | 6/2018 |
| WO | 0170987 A2 | 9/2001 |
| WO | 03093450 A2 | 11/2003 |
| WO | 2008062049 A1 | 5/2008 |
| WO | 2013138544 A1 | 9/2013 |

(Continued)

OTHER PUBLICATIONS

Somssich et al. 2016 "Shared and distinct functions of the pseudokinase Coryne (CRN) in shoot and root stem cell maintenance of *Arabidopsis*" J. Exp. Botany 67(14): 4901-4915 (Year: 2016).*

(Continued)

*Primary Examiner* — Matthew R Keogh
*Assistant Examiner* — Rebecca Stephens
(74) *Attorney, Agent, or Firm* — Myers Bigel, P.A.

(57) ABSTRACT

This invention relates to compositions and methods for modifying CORYNE (CRN) genes in plants to optionally increase kernel row number and/or improve one or more yield traits. The invention further relates to plants having increased kernel row number and/or one or more improved yield traits produced using the methods and compositions of the invention.

8 Claims, 3 Drawing Sheets

Specification includes a Sequence Listing.

(56) References Cited

FOREIGN PATENT DOCUMENTS

| WO | 2017139309 A1 | 8/2017 |
| WO | 2020023258 A1 | 1/2020 |
| WO | 2021195458 A1 | 9/2021 |

OTHER PUBLICATIONS

Somssich 2014 (Nov. 18, 2014 dissertation entitled "On Receptor Kinase Interactions and Complex Formations" online by Apr. 3, 2015 via WorldCat OCLC Number/Unique Identifier 1106976740 at https://docserv.uni-duesseldorf.de/servlets/DerivateServlet/Derivate-36032/DissertationRev.pdf; (Year: 2015).*

Je et al. (2018 eLife: e35673, DOI:https://doi.org/10.7554/eLife.35673; of record IDS Dec. 20, 2021) (Year: 2018).*

EMBL/GenBank Accession No. ONM34918.1 (Feb. 6, 2017) entitled "Receptor-like protein kinase 5 [*Zea mays*]" (Year: 2017).*

Sequence published as GenBank Accession No. XM_044495660.1 entitled "Predicted: Triticum aestibum inactive leucine-rich repeat receptor-like protein kinase Coryne (LOC123072101), mRNA" dated Oct. 25, 2021, 2 total pages. (Year: 2021).*

Sequence published as GenBank Accession No. XP_044351595.1 entitled "inactive leucine-rich repeat receptor-like protein kinase Coryne [Triticum aestivum]" dated Oct. 25, 2021, 2 total pages. (Year: 2021).*

Bleckmann et al. "Stem Cell Signaling in *Arabidopsis* Requires CRN to Localize CLV2 to the Plasma Membrane" Plant Physiology, 152:166-176 2010.

Byoung II et al "The Clavata receptor Fasciated EAR2 responds to distinct CLE peptides by signaling through two downstream effectors" eLife, Mar. 15, 2018 Retrieved from Internet Sep. 7, 2021 https://www.ncbi.nlm.nih.gov/pmc/articles/PMC5854466/pdf/elife-35673.pdf.

Fletcher, J.C. (2018). The CLV-WUS Stem Cell Signaling Pathway: A Roadmap to Crop Yield Optimization. Plants 7:87.

Guo, Y., Han, L., Hymes, M., Denver, R., and Clark, S.E. (2010). CLAVATA2 forms a distinct CLE-binding receptor complex regulating *Arabidopsis* stem cell specification. Plant J 63: 889-900.

International Search Report and Written Opinion corresponding to International Application No. PCT/US2021/035114, mailed Sep. 21, 2021, 14 pages.

Je, B. el. (2018). The Clavata receptor Fasciated EAR2 responds to distinct CLE peptides by signaling through two downstream effectors. eLife 7: e35673.

Je, B.I. et al. (2016). Signaling from maize organ primordia via Fasciated EAR3 regulates stem cell proliferation and yield traits. Nat Genet 48: ng.3567.

Laux, T., Mayer, K., Berger, J., and Jürgens, G. The Wuschel gene is required for shoot and floral meristem integrity in *Arabidopsis*. Development (Cambridge, England) 122: 87-96.

Miwa, H., Betsuyaku, S., Iwamoto, K., Kinoshita, A., Fukuda, H., and Sawa, S. (2008). The Receptor-Like Kinase SOL2 Mediates CLE Signaling in *Arabidopsis*. Plant Cell Physiol 49: 1752-1757.

Muller, R., Bleckmann, A., and Simon, R. (2008). The Receptor Kinase Coryne of *Arabidopsis* Transmits the Stem Cell-Limiting Signal CLAVATA3 Independently of CLAVATA1. The Plant Cell Online 20: 934-946.

Nimchuk, Z.L., Tarr, P.T., and Meyerowitz, E.M. (2011). An Evolutionarily Conserved Pseudokinase Mediates Stem Cell Production in Plants. Plant Cell 23: 851-854.

Schoof, H., Lenhard, M., Haecker, A., Mayer, K.F.X., Jürgens, G., and Laux, T. (2000). The Stem Cell Population of *Arabidopsis* Shoot Meristems Is Maintained by a Regulatory Loop between the Clavata and Wuschel Genes. Cell 100: 635-644.

Somssich, Marc "On Receptor Kinase Interactions and Complex Formations—Inauguraldissertation zur Erlangung des Doktorgrades der Mathematisch-Naturwissenschaftlichen Fakultat der Heinrich-Heine-Universitat Düsseldorf vorgelegt van" Nov. 18, 2014 Dissertation.

Taguchi-Shiobara, F., Yuan, Z., Hake, S., and Jackson, D. (2001). The fasciated ear2 gene encodes a leucine-rich repeat receptor-like protein that regulates shoot meristem proliferation in maize. Gene Dev 15: 2755-2766.

Wu Qingyu et al. "All together now, a magical mystery tour of the maize shoot meristem" Current Opinion in Plant Biology, Elsevier, Amsterdam, NL, 45:26-35 2018.

Zhu, Y., Wang, Y., Li, R., Song, X., Wang, Q., Huang, S., Jin, J.B., Liu, C.-M., and Lin, J. (2009). Analysis of interactions among the CLAVATA3 receptors reveals a direct interaction between CLAVATA2 and Coryne in *Arabidopsis*. Plant J 61: 223-233.

Dievart, Anne, et al., "CLAVATA1 Dominant-Negative Alleles Reveal Functional Overlap between Multiple Receptor Kinases That Regulate Meristem and Organ Development", The Plant Cell. 15(5), 2003, 1198-1211.

Ellison, Erika L., et al., "Mutator transposon insertions within maize genes often provide a novel outward reading promoter", bioRxiv. https://doi.org/10.1101/2023.06.05.543741, 2023, 1-33.

FEA2_MAIZE, version 102, UniProtKB Accession No. Q940E8 (B4G061); dated Feb. 13, 2019.

International Search Report and Written Opinion corresponding to International Application No. PCT/US2021/024283; dated Jul. 16, 2021, 13 pages.

International Search Report and Written Opinion corresponding to International Application No. PCT/US2021/027609 dated Sep. 28, 2021, 22 pages.

International Search Report and Written Opinion corresponding to International Application No. PCT/US2021/037740, mailed Dec. 2, 2021, 22 pages.

International Search Report and Written Opinion corresponding to International Application No. PCT/US2023/069210, mailed Oct. 16, 2023, 21 pages.

International Search Report and Written Opinion corresponding to International Application No. PCT/US2023/069211, mailed Oct. 16, 2023, 21 pages.

Leucine-rich repeat receptor-like protein fasciatef ear2, Uniprot Database Accession No. Q940E8 (2001-12-01).

Database: UniProt [online]: A0A5J9V4K0_9POAL. Protein Recommended Name: Protein kinase domain-containing protein, Dec. 11, 2019. Retrieved from: https://www.uniprot.org/uniprot/A0A5J9V4K0, 2 pages.

Fon2-like cle protein1 [*Zea mays*], Retrieved from https://www.ncbi.nlm.nih.gov/protein/ONM16738.1?report=genbank&log$=protalign&blast_rank=1&RID=BF2FPXGG013 on Jul. 19, 2023.

Hypothetical protein ZEAMMB73_Zm00001d007576 [*Zea mays*], Retrieved from https://www.ncbi.nlm.nih.gov/protein/ONM27114.1?report=genbank&log$=protalign&blast_rank=1&RID=BHMXAB2Y016 on Jul. 20, 2023, 2023.

*Zea mays* clone 462207 mRNA sequence, Retrieved from https://www.ncbi.nlm.nih.gov/nucleotide/EU974983.1?report=genbank&log$=nuclalign&blast_rank=2&RID=BF1RUX1A013 on Jul. 19, 2023, 2023.

Bettembourg, Mathilde, et al., "Root cone angle is enlarged in docs1 LRR-RLK mutants in rice", Rice, 10(1), 2017, 1-8.

Bommert, Peter, et al., "Quantitative variation in maize kernel row number is controlled by the Fasciated EAR2 locus", Nature Genetics 45(3), 2013, 334-337.

Bommert, Peter, et al., "thick tassel dwarf1 encodes a putative maize ortholog of the *Arabidopsis* CLAVATA1 leucine-rich repeat receptor-like kinase", Development, 132(6), 2005, 1235-1245.

Carballo, Jose, et al., "A high-quality genome of Eragrostis curvula grass provides insights into Poaceae evolution and supports new strategies to enhance forage quality", Scientific Reports, 9(Article: 10250), 2019, 1-15.

Crook, Ashley D., et al., "The systemic nodule number regulation kinase SUNN in Medicago truncatula interacts with MtCLV2 and MtCRN", The Plant Journal 88, 2016, 108-119.

Czyzewicz, Nathan, et al., "Antagonistic peptide technology for functional dissection of CLE peptides revisited", Journal of Experimental Botany 66, 2015, 5367-5374.

(56) References Cited

OTHER PUBLICATIONS

Deyoung, Brody J., et al., "The CLAVATA1-related BAM1, BAM2 and BAM3 receptor kinase-like proteins are required for meristem function in *Arabidopsis*", The Plant Journal, 45(1), 2006, 1-16.
Fan, C., et al., "A Novel Single-Nucleotide Mutation in a CLAVATA3 Gene Homolog Controls a Multilocular Silique Trait in *Brassica rapa* L", Mol Plant 7, 2014, 1788-1792.
Goad, David M., et al., "Comprehensive identification and clustering of CLV3/ESR-related (CLE) genes in plants finds groups with potentially shared function", New Phytologist 216, 2017, 605-616.
Hu, Chong, et al., "A group of receptor kinases are essential for Clavata signalling to maintain stem cell homeostasis", Nature Plants, 4, 2018, 205-211.
Kinoshita, Atsuko, et al., "RPK2 is an essential receptor-like kinase that transmits the CLV3 signal in *Arabidopsis*", Development, 137(22), 2010, 3911-3920.
Li, Manfei, et al., "Genetic and Molecular Mechanisms of Quantitative Trait Loci Controlling Maize Inflorescence Architecture", 2018 Plant Cell Physiology 59 (3), 2018, 448-457.
Liu, Lei, et al., "Enhancing grain-yield-related traits by CRISPR-Cas9 promoter editing of maize CLE genes", Nature plants, 7(3), 2021, 287-294.
Liu, Chang, et al., "Natural variation in the Thick Tassel DWARF1 (TD1) gene in the regulation of maize (*Zea mays* L.) ear-related traits", Breeding Science, 69(2), 2019, 323-331.
Nimchuk, Zachary L., "Plant stem cell maintenance by transcriptional cross-regulation of related receptor kinases", Development, 142(6), 2015, 1043-1049.
Nowak, Stephen, et al., "The Medicago truncatula CLAVATA3-Like CLE12/13 signaling peptides regulate nodule number depending on the Coryne but not the Compact Root Architecture2 receptor", Plant Signaling & Behavior. vol. 14, No. 6, 2019, e1598730.
Rodriguez-Leal, Daniel, et al., "Evolution of buffering in a genetic circuit controlling plant stem cell proliferation", Nature Genetics. 51, 2019, 786-792.
Rodriguez-Villalon, Antia, et al., "Molecular genetic framework for protophloem formation", Proceedings of the National Academy of Sciences 111, 2014, 11551-11556.
Shpak, Elena D., et al., "Dominant-Negative Receptor Uncovers Redundancy in the *Arabidopsis* Erecta Leucine-Rich Repeat Receptor-Like Kinase Signaling Pathway That Regulates Organ Shape", The Plant Cell, 15(5), 2003, 1095-1110.
Song, Xiu-Fen, et al., "Antagonistic Peptide Technology for Functional Dissection of CLV3/ESR Genes in *Arabidopsis*", Plant Physiol 161, 2013, 1076-1085.
Song, Xiu-Fen, et al., "Contributions of Individual Amino Acid Residues to the Endogenous CLV3 Function in Shoot Apical Meristem Maintenance in *Arabidopsis*", Mol Plant 5, 2012, 515-523.
Tran, Quan Hong, et al., "Mapping-by-Sequencing via MutMap Identifies a Mutation in ZmCLE7 Underlying Fasciation in a Newly Developed EMS Mutant Population in an Elite Tropical Maize Inbred", Genes vol. 11, No. 3, 2020.
Trung, Khuat Huu, et al., "A Weak Allele of Fasciated Ear 2 (FEA2) Increases Maize Kernel Row Number (KRN) and Yield in Elite Maize Hybrids", Agronomy 10, 2020, 1774.
Xu, Cao, et al., "A cascade of arabinosyltransferases controls shoot meristem size in tomato", Nature Genetics, 47 (7), 2015, 784-792.
Yamaguchi, Yasuka L., et al., "A Collection of Mutants for CLE-Peptide-Encoding Genes in *Arabidopsis* Generated by CRISPR/Cas9-Mediated Gene Targeting", Plant and Cell Phsiology vol. 58, No. 11, 2017, 1848-1856.
Yang, Yang, et al., "Precise editing of Clavata genes in *Brassica napus* L. regulates multilocular silique development", Plant Biotechnol J 16, 2018, 1322-1335.
Zsogon, Agustin, et al., "Genome editing as a tool to achieve the crop ideotype and de novo domestication of wild relatives: Case study in tomato", Plant Science 256, 2017, 120-130.
"*Zea mays* cultivar B73 chromosome 3, whole genome shotgun sequence." GenBank Accession No. CM007649.1 (2017).
Mendes-Moreira, et al., "Genetic Architecture of Ear Fasciation in Maize (*Zea mays*) under QTL Scrutiny", PLoS ONE 10(4):e0124543. doi:10.1371/journal.pone.0124543.

\* cited by examiner

```
                        SEQUENCE LISTING

<160> NUMBER OF SEQ ID NOS: 191

<210> SEQ ID NO 1
    <211> LENGTH: 1228
    <212> TYPE: PRT
    <213> ORGANISM: Lachnospiraceae sp.

<400> SEQUENCE: 1

Met Ser Lys Leu Glu Lys Phe Thr Asn Cys Tyr Ser Leu Ser Lys Thr
    1               5                   10                  15

Leu Arg Phe Lys Ala Ile Pro Val Gly Lys Thr Gln Glu Asn Ile Asp
                20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
    65                  70                  75                  80

Phe Arg Lys Lys Thr Arg Thr Glu Lys Glu Asn Lys Glu Leu Glu Asn
                    85                  90                  95

Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
    145                 150                 155                 160

Met Phe Ser Glu Glu Ala Lys Ser Thr Ser Ile Ala Phe Arg Cys Ile
                    165                 170                 175

Asn Glu Asn Leu Thr Arg Tyr Ile Ser Asn Met Asp Ile Phe Glu Lys
                180                 185                 190

Val Asp Ala Ile Phe Asp Lys His Glu Val Gln Glu Ile Lys Glu Lys
            195                 200                 205

Ile Leu Asn Ser Asp Tyr Asp Val Glu Phe Phe Glu Gly Glu Phe
        210                 215                 220

Phe Asn Phe Val Leu Thr Gln Glu Gly Ile Asp Val Tyr Asn Ala Ile
    225                 230                 235                 240

Ile Gly Gly Phe Val Thr Glu Ser Gly Glu Lys Ile Lys Gly Leu Asn
```

```
                    245                 250                 255
Glu Tyr Ile Asn Leu Tyr Asn Gln Lys Thr Lys Gln Lys Leu Pro Lys
                260                 265                 270

Phe Lys Pro Leu Tyr Lys Gln Val Leu Ser Asp Arg Glu Ser Leu Ser
            275                 280                 285

Phe Tyr Gly Glu Gly Tyr Thr Ser Asp Glu Glu Val Leu Glu Val Phe
        290                 295                 300

Arg Asn Thr Leu Asn Lys Asn Ser Glu Ile Phe Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
                340                 345                 350

Gly Glu Trp Asn Val Ile Arg Asp Lys Trp Asn Ala Glu Tyr Asp Asp
                355                 360                 365

Ile His Leu Lys Lys Lys Ala Val Val Thr Glu Lys Tyr Glu Asp Asp
                370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
            530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670
```

```
Val Glu Glu Gln Gly Tyr Lys Val Ser Phe Glu Ser Ala Ser Lys Lys
            675                 680                 685

Glu Val Asp Lys Leu Val Glu Gly Lys Leu Tyr Met Phe Gln Ile
690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
        820                 825                 830

Arg Gly Glu Arg Asn Leu Leu Tyr Ile Val Val Asp Gly Lys Gly
        835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
        900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
                980                 985                 990

Ile Phe Tyr Ile Pro Ala Trp Leu Thr Ser Lys Ile Asp Pro Ser Thr
            995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080
```

-continued

```
Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 2
<211> LENGTH: 1307
<212> TYPE: PRT
<213> ORGANISM: Acidaminococcus sp.

<400> SEQUENCE: 2

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220
```

```
Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640
```

-continued

```
Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
        995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
```

```
            1055                1060                1065

Tyr Thr Ser Lys Ile Asp Pro Leu Thr Gly Phe Val Asp Pro Phe
        1070                1075                1080

Val Trp Lys Thr Ile Lys Asn His Glu Ser Arg Lys His Phe Leu
1085                1090                1095

Glu Gly Phe Asp Phe Leu His Tyr Asp Val Lys Thr Gly Asp Phe
        1100                1105                1110

Ile Leu His Phe Lys Met Asn Arg Asn Leu Ser Phe Gln Arg Gly
        1115                1120                1125

Leu Pro Gly Phe Met Pro Ala Trp Asp Ile Val Phe Glu Lys Asn
        1130                1135                1140

Glu Thr Gln Phe Asp Ala Lys Gly Thr Pro Phe Ile Ala Gly Lys
        1145                1150                1155

Arg Ile Val Pro Val Ile Glu Asn His Arg Phe Thr Gly Arg Tyr
        1160                1165                1170

Arg Asp Leu Tyr Pro Ala Asn Glu Leu Ile Ala Leu Leu Glu Glu
        1175                1180                1185

Lys Gly Ile Val Phe Arg Asp Gly Ser Asn Ile Leu Pro Lys Leu
        1190                1195                1200

Leu Glu Asn Asp Asp Ser His Ala Ile Asp Thr Met Val Ala Leu
        1205                1210                1215

Ile Arg Ser Val Leu Gln Met Arg Asn Ser Asn Ala Ala Thr Gly
        1220                1225                1230

Glu Asp Tyr Ile Asn Ser Pro Val Arg Asp Leu Asn Gly Val Cys
        1235                1240                1245

Phe Asp Ser Arg Phe Gln Asn Pro Glu Trp Pro Met Asp Ala Asp
        1250                1255                1260

Ala Asn Gly Ala Tyr His Ile Ala Leu Lys Gly Gln Leu Leu Leu
        1265                1270                1275

Asn His Leu Lys Glu Ser Lys Asp Leu Lys Leu Gln Asn Gly Ile
        1280                1285                1290

Ser Asn Gln Asp Trp Leu Ala Tyr Ile Gln Glu Leu Arg Asn
        1295                1300                1305

<210> SEQ ID NO 3
<211> LENGTH: 1241
<212> TYPE: PRT
<213> ORGANISM: Butyrivibrio proteoclasticus

<400> SEQUENCE: 3

Met Leu Leu Tyr Glu Asn Tyr Thr Lys Arg Asn Gln Ile Thr Lys Ser
1               5                   10                  15

Leu Arg Leu Glu Leu Arg Pro Gln Gly Lys Thr Leu Arg Asn Ile Lys
            20                  25                  30

Glu Leu Asn Leu Leu Glu Gln Asp Lys Ala Ile Tyr Ala Leu Leu Glu
        35                  40                  45

Arg Leu Lys Pro Val Ile Asp Glu Gly Ile Lys Asp Ile Ala Arg Asp
    50                  55                  60

Thr Leu Lys Asn Cys Glu Leu Ser Phe Glu Lys Leu Tyr Glu His Phe
65                  70                  75                  80

Leu Ser Gly Asp Lys Lys Ala Tyr Ala Lys Glu Ser Glu Arg Leu Lys
                85                  90                  95

Lys Glu Ile Val Lys Thr Leu Ile Lys Asn Leu Pro Glu Gly Ile Gly
            100                 105                 110
```

-continued

Lys Ile Ser Glu Ile Asn Ser Ala Lys Tyr Leu Asn Gly Val Leu Tyr
115                 120                 125

Asp Phe Ile Asp Lys Thr His Lys Asp Ser Glu Glu Lys Gln Asn Ile
130                 135                 140

Leu Ser Asp Ile Leu Glu Thr Lys Gly Tyr Leu Ala Leu Phe Ser Lys
145                 150                 155                 160

Phe Leu Thr Ser Arg Ile Thr Thr Leu Glu Gln Ser Met Pro Lys Arg
            165                 170                 175

Val Ile Glu Asn Phe Glu Ile Tyr Ala Ala Asn Ile Pro Lys Met Gln
                180                 185                 190

Asp Ala Leu Glu Arg Gly Ala Val Ser Phe Ala Ile Glu Tyr Glu Ser
            195                 200                 205

Ile Cys Ser Val Asp Tyr Tyr Asn Gln Ile Leu Ser Gln Glu Asp Ile
        210                 215                 220

Asp Ser Tyr Asn Arg Leu Ile Ser Gly Ile Met Asp Glu Asp Gly Ala
225                 230                 235                 240

Lys Glu Lys Gly Ile Asn Gln Thr Ile Ser Glu Lys Asn Ile Lys Ile
                245                 250                 255

Lys Ser Glu His Leu Glu Glu Lys Pro Phe Arg Ile Leu Lys Gln Leu
            260                 265                 270

His Lys Gln Ile Leu Glu Glu Arg Glu Lys Ala Phe Thr Ile Asp His
    275                 280                 285

Ile Asp Ser Asp Glu Glu Val Val Gln Val Thr Lys Glu Ala Phe Glu
        290                 295                 300

Gln Thr Lys Glu Gln Trp Glu Asn Ile Lys Lys Ile Asn Gly Phe Tyr
305                 310                 315                 320

Ala Lys Asp Pro Gly Asp Ile Thr Leu Phe Ile Val Val Gly Pro Asn
                325                 330                 335

Gln Thr His Val Leu Ser Gln Leu Ile Tyr Gly Glu His Asp Arg Ile
            340                 345                 350

Arg Leu Leu Leu Glu Glu Tyr Glu Lys Asn Thr Leu Glu Val Leu Pro
        355                 360                 365

Arg Arg Thr Lys Ser Glu Asp Ala Arg Tyr Asp Lys Phe Val Asn Ala
370                 375                 380

Val Pro Lys Lys Val Ala Lys Glu Ser His Thr Phe Asp Gly Leu Gln
385                 390                 395                 400

Lys Met Thr Gly Asp Asp Arg Leu Phe Ile Leu Tyr Arg Asp Glu Leu
                405                 410                 415

Ala Arg Asn Tyr Met Arg Ile Lys Glu Ala Tyr Gly Thr Phe Glu Arg
            420                 425                 430

Asp Ile Leu Lys Ser Arg Arg Gly Ile Lys Gly Asn Arg Asp Val Gln
        435                 440                 445

Glu Ser Leu Val Ser Phe Tyr Asp Glu Leu Thr Lys Phe Arg Ser Ala
            450                 455                 460

Leu Arg Ile Ile Asn Ser Gly Asn Asp Glu Lys Ala Asp Pro Ile Phe
465                 470                 475                 480

Tyr Asn Thr Phe Asp Gly Ile Phe Glu Lys Ala Asn Arg Thr Tyr Lys
                485                 490                 495

Ala Glu Asn Leu Cys Arg Asn Tyr Val Thr Lys Ser Pro Ala Asp Asp
            500                 505                 510

Ala Arg Ile Met Ala Ser Cys Leu Gly Thr Pro Ala Arg Leu Arg Thr
        515                 520                 525

His Trp Trp Asn Gly Glu Glu Asn Phe Ala Ile Asn Asp Val Ala Met

```
                 530              535              540
Ile Arg Arg Gly Asp Glu Tyr Tyr Phe Val Leu Thr Pro Asp Val
545                  550              555              560

Lys Pro Val Asp Leu Lys Thr Lys Asp Glu Thr Asp Ala Gln Ile Phe
                 565              570              575

Val Gln Arg Lys Gly Ala Lys Ser Phe Leu Gly Leu Pro Lys Ala Leu
                 580              585              590

Phe Lys Cys Ile Leu Glu Pro Tyr Phe Glu Ser Pro Glu His Lys Asn
                 595              600              605

Asp Lys Asn Cys Val Ile Glu Glu Tyr Val Ser Lys Pro Leu Thr Ile
                 610              615              620

Asp Arg Arg Ala Tyr Asp Ile Phe Lys Asn Gly Thr Phe Lys Lys Thr
625              630              635              640

Asn Ile Gly Ile Asp Gly Leu Thr Glu Glu Lys Phe Lys Asp Asp Cys
                 645              650              655

Arg Tyr Leu Ile Asp Val Tyr Lys Glu Phe Ile Ala Val Tyr Thr Arg
                 660              665              670

Tyr Ser Cys Phe Asn Met Ser Gly Leu Lys Arg Ala Asp Glu Tyr Asn
                 675              680              685

Asp Ile Gly Glu Phe Phe Ser Asp Val Asp Thr Arg Leu Cys Thr Met
                 690              695              700

Glu Trp Ile Pro Val Ser Phe Glu Arg Ile Asn Asp Met Val Asp Lys
705              710              715              720

Lys Glu Gly Leu Leu Phe Leu Val Arg Ser Met Phe Leu Tyr Asn Arg
                 725              730              735

Pro Arg Lys Pro Tyr Glu Arg Thr Phe Ile Gln Leu Phe Ser Asp Ser
                 740              745              750

Asn Met Glu His Thr Ser Met Leu Leu Asn Ser Arg Ala Met Ile Gln
                 755              760              765

Tyr Arg Ala Ala Ser Leu Pro Arg Arg Val Thr His Lys Lys Gly Ser
                 770              775              780

Ile Leu Val Ala Leu Arg Asp Ser Asn Gly Glu His Ile Pro Met His
785              790              795              800

Ile Arg Glu Ala Ile Tyr Lys Met Lys Asn Asn Phe Asp Ile Ser Ser
                 805              810              815

Glu Asp Phe Ile Met Ala Lys Ala Tyr Leu Ala Glu His Asp Val Ala
                 820              825              830

Ile Lys Lys Ala Asn Glu Asp Ile Ile Arg Asn Arg Arg Tyr Thr Glu
                 835              840              845

Asp Lys Phe Phe Leu Ser Leu Ser Tyr Thr Lys Asn Ala Asp Ile Ser
850              855              860

Ala Arg Thr Leu Asp Tyr Ile Asn Asp Lys Val Glu Glu Asp Thr Gln
865              870              875              880

Asp Ser Arg Met Ala Val Ile Val Thr Arg Asn Leu Lys Asp Leu Thr
                 885              890              895

Tyr Val Ala Val Val Asp Glu Lys Asn Asn Val Leu Glu Glu Lys Ser
                 900              905              910

Leu Asn Glu Ile Asp Gly Val Asn Tyr Arg Glu Leu Leu Lys Glu Arg
                 915              920              925

Thr Lys Ile Lys Tyr His Asp Lys Thr Arg Leu Trp Gln Tyr Asp Val
                 930              935              940

Ser Ser Lys Gly Leu Lys Glu Ala Tyr Val Glu Leu Ala Val Thr Gln
945              950              955              960
```

```
Ile Ser Lys Leu Ala Thr Lys Tyr Asn Ala Val Val Val Glu Ser
            965                 970                 975

Met Ser Ser Thr Phe Lys Asp Lys Phe Ser Phe Leu Asp Glu Gln Ile
            980                 985                 990

Phe Lys Ala Phe Glu Ala Arg Leu Cys Ala Arg Met Ser Asp Leu Ser
            995                 1000                1005

Phe Asn Thr Ile Lys Glu Gly Glu Ala Gly Ser Ile Ser Asn Pro
        1010                1015                1020

Ile Gln Val Ser Asn Asn Asn Gly Asn Ser Tyr Gln Asp Gly Val
        1025                1030                1035

Ile Tyr Phe Leu Asn Asn Ala Tyr Thr Arg Thr Leu Cys Pro Asp
        1040                1045                1050

Thr Gly Phe Val Asp Val Phe Asp Lys Thr Arg Leu Ile Thr Met
        1055                1060                1065

Gln Ser Lys Arg Gln Phe Phe Ala Lys Met Lys Asp Ile Arg Ile
        1070                1075                1080

Asp Asp Gly Glu Met Leu Phe Thr Phe Asn Leu Glu Glu Tyr Pro
        1085                1090                1095

Thr Lys Arg Leu Leu Asp Arg Lys Glu Trp Thr Val Lys Ile Ala
        1100                1105                1110

Gly Asp Gly Ser Tyr Phe Asp Lys Asp Lys Gly Glu Tyr Val Tyr
        1115                1120                1125

Val Asn Asp Ile Val Arg Glu Gln Ile Ile Pro Ala Leu Leu Glu
        1130                1135                1140

Asp Lys Ala Val Phe Asp Gly Asn Met Ala Glu Lys Phe Leu Asp
        1145                1150                1155

Lys Thr Ala Ile Ser Gly Lys Ser Val Glu Leu Ile Tyr Lys Trp
        1160                1165                1170

Phe Ala Asn Ala Leu Tyr Gly Ile Ile Thr Lys Lys Asp Gly Glu
        1175                1180                1185

Lys Ile Tyr Arg Ser Pro Ile Thr Gly Thr Glu Ile Asp Val Ser
        1190                1195                1200

Lys Asn Thr Thr Tyr Asn Phe Gly Lys Lys Phe Met Phe Lys Gln
        1205                1210                1215

Glu Tyr Arg Gly Asp Gly Asp Phe Leu Asp Ala Phe Leu Asn Tyr
        1220                1225                1230

Met Gln Ala Gln Asp Ile Ala Val
        1235                1240

<210> SEQ ID NO 4
<211> LENGTH: 1238
<212> TYPE: PRT
<213> ORGANISM: Candidatus Methanoplasma termitum

<400> SEQUENCE: 4

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
            20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Lys Phe Ile Asp Glu
    50                  55                  60

His Leu Thr Asn Met Ser Leu Asp Trp Asn Ser Leu Lys Gln Ile Ser
```

```
            65                  70                  75                  80
Glu Lys Tyr Tyr Lys Ser Arg Glu Gly Lys Asp Lys Val Phe Leu
                85                  90                  95
Ser Glu Gln Lys Arg Met Arg Gln Glu Ile Val Ser Glu Phe Lys Lys
                    100                 105                 110
Asp Asp Arg Phe Lys Asp Leu Phe Ser Lys Lys Leu Phe Ser Glu Leu
                    115                 120                 125
Leu Lys Glu Glu Ile Tyr Lys Lys Gly Asn His Gln Glu Ile Asp Ala
            130                 135                 140
Leu Lys Ser Phe Asp Lys Phe Ser Gly Tyr Phe Ile Gly Leu His Glu
145                 150                 155                 160
Asn Arg Lys Asn Met Tyr Ser Asp Gly Asp Glu Ile Thr Ala Ile Ser
                        165                 170                 175
Asn Arg Ile Val Asn Glu Asn Phe Pro Lys Phe Leu Asp Asn Leu Gln
                    180                 185                 190
Lys Tyr Gln Glu Ala Arg Lys Lys Tyr Pro Glu Trp Ile Ile Lys Ala
                195                 200                 205
Glu Ser Ala Leu Val Ala His Asn Ile Lys Met Asp Ile Val Phe Ser
            210                 215                 220
Leu Glu Tyr Phe Asn Lys Val Leu Asn Gln Glu Gly Ile Gln Arg Tyr
225                 230                 235                 240
Asn Leu Ala Leu Gly Gly Tyr Val Thr Lys Ser Gly Glu Lys Met Met
                    245                 250                 255
Gly Leu Asn Asp Ala Leu Asn Leu Ala His Gln Ser Glu Lys Ser Ser
                260                 265                 270
Lys Gly Arg Ile His Met Thr Pro Leu Phe Lys Gln Ile Leu Ser Glu
            275                 280                 285
Lys Glu Ser Phe Ser Tyr Ile Pro Asp Val Phe Thr Glu Asp Ser Gln
            290                 295                 300
Leu Leu Pro Ser Ile Gly Gly Phe Phe Ala Gln Ile Glu Asn Asp Lys
305                 310                 315                 320
Asp Gly Asn Ile Phe Asp Arg Ala Leu Glu Leu Ile Ser Ser Tyr Ala
                    325                 330                 335
Glu Tyr Asp Thr Glu Arg Ile Tyr Ile Arg Gln Ala Asp Ile Asn Arg
                340                 345                 350
Val Ser Asn Val Ile Phe Gly Glu Trp Gly Thr Leu Gly Gly Leu Met
            355                 360                 365
Arg Glu Tyr Lys Ala Asp Ser Ile Asn Asp Ile Asn Leu Glu Arg Thr
    370                 375                 380
Cys Lys Lys Val Asp Lys Trp Leu Asp Ser Lys Glu Phe Ala Leu Ser
385                 390                 395                 400
Asp Val Leu Glu Ala Ile Asp Arg Thr Gly Asn Asn Asp Ala Phe Asn
                    405                 410                 415
Glu Tyr Ile Ser Lys Met Arg Thr Ala Arg Glu Lys Ile Asp Ala Ala
                420                 425                 430
Arg Lys Glu Met Lys Phe Ile Ser Glu Lys Ile Ser Gly Asp Glu Glu
            435                 440                 445
Ser Ile His Ile Ile Lys Thr Leu Leu Asp Ser Val Gln Gln Phe Leu
            450                 455                 460
His Phe Phe Asn Leu Phe Lys Ala Arg Gln Asp Ile Pro Leu Asp Gly
465                 470                 475                 480
Ala Phe Tyr Ala Glu Phe Asp Glu Val His Ser Lys Leu Phe Ala Ile
                    485                 490                 495
```

```
Val Pro Leu Tyr Asn Lys Val Arg Asn Tyr Leu Thr Lys Asn Asn Leu
            500                 505                 510

Asn Thr Lys Lys Ile Lys Leu Asn Phe Lys Asn Pro Thr Leu Ala Asn
        515                 520                 525

Gly Trp Asp Gln Asn Lys Val Tyr Asp Tyr Ala Ser Leu Ile Phe Leu
    530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
                565                 570                 575

Met Val Tyr Lys Gln Ile Pro Gly Pro Asn Lys Asn Leu Arg Pro Val
            580                 585                 590

Phe Leu Thr Ser Thr Lys Gly Lys Lys Glu Tyr Lys Pro Ser Lys Glu
        595                 600                 605

Ile Ile Glu Gly Tyr Glu Ala Asp Lys His Ile Arg Gly Asp Lys Phe
        610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
                645                 650                 655

Glu Ser Tyr Gly Asp Ile Ser Glu Phe Tyr Leu Asp Val Glu Lys Gln
            660                 665                 670

Gly Tyr Arg Met His Phe Glu Asn Ile Ser Ala Glu Thr Ile Asp Glu
        675                 680                 685

Tyr Val Glu Lys Gly Asp Leu Phe Leu Phe Gln Ile Tyr Asn Lys Asp
            690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Lys Leu
                725                 730                 735

Asn Gly Glu Ala Glu Leu Phe Tyr Arg Asp Lys Ser Asp Ile Lys Glu
            740                 745                 750

Ile Val His Arg Glu Gly Glu Ile Leu Val Asn Arg Thr Tyr Asn Gly
        755                 760                 765

Arg Thr Pro Val Pro Asp Lys Ile His Lys Lys Leu Thr Asp Tyr His
770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
                805                 810                 815

Leu Asn Asp Lys Ile Tyr Phe His Val Pro Leu Thr Leu Asn Phe Lys
            820                 825                 830

Ala Asn Gly Lys Lys Asn Leu Asn Lys Met Val Ile Glu Lys Phe Leu
        835                 840                 845

Ser Asp Glu Lys Ala His Ile Ile Gly Ile Asp Arg Gly Glu Arg Asn
        850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
            900                 905                 910
```

Gly Lys Ile Lys Asp Leu Lys Glu Gly Tyr Leu Ser Lys Ala Val His
        915                 920                 925

Glu Ile Thr Lys Met Ala Ile Gln Tyr Asn Ala Ile Val Val Met Glu
        930                 935                 940

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
                965                 970                 975

Val Phe Lys Asp Ala Pro Asp Glu Ser Pro Gly Val Leu Asn Ala
        980                 985                 990

Tyr Gln Leu Thr Asn Pro Leu Glu Ser Phe Ala Lys Leu Gly Lys Gln
        995                 1000                1005

Thr Gly Ile Leu Phe Tyr Val Pro Ala Ala Tyr Thr Ser Lys Ile
        1010                1015                1020

Asp Pro Thr Thr Gly Phe Val Asn Leu Phe Asn Thr Ser Ser Lys
        1025                1030                1035

Thr Asn Ala Gln Glu Arg Lys Glu Phe Leu Gln Lys Phe Glu Ser
        1040                1045                1050

Ile Ser Tyr Ser Ala Lys Asp Gly Gly Ile Phe Ala Phe Ala Phe
        1055                1060                1065

Asp Tyr Arg Lys Phe Gly Thr Ser Lys Thr Asp His Lys Asn Val
        1070                1075                1080

Trp Thr Ala Tyr Thr Asn Gly Glu Arg Met Arg Tyr Ile Lys Glu
        1085                1090                1095

Lys Lys Arg Asn Glu Leu Phe Asp Pro Ser Lys Glu Ile Lys Glu
        1100                1105                1110

Ala Leu Thr Ser Ser Gly Ile Lys Tyr Asp Gly Gly Gln Asn Ile
        1115                1120                1125

Leu Pro Asp Ile Leu Arg Ser Asn Asn Asn Gly Leu Ile Tyr Thr
        1130                1135                1140

Met Tyr Ser Ser Phe Ile Ala Ala Ile Gln Met Arg Val Tyr Asp
        1145                1150                1155

Gly Lys Glu Asp Tyr Ile Ile Ser Pro Ile Lys Asn Ser Lys Gly
        1160                1165                1170

Glu Phe Phe Arg Thr Asp Pro Lys Arg Arg Glu Leu Pro Ile Asp
        1175                1180                1185

Ala Asp Ala Asn Gly Ala Tyr Asn Ile Ala Leu Arg Gly Glu Leu
        1190                1195                1200

Thr Met Arg Ala Ile Ala Glu Lys Phe Asp Pro Asp Ser Glu Lys
        1205                1210                1215

Met Ala Lys Leu Glu Leu Lys His Lys Asp Trp Phe Glu Phe Met
        1220                1225                1230

Gln Thr Arg Gly Asp
        1235

<210> SEQ ID NO 5
<211> LENGTH: 1281
<212> TYPE: PRT
<213> ORGANISM: Eubacterium eligens

<400> SEQUENCE: 5

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
            20                  25                  30

-continued

```
Gln Glu His Ile Ile Gln Asn Gly Leu Ile Gln Glu Asp Glu Leu Arg
            35                  40                  45
Gln Glu Lys Ser Thr Glu Leu Lys Asn Ile Met Asp Asp Tyr Tyr Arg
        50                  55                  60
Glu Tyr Ile Asp Lys Ser Leu Ser Gly Val Thr Asp Leu Asp Phe Thr
65                  70                  75                  80
Leu Leu Phe Glu Leu Met Asn Leu Val Gln Ser Ser Pro Ser Lys Asp
                85                  90                  95
Asn Lys Lys Ala Leu Glu Lys Glu Gln Ser Lys Met Arg Glu Gln Ile
            100                 105                 110
Cys Thr His Leu Gln Ser Asp Ser Asn Tyr Lys Asn Ile Phe Asn Ala
            115                 120                 125
Lys Leu Leu Lys Glu Ile Leu Pro Asp Phe Ile Lys Asn Tyr Asn Gln
        130                 135                 140
Tyr Asp Val Lys Asp Lys Ala Gly Lys Leu Glu Thr Leu Ala Leu Phe
145                 150                 155                 160
Asn Gly Phe Ser Thr Tyr Phe Thr Asp Phe Phe Glu Lys Arg Lys Asn
                165                 170                 175
Val Phe Thr Lys Glu Ala Val Ser Thr Ser Ile Ala Tyr Arg Ile Val
            180                 185                 190
His Glu Asn Ser Leu Ile Phe Leu Ala Asn Met Thr Ser Tyr Lys Lys
            195                 200                 205
Ile Ser Glu Lys Ala Leu Asp Glu Ile Glu Val Ile Glu Lys Asn Asn
        210                 215                 220
Gln Asp Lys Met Gly Asp Trp Glu Leu Asn Gln Ile Phe Asn Pro Asp
225                 230                 235                 240
Phe Tyr Asn Met Val Leu Ile Gln Ser Gly Ile Asp Phe Tyr Asn Glu
                245                 250                 255
Ile Cys Gly Val Val Asn Ala His Met Asn Leu Tyr Cys Gln Gln Thr
            260                 265                 270
Lys Asn Asn Tyr Asn Leu Phe Lys Met Arg Lys Leu His Lys Gln Ile
        275                 280                 285
Leu Ala Tyr Thr Ser Thr Ser Phe Glu Val Pro Lys Met Phe Glu Asp
        290                 295                 300
Asp Met Ser Val Tyr Asn Ala Val Asn Ala Phe Ile Asp Glu Thr Glu
305                 310                 315                 320
Lys Gly Asn Ile Ile Gly Lys Leu Lys Asp Ile Val Asn Lys Tyr Asp
                325                 330                 335
Glu Leu Asp Glu Lys Arg Ile Tyr Ile Ser Lys Asp Phe Tyr Glu Thr
            340                 345                 350
Leu Ser Cys Phe Met Ser Gly Asn Trp Asn Leu Ile Thr Gly Cys Val
            355                 360                 365
Glu Asn Phe Tyr Asp Glu Asn Ile His Ala Lys Gly Lys Ser Lys Glu
        370                 375                 380
Glu Lys Val Lys Lys Ala Val Lys Glu Asp Lys Tyr Lys Ser Ile Asn
385                 390                 395                 400
Asp Val Asn Asp Leu Val Glu Lys Tyr Ile Asp Glu Lys Glu Arg Asn
                405                 410                 415
Glu Phe Lys Asn Ser Asn Ala Lys Gln Tyr Ile Arg Glu Ile Ser Asn
            420                 425                 430
Ile Ile Thr Asp Thr Glu Thr Ala His Leu Glu Tyr Asp Asp His Ile
        435                 440                 445
```

```
Ser Leu Ile Glu Ser Glu Glu Lys Ala Asp Glu Met Lys Lys Arg Leu
450                 455                 460

Asp Met Tyr Met Asn Met Tyr His Trp Ala Lys Ala Phe Ile Val Asp
465                 470                 475                 480

Glu Val Leu Asp Arg Asp Glu Met Phe Tyr Ser Asp Ile Asp Asp Ile
            485                 490                 495

Tyr Asn Ile Leu Glu Asn Ile Val Pro Leu Tyr Asn Arg Val Arg Asn
                500                 505                 510

Tyr Val Thr Gln Lys Pro Tyr Asn Ser Lys Lys Ile Lys Leu Asn Phe
            515                 520                 525

Gln Ser Pro Thr Leu Ala Asn Gly Trp Ser Gln Ser Lys Glu Phe Asp
530                 535                 540

Asn Asn Ala Ile Ile Leu Ile Arg Asp Asn Lys Tyr Tyr Leu Ala Ile
545                 550                 555                 560

Phe Asn Ala Lys Asn Lys Pro Asp Lys Lys Ile Ile Gln Gly Asn Ser
                565                 570                 575

Asp Lys Lys Asn Asp Asn Asp Tyr Lys Lys Met Val Tyr Asn Leu Leu
            580                 585                 590

Pro Gly Ala Asn Lys Met Leu Pro Lys Val Phe Leu Ser Lys Lys Gly
            595                 600                 605

Ile Glu Thr Phe Lys Pro Ser Asp Tyr Ile Ile Ser Gly Tyr Asn Ala
            610                 615                 620

His Lys His Ile Lys Thr Ser Glu Asn Phe Asp Ile Ser Phe Cys Arg
625                 630                 635                 640

Asp Leu Ile Asp Tyr Phe Lys Asn Ser Ile Glu Lys His Ala Glu Trp
                645                 650                 655

Arg Lys Tyr Glu Phe Lys Phe Ser Ala Thr Asp Ser Tyr Ser Asp Ile
            660                 665                 670

Ser Glu Phe Tyr Arg Glu Val Glu Met Gln Gly Tyr Arg Ile Asp Trp
            675                 680                 685

Thr Tyr Ile Ser Glu Ala Asp Ile Asn Lys Leu Asp Glu Glu Gly Lys
            690                 695                 700

Ile Tyr Leu Phe Gln Ile Tyr Asn Lys Asp Phe Ala Glu Asn Ser Thr
705                 710                 715                 720

Gly Lys Glu Asn Leu His Thr Met Tyr Phe Lys Asn Ile Phe Ser Glu
                725                 730                 735

Glu Asn Leu Asp Lys Ile Ile Lys Leu Asn Gly Gln Ala Glu Leu Phe
            740                 745                 750

Tyr Arg Arg Ala Ser Val Lys Asn Pro Val Lys His Lys Lys Asp Ser
            755                 760                 765

Val Leu Val Asn Lys Thr Tyr Lys Asn Gln Leu Asp Asn Gly Asp Val
770                 775                 780

Val Arg Ile Pro Ile Pro Asp Asp Ile Tyr Asn Glu Ile Tyr Lys Met
785                 790                 795                 800

Tyr Asn Gly Tyr Ile Lys Glu Ser Asp Leu Ser Glu Ala Ala Lys Glu
                805                 810                 815

Tyr Leu Asp Lys Val Glu Val Arg Thr Ala Gln Lys Asp Ile Val Lys
            820                 825                 830

Asp Tyr Arg Tyr Thr Val Asp Lys Tyr Phe Ile His Thr Pro Ile Thr
            835                 840                 845

Ile Asn Tyr Lys Val Thr Ala Arg Asn Asn Val Asn Asp Met Val Val
850                 855                 860

Lys Tyr Ile Ala Gln Asn Asp Asp Ile His Val Ile Gly Ile Asp Arg
```

-continued

```
             865                 870                 875                 880
Gly Glu Arg Asn Leu Ile Tyr Ile Ser Val Ile Asp Ser His Gly Asn
                 885                 890                 895

Ile Val Lys Gln Lys Ser Tyr Asn Ile Leu Asn Asn Tyr Asp Tyr Lys
                 900                 905                 910

Lys Lys Leu Val Glu Lys Glu Lys Thr Arg Glu Tyr Ala Arg Lys Asn
                 915                 920                 925

Trp Lys Ser Ile Gly Asn Ile Lys Glu Leu Lys Glu Gly Tyr Ile Ser
                 930                 935                 940

Gly Val Val His Glu Ile Ala Met Leu Ile Val Glu Tyr Asn Ala Ile
945                 950                 955                 960

Ile Ala Met Glu Asp Leu Asn Tyr Gly Phe Lys Arg Gly Arg Phe Lys
                 965                 970                 975

Val Glu Arg Gln Val Tyr Gln Lys Phe Glu Ser Met Leu Ile Asn Lys
                 980                 985                 990

Leu Asn Tyr Phe Ala Ser Lys Glu Lys Ser Val Asp Glu Pro Gly Gly
                 995                1000                1005

Leu Leu Lys Gly Tyr Gln Leu Thr Tyr Val Pro Asp Asn Ile Lys
    1010                1015                1020

Asn Leu Gly Lys Gln Cys Gly Val Ile Phe Tyr Val Pro Ala Ala
    1025                1030                1035

Phe Thr Ser Lys Ile Asp Pro Ser Thr Gly Phe Ile Ser Ala Phe
    1040                1045                1050

Asn Phe Lys Ser Ile Ser Thr Asn Ala Ser Arg Lys Gln Phe Phe
    1055                1060                1065

Met Gln Phe Asp Glu Ile Arg Tyr Cys Ala Glu Lys Asp Met Phe
    1070                1075                1080

Ser Phe Gly Phe Asp Tyr Asn Asn Phe Asp Thr Tyr Asn Ile Thr
    1085                1090                1095

Met Gly Lys Thr Gln Trp Thr Val Tyr Thr Asn Gly Glu Arg Leu
    1100                1105                1110

Gln Ser Glu Phe Asn Asn Ala Arg Arg Thr Gly Lys Thr Lys Ser
    1115                1120                1125

Ile Asn Leu Thr Glu Thr Ile Lys Leu Leu Leu Glu Asp Asn Glu
    1130                1135                1140

Ile Asn Tyr Ala Asp Gly His Asp Ile Arg Ile Asp Met Glu Lys
    1145                1150                1155

Met Asp Glu Asp Lys Lys Ser Glu Phe Phe Ala Gln Leu Leu Ser
    1160                1165                1170

Leu Tyr Lys Leu Thr Val Gln Met Arg Asn Ser Tyr Thr Glu Ala
    1175                1180                1185

Glu Glu Gln Glu Asn Gly Ile Ser Tyr Asp Lys Ile Ile Ser Pro
    1190                1195                1200

Val Ile Asn Asp Glu Gly Glu Phe Phe Asp Ser Asp Asn Tyr Lys
    1205                1210                1215

Glu Ser Asp Asp Lys Glu Cys Lys Met Pro Lys Asp Ala Asp Ala
    1220                1225                1230

Asn Gly Ala Tyr Cys Ile Ala Leu Lys Gly Leu Tyr Glu Val Leu
    1235                1240                1245

Lys Ile Lys Ser Glu Trp Thr Glu Asp Gly Phe Asp Arg Asn Cys
    1250                1255                1260

Leu Lys Leu Pro His Ala Glu Trp Leu Asp Phe Ile Gln Asn Lys
    1265                1270                1275
```

Arg Tyr Glu
    1280

<210> SEQ ID NO 6
<211> LENGTH: 1300
<212> TYPE: PRT
<213> ORGANISM: Francisella novicida

<400> SEQUENCE: 6

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Val Asn Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys

```
                355                 360                 365
Ser Ile Lys Glu Thr Leu Ser Leu Leu Phe Asp Asp Leu Lys Ala Gln
370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
                420                 425                 430

Pro Ser Lys Lys Glu Gln Leu Ile Ala Lys Lys Thr Glu Lys Ala
                435                 440                 445

Lys Tyr Leu Ser Leu Glu Thr Ile Lys Leu Ala Leu Glu Glu Phe Asn
                450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
                500                 505                 510

Asp Leu Leu Gln Ala Ser Ala Glu Asp Val Lys Ala Ile Lys Asp
                515                 520                 525

Leu Leu Asp Gln Thr Asn Asn Leu Leu His Lys Leu Lys Ile Phe His
530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
                580                 585                 590

Asp Glu Lys Phe Lys Leu Asn Phe Glu Asn Ser Thr Leu Ala Asn Gly
                595                 600                 605

Trp Asp Lys Asn Lys Glu Pro Asp Asn Thr Ala Ile Leu Phe Ile Lys
                610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
                660                 665                 670

Phe Phe Ser Ala Lys Ser Ile Lys Phe Tyr Asn Pro Ser Glu Asp Ile
                675                 680                 685

Leu Arg Ile Arg Asn His Ser Thr His Thr Lys Asn Gly Ser Pro Gln
                690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
                740                 745                 750

Phe Tyr Arg Glu Val Glu Asn Gln Gly Tyr Lys Leu Thr Phe Glu Asn
                755                 760                 765

Ile Ser Glu Ser Tyr Ile Asp Ser Val Val Asn Gln Gly Lys Leu Tyr
770                 775                 780
```

-continued

```
Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Ile Thr His Pro Ala Lys Glu Ala
        835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
        995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185
```

-continued

```
Glu Cys Ile Lys Ala Ala Ile Cys Gly Glu Ser Asp Lys Lys Phe
1190                1195                1200

Phe Ala Lys Leu Thr Ser Val Leu Asn Thr Ile Leu Gln Met Arg
1205                1210                1215

Asn Ser Lys Thr Gly Thr Glu Leu Asp Tyr Leu Ile Ser Pro Val
1220                1225                1230

Ala Asp Val Asn Gly Asn Phe Phe Asp Ser Arg Gln Ala Pro Lys
1235                1240                1245

Asn Met Pro Gln Asp Ala Asp Ala Asn Gly Ala Tyr His Ile Gly
1250                1255                1260

Leu Lys Gly Leu Met Leu Leu Gly Arg Ile Lys Asn Asn Gln Glu
1265                1270                1275

Gly Lys Lys Leu Asn Leu Val Ile Lys Asn Glu Glu Tyr Phe Glu
1280                1285                1290

Phe Val Gln Asn Arg Asn Asn
1295                1300

<210> SEQ ID NO 7
<211> LENGTH: 1206
<212> TYPE: PRT
<213> ORGANISM: Lachnospiraceae sp.

<400> SEQUENCE: 7

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
                20                  25                  30

Asn Asn Ile Leu Glu Ser Asp Val Lys Arg Lys Gln Asn Tyr Glu His
            35                  40                  45

Val Lys Gly Ile Leu Asp Glu Tyr His Lys Gln Leu Ile Asn Glu Ala
        50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Gln Asp
        195                 200                 205

Ser Leu Phe Ile Val Glu Thr Phe Asn Lys Thr Leu Thr Gln Asp Gly
    210                 215                 220

Ile Asp Thr Tyr Asn Ser Gln Val Gly Lys Ile Asn Ser Ser Ile Asn
225                 230                 235                 240

Leu Tyr Asn Gln Lys Asn Gln Lys Ala Asn Gly Phe Arg Lys Ile Pro
                245                 250                 255
```

```
Lys Met Lys Met Leu Tyr Lys Gln Ile Leu Ser Asp Arg Glu Glu Ser
            260                 265                 270

Phe Ile Asp Glu Phe Gln Ser Asp Glu Val Leu Ile Asp Asn Val Glu
        275                 280                 285

Ser Tyr Gly Ser Val Leu Ile Glu Ser Leu Lys Ser Ser Lys Val Ser
    290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Val Ile Val Phe Glu Asn
            325                 330                 335

Trp Arg Thr Phe Asp Asp Leu Leu Asn Gln Glu Tyr Asp Leu Ala Asn
            340                 345                 350

Glu Asn Lys Lys Lys Asp Asp Lys Tyr Phe Glu Lys Arg Gln Lys Glu
        355                 360                 365

Leu Lys Lys Asn Lys Ser Tyr Ser Leu Glu His Leu Cys Asn Leu Ser
    370                 375                 380

Glu Asp Ser Cys Asn Leu Ile Glu Asn Tyr Ile His Gln Ile Ser Asp
385                 390                 395                 400

Asp Ile Glu Asn Ile Ile Asn Asn Glu Thr Phe Leu Arg Ile Val
            405                 410                 415

Ile Asn Glu His Asp Arg Ser Arg Lys Leu Ala Lys Asn Arg Lys Ala
            420                 425                 430

Val Lys Ala Ile Lys Asp Phe Leu Asp Ser Ile Lys Val Leu Glu Arg
        435                 440                 445

Glu Leu Lys Leu Ile Asn Ser Ser Gly Gln Glu Leu Glu Lys Asp Leu
        450                 455                 460

Ile Val Tyr Ser Ala His Glu Glu Leu Leu Val Glu Leu Lys Gln Val
465                 470                 475                 480

Asp Ser Leu Tyr Asn Met Thr Arg Asn Tyr Leu Thr Lys Lys Pro Phe
            485                 490                 495

Ser Thr Glu Lys Val Lys Leu Asn Phe Asn Arg Ser Thr Leu Leu Asn
        500                 505                 510

Gly Trp Asp Arg Asn Lys Glu Thr Asp Asn Leu Gly Val Leu Leu Leu
        515                 520                 525

Lys Asp Gly Lys Tyr Tyr Leu Gly Ile Met Asn Thr Ser Ala Asn Lys
530                 535                 540

Ala Phe Val Asn Pro Pro Val Ala Lys Thr Glu Lys Val Phe Lys Lys
545                 550                 555                 560

Val Asp Tyr Lys Leu Leu Pro Val Pro Asn Gln Met Leu Pro Lys Val
            565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
        595                 600                 605

Leu Glu Asp Cys His Asn Leu Ile Asp Phe Phe Lys Glu Ser Ile Ser
        610                 615                 620

Lys His Glu Asp Trp Ser Lys Phe Gly Phe Lys Phe Asp Thr Gln Ala
625                 630                 635                 640

Ser Tyr Asn Asp Ile Ser Glu Phe Tyr Arg Glu Val Glu Lys Gln Gly
            645                 650                 655

Tyr Lys Leu Thr Tyr Thr Asp Ile Asp Glu Thr Tyr Ile Asn Asp Leu
            660                 665                 670
```

```
Ile Glu Arg Asn Glu Leu Tyr Leu Phe Gln Ile Tyr Asn Lys Asp Phe
            675                 680                 685

Ser Met Tyr Ser Lys Gly Lys Leu Asn Leu His Thr Leu Tyr Phe Met
        690                 695                 700

Met Leu Phe Asp Gln Arg Asn Ile Asp Asp Val Val Tyr Lys Leu Asn
705                 710                 715                 720

Gly Glu Ala Glu Val Phe Tyr Arg Pro Ala Ser Ile Ser Glu Asp Glu
                725                 730                 735

Leu Ile Ile His Lys Ala Gly Glu Glu Ile Lys Asn Lys Asn Pro Asn
            740                 745                 750

Arg Ala Arg Thr Lys Glu Thr Ser Thr Phe Ser Tyr Asp Ile Val Lys
        755                 760                 765

Asp Lys Arg Tyr Ser Lys Asp Lys Phe Thr Leu His Ile Pro Ile Thr
        770                 775                 780

Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
                805                 810                 815

Gly Glu Arg Asn Leu Leu Tyr Val Val Val Ile Asp Ser Lys Gly Asn
            820                 825                 830

Ile Leu Glu Gln Ile Ser Leu Asn Ser Ile Ile Asn Lys Glu Tyr Asp
            835                 840                 845

Ile Glu Thr Asp Tyr His Ala Leu Leu Asp Glu Arg Glu Gly Gly Arg
            850                 855                 860

Asp Lys Ala Arg Lys Asp Trp Asn Thr Val Glu Asn Ile Arg Asp Leu
865                 870                 875                 880

Lys Ala Gly Leu Tyr Leu Gln Val Val Asn Val Val Ala Lys Leu Val
                885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
            915                 920                 925

Lys Met Leu Ile Asp Lys Leu Asn Tyr Leu Val Ile Asp Lys Ser Arg
930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
                965                 970                 975

Val Ile Tyr Tyr Val Pro Ala Tyr Leu Thr Ser Lys Ile Asp Pro Thr
            980                 985                 990

Thr Gly Phe Ala Asn Leu Phe Tyr  Met Lys Cys Glu Asn  Val Glu Lys
            995                 1000                1005

Ser Lys Arg Phe Phe Asp Gly  Phe Asp Phe Ile Arg  Phe Asn Ala
            1010                1015                1020

Leu Glu Asn Val Phe Glu Phe  Gly Phe Asp Tyr Arg  Ser Phe Thr
            1025                1030                1035

Gln Arg Ala Cys Gly Ile Asn  Ser Lys Trp Thr Val  Cys Thr Asn
            1040                1045                1050

Gly Glu Arg Ile Ile Lys Tyr  Arg Asn Pro Asp Lys  Asn Asn Met
            1055                1060                1065

Phe Asp Glu Lys Val Val Val  Thr Asp Glu Met  Lys Asn Leu
            1070                1075                1080

Phe Glu Gln Tyr Lys Ile Pro  Tyr Glu Asp Gly Arg  Asn Val Lys
```

-continued

```
            1085                1090                1095

Asp Met Ile Ile Ser Asn Glu Glu Ala Glu Phe Tyr Arg Arg Leu
    1100                1105                1110

Tyr Arg Leu Leu Gln Gln Thr Leu Gln Met Arg Asn Ser Thr Ser
    1115                1120                1125

Asp Gly Thr Arg Asp Tyr Ile Ile Ser Pro Val Lys Asn Lys Arg
    1130                1135                1140

Glu Ala Tyr Phe Asn Ser Glu Leu Ser Asp Gly Ser Val Pro Lys
    1145                1150                1155

Asp Ala Asp Ala Asn Gly Ala Tyr Asn Ile Ala Arg Lys Gly Leu
    1160                1165                1170

Trp Val Leu Glu Gln Ile Arg Gln Lys Ser Glu Gly Glu Lys Ile
    1175                1180                1185

Asn Leu Ala Met Thr Asn Ala Glu Trp Leu Glu Tyr Ala Gln Thr
    1190                1195                1200

His Leu Leu
    1205

<210> SEQ ID NO 8
<211> LENGTH: 1233
<212> TYPE: PRT
<213> ORGANISM: Lachnospiraceae sp.

<400> SEQUENCE: 8

Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
                20                  25                  30

Arg Glu Gln Lys Leu Leu Glu Gln Asp Ala Ala Phe Arg Lys Leu Val
            35                  40                  45

Glu Thr Val Thr Pro Ile Val Asp Asp Cys Ile Arg Lys Ile Ala Asp
        50                  55                  60

Asn Ala Leu Cys His Phe Gly Thr Glu Tyr Asp Phe Ser Cys Leu Gly
65                  70                  75                  80

Asn Ala Ile Ser Lys Asn Asp Ser Lys Ala Ile Lys Lys Glu Thr Glu
                85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
        115                 120                 125

Thr Leu Thr Ser Phe Val Gln Asp Asp Ala Asp Lys Arg Val Leu Ile
    130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
    210                 215                 220

Asp Ser Tyr Asn Leu Ile Ile Ser Gly Ile Tyr Ala Asp Asp Glu Val
225                 230                 235                 240
```

-continued

Lys Asn Pro Gly Ile Asn Glu Ile Val Lys Glu Tyr Asn Gln Gln Ile
            245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
            275                 280                 285

Ser Asn Asp Ser Asp Ala Arg Ser Ile Leu Glu Lys Ile Leu Lys Asp
            290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
            325                 330                 335

Val Ile Tyr Gly Asp His Gly Lys Leu Ser Gln Ile Ile Tyr Asp Lys
            340                 345                 350

Glu Ser Lys Arg Ile Ser Glu Leu Met Glu Thr Leu Ser Pro Lys Glu
            355                 360                 365

Arg Lys Glu Ser Lys Lys Arg Leu Glu Gly Leu Glu Glu His Ile Arg
            370                 375                 380

Lys Ser Thr Tyr Thr Phe Asp Glu Leu Asn Arg Tyr Ala Glu Lys Asn
385                 390                 395                 400

Val Met Ala Ala Tyr Ile Ala Ala Val Glu Glu Ser Cys Ala Glu Ile
            405                 410                 415

Met Arg Lys Glu Lys Asp Leu Arg Thr Leu Leu Ser Lys Glu Asp Val
            420                 425                 430

Lys Ile Arg Gly Asn Arg His Asn Thr Leu Ile Val Lys Asn Tyr Phe
            435                 440                 445

Asn Ala Trp Thr Val Phe Arg Asn Leu Ile Arg Ile Leu Arg Arg Lys
450                 455                 460

Ser Glu Ala Glu Ile Asp Ser Asp Phe Tyr Asp Val Leu Asp Asp Ser
465                 470                 475                 480

Val Glu Val Leu Ser Leu Thr Tyr Lys Gly Asn Leu Cys Arg Ser
            485                 490                 495

Tyr Ile Thr Lys Lys Ile Gly Ser Asp Leu Lys Pro Glu Ile Ala Thr
            500                 505                 510

Tyr Gly Ser Ala Leu Arg Pro Asn Ser Arg Trp Trp Ser Pro Gly Glu
            515                 520                 525

Lys Phe Asn Val Lys Phe His Thr Ile Val Arg Arg Asp Gly Arg Leu
            530                 535                 540

Tyr Tyr Phe Ile Leu Pro Lys Gly Ala Lys Pro Val Glu Leu Glu Asp
545                 550                 555                 560

Met Asp Gly Asp Ile Glu Cys Leu Gln Met Arg Lys Ile Pro Asn Pro
            565                 570                 575

Thr Ile Phe Leu Pro Lys Leu Val Phe Lys Asp Pro Glu Ala Phe Phe
            580                 585                 590

Arg Asp Asn Pro Glu Ala Asp Glu Phe Val Phe Leu Ser Gly Met Lys
            595                 600                 605

Ala Pro Val Thr Ile Thr Arg Glu Thr Tyr Glu Ala Tyr Arg Tyr Lys
            610                 615                 620

Leu Tyr Thr Val Gly Lys Leu Arg Asp Gly Glu Val Ser Glu Glu Glu
625                 630                 635                 640

Tyr Lys Arg Ala Leu Leu Gln Val Leu Thr Ala Tyr Lys Glu Phe Leu
            645                 650                 655

Glu Asn Arg Met Ile Tyr Ala Asp Leu Asn Phe Gly Phe Lys Asp Leu

-continued

```
                660                 665                 670
Glu Glu Tyr Lys Asp Ser Ser Glu Phe Ile Lys Gln Val Glu Thr His
            675                 680                 685

Asn Thr Phe Met Cys Trp Ala Lys Val Ser Ser Gln Leu Asp Asp
        690                 695                 700

Leu Val Lys Ser Gly Asn Gly Leu Leu Phe Glu Ile Trp Ser Glu Arg
705                 710                 715                 720

Leu Glu Ser Tyr Tyr Lys Tyr Gly Asn Glu Lys Val Leu Arg Gly Tyr
                725                 730                 735

Glu Gly Val Leu Leu Ser Ile Leu Lys Asp Glu Asn Leu Val Ser Met
            740                 745                 750

Arg Thr Leu Leu Asn Ser Arg Pro Met Leu Val Tyr Arg Pro Lys Glu
        755                 760                 765

Ser Ser Lys Pro Met Val Val His Arg Asp Gly Ser Arg Val Val Asp
        770                 775                 780

Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
                805                 810                 815

Lys Ala Arg Lys Ile Leu Asp Asn Lys Lys Val Lys Val Lys Val Leu
            820                 825                 830

Glu Ser Glu Arg Val Lys Trp Ser Lys Phe Tyr Asp Glu Gln Phe Ala
        835                 840                 845

Val Thr Phe Ser Val Lys Lys Asn Ala Asp Cys Leu Asp Thr Thr Lys
        850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
                885                 890                 895

Lys Asn Gly Lys Val Leu Lys Gln Arg Ser Leu Asn Ile Ile Asn Asp
            900                 905                 910

Gly Ala Arg Asp Val Asp Trp Lys Glu Arg Phe Arg Gln Val Thr Lys
        915                 920                 925

Asp Arg Asn Glu Gly Tyr Asn Glu Trp Asp Tyr Ser Arg Thr Ser Asn
        930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Ile Glu Lys Met Ser Asn
                965                 970                 975

Ala Phe Lys Asp Lys Tyr Ser Phe Leu Asp Asp Val Thr Phe Lys Gly
            980                 985                 990

Phe Glu Thr Lys Lys Leu Ala Lys  Leu Ser Asp Leu His  Phe Arg Gly
        995                 1000                1005

Ile Lys  Asp Gly Glu Pro  Cys  Ser Phe Thr Asn Pro  Leu Gln Leu
    1010                1015                1020

Cys Gln  Asn Asp Ser Asn  Lys  Ile Leu Gln Asp Gly  Val Ile Phe
    1025                1030                1035

Met Val  Pro Asn Ser Met  Thr  Arg Ser Leu Asp Pro  Asp Thr Gly
    1040                1045                1050

Phe Ile  Phe Ala Ile Asn Asp  His Asn Ile Arg Thr  Lys Lys Ala
    1055                1060                1065

Lys Leu  Asn Phe Leu Ser Lys  Phe Asp Gln Leu Lys  Val Ser Ser
    1070                1075                1080
```

-continued

Glu Gly Cys Leu Ile Met Lys Tyr Ser Gly Asp Ser Leu Pro Thr
    1085                1090                1095

His Asn Thr Asp Asn Arg Val Trp Asn Cys Cys Cys Asn His Pro
    1100                1105                1110

Ile Thr Asn Tyr Asp Arg Glu Thr Lys Lys Val Glu Phe Ile Glu
    1115                1120                1125

Glu Pro Val Glu Glu Leu Ser Arg Val Leu Glu Asn Gly Ile
    1130                1135                1140

Glu Thr Asp Thr Glu Leu Asn Lys Leu Asn Glu Arg Glu Asn Val
    1145                1150                1155

Pro Gly Lys Val Val Asp Ala Ile Tyr Ser Leu Val Leu Asn Tyr
    1160                1165                1170

Leu Arg Gly Thr Val Ser Gly Val Ala Gly Gln Arg Ala Val Tyr
    1175                1180                1185

Tyr Ser Pro Val Thr Gly Lys Lys Tyr Asp Ile Ser Phe Ile Gln
    1190                1195                1200

Ala Met Asn Leu Asn Arg Lys Cys Asp Tyr Tyr Arg Ile Gly Ser
    1205                1210                1215

Lys Glu Arg Gly Glu Trp Thr Asp Phe Val Ala Gln Leu Ile Asn
    1220                1225                1230

<210> SEQ ID NO 9
<211> LENGTH: 1227
<212> TYPE: PRT
<213> ORGANISM: Lachnospiraceae sp.

<400> SEQUENCE: 9

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
                20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
                180                 185                 190

Val Asp Ala Ile Phe Asp Lys His Glu Val Gln Glu Ile Lys Glu Lys
            195                 200                 205

Ile Leu Asn Ser Asp Tyr Asp Val Glu Asp Phe Phe Glu Gly Glu Phe

```
            210                 215                 220
Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
                260                 265                 270

Phe Lys Pro Leu Tyr Lys Gln Val Leu Ser Asp Arg Glu Ser Leu Ser
            275                 280                 285

Phe Tyr Gly Glu Gly Tyr Thr Ser Asp Glu Glu Val Leu Glu Val Phe
            290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
                340                 345                 350

Gly Glu Trp Asn Val Ile Arg Asp Lys Trp Asn Ala Glu Tyr Asp Asp
            355                 360                 365

Ile His Leu Lys Lys Lys Ala Val Val Thr Glu Lys Tyr Glu Asp Asp
            370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
            530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640
```

```
Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
                675                 680                 685

Glu Val Asp Lys Leu Val Glu Glu Gly Lys Leu Tyr Met Phe Gln Ile
                690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
                755                 760                 765

Asn Pro Asp Asn Pro Lys Lys Thr Thr Thr Leu Ser Tyr Asp Val Tyr
                770                 775                 780

Lys Asp Lys Arg Phe Ser Glu Asp Gln Tyr Glu Leu His Ile Pro Ile
785                 790                 795                 800

Ala Asn Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
                820                 825                 830

Asp Arg Gly Glu Arg Asn Leu Leu Tyr Ile Val Val Val Asp Gly Lys
                835                 840                 845

Gly Asn Ile Val Glu Gln Tyr Ser Leu Asn Glu Ile Ile Asn Asn Phe
                850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
                900                 905                 910

Cys Glu Leu Val Glu Lys Tyr Asp Ala Val Ile Ala Leu Glu Asp Leu
                915                 920                 925

Asn Ser Gly Phe Lys Asn Ser Arg Val Lys Val Glu Lys Gln Val Tyr
                930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
                965                 970                 975

Ile Thr Asn Lys Phe Glu Ser Phe Lys Ser Met Ser Thr Gln Asn Gly
                980                 985                 990

Phe Ile Phe Tyr Ile Pro Ala Trp Leu Thr Ser Lys Ile Asp Pro Ser
                995                 1000                1005

Thr Gly Phe Val Asn Leu Leu Lys Thr Lys Tyr Thr Ser Ile Ala
                1010                1015                1020

Asp Lys Lys Phe Ile Ser Ser Phe Asp Arg Ile Met Tyr Val Pro
                1025                1030                1035

Glu Glu Asp Leu Phe Glu Phe Ala Leu Asp Tyr Lys Asn Phe Ser
                1040                1045                1050
```

-continued

```
Arg Thr Asp Ala Asp Tyr Ile Lys Lys Trp Lys Leu Tyr Ser Tyr
    1055            1060                1065

Gly Asn Arg Ile Arg Ile Phe Arg Asn Pro Lys Lys Asn Asn Val
    1070            1075                1080

Phe Asp Trp Glu Glu Val Cys Leu Thr Ser Ala Tyr Lys Glu Leu
    1085            1090                1095

Phe Asn Lys Tyr Gly Ile Asn Tyr Gln Gln Gly Asp Ile Arg Ala
    1100            1105                1110

Leu Leu Cys Glu Gln Ser Asp Lys Ala Phe Tyr Ser Ser Phe Met
    1115            1120                1125

Ala Leu Met Ser Leu Met Leu Gln Met Arg Asn Ser Ile Thr Gly
    1130            1135                1140

Arg Thr Asp Val Asp Phe Leu Ile Ser Pro Val Lys Asn Ser Asp
    1145            1150                1155

Gly Ile Phe Tyr Asp Ser Arg Asn Tyr Glu Ala Gln Glu Asn Ala
    1160            1165                1170

Ile Leu Pro Lys Asn Ala Asp Ala Asn Gly Ala Tyr Asn Ile Ala
    1175            1180                1185

Arg Lys Val Leu Trp Ala Ile Gly Gln Phe Lys Lys Ala Glu Asp
    1190            1195                1200

Glu Lys Leu Asp Lys Val Lys Ile Ala Ser Asn Lys Glu Trp Leu
    1205            1210                1215

Glu Tyr Ala Gln Thr Ser Val Lys His
    1220            1225

<210> SEQ ID NO 10
<211> LENGTH: 1264
<212> TYPE: PRT
<213> ORGANISM: Leptospira inadai

<400> SEQUENCE: 10

Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
            20                  25                  30

Lys Lys Gly Phe Leu Lys Lys Asp Lys Ile Arg Ala Glu Asp Tyr Lys
        35                  40                  45

Ala Val Lys Lys Ile Ile Asp Lys Tyr His Arg Ala Tyr Ile Glu Glu
    50                  55                  60

Val Phe Asp Ser Val Leu His Gln Lys Lys Lys Asp Lys Thr Arg
65                  70                  75                  80

Phe Ser Thr Gln Phe Ile Lys Glu Ile Lys Glu Phe Ser Leu Tyr
                85                  90                  95

Tyr Lys Thr Glu Lys Asn Ile Pro Asp Lys Glu Arg Leu Glu Ala Leu
            100                 105                 110

Ser Glu Lys Leu Arg Lys Met Leu Val Gly Ala Phe Lys Gly Glu Phe
        115                 120                 125

Ser Glu Glu Val Ala Glu Lys Tyr Asn Lys Asn Leu Phe Ser Lys Glu
    130                 135                 140

Leu Ile Arg Asn Glu Ile Glu Lys Phe Cys Glu Thr Asp Glu Glu Arg
145                 150                 155                 160

Lys Gln Val Ser Asn Phe Lys Ser Phe Thr Thr Tyr Phe Thr Gly Phe
                165                 170                 175

His Ser Asn Arg Gln Asn Ile Tyr Ser Asp Glu Lys Lys Ser Thr Ala
            180                 185                 190
```

```
Ile Gly Tyr Arg Ile Ile His Gln Asn Leu Pro Lys Phe Leu Asp Asn
        195                 200                 205

Leu Lys Ile Ile Glu Ser Ile Gln Arg Arg Phe Lys Asp Phe Pro Trp
210                 215                 220

Ser Asp Leu Lys Lys Asn Leu Lys Lys Ile Asp Lys Asn Ile Lys Leu
225                 230                 235                 240

Thr Glu Tyr Phe Ser Ile Asp Gly Phe Val Asn Val Leu Asn Gln Lys
                245                 250                 255

Gly Ile Asp Ala Tyr Asn Thr Ile Leu Gly Gly Lys Ser Glu Glu Ser
                260                 265                 270

Gly Glu Lys Ile Gln Gly Leu Asn Glu Tyr Ile Asn Leu Tyr Arg Gln
            275                 280                 285

Lys Asn Asn Ile Asp Arg Lys Asn Pro Leu Asn Val Lys Ile Leu Phe
290                 295                 300

Lys Gln Ile Leu Gly Asp Arg Glu Thr Lys Ser Phe Ile Pro Glu Ala
305                 310                 315                 320

Phe Pro Asp Asp Gln Ser Val Leu Asn Ser Ile Thr Glu Phe Ala Lys
                325                 330                 335

Tyr Leu Lys Leu Asp Lys Lys Lys Ser Ile Ala Glu Leu Lys
                340                 345                 350

Lys Phe Leu Ser Ser Phe Asn Arg Tyr Glu Leu Asp Gly Ile Tyr Leu
            355                 360                 365

Ala Asn Asp Asn Ser Leu Ala Ser Ile Ser Thr Phe Leu Phe Asp Asp
        370                 375                 380

Trp Ser Phe Ile Lys Lys Ser Val Ser Phe Lys Tyr Asp Glu Ser Val
385                 390                 395                 400

Gly Asp Pro Lys Lys Lys Ile Lys Ser Pro Leu Lys Tyr Glu Lys Glu
                405                 410                 415

Lys Glu Lys Trp Leu Lys Gln Lys Tyr Tyr Thr Ile Ser Phe Leu Asn
            420                 425                 430

Asp Ala Ile Glu Ser Tyr Ser Lys Ser Gln Asp Glu Lys Arg Val Lys
        435                 440                 445

Ile Arg Leu Glu Ala Tyr Phe Ala Glu Phe Lys Ser Lys Asp Asp Ala
    450                 455                 460

Lys Lys Gln Phe Asp Leu Leu Glu Arg Ile Glu Glu Ala Tyr Ala Ile
465                 470                 475                 480

Val Glu Pro Leu Leu Gly Ala Glu Tyr Pro Arg Asp Arg Asn Leu Lys
                485                 490                 495

Ala Asp Lys Lys Glu Val Gly Lys Ile Lys Asp Phe Leu Asp Ser Ile
            500                 505                 510

Lys Ser Leu Gln Phe Phe Leu Lys Pro Leu Leu Ser Ala Glu Ile Phe
        515                 520                 525

Asp Glu Lys Asp Leu Gly Phe Tyr Asn Gln Leu Glu Gly Tyr Tyr Glu
    530                 535                 540

Glu Ile Asp Ile Ser Gly His Leu Tyr Asn Lys Val Arg Asn Tyr Leu
545                 550                 555                 560

Thr Gly Lys Ile Tyr Ser Lys Glu Lys Phe Lys Leu Asn Phe Glu Asn
                565                 570                 575

Ser Thr Leu Leu Lys Gly Trp Asp Glu Asn Arg Glu Val Ala Asn Leu
            580                 585                 590

Cys Val Ile Phe Arg Glu Asp Gln Lys Tyr Tyr Leu Gly Val Met Asp
        595                 600                 605
```

-continued

```
Lys Glu Asn Asn Thr Ile Leu Ser Asp Ile Pro Lys Val Lys Pro Asn
    610                 615                 620

Glu Leu Phe Tyr Glu Lys Met Val Tyr Lys Leu Ile Pro Thr Pro His
625                 630                 635                 640

Met Gln Leu Pro Arg Ile Ile Phe Ser Ser Asp Asn Leu Ser Ile Tyr
                645                 650                 655

Asn Pro Ser Lys Ser Ile Leu Lys Ile Arg Glu Ala Lys Ser Phe Lys
            660                 665                 670

Glu Gly Lys Asn Phe Lys Leu Lys Asp Cys His Lys Phe Ile Asp Phe
        675                 680                 685

Tyr Lys Glu Ser Ile Ser Lys Asn Glu Asp Trp Ser Arg Phe Asp Phe
690                 695                 700

Lys Phe Ser Lys Thr Ser Ser Tyr Glu Asn Ile Ser Glu Phe Tyr Arg
705                 710                 715                 720

Glu Val Glu Arg Gln Gly Tyr Asn Leu Asp Phe Lys Lys Val Ser Lys
                725                 730                 735

Phe Tyr Ile Asp Ser Leu Val Glu Asp Gly Lys Leu Tyr Leu Phe Gln
            740                 745                 750

Ile Tyr Asn Lys Asp Phe Ser Ile Phe Ser Lys Gly Lys Pro Asn Leu
        755                 760                 765

His Thr Ile Tyr Phe Arg Ser Leu Phe Ser Lys Glu Asn Leu Lys Asp
770                 775                 780

Val Cys Leu Lys Leu Asn Gly Glu Ala Glu Met Phe Phe Arg Lys Lys
785                 790                 795                 800

Ser Ile Asn Tyr Asp Glu Lys Lys Lys Arg Glu Gly His His Pro Glu
                805                 810                 815

Leu Phe Glu Lys Leu Lys Tyr Pro Ile Leu Lys Asp Lys Arg Tyr Ser
            820                 825                 830

Glu Asp Lys Phe Gln Phe His Leu Pro Ile Ser Leu Asn Phe Lys Ser
        835                 840                 845

Lys Glu Arg Leu Asn Phe Asn Leu Lys Val Asn Glu Phe Leu Lys Arg
850                 855                 860

Asn Lys Asp Ile Asn Ile Ile Gly Ile Asp Arg Gly Glu Arg Asn Leu
865                 870                 875                 880

Leu Tyr Leu Val Met Ile Asn Gln Lys Gly Glu Ile Leu Lys Gln Thr
                885                 890                 895

Leu Leu Asp Ser Met Gln Ser Gly Lys Gly Arg Pro Glu Ile Asn Tyr
            900                 905                 910

Lys Glu Lys Leu Gln Glu Lys Glu Ile Glu Arg Asp Lys Ala Arg Lys
        915                 920                 925

Ser Trp Gly Thr Val Glu Asn Ile Lys Glu Leu Lys Glu Gly Tyr Leu
930                 935                 940

Ser Ile Val Ile His Gln Ile Ser Lys Leu Met Val Glu Asn Asn Ala
945                 950                 955                 960

Ile Val Val Leu Glu Asp Leu Asn Ile Gly Phe Lys Arg Gly Arg Gln
                965                 970                 975

Lys Val Glu Arg Gln Val Tyr Gln Lys Phe Glu Lys Met Leu Ile Asp
            980                 985                 990

Lys Leu Asn Phe Leu Val Phe Lys  Glu Asn Lys Pro Thr Glu Pro Gly
        995                 1000                1005

Gly Val Leu Lys Ala Tyr Gln  Leu Thr Asp Glu Phe  Gln Ser Phe
        1010                1015                1020

Glu Lys  Leu Ser Lys Gln Thr  Gly Phe Leu Phe Tyr  Val Pro Ser
```

-continued

```
                  1025                1030                1035
Trp Asn Thr Ser Lys Ile Asp Pro Arg Thr Gly Phe Ile Asp Phe
        1040                1045                1050
Leu His Pro Ala Tyr Glu Asn Ile Glu Lys Ala Lys Gln Trp Ile
        1055                1060                1065
Asn Lys Phe Asp Ser Ile Arg Phe Asn Ser Lys Met Asp Trp Phe
        1070                1075                1080
Glu Phe Thr Ala Asp Thr Arg Lys Phe Ser Glu Asn Leu Met Leu
        1085                1090                1095
Gly Lys Asn Arg Val Trp Val Ile Cys Thr Thr Asn Val Glu Arg
        1100                1105                1110
Tyr Phe Thr Ser Lys Thr Ala Asn Ser Ser Ile Gln Tyr Asn Ser
        1115                1120                1125
Ile Gln Ile Thr Glu Lys Leu Lys Glu Leu Phe Val Asp Ile Pro
        1130                1135                1140
Phe Ser Asn Gly Gln Asp Leu Lys Pro Glu Ile Leu Arg Lys Asn
        1145                1150                1155
Asp Ala Val Phe Phe Lys Ser Leu Leu Phe Tyr Ile Lys Thr Thr
        1160                1165                1170
Leu Ser Leu Arg Gln Asn Asn Gly Lys Lys Gly Glu Glu Lys
        1175                1180                1185
Asp Phe Ile Leu Ser Pro Val Val Asp Ser Lys Gly Arg Phe Phe
        1190                1195                1200
Asn Ser Leu Glu Ala Ser Asp Asp Glu Pro Lys Asp Ala Asp Ala
        1205                1210                1215
Asn Gly Ala Tyr His Ile Ala Leu Lys Gly Leu Met Asn Leu Leu
        1220                1225                1230
Val Leu Asn Glu Thr Lys Glu Glu Asn Leu Ser Arg Pro Lys Trp
        1235                1240                1245
Lys Ile Lys Asn Lys Asp Trp Leu Glu Phe Val Trp Glu Arg Asn
        1250                1255                1260
Arg
```

<210> SEQ ID NO 11
<211> LENGTH: 1373
<212> TYPE: PRT
<213> ORGANISM: Moraxella bovoculi

<400> SEQUENCE: 11

```
Met Leu Phe Gln Asp Phe Thr His Leu Tyr Pro Leu Ser Lys Thr Val
1               5                   10                  15
Arg Phe Glu Leu Phe Ile Asp Arg Thr Leu Glu His Ile His Ala Lys
                20                  25                  30
Asn Phe Leu Ser Gln Asp Glu Thr Met Ala Asp Met His Gln Lys Val
            35                  40                  45
Lys Val Ile Leu Asp Asp Tyr His Arg Asp Phe Ile Ala Asp Met Met
        50                  55                  60
Gly Glu Val Lys Leu Thr Lys Leu Ala Glu Phe Tyr Asp Val Tyr Leu
65                  70                  75                  80
Lys Phe Arg Lys Asn Pro Lys Asp Asp Glu Leu Gln Lys Ala Gln Leu
                85                  90                  95
Lys Asp Leu Gln Ala Val Leu Arg Lys Glu Ile Val Lys Pro Ile Gly
            100                 105                 110
Asn Gly Gly Lys Tyr Lys Ala Gly Tyr Asp Arg Leu Phe Gly Ala Lys
```

```
            115                 120                 125
Leu Phe Lys Asp Gly Lys Glu Leu Gly Asp Leu Ala Lys Phe Val Ile
130                 135                 140
Ala Gln Glu Gly Glu Ser Ser Pro Lys Leu Ala His Leu Ala His Phe
145                 150                 155                 160
Glu Lys Phe Ser Thr Tyr Phe Thr Gly Phe His Asp Asn Arg Lys Asn
                165                 170                 175
Met Tyr Ser Asp Glu Asp Lys His Thr Ala Ile Ala Tyr Arg Leu Ile
                180                 185                 190
His Glu Asn Leu Pro Arg Phe Ile Asp Asn Leu Gln Ile Leu Thr Thr
                195                 200                 205
Ile Lys Gln Lys His Ser Ala Leu Tyr Asp Gln Ile Ile Asn Glu Leu
210                 215                 220
Thr Ala Ser Gly Leu Asp Val Ser Leu Ala Ser His Leu Asp Gly Tyr
225                 230                 235                 240
His Lys Leu Leu Thr Gln Glu Gly Ile Thr Ala Tyr Asn Thr Leu Leu
                245                 250                 255
Gly Gly Ile Ser Gly Glu Ala Gly Ser Pro Lys Ile Gln Gly Ile Asn
                260                 265                 270
Glu Leu Ile Asn Ser His His Asn Gln His Cys His Lys Ser Glu Arg
                275                 280                 285
Ile Ala Lys Leu Arg Pro Leu His Lys Gln Ile Leu Ser Asp Gly Met
290                 295                 300
Ser Val Ser Phe Leu Pro Ser Lys Phe Ala Asp Ser Glu Met Cys
305                 310                 315                 320
Gln Ala Val Asn Glu Phe Tyr Arg His Tyr Ala Asp Val Phe Ala Lys
                325                 330                 335
Val Gln Ser Leu Phe Asp Gly Phe Asp Asp His Gln Lys Asp Gly Ile
                340                 345                 350
Tyr Val Glu His Lys Asn Leu Asn Glu Leu Ser Lys Gln Ala Phe Gly
                355                 360                 365
Asp Phe Ala Leu Leu Gly Arg Val Leu Asp Gly Tyr Tyr Val Asp Val
370                 375                 380
Val Asn Pro Glu Phe Asn Glu Arg Phe Ala Lys Ala Lys Thr Asp Asn
385                 390                 395                 400
Ala Lys Ala Lys Leu Thr Lys Glu Lys Asp Lys Phe Ile Lys Gly Val
                405                 410                 415
His Ser Leu Ala Ser Leu Glu Gln Ala Ile Glu His Tyr Thr Ala Arg
                420                 425                 430
His Asp Asp Glu Ser Val Gln Ala Gly Lys Leu Gly Gln Tyr Phe Lys
                435                 440                 445
His Gly Leu Ala Gly Val Asp Asn Pro Ile Gln Lys Ile His Asn Asn
                450                 455                 460
His Ser Thr Ile Lys Gly Phe Leu Glu Arg Glu Arg Pro Ala Gly Glu
465                 470                 475                 480
Arg Ala Leu Pro Lys Ile Lys Ser Gly Lys Asn Pro Glu Met Thr Gln
                485                 490                 495
Leu Arg Gln Leu Lys Glu Leu Leu Asp Asn Ala Leu Asn Val Ala His
                500                 505                 510
Phe Ala Lys Leu Leu Thr Thr Lys Thr Thr Leu Asp Asn Gln Asp Gly
                515                 520                 525
Asn Phe Tyr Gly Glu Phe Gly Val Leu Tyr Asp Glu Leu Ala Lys Ile
                530                 535                 540
```

```
Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
        595                 600                 605

Val Phe Asp Asn Ala Pro Asn Thr Gly Lys Ser Ile Tyr Gln Lys Met
610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
        675                 680                 685

Lys Lys Phe Glu Gly Ala Ile Gly Asp Ile Gln Leu Phe Lys Lys Asp
690                 695                 700

Lys Lys Gly Arg Glu Val Pro Ile Ser Glu Lys Asp Leu Phe Lys Asp
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
        755                 760                 765

Glu Asn Phe Tyr Asn Asn His Pro Lys Phe Lys Lys Asp Leu Val Arg
770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
                805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
        835                 840                 845

Gln Leu Tyr Leu Phe Gln Ile Tyr Asn Lys Asp Phe Ser Pro Lys Ala
        850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
            885                 890                 895

Ile Phe Tyr Arg Lys Ala Ser Leu Asp Met Asn Glu Thr Thr Ile His
        900                 905                 910

Arg Ala Gly Glu Val Leu Glu Asn Lys Asn Pro Asp Asn Pro Lys Lys
        915                 920                 925

Arg Gln Phe Val Tyr Asp Ile Ile Lys Asp Lys Arg Tyr Thr Gln Lys
        930                 935                 940

Asp Phe Met Leu His Val Pro Ile Thr Met Asn Phe Gly Val Gln Gly
945                 950                 955                 960
```

```
Met Thr Ile Lys Glu Phe Asn Lys Lys Val Asn Gln Ser Ile Gln Gln
            965                 970                 975

Tyr Asp Glu Val Asn Val Ile Gly Ile Asp Arg Gly Glu Arg His Leu
        980                 985                 990

Leu Tyr Leu Thr Val Ile Asn Ser Lys Gly Glu Ile Leu Glu Gln Cys
        995                 1000                1005

Ser Leu Asn Asp Ile Thr Thr Ala Ser Ala Asn Gly Thr Gln Met
    1010                1015                1020

Thr Thr Pro Tyr His Lys Ile Leu Asp Lys Arg Glu Ile Glu Arg
    1025                1030                1035

Leu Asn Ala Arg Val Gly Trp Gly Glu Ile Glu Thr Ile Lys Glu
    1040                1045                1050

Leu Lys Ser Gly Tyr Leu Ser His Val Val His Gln Ile Ser Gln
    1055                1060                1065

Leu Met Leu Lys Tyr Asn Ala Ile Val Val Leu Glu Asp Leu Asn
    1070                1075                1080

Phe Gly Phe Lys Arg Gly Arg Phe Lys Val Glu Lys Gln Ile Tyr
    1085                1090                1095

Gln Asn Phe Glu Asn Ala Leu Ile Lys Lys Leu Asn His Leu Val
    1100                1105                1110

Leu Lys Asp Lys Ala Asp Asp Glu Ile Gly Ser Tyr Lys Asn Ala
    1115                1120                1125

Leu Gln Leu Thr Asn Asn Phe Thr Asp Leu Lys Ser Ile Gly Lys
    1130                1135                1140

Gln Thr Gly Phe Leu Phe Tyr Val Pro Ala Trp Asn Thr Ser Lys
    1145                1150                1155

Ile Asp Pro Glu Thr Gly Phe Val Asp Leu Leu Lys Pro Arg Tyr
    1160                1165                1170

Glu Asn Ile Gln Ala Ser Gln Ala Phe Phe Gly Lys Phe Asp Lys
    1175                1180                1185

Ile Cys Tyr Asn Ala Asp Lys Asp Tyr Phe Glu Phe His Ile Asp
    1190                1195                1200

Tyr Ala Lys Phe Thr Asp Lys Ala Lys Asn Ser Arg Gln Ile Trp
    1205                1210                1215

Thr Ile Cys Ser His Gly Asp Lys Arg Tyr Val Tyr Asp Lys Thr
    1220                1225                1230

Ala Asn Gln Asn Lys Gly Ala Ala Lys Gly Ile Asn Val Asn Asp
    1235                1240                1245

Ile Leu Lys Ser Leu Phe Ala Arg His His Ile Asn Glu Lys Gln
    1250                1255                1260

Pro Asn Leu Val Met Asp Ile Cys Gln Asn Asn Asp Lys Glu Phe
    1265                1270                1275

His Lys Ser Leu Met Tyr Leu Leu Lys Thr Leu Leu Ala Leu Arg
    1280                1285                1290

Tyr Ser Asn Ala Ser Ser Asp Glu Asp Phe Ile Leu Ser Pro Val
    1295                1300                1305

Ala Asn Asp Glu Gly Val Phe Phe Asn Ser Ala Leu Ala Asp Asp
    1310                1315                1320

Thr Gln Pro Gln Asn Ala Asp Ala Asn Gly Ala Tyr His Ile Ala
    1325                1330                1335

Leu Lys Gly Leu Trp Leu Leu Asn Glu Leu Lys Asn Ser Asp Asp
    1340                1345                1350

Leu Asn Lys Val Lys Leu Ala Ile Asp Asn Gln Thr Trp Leu Asn
```

Phe Ala  Gln Asn Arg
    1370

<210> SEQ ID NO 12
<211> LENGTH: 1352
<212> TYPE: PRT
<213> ORGANISM: Parcubacteria bacterium

<400> SEQUENCE: 12

Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
            20                  25                  30

Lys Ile Asn Lys Val Phe Glu Lys Asp Gln Thr Ile Asp Asp Ser Tyr
        35                  40                  45

Asn Gln Ala Lys Phe Tyr Phe Asp Ser Leu His Gln Lys Phe Ile Asp
    50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
            100                 105                 110

Arg Leu Gln Lys Glu Ile Asn Asp Ala Glu Asp Ile Ile Gln Lys Glu
        115                 120                 125

Lys Glu Lys Ile Tyr Lys Asp Val Arg Thr Leu Phe Asp Asn Glu Ala
    130                 135                 140

Glu Ser Trp Lys Thr Tyr Tyr Gln Glu Arg Glu Val Asp Gly Lys Lys
145                 150                 155                 160

Ile Thr Glu Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
            180                 185                 190

Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
    210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
            260                 265                 270

Lys Asn Asn His Thr Asp Leu Gly Phe Asp Glu Glu Asn Ile Phe Glu
        275                 280                 285

Ile Glu Arg Tyr Lys Asn Cys Leu Leu Gln Arg Glu Ile Glu His Ile
    290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

-continued

```
Val Glu Lys Glu Lys Gln Leu Ile Glu Lys Thr Arg Glu Lys Thr Glu
            355                 360                 365

Glu Asp Val Leu Ile Glu Arg Phe Lys Glu Phe Ile Glu Asn Asn Glu
        370                 375                 380

Glu Arg Phe Thr Ala Ala Lys Lys Leu Met Asn Ala Phe Cys Asn Gly
385                 390                 395                 400

Glu Phe Glu Ser Glu Tyr Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
    530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
            660                 665                 670

Gln Lys Met Ile Tyr Lys Gln Ile Ala Asp Ala Ser Lys Asp Val Pro
        675                 680                 685

Arg Leu Leu Leu Thr Ser Lys Lys Ala Met Glu Lys Phe Lys Pro Ser
    690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
            740                 745                 750

Gln Asp Thr Gly Lys Tyr Gln Asn Ile Lys Glu Phe Thr Asp Val
        755                 760                 765

Gln Lys Tyr Gly Tyr Lys Ile Ser Phe Arg Asp Ile Asp Asp Glu Tyr
```

```
              770              775              780
Ile Asn Gln Ala Leu Asn Glu Gly Lys Met Tyr Leu Phe Glu Val Val
785              790              795              800

Asn Lys Asp Ile Tyr Asn Thr Lys Asn Gly Ser Lys Asn Leu His Thr
              805              810              815

Leu Tyr Phe Glu His Ile Leu Ser Ala Glu Asn Leu Asn Asp Pro Val
              820              825              830

Phe Lys Leu Ser Gly Met Ala Glu Ile Phe Gln Arg Gln Pro Ser Val
              835              840              845

Asn Glu Arg Glu Lys Ile Thr Thr Gln Lys Asn Gln Cys Ile Leu Asp
850              855              860

Lys Gly Asp Arg Ala Tyr Lys Tyr Arg Arg Tyr Thr Glu Lys Lys Ile
865              870              875              880

Met Phe His Met Ser Leu Val Leu Asn Thr Gly Lys Gly Glu Ile Lys
              885              890              895

Gln Val Gln Phe Asn Lys Ile Ile Asn Gln Arg Ile Ser Ser Ser Asp
              900              905              910

Asn Glu Met Arg Val Asn Val Ile Gly Ile Asp Arg Gly Glu Lys Asn
              915              920              925

Leu Leu Tyr Tyr Ser Val Val Lys Gln Asn Gly Glu Ile Ile Glu Gln
930              935              940

Ala Ser Leu Asn Glu Ile Asn Gly Val Asn Tyr Arg Asp Lys Leu Ile
945              950              955              960

Glu Arg Glu Lys Glu Arg Leu Lys Asn Arg Gln Ser Trp Lys Pro Val
              965              970              975

Val Lys Ile Lys Asp Leu Lys Lys Gly Tyr Ile Ser His Val Ile His
              980              985              990

Lys Ile Cys Gln Leu Ile Glu Lys Tyr Ser Ala Ile Val Val Leu Glu
              995              1000             1005

Asp Leu Asn Met Arg Phe Lys Gln Ile Arg Gly Gly Ile Glu Arg
1010             1015             1020

Ser Val Tyr Gln Gln Phe Glu Lys Ala Leu Ile Asp Lys Leu Gly
1025             1030             1035

Tyr Leu Val Phe Lys Asp Asn Arg Asp Leu Arg Ala Pro Gly Gly
1040             1045             1050

Val Leu Asn Gly Tyr Gln Leu Ser Ala Pro Phe Val Ser Phe Glu
1055             1060             1065

Lys Met Arg Lys Gln Thr Gly Ile Leu Phe Tyr Thr Gln Ala Glu
1070             1075             1080

Tyr Thr Ser Lys Thr Asp Pro Ile Thr Gly Phe Arg Lys Asn Val
1085             1090             1095

Tyr Ile Ser Asn Ser Ala Ser Leu Asp Lys Ile Lys Glu Ala Val
1100             1105             1110

Lys Lys Phe Asp Ala Ile Gly Trp Asp Gly Lys Glu Gln Ser Tyr
1115             1120             1125

Phe Phe Lys Tyr Asn Pro Tyr Asn Leu Ala Asp Glu Lys Tyr Lys
1130             1135             1140

Asn Ser Thr Val Ser Lys Glu Trp Ala Ile Phe Ala Ser Ala Pro
1145             1150             1155

Arg Ile Arg Arg Gln Lys Gly Glu Asp Gly Tyr Trp Lys Tyr Asp
1160             1165             1170

Arg Val Lys Val Asn Glu Glu Phe Glu Lys Leu Leu Lys Val Trp
1175             1180             1185
```

-continued

```
Asn Phe Val Asn Pro Lys Ala Thr Asp Ile Lys Gln Glu Ile Ile
    1190                1195                1200

Lys Lys Ile Lys Ala Gly Asp Leu Gln Gly Glu Lys Glu Leu Asp
    1205                1210                1215

Gly Arg Leu Arg Asn Phe Trp His Ser Phe Ile Tyr Leu Phe Asn
    1220                1225                1230

Leu Val Leu Glu Leu Arg Asn Ser Phe Ser Leu Gln Ile Lys Ile
    1235                1240                1245

Lys Ala Gly Glu Val Ile Ala Val Asp Glu Gly Val Asp Phe Ile
    1250                1255                1260

Ala Ser Pro Val Lys Pro Phe Phe Thr Thr Pro Asn Pro Tyr Ile
    1265                1270                1275

Pro Ser Asn Leu Cys Trp Leu Ala Val Glu Asn Ala Asp Ala Asn
    1280                1285                1290

Gly Ala Tyr Asn Ile Ala Arg Lys Gly Val Met Ile Leu Lys Lys
    1295                1300                1305

Ile Arg Glu His Ala Lys Lys Asp Pro Glu Phe Lys Lys Leu Pro
    1310                1315                1320

Asn Leu Phe Ile Ser Asn Ala Glu Trp Asp Glu Ala Ala Arg Asp
    1325                1330                1335

Trp Gly Lys Tyr Ala Gly Thr Thr Ala Leu Asn Leu Asp His
    1340                1345                1350

<210> SEQ ID NO 13
<211> LENGTH: 1260
<212> TYPE: PRT
<213> ORGANISM: Porphyromonas crevioricanis

<400> SEQUENCE: 13

Met Asp Ser Leu Lys Asp Phe Thr Asn Leu Tyr Pro Val Ser Lys Thr
1                   5                   10                  15

Leu Arg Phe Glu Leu Lys Pro Val Gly Lys Thr Leu Glu Asn Ile Glu
                20                  25                  30

Lys Ala Gly Ile Leu Lys Glu Asp Glu His Arg Ala Glu Ser Tyr Arg
            35                  40                  45

Arg Val Lys Lys Ile Ile Asp Thr Tyr His Lys Val Phe Ile Asp Ser
        50                  55                  60

Ser Leu Glu Asn Met Ala Lys Met Gly Ile Glu Asn Glu Ile Lys Ala
65                  70                  75                  80

Met Leu Gln Ser Phe Cys Glu Leu Tyr Lys Lys Asp His Arg Thr Glu
                85                  90                  95

Gly Glu Asp Lys Ala Leu Asp Lys Ile Arg Ala Val Leu Arg Gly Leu
            100                 105                 110

Ile Val Gly Ala Phe Thr Gly Val Cys Gly Arg Arg Glu Asn Thr Val
        115                 120                 125

Gln Asn Glu Lys Tyr Glu Ser Leu Phe Lys Glu Lys Leu Ile Lys Glu
    130                 135                 140

Ile Leu Pro Asp Phe Val Leu Ser Thr Glu Ala Glu Ser Leu Pro Phe
145                 150                 155                 160

Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
            180                 185                 190

Lys Pro Gln Ser Thr Ala Ile Ala Tyr Arg Leu Ile His Glu Asn Leu
```

-continued

```
            195                 200                 205
Pro Lys Phe Ile Asp Asn Ile Leu Val Phe Gln Lys Ile Lys Glu Pro
210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
                260                 265                 270

Ile Gly Lys Ile Val Thr Glu Gly Asp Gly Glu Met Lys Gly Leu Asn
                275                 280                 285

Glu His Ile Asn Leu Tyr Asn Gln Gln Arg Gly Arg Glu Asp Arg Leu
                290                 295                 300

Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
                340                 345                 350

Thr Gln Gln Leu Met Thr Ser Ile Ser Glu Tyr Asp Leu Ser Arg Ile
                355                 360                 365

Tyr Val Arg Asn Asp Ser Gln Leu Thr Asp Ile Ser Lys Lys Met Leu
370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
                420                 425                 430

Cys Ile Ala Phe Leu Asp Asn Val Arg Asp Cys Arg Val Asp Thr Tyr
                435                 440                 445

Leu Ser Thr Leu Gly Gln Lys Glu Gly Pro His Gly Leu Ser Asn Leu
450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
                500                 505                 510

Leu Lys Pro Leu Trp Gly Met Gly Asp Glu Pro Asp Lys Asp Glu Arg
                515                 520                 525

Phe Tyr Gly Glu Tyr Asn Tyr Ile Arg Gly Ala Leu Asp Gln Val Ile
                530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575

Trp Asp Arg Asn Lys Glu Lys Asp Asn Ser Cys Val Ile Leu Arg Lys
                580                 585                 590

Gly Gln Asn Phe Tyr Leu Ala Ile Met Asn Asn Arg His Lys Arg Ser
                595                 600                 605

Phe Glu Asn Lys Met Leu Pro Glu Tyr Lys Glu Gly Glu Pro Tyr Phe
610                 615                 620
```

```
Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655

Lys Leu Leu Glu Gln Tyr Gly His Gly Thr His Lys Lys Gly Asp Thr
            660                 665                 670

Phe Ser Met Asp Asp Leu His Glu Leu Ile Asp Phe Lys His Ser
        675                 680                 685

Ile Glu Ala His Glu Asp Trp Lys Gln Phe Gly Phe Lys Phe Ser Asp
690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
                725                 730                 735

Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
        755                 760                 765

Trp Arg Met Leu Phe Asp Glu Arg Asn Leu Ala Asp Val Ile Tyr Lys
770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Ser Arg
                805                 810                 815

Gln Lys Lys Gly Glu Glu Ser Leu Phe Glu Tyr Asp Leu Val Lys Asp
                820                 825                 830

Arg Arg Tyr Thr Met Asp Lys Phe Gln Phe His Val Pro Ile Thr Met
                835                 840                 845

Asn Phe Lys Cys Ser Ala Gly Ser Lys Val Asn Asp Met Val Asn Ala
850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
            900                 905                 910

Leu Leu Glu Ser Arg Asp Lys Asp Arg Gln Gln Glu His Arg Asn Trp
        915                 920                 925

Gln Thr Ile Glu Gly Ile Lys Glu Leu Lys Gln Gly Tyr Leu Ser Gln
        930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
            980                 985                 990

Asn Tyr Leu Val Asp Lys Lys Lys Arg Pro Glu Asp Ile Gly Gly Leu
        995                 1000                1005

Leu Arg Ala Tyr Gln Phe Thr Ala Pro Phe Lys Ser Phe Lys Glu
    1010                1015                1020

Met Gly Lys Gln Asn Gly Phe Leu Phe Tyr Ile Pro Ala Trp Asn
    1025                1030                1035
```

```
Thr Ser Asn Ile Asp Pro Thr Thr Gly Phe Val Asn Leu Phe His
    1040                1045                1050

Val Gln Tyr Glu Asn Val Asp Lys Ala Lys Ser Phe Phe Gln Lys
    1055                1060                1065

Phe Asp Ser Ile Ser Tyr Asn Pro Lys Lys Asp Trp Phe Glu Phe
    1070                1075                1080

Ala Phe Asp Tyr Lys Asn Phe Thr Lys Lys Ala Glu Gly Ser Arg
    1085                1090                1095

Ser Met Trp Ile Leu Cys Thr His Gly Ser Arg Ile Lys Asn Phe
    1100                1105                1110

Arg Asn Ser Gln Lys Asn Gly Gln Trp Asp Ser Glu Glu Phe Ala
    1115                1120                1125

Leu Thr Glu Ala Phe Lys Ser Leu Phe Val Arg Tyr Glu Ile Asp
    1130                1135                1140

Tyr Thr Ala Asp Leu Lys Thr Ala Ile Val Asp Glu Lys Gln Lys
    1145                1150                1155

Asp Phe Phe Val Asp Leu Leu Lys Leu Phe Lys Leu Thr Val Gln
    1160                1165                1170

Met Arg Asn Ser Trp Lys Glu Lys Asp Leu Asp Tyr Leu Ile Ser
    1175                1180                1185

Pro Val Ala Gly Ala Asp Gly Arg Phe Phe Asp Thr Arg Glu Gly
    1190                1195                1200

Asn Lys Ser Leu Pro Lys Asp Ala Asp Ala Asn Gly Ala Tyr Asn
    1205                1210                1215

Ile Ala Leu Lys Gly Leu Trp Ala Leu Arg Gln Ile Arg Gln Thr
    1220                1225                1230

Ser Glu Gly Gly Lys Leu Lys Leu Ala Ile Ser Asn Lys Glu Trp
    1235                1240                1245

Leu Gln Phe Val Gln Glu Arg Ser Tyr Glu Lys Asp
    1250                1255                1260

<210> SEQ ID NO 14
<211> LENGTH: 1324
<212> TYPE: PRT
<213> ORGANISM: Prevotella disiens

<400> SEQUENCE: 14

Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Val Lys Lys Thr Ala Leu Arg
            100                 105                 110

Asn Lys Cys Thr Ser Ile Gln Arg Ala Met Arg Glu Ala Ile Ser Gln
        115                 120                 125

Ala Phe Leu Lys Ser Pro Gln Lys Lys Leu Leu Ala Ile Lys Asn Leu
    130                 135                 140
```

```
Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
            195                 200                 205

Glu Gln Phe Asp Ala Lys Thr Leu Ser Glu Ile Phe Glu Asn Tyr Lys
210                 215                 220

Leu Tyr Val Ala Gly Ser Ser Leu Asp Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
            275                 280                 285

Phe Phe Ile Ser Leu Lys Lys Gln Ile Leu Ser Asp Arg Glu Ala Leu
290                 295                 300

Ser Trp Leu Pro Asp Met Phe Lys Asn Asp Ser Glu Val Ile Asp Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
            355                 360                 365

Tyr Arg Asn Phe Ser Ile Asp Glu Ala Ile Asp Ala Gln Asn Ala Glu
370                 375                 380

Leu Gln Thr Phe Asn Asn Tyr Glu Leu Ile Ala Asn Ala Leu Arg Ala
385                 390                 395                 400

Lys Ile Lys Lys Glu Thr Lys Gln Gly Arg Lys Ser Phe Glu Lys Tyr
                405                 410                 415

Glu Glu Tyr Ile Asp Lys Lys Val Lys Ala Ile Asp Ser Leu Ser Ile
            420                 425                 430

Gln Glu Ile Asn Glu Leu Val Glu Asn Tyr Val Ser Glu Phe Asn Ser
            435                 440                 445

Asn Ser Gly Asn Met Pro Arg Lys Val Glu Asp Tyr Phe Ser Leu Met
450                 455                 460

Arg Lys Gly Asp Phe Gly Ser Asn Asp Leu Ile Glu Asn Ile Lys Thr
465                 470                 475                 480

Lys Leu Ser Ala Ala Glu Lys Leu Leu Gly Thr Lys Tyr Gln Glu Thr
                485                 490                 495

Ala Lys Asp Ile Phe Lys Lys Asp Glu Asn Ser Lys Leu Ile Lys Glu
            500                 505                 510

Leu Leu Asp Ala Thr Lys Gln Phe Gln His Phe Ile Lys Pro Leu Leu
            515                 520                 525

Gly Thr Gly Glu Glu Ala Asp Arg Asp Leu Val Phe Tyr Gly Asp Phe
530                 535                 540

Leu Pro Leu Tyr Glu Lys Phe Glu Glu Leu Thr Leu Leu Tyr Asn Lys
545                 550                 555                 560
```

-continued

Val Arg Asn Arg Leu Thr Gln Lys Pro Tyr Ser Lys Asp Lys Ile Arg
                565                 570                 575

Leu Cys Phe Asn Lys Pro Lys Leu Met Thr Gly Trp Val Asp Ser Lys
                580                 585                 590

Thr Glu Lys Ser Asp Asn Gly Thr Gln Tyr Gly Gly Tyr Leu Phe Arg
                595                 600                 605

Lys Lys Asn Glu Ile Gly Glu Tyr Asp Tyr Phe Leu Gly Ile Ser Ser
            610                 615                 620

Lys Ala Gln Leu Phe Arg Lys Asn Glu Ala Val Ile Gly Asp Tyr Glu
625                 630                 635                 640

Arg Leu Asp Tyr Tyr Gln Pro Lys Ala Asn Thr Ile Tyr Gly Ser Ala
                645                 650                 655

Tyr Glu Gly Glu Asn Ser Tyr Lys Glu Asp Lys Lys Arg Leu Asn Lys
                660                 665                 670

Val Ile Ile Ala Tyr Ile Glu Gln Ile Lys Gln Thr Asn Ile Lys Lys
                675                 680                 685

Ser Ile Ile Glu Ser Ile Ser Lys Tyr Pro Asn Ile Ser Asp Asp Asp
                690                 695                 700

Lys Val Thr Pro Ser Ser Leu Leu Glu Lys Ile Lys Lys Val Ser Ile
705                 710                 715                 720

Asp Ser Tyr Asn Gly Ile Leu Ser Phe Lys Ser Phe Gln Ser Val Asn
                725                 730                 735

Lys Glu Val Ile Asp Asn Leu Leu Lys Thr Ile Ser Pro Leu Lys Asn
                740                 745                 750

Lys Ala Glu Phe Leu Asp Leu Ile Asn Lys Asp Tyr Gln Ile Phe Thr
                755                 760                 765

Glu Val Gln Ala Val Ile Asp Glu Ile Cys Lys Gln Lys Thr Phe Ile
                770                 775                 780

Tyr Phe Pro Ile Ser Asn Val Glu Leu Glu Lys Glu Met Gly Asp Lys
785                 790                 795                 800

Asp Lys Pro Leu Cys Leu Phe Gln Ile Ser Asn Lys Asp Leu Ser Phe
                805                 810                 815

Ala Lys Thr Phe Ser Ala Asn Leu Arg Lys Lys Arg Gly Ala Glu Asn
                820                 825                 830

Leu His Thr Met Leu Phe Lys Ala Leu Met Glu Gly Asn Gln Asp Asn
                835                 840                 845

Leu Asp Leu Gly Ser Gly Ala Ile Phe Tyr Arg Ala Lys Ser Leu Asp
                850                 855                 860

Gly Asn Lys Pro Thr His Pro Ala Asn Glu Ala Ile Lys Cys Arg Asn
865                 870                 875                 880

Val Ala Asn Lys Asp Lys Val Ser Leu Phe Thr Tyr Asp Ile Tyr Lys
                885                 890                 895

Asn Arg Arg Tyr Met Glu Asn Lys Phe Leu Phe His Leu Ser Ile Val
                900                 905                 910

Gln Asn Tyr Lys Ala Ala Asn Asp Ser Ala Gln Leu Asn Ser Ser Ala
                915                 920                 925

Thr Glu Tyr Ile Arg Lys Ala Asp Asp Leu His Ile Ile Gly Ile Asp
                930                 935                 940

Arg Gly Glu Arg Asn Leu Leu Tyr Tyr Ser Val Ile Asp Met Lys Gly
945                 950                 955                 960

Asn Ile Val Glu Gln Asp Ser Leu Asn Ile Ile Arg Asn Asn Asp Leu
                965                 970                 975

Glu Thr Asp Tyr His Asp Leu Leu Asp Lys Arg Glu Lys Glu Arg Lys

```
                    980             985             990
Ala Asn Arg Gln Asn Trp Glu Ala Val Glu Gly Ile Lys Asp Leu Lys
                995            1000             1005

Lys Gly Tyr Leu Ser Gln Ala Val His Gln Ile Ala Gln Leu Met
    1010             1015             1020

Leu Lys Tyr Asn Ala Ile Ile Ala Leu Glu Asp Leu Gly Gln Met
    1025             1030             1035

Phe Val Thr Arg Gly Gln Lys Ile Glu Lys Ala Val Tyr Gln Gln
    1040             1045             1050

Phe Glu Lys Ser Leu Val Asp Lys Leu Ser Tyr Leu Val Asp Lys
    1055             1060             1065

Lys Arg Pro Tyr Asn Glu Leu Gly Gly Ile Leu Lys Ala Tyr Gln
    1070             1075             1080

Leu Ala Ser Ser Ile Thr Lys Asn Asn Ser Asp Lys Gln Asn Gly
    1085             1090             1095

Phe Leu Phe Tyr Val Pro Ala Trp Asn Thr Ser Lys Ile Asp Pro
    1100             1105             1110

Val Thr Gly Phe Thr Asp Leu Leu Arg Pro Lys Ala Met Thr Ile
    1115             1120             1125

Lys Glu Ala Gln Asp Phe Phe Gly Ala Phe Asp Asn Ile Ser Tyr
    1130             1135             1140

Asn Asp Lys Gly Tyr Phe Glu Phe Glu Thr Asn Tyr Asp Lys Phe
    1145             1150             1155

Lys Ile Arg Met Lys Ser Ala Gln Thr Arg Trp Thr Ile Cys Thr
    1160             1165             1170

Phe Gly Asn Arg Ile Lys Arg Lys Lys Asp Lys Asn Tyr Trp Asn
    1175             1180             1185

Tyr Glu Glu Val Glu Leu Thr Glu Glu Phe Lys Lys Leu Phe Lys
    1190             1195             1200

Asp Ser Asn Ile Asp Tyr Glu Asn Cys Asn Leu Lys Glu Glu Ile
    1205             1210             1215

Gln Asn Lys Asp Asn Arg Lys Phe Phe Asp Asp Leu Ile Lys Leu
    1220             1225             1230

Leu Gln Leu Thr Leu Gln Met Arg Asn Ser Asp Asp Lys Gly Asn
    1235             1240             1245

Asp Tyr Ile Ile Ser Pro Val Ala Asn Ala Glu Gly Gln Phe Phe
    1250             1255             1260

Asp Ser Arg Asn Gly Asp Lys Lys Leu Pro Leu Asp Ala Asp Ala
    1265             1270             1275

Asn Gly Ala Tyr Asn Ile Ala Arg Lys Gly Leu Trp Asn Ile Arg
    1280             1285             1290

Gln Ile Lys Gln Thr Lys Asn Lys Asp Asp Leu Asn Leu Ser Ile
    1295             1300             1305

Ser Ser Thr Glu Trp Leu Asp Phe Val Arg Glu Lys Pro Tyr Leu
    1310             1315             1320

Lys

<210> SEQ ID NO 15
<211> LENGTH: 1484
<212> TYPE: PRT
<213> ORGANISM: Peregrinibacteria bacterium
<220> FEATURE:
<221> NAME/KEY: misc_feature
<222> LOCATION: (1073)..(1073)
<223> OTHER INFORMATION: Xaa can be any naturally occurring amino acid
```

<400> SEQUENCE: 15

```
Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
            20                  25                  30

Lys Asp His Leu Glu Tyr Asp Glu Lys Leu Gln Thr Phe Leu Lys Asp
        35                  40                  45

Gln Asn Ile Asp Asp Ala Tyr Gln Ala Leu Lys Pro Gln Phe Asp Glu
    50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
    130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
        195                 200                 205

Phe Cys Asp Asn Val Ile Gln Phe Lys His Ile Ile Lys Arg Lys Lys
210                 215                 220

Asp Gly Thr Val Glu Lys Thr Glu Arg Lys Thr Glu Tyr Leu Asn Ala
225                 230                 235                 240

Tyr Gln Tyr Leu Lys Asn Asn Asn Lys Ile Thr Gln Ile Lys Asp Ala
                245                 250                 255

Glu Thr Glu Lys Met Ile Glu Ser Thr Pro Ile Ala Glu Lys Ile Phe
            260                 265                 270

Asp Val Tyr Tyr Phe Ser Ser Cys Leu Ser Gln Lys Gln Ile Glu Glu
        275                 280                 285

Tyr Asn Arg Ile Ile Gly His Tyr Asn Leu Leu Ile Asn Leu Tyr Asn
290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
            340                 345                 350

Glu Ala Asn Lys Ser Arg Asn Glu Gly Lys Glu Ser His Ser Val Glu
        355                 360                 365

Glu Ile Ile Asn Lys Ala Gln Glu Ala Ile Asn Lys Tyr Phe Lys Ser
370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
```

```
                405                 410                 415
Met Asn Thr Ile Ser Asp Lys Tyr Phe Ala Asn Tyr His Asp Leu Gln
            420                 425                 430

Asp Arg Leu Lys Glu Ala Lys Val Phe Gln Lys Ala Asp Lys Lys Ser
            435                 440                 445

Glu Asp Ile Lys Ile Pro Glu Ala Ile Glu Leu Ser Gly Leu Phe
        450                 455                 460

Gly Val Leu Asp Ser Leu Ala Asp Trp Gln Thr Thr Leu Phe Lys Ser
465                 470                 475                 480

Ser Ile Leu Ser Asn Glu Lys Leu Lys Ile Ile Thr Asp Ser Gln Thr
                485                 490                 495

Pro Ser Glu Ala Leu Leu Lys Met Ile Phe Asn Asp Ile Glu Lys Asn
            500                 505                 510

Met Glu Ser Phe Leu Lys Glu Thr Asn Asp Ile Ile Thr Leu Lys Lys
            515                 520                 525

Tyr Lys Gly Asn Lys Glu Gly Thr Glu Lys Ile Lys Gln Trp Phe Asp
            530                 535                 540

Tyr Thr Leu Ala Ile Asn Arg Met Leu Lys Tyr Phe Leu Val Lys Glu
545                 550                 555                 560

Asn Lys Ile Lys Gly Asn Ser Leu Asp Thr Asn Ile Ser Glu Ala Leu
                565                 570                 575

Lys Thr Leu Ile Tyr Ser Asp Asp Ala Glu Trp Phe Lys Trp Tyr Asp
            580                 585                 590

Ala Leu Arg Asn Tyr Leu Thr Gln Lys Pro Gln Asp Glu Ala Lys Glu
                595                 600                 605

Asn Lys Leu Lys Leu Asn Phe Asp Asn Pro Ser Leu Ala Gly Gly Trp
            610                 615                 620

Asp Val Asn Lys Glu Cys Ser Asn Phe Cys Val Ile Leu Lys Asp Lys
625                 630                 635                 640

Asn Glu Lys Lys Tyr Leu Ala Met Ile Lys Lys Gly Glu Asn Thr Leu
                645                 650                 655

Phe Gln Lys Glu Trp Thr Glu Gly Arg Gly Lys Asn Leu Thr Lys Lys
            660                 665                 670

Ser Asn Pro Leu Phe Glu Ile Asn Asn Cys Glu Ile Leu Ser Lys Met
            675                 680                 685

Glu Tyr Asp Phe Trp Ala Asp Val Ser Lys Met Ile Pro Lys Cys Ser
            690                 695                 700

Thr Gln Leu Lys Ala Val Val Asn His Phe Lys Gln Ser Asp Asn Glu
705                 710                 715                 720

Phe Ile Phe Pro Ile Gly Tyr Lys Val Thr Ser Gly Glu Lys Phe Arg
                725                 730                 735

Glu Glu Cys Lys Ile Ser Lys Gln Asp Phe Glu Leu Asn Asn Lys Val
            740                 745                 750

Phe Asn Lys Asn Glu Leu Ser Val Thr Ala Met Arg Tyr Asp Leu Ser
            755                 760                 765

Ser Thr Gln Glu Lys Gln Tyr Ile Lys Ala Phe Gln Lys Glu Tyr Trp
            770                 775                 780

Glu Leu Leu Phe Lys Gln Glu Lys Arg Asp Thr Lys Leu Thr Asn Asn
785                 790                 795                 800

Glu Ile Phe Asn Glu Trp Ile Asn Phe Cys Asn Lys Lys Tyr Ser Glu
                805                 810                 815

Leu Leu Ser Trp Glu Arg Lys Tyr Lys Asp Ala Leu Thr Asn Trp Ile
            820                 825                 830
```

```
Asn Phe Cys Lys Tyr Phe Leu Ser Lys Tyr Pro Lys Thr Thr Leu Phe
        835                 840                 845

Asn Tyr Ser Phe Lys Glu Ser Glu Asn Tyr Asn Ser Leu Asp Glu Phe
        850                 855                 860

Tyr Arg Asp Val Asp Ile Cys Ser Tyr Lys Leu Asn Ile Asn Thr Thr
865                 870                 875                 880

Ile Asn Lys Ser Ile Leu Asp Arg Leu Val Glu Glu Gly Lys Leu Tyr
            885                 890                 895

Leu Phe Glu Ile Lys Asn Gln Asp Ser Asn Asp Gly Lys Ser Ile Gly
            900                 905                 910

His Lys Asn Asn Leu His Thr Ile Tyr Trp Asn Ala Ile Phe Glu Asn
            915                 920                 925

Phe Asp Asn Arg Pro Lys Leu Asn Gly Glu Ala Glu Ile Phe Tyr Arg
            930                 935                 940

Lys Ala Ile Ser Lys Asp Lys Leu Gly Ile Val Lys Gly Lys Lys Thr
945                 950                 955                 960

Lys Asn Gly Thr Trp Ile Ile Lys Asn Tyr Arg Phe Ser Lys Glu Lys
                965                 970                 975

Phe Ile Leu His Val Pro Ile Thr Leu Asn Phe Cys Ser Asn Asn Glu
            980                 985                 990

Tyr Val Asn Asp Ile Val Asn Thr Lys Phe Tyr Asn Phe Ser Asn Leu
            995                 1000                1005

His Phe Leu Gly Ile Asp Arg Gly Glu Lys His Leu Ala Tyr Tyr
        1010                1015                1020

Ser Leu Val Asn Lys Asn Gly Glu Ile Val Asp Gln Gly Thr Leu
        1025                1030                1035

Asn Leu Pro Phe Thr Asp Lys Asp Gly Asn Gln Arg Ser Ile Lys
        1040                1045                1050

Lys Glu Lys Tyr Phe Tyr Asn Lys Gln Glu Asp Lys Trp Glu Ala
        1055                1060                1065

Lys Glu Val Asp Xaa Trp Asn Tyr Asn Asp Leu Leu Asp Ala Met
        1070                1075                1080

Ala Ser Asn Arg Asp Met Ala Arg Lys Asn Trp Gln Arg Ile Gly
        1085                1090                1095

Thr Ile Lys Glu Ala Lys Asn Gly Tyr Val Ser Leu Val Ile Arg
        1100                1105                1110

Lys Ile Ala Asp Leu Ala Val Asn Asn Glu Arg Pro Ala Phe Ile
        1115                1120                1125

Val Leu Glu Asp Leu Asn Thr Gly Phe Lys Arg Ser Arg Gln Lys
        1130                1135                1140

Ile Asp Lys Ser Val Tyr Gln Lys Phe Glu Leu Ala Leu Ala Lys
        1145                1150                1155

Lys Leu Asn Phe Leu Val Asp Lys Asn Ala Lys Arg Asp Glu Ile
        1160                1165                1170

Gly Ser Pro Thr Lys Ala Leu Gln Leu Thr Pro Pro Val Asn Asn
        1175                1180                1185

Tyr Gly Asp Ile Glu Asn Lys Lys Gln Ala Gly Ile Met Leu Tyr
        1190                1195                1200

Thr Arg Ala Asn Tyr Thr Ser Gln Thr Asp Pro Ala Thr Gly Trp
        1205                1210                1215

Arg Lys Thr Ile Tyr Leu Lys Ala Gly Pro Glu Glu Thr Thr Tyr
        1220                1225                1230
```

-continued

```
Lys Lys Asp Gly Lys Ile Lys Asn Lys Ser Val Lys Asp Gln Ile
    1235                1240                1245

Ile Glu Thr Phe Thr Asp Ile Gly Phe Asp Gly Lys Asp Tyr Tyr
    1250                1255                1260

Phe Glu Tyr Asp Lys Gly Glu Phe Val Asp Glu Lys Thr Gly Glu
    1265                1270                1275

Ile Lys Pro Lys Lys Trp Arg Leu Tyr Ser Gly Glu Asn Gly Lys
    1280                1285                1290

Ser Leu Asp Arg Phe Arg Gly Glu Arg Glu Lys Asp Lys Tyr Glu
    1295                1300                1305

Trp Lys Ile Asp Lys Ile Asp Ile Val Lys Ile Leu Asp Asp Leu
    1310                1315                1320

Phe Val Asn Phe Asp Lys Asn Ile Ser Leu Leu Lys Gln Leu Lys
    1325                1330                1335

Glu Gly Val Glu Leu Thr Arg Asn Asn Glu His Gly Thr Gly Glu
    1340                1345                1350

Ser Leu Arg Phe Ala Ile Asn Leu Ile Gln Gln Ile Arg Asn Thr
    1355                1360                1365

Gly Asn Asn Glu Arg Asp Asn Asp Phe Ile Leu Ser Pro Val Arg
    1370                1375                1380

Asp Glu Asn Gly Lys His Phe Asp Ser Arg Glu Tyr Trp Asp Lys
    1385                1390                1395

Glu Thr Lys Gly Glu Lys Ile Ser Met Pro Ser Ser Gly Asp Ala
    1400                1405                1410

Asn Gly Ala Phe Asn Ile Ala Arg Lys Gly Ile Ile Met Asn Ala
    1415                1420                1425

His Ile Leu Ala Asn Ser Asp Ser Lys Asp Leu Ser Leu Phe Val
    1430                1435                1440

Ser Asp Glu Glu Trp Asp Leu His Leu Asn Asn Lys Thr Glu Trp
    1445                1450                1455

Lys Lys Gln Leu Asn Ile Phe Ser Ser Arg Lys Ala Met Ala Lys
    1460                1465                1470

Arg Lys Lys Lys Arg Pro Ala Ala Thr Lys Lys
    1475                1480

<210> SEQ ID NO 16
<211> LENGTH: 1245
<212> TYPE: PRT
<213> ORGANISM: Porphyromonas macacae

<400> SEQUENCE: 16

Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
                20                  25                  30

Asn Ile Lys Lys Asn Gly Leu Ile Arg Arg Asp Glu Gln Arg Leu Asp
            35                  40                  45

Asp Tyr Glu Lys Leu Lys Lys Val Ile Asp Glu Tyr His Glu Asp Phe
        50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Ile Ser Glu Ala Arg Ala Lys Ile Glu
                85                  90                  95

Lys Thr Met Arg Asp Thr Leu Ala Lys Ala Phe Ser Glu Asp Glu Arg
            100                 105                 110
```

```
Tyr Lys Ser Ile Phe Lys Lys Glu Leu Val Lys Lys Asp Ile Pro Val
        115                 120                 125
Trp Cys Pro Ala Tyr Lys Ser Leu Cys Lys Lys Phe Asp Asn Phe Thr
130                 135                 140
Thr Ser Leu Val Pro Phe His Glu Asn Arg Lys Asn Leu Tyr Thr Ser
145                 150                 155                 160
Asn Glu Ile Thr Ala Ser Ile Pro Tyr Arg Ile Val His Val Asn Leu
                165                 170                 175
Pro Lys Phe Ile Gln Asn Ile Glu Ala Leu Cys Glu Leu Gln Lys Lys
                180                 185                 190
Met Gly Ala Asp Leu Tyr Leu Glu Met Met Glu Asn Leu Arg Asn Val
        195                 200                 205
Trp Pro Ser Phe Val Lys Thr Pro Asp Asp Leu Cys Asn Leu Lys Thr
        210                 215                 220
Tyr Asn His Leu Met Val Gln Ser Ser Ile Ser Glu Tyr Asn Arg Phe
225                 230                 235                 240
Val Gly Gly Tyr Ser Thr Glu Asp Gly Thr Lys His Gln Gly Ile Asn
                245                 250                 255
Glu Trp Ile Asn Ile Tyr Arg Gln Arg Asn Lys Glu Met Arg Leu Pro
            260                 265                 270
Gly Leu Val Phe Leu His Lys Gln Ile Leu Ala Lys Val Asp Ser Ser
        275                 280                 285
Ser Phe Ile Ser Asp Thr Leu Glu Asn Asp Asp Gln Val Phe Cys Val
        290                 295                 300
Leu Arg Gln Phe Arg Lys Leu Phe Trp Asn Thr Val Ser Ser Lys Glu
305                 310                 315                 320
Asp Asp Ala Ala Ser Leu Lys Asp Leu Phe Cys Gly Leu Ser Gly Tyr
                325                 330                 335
Asp Pro Glu Ala Ile Tyr Val Ser Asp Ala His Leu Ala Thr Ile Ser
                340                 345                 350
Lys Asn Ile Phe Asp Arg Trp Asn Tyr Ile Ser Asp Ala Ile Arg Arg
            355                 360                 365
Lys Thr Glu Val Leu Met Pro Arg Lys Lys Glu Ser Val Glu Arg Tyr
        370                 375                 380
Ala Glu Lys Ile Ser Lys Gln Ile Lys Lys Arg Gln Ser Tyr Ser Leu
385                 390                 395                 400
Ala Glu Leu Asp Asp Leu Leu Ala His Tyr Ser Glu Glu Ser Leu Pro
                405                 410                 415
Ala Gly Phe Ser Leu Leu Ser Tyr Phe Thr Ser Leu Gly Gly Gln Lys
                420                 425                 430
Tyr Leu Val Ser Asp Gly Glu Val Ile Leu Tyr Glu Glu Gly Ser Asn
        435                 440                 445
Ile Trp Asp Glu Val Leu Ile Ala Phe Arg Asp Leu Gln Val Ile Leu
        450                 455                 460
Asp Lys Asp Phe Thr Glu Lys Lys Leu Gly Lys Asp Glu Glu Ala Val
465                 470                 475                 480
Ser Val Ile Lys Lys Ala Leu Asp Ser Ala Leu Arg Leu Arg Lys Phe
                485                 490                 495
Phe Asp Leu Leu Ser Gly Thr Gly Ala Glu Ile Arg Arg Asp Ser Ser
                500                 505                 510
Phe Tyr Ala Leu Tyr Thr Asp Arg Met Asp Lys Leu Lys Gly Leu Leu
        515                 520                 525
```

-continued

```
Lys Met Tyr Asp Lys Val Arg Asn Tyr Leu Thr Lys Lys Pro Tyr Ser
    530                 535                 540
Ile Glu Lys Phe Lys Leu His Phe Asp Asn Pro Ser Leu Leu Ser Gly
545                 550                 555                 560
Trp Asp Lys Asn Lys Glu Leu Asn Asn Leu Ser Val Ile Phe Arg Gln
                565                 570                 575
Asn Gly Tyr Tyr Tyr Leu Gly Ile Met Thr Pro Lys Gly Lys Asn Leu
            580                 585                 590
Phe Lys Thr Leu Pro Lys Leu Gly Ala Glu Met Phe Tyr Glu Lys
        595                 600                 605
Met Glu Tyr Lys Gln Ile Ala Glu Pro Met Leu Met Leu Pro Lys Val
    610                 615                 620
Phe Phe Pro Lys Lys Thr Lys Pro Ala Phe Ala Pro Asp Gln Ser Val
625                 630                 635                 640
Val Asp Ile Tyr Asn Lys Lys Thr Phe Lys Thr Gly Gln Lys Gly Phe
                645                 650                 655
Asn Lys Lys Asp Leu Tyr Arg Leu Ile Asp Phe Tyr Lys Glu Ala Leu
            660                 665                 670
Thr Val His Glu Trp Lys Leu Phe Asn Phe Ser Phe Ser Pro Thr Glu
        675                 680                 685
Gln Tyr Arg Asn Ile Gly Glu Phe Phe Asp Glu Val Arg Glu Gln Ala
    690                 695                 700
Tyr Lys Val Ser Met Val Asn Val Pro Ala Ser Tyr Ile Asp Glu Ala
705                 710                 715                 720
Val Glu Asn Gly Lys Leu Tyr Leu Phe Gln Ile Tyr Asn Lys Asp Phe
                725                 730                 735
Ser Pro Tyr Ser Lys Gly Ile Pro Asn Leu His Thr Leu Tyr Trp Lys
            740                 745                 750
Ala Leu Phe Ser Glu Gln Asn Gln Ser Arg Val Tyr Lys Leu Cys Gly
        755                 760                 765
Gly Gly Glu Leu Phe Tyr Arg Lys Ala Ser Leu His Met Gln Asp Thr
    770                 775                 780
Thr Val His Pro Lys Gly Ile Ser Ile His Lys Lys Asn Leu Asn Lys
785                 790                 795                 800
Lys Gly Glu Thr Ser Leu Phe Asn Tyr Asp Leu Val Lys Asp Lys Arg
                805                 810                 815
Phe Thr Glu Asp Lys Phe Phe His Val Pro Ile Ser Ile Asn Tyr
            820                 825                 830
Lys Asn Lys Lys Ile Thr Asn Val Asn Gln Met Val Arg Asp Tyr Ile
        835                 840                 845
Ala Gln Asn Asp Asp Leu Gln His Gly Ile Asp Arg Gly Glu Arg Asn
    850                 855                 860
Leu Leu Tyr Ile Ser Arg Ile Asp Thr Arg Gly Asn Leu Leu Glu Gln
865                 870                 875                 880
Phe Ser Leu Asn Val Ile Glu Ser Asp Lys Gly Asp Leu Arg Thr Asp
                885                 890                 895
Tyr Gln Lys Ile Leu Gly Asp Arg Glu Gln Glu Arg Leu Arg Arg Arg
            900                 905                 910
Gln Glu Trp Lys Ser Ile Glu Ser Ile Lys Asp Leu Lys Asp Gly Tyr
        915                 920                 925
Met Ser Gln Val Val His Lys Ile Cys Asn Met Val Val Glu His Lys
    930                 935                 940
Ala Ile Val Val Leu Glu Asn Leu Asn Leu Ser Phe Met Lys Gly Arg
```

```
                                945             950             955             960
                Lys Lys Val Glu Lys Ser Val Tyr Glu Lys Phe Glu Arg Met Leu Val
                                    965             970             975
                Asp Lys Leu Asn Tyr Leu Val Val Asp Lys Lys Asn Leu Ser Asn Glu
                                    980             985             990
                Pro Gly Gly Leu Tyr Ala Ala Tyr Gln Leu Thr Asn Pro Leu Phe Ser
                        995             1000            1005
                Phe Glu Glu Leu His Arg Tyr Pro Gln Ser Gly Ile Leu Phe Phe
                    1010            1015            1020
                Val Asp Pro Trp Asn Thr Ser Leu Thr Asp Pro Ser Thr Gly Phe
                    1025            1030            1035
                Val Asn Leu Leu Gly Arg Ile Asn Tyr Thr Asn Val Gly Asp Ala
                    1040            1045            1050
                Arg Lys Phe Phe Asp Arg Phe Asn Ala Ile Arg Tyr Asp Gly Lys
                    1055            1060            1065
                Gly Asn Ile Leu Phe Asp Leu Asp Leu Ser Arg Phe Asp Val Arg
                    1070            1075            1080
                Val Glu Thr Gln Arg Lys Leu Trp Thr Leu Thr Thr Phe Gly Ser
                    1085            1090            1095
                Arg Ile Ala Lys Ser Lys Lys Ser Gly Lys Trp Met Val Glu Arg
                    1100            1105            1110
                Ile Glu Asn Leu Ser Leu Cys Phe Leu Glu Leu Phe Glu Gln Phe
                    1115            1120            1125
                Asn Ile Gly Tyr Arg Val Glu Lys Asp Leu Lys Lys Ala Ile Leu
                    1130            1135            1140
                Ser Gln Asp Arg Lys Glu Phe Tyr Val Arg Leu Ile Tyr Leu Phe
                    1145            1150            1155
                Asn Leu Met Met Gln Ile Arg Asn Ser Asp Gly Glu Glu Asp Tyr
                    1160            1165            1170
                Ile Leu Ser Pro Ala Leu Asn Glu Lys Asn Leu Gln Phe Asp Ser
                    1175            1180            1185
                Arg Leu Ile Glu Ala Lys Asp Leu Pro Val Asp Ala Asp Ala Asn
                    1190            1195            1200
                Gly Ala Tyr Asn Val Ala Arg Lys Gly Leu Met Val Val Gln Arg
                    1205            1210            1215
                Ile Lys Arg Gly Asp His Glu Ser Ile His Arg Ile Gly Arg Ala
                    1220            1225            1230
                Gln Trp Leu Arg Tyr Val Glu Gly Ile Val Glu
                    1235            1240            1245

<210> SEQ ID NO 17
<211> LENGTH: 1250
<212> TYPE: PRT
<213> ORGANISM: Smithella sp.

<400> SEQUENCE: 17

Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
                20                  25                  30

Glu Gln Lys Gly Leu Leu Lys Lys Asp Glu Asp Arg Ala Glu Lys Tyr
            35                  40                  45

Lys Lys Val Lys Asn Ile Ile Asp Glu Tyr His Lys Asp Phe Ile Glu
        50                  55                  60
```

-continued

```
Lys Ser Leu Asn Gly Leu Lys Leu Asp Gly Leu Glu Lys Tyr Lys Thr
 65                  70                  75                  80

Leu Tyr Leu Lys Gln Glu Lys Asp Asp Lys Asp Lys Lys Ala Phe Asp
                 85                  90                  95

Lys Glu Lys Glu Asn Leu Arg Lys Gln Ile Ala Asn Ala Phe Arg Asn
            100                 105                 110

Asn Glu Lys Phe Lys Thr Leu Phe Ala Lys Glu Leu Ile Lys Asn Asp
            115                 120                 125

Leu Met Ser Phe Ala Cys Glu Asp Lys Lys Asn Val Lys Glu Phe
    130                 135                 140

Glu Ala Phe Thr Thr Tyr Phe Thr Gly Phe His Gln Asn Arg Ala Asn
145                 150                 155                 160

Met Tyr Val Ala Asp Glu Lys Arg Thr Ala Ile Ala Ser Arg Leu Ile
                165                 170                 175

His Glu Asn Leu Pro Lys Phe Ile Asp Asn Ile Lys Ile Phe Glu Lys
            180                 185                 190

Met Lys Lys Glu Ala Pro Glu Leu Leu Ser Pro Phe Asn Gln Thr Leu
            195                 200                 205

Lys Asp Met Lys Asp Val Ile Lys Gly Thr Thr Leu Glu Glu Ile Phe
210                 215                 220

Ser Leu Asp Tyr Phe Asn Lys Thr Leu Thr Gln Ser Gly Ile Asp Ile
225                 230                 235                 240

Tyr Asn Ser Val Ile Gly Gly Arg Thr Pro Glu Glu Gly Lys Thr Lys
                245                 250                 255

Ile Lys Gly Leu Asn Glu Tyr Ile Asn Thr Asp Phe Asn Gln Lys Gln
            260                 265                 270

Thr Asp Lys Lys Lys Arg Gln Pro Lys Phe Lys Gln Leu Tyr Lys Gln
            275                 280                 285

Ile Leu Ser Asp Arg Gln Ser Leu Ser Phe Ile Ala Glu Ala Phe Lys
    290                 295                 300

Asn Asp Thr Glu Ile Leu Glu Ala Ile Glu Lys Phe Tyr Val Asn Glu
305                 310                 315                 320

Leu Leu His Phe Ser Asn Glu Gly Lys Ser Thr Asn Val Leu Asp Ala
                325                 330                 335

Ile Lys Asn Ala Val Ser Asn Leu Glu Ser Phe Asn Leu Thr Lys Met
            340                 345                 350

Tyr Phe Arg Ser Gly Ala Ser Leu Thr Asp Val Ser Arg Lys Val Phe
            355                 360                 365

Gly Glu Trp Ser Ile Ile Asn Arg Ala Leu Asp Asn Tyr Tyr Ala Thr
    370                 375                 380

Thr Tyr Pro Ile Lys Pro Arg Glu Lys Ser Glu Lys Tyr Glu Glu Arg
385                 390                 395                 400

Lys Glu Lys Trp Leu Lys Gln Asp Phe Asn Val Ser Leu Ile Gln Thr
                405                 410                 415

Ala Ile Asp Glu Tyr Asp Asn Glu Thr Val Lys Gly Lys Asn Ser Gly
            420                 425                 430

Lys Val Ile Ala Asp Tyr Phe Ala Lys Phe Cys Asp Asp Lys Glu Thr
            435                 440                 445

Asp Leu Ile Gln Lys Val Asn Glu Gly Tyr Ile Ala Val Lys Asp Leu
    450                 455                 460

Leu Asn Thr Pro Cys Pro Glu Asn Glu Lys Leu Gly Ser Asn Lys Asp
465                 470                 475                 480

Gln Val Lys Gln Ile Lys Ala Phe Met Asp Ser Ile Met Asp Ile Met
```

```
                    485                 490                 495
His Phe Val Arg Pro Leu Ser Leu Lys Asp Thr Asp Lys Glu Lys Asp
                500                 505                 510

Glu Thr Phe Tyr Ser Leu Phe Thr Pro Leu Tyr Asp His Leu Thr Gln
                515                 520                 525

Thr Ile Ala Leu Tyr Asn Lys Val Arg Asn Tyr Leu Thr Gln Lys Pro
            530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                565                 570                 575

Arg Lys Asp Asn Leu Tyr Tyr Leu Gly Ile Met Asp Lys Arg His Asn
                580                 585                 590

Arg Ile Phe Arg Asn Val Pro Lys Ala Asp Lys Lys Asp Phe Cys Tyr
            595                 600                 605

Glu Lys Met Val Tyr Lys Leu Leu Pro Gly Ala Asn Lys Met Leu Pro
        610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                645                 650                 655

Phe Asn Leu Asn His Cys His Lys Leu Ile Asp Phe Phe Lys Asp Ser
            660                 665                 670

Ile Asn Lys His Glu Asp Trp Lys Asn Phe Asp Phe Arg Phe Ser Ala
        675                 680                 685

Thr Ser Thr Tyr Ala Asp Leu Ser Gly Phe Tyr His Glu Val Glu His
            690                 695                 700

Gln Gly Tyr Lys Ile Ser Phe Gln Ser Val Ala Asp Ser Phe Ile Asp
705                 710                 715                 720

Asp Leu Val Asn Glu Gly Lys Leu Tyr Leu Phe Gln Ile Tyr Asn Lys
                725                 730                 735

Asp Phe Ser Pro Phe Ser Lys Gly Lys Pro Asn Leu His Thr Leu Tyr
            740                 745                 750

Trp Lys Met Leu Phe Asp Glu Asn Asn Leu Lys Asp Val Val Tyr Lys
        755                 760                 765

Leu Asn Gly Glu Ala Glu Val Phe Tyr Arg Lys Lys Ser Ile Ala Glu
        770                 775                 780

Lys Asn Thr Thr Ile His Lys Ala Asn Glu Ser Ile Ile Asn Lys Asn
785                 790                 795                 800

Pro Asp Asn Pro Lys Ala Thr Ser Thr Phe Asn Tyr Asp Ile Val Lys
                805                 810                 815

Asp Lys Arg Tyr Thr Ile Asp Lys Phe Gln Phe His Ile Pro Ile Thr
                820                 825                 830

Met Asn Phe Lys Ala Glu Gly Ile Phe Asn Met Asn Gln Arg Val Asn
            835                 840                 845

Gln Phe Leu Lys Ala Asn Pro Asp Ile Asn Ile Ile Gly Ile Asp Arg
        850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
                885                 890                 895

Val Asp Tyr His Asn Leu Leu Asp Lys Lys Glu Gly Asp Arg Ala Thr
            900                 905                 910
```

Ala Arg Gln Glu Trp Gly Val Ile Glu Thr Ile Lys Glu Leu Lys Glu
        915                 920                 925

Gly Tyr Leu Ser Gln Val Ile His Lys Leu Thr Asp Leu Met Ile Glu
    930                 935                 940

Asn Asn Ala Ile Ile Val Met Glu Asp Leu Asn Phe Gly Phe Lys Arg
945                 950                 955                 960

Gly Arg Gln Lys Val Glu Lys Gln Val Tyr Gln Lys Phe Glu Lys Met
                965                 970                 975

Leu Ile Asp Lys Leu Asn Tyr Leu Val Asp Lys Asn Lys Lys Ala Asn
            980                 985                 990

Glu Leu Gly Gly Leu Leu Asn Ala Phe Gln Leu Ala Asn Lys Phe Glu
        995                 1000                1005

Ser Phe Gln Lys Met Gly Lys Gln Asn Gly Phe Ile Phe Tyr Val
    1010                1015                1020

Pro Ala Trp Asn Thr Ser Lys Thr Asp Pro Ala Thr Gly Phe Ile
    1025                1030                1035

Asp Phe Leu Lys Pro Arg Tyr Glu Asn Leu Asn Gln Ala Lys Asp
    1040                1045                1050

Phe Phe Glu Lys Phe Asp Ser Ile Arg Leu Asn Ser Lys Ala Asp
    1055                1060                1065

Tyr Phe Glu Phe Ala Phe Asp Phe Lys Asn Phe Thr Glu Lys Ala
    1070                1075                1080

Asp Gly Gly Arg Thr Lys Trp Thr Val Cys Thr Thr Asn Glu Asp
    1085                1090                1095

Arg Tyr Gln Trp Asn Arg Ala Leu Asn Asn Arg Gly Ser Gln
    1100                1105                1110

Glu Lys Tyr Asp Ile Thr Ala Glu Leu Lys Ser Leu Phe Asp Gly
    1115                1120                1125

Lys Val Asp Tyr Lys Ser Gly Lys Asp Leu Lys Gln Gln Ile Ala
    1130                1135                1140

Ser Gln Glu Ser Ala Asp Phe Phe Lys Ala Leu Met Lys Asn Leu
    1145                1150                1155

Ser Ile Thr Leu Ser Leu Arg His Asn Asn Gly Glu Lys Gly Asp
    1160                1165                1170

Asn Glu Gln Asp Tyr Ile Leu Ser Pro Val Ala Asp Ser Lys Gly
    1175                1180                1185

Arg Phe Phe Asp Ser Arg Lys Ala Asp Asp Met Pro Lys Asn
    1190                1195                1200

Ala Asp Ala Asn Gly Ala Tyr His Ile Ala Leu Lys Gly Leu Trp
    1205                1210                1215

Cys Leu Glu Gln Ile Ser Lys Thr Asp Asp Leu Lys Lys Val Lys
    1220                1225                1230

Leu Ala Ile Ser Asn Lys Glu Trp Leu Glu Phe Val Gln Thr Leu
    1235                1240                1245

Lys Gly
    1250

<210> SEQ ID NO 18
<211> LENGTH: 3987
<212> TYPE: DNA
<213> ORGANISM: Artificial sequence
<220> FEATURE:
<223> OTHER INFORMATION: Synthetic polynucleotide

<400> SEQUENCE: 18

```
atggccggga gcaagaagcg ccggataaag caggacacgc agttcgaggg cttcaccaac      60
ctgtaccaag tctccaagac gctccggttc gagcttatcc cgcaagggaa gaccctgaaa     120
cacatccagg aacaaggttt catcgaggag gacaaggccc gcaacgacca ctacaaggag     180
ctcaagccca taatcgatcg gatctacaag acgtacgccg accagtgcct ccaactggtg     240
cagctcgact gggagaacct gagcgccgcc attgacagct accgcaagga aaagacggag     300
gagacgcgca acgcccttat tgaggagcaa gccacctacc gcaacgccat ccacgactac     360
ttcatcgggc gcaccgacaa cctgacggac gcgatcaaca agcgccacgc ggaaatctac     420
aagggccttt tcaaggccga gctcttcaac gggaaggtcc taaaacagct cgggactgtc     480
acgacaaccg agcatgagaa cgccctcctt cgcagcttcg acaagttcac cacatacttc     540
tcgggcttct accggaaccg caagaacgtt ttcagcgccg aggacatctc caccgccatc     600
ccgcacagga tcgtccagga caacttcccc aagttcaagg agaactgcca catcttcacg     660
cgcctgatta cagccgtacc ttcacttcgt gagcacttcg agaacgtcaa aaaggccatc     720
gggatcttcg tctccacgtc catcgaggag gtattctctt tcccgttcta taaccagctc     780
ctgacccaga cgcagatcga cctctacaac cagctactgg gcggcatcag ccggaggcc      840
gggaccgaga aaataaaggg cctcaacgaa gttctcaacc tggccatcca agaacgac       900
gagaccgcgc atatcatcgc atccctgccg catcgcttca ttcctttgtt caagcagata     960
ttgagcgacc ggaacaccct ctcgttcatc ctcgaagaat caagagcga cgaggaggtc    1020
attcagtctt tctgcaagta caagacgctc ctacggaatg agaatgtgct ggagaccgcg    1080
gaggcactct tcaatgagct gaactccatt gacctgaccc acatcttcat tagccacaag    1140
aaactggaga cgatctccag cgccctgtgc gaccactggg acactctccg caacgccctc    1200
tacgaacgcc ggatctccga acttaccggc aagataacta agtcggctaa ggagaaggtg    1260
caacggagcc tcaagcacga ggacatcaac cttcaggaaa tcatctcagc cgcgggcaag    1320
gagctgagcg aggcgtttaa gcagaaaaca tcggagatac tgagccacgc gcacgcggcc    1380
ctggatcaac cgctgccgac gactctcaag aagcaagagg agaaggaaat ccttaagtcc    1440
cagctcgact cgctgctcgg cctctatcac ttgctcgact ggttcgcggt tgatgagtcc    1500
aacgaggtgg acccggagtt ctccgcgcgc ctcacgggta ttaagctgga gatggagcca    1560
agcttaagct tctacaacaa ggcccgcaac tacgcgacca aaaaaccgta tcagtcgag    1620
aaattcaagc tgaatttcca gatgcctaca ttggcgaggg ggtgggacgt gaaccgcgag    1680
aagaacaatg gagccatcct gttcgtcaaa aatgggttgt actacctggg catcatgccc    1740
aagcagaagg gccgttacaa ggccctgtca ttcgagccta ccgagaagac ctcggagggc    1800
ttcgacaaga tgtactacga ctatttcccg gacgccgcca agatgatccc gaagtgctcc    1860
acgcagctca agccgtcac ggcccacttc cagacgcata ccacgccgat acttctgagc    1920
aacaacttca ttgagccgct agagatcacg aaggagatat acgacctaaa caaccccgaa    1980
aaggagccca agaagttcca gacagcctac gctaagaaga caggtgatca gaagggatat    2040
agggaggcac tctgcaagtg gatcgacttc acgcgcgact cctgtcgaa atatacaaag    2100
acgaccagca ttgacctaag ttctctccgc ccatcctccc agtacaagga tctgggcgag    2160
tattatgcgg agctgaaccc attgctgtac cacatcagct ccagaggat cgccgagaag    2220
gagattatgg acgcggtgga gacggggaaa ctataccttgt tccaaatata taacaaggac    2280
ttcgctaaag ggcaccacgg gaagcccaac ctgcacacac tctactggac gggcttgttt    2340
```

```
tcgccagaaa atttggccaa gacttcgatc aagctcaacg gccaggcgga gttgttttac    2400
cgtcccaagt ctcgcatgaa gcgcatggcg catcgcctcg agagaaaat gcttaacaag     2460 aagctcaagg atcagaagac gcccatacct gatacgttgt accaggaatt gtacgactac    2520
gtgaaccacc gcctatcgca cgacctctca gacgaggccc gcgccctcct cccaaacgtg    2580
attactaagg aggtttccca tgaaataatc aaggaccgac ggttcaccag cgacaaattt    2640
tttttccacg tgcctatcac gctcaattac caggcggcca actccccatc gaagttcaac    2700
cagcgcgtga acgcctacct taaggagcac ccggagaccc aatcatcgg gatcgaccgt     2760 ggcgagcgga acctgatcta tattacggtg atcgatagca ccgggaagat cctggagcag    2820
cgctccctga acacaatcca gcagtttgac taccagaaga aactcgacaa ccgggagaag    2880
gagcgcgtcg cagcccggca agcatggagt gtggtcggca ccataaagga cctgaaacag    2940
ggttacctaa gtcaagttat ccacgagatc gttgacctga tgatacacta tcaagccgta    3000
gtcgtgctgg agaacctcaa cttcgggttt aagtccaagc gcaccggcat cgcggagaag    3060
gcggtgtacc agcagttcga aagatgctg atcgacaagc tgaactgcct ggtgctcaag     3120
gactaccctg cggagaaggt cggcgggtc ttgaacccgt accagctaac cgaccagttc     3180
acgagcttcg ccaaaatggg cacgcagtcc ggattcttgt tttatgtccc ggctccatat    3240
acaagtaaga tcgacccgct gacagggttt gttgacccat tcgtgtggaa gaccatcaag    3300
aaccacgaga gcaggaaaca cttcttagag ggcttcgact tcctgcatta cgacgttaag    3360
acaggcgact tcatcctgca cttcaagatg aaccgcaacc tgtcgttcca gaggggcctg    3420
cccggcttca tgcccgcctg ggatatcgtc tttgagaaga atgagacgca gttcgacgcg    3480
aaggggacgc cgttcatcgc tggaaagcgg atcgtgccgg tcatcgagaa ccaccgcttc    3540
acgggtcgct accgagattt ataccccgcc aacgaactaa ttgcgctgct ggaggagaag    3600
gggatcgtgt tccgagatgg cagcaacatt ctcccgaagc tgctggagaa cgacgactcg    3660
cacgctattg acacgatggt cgccctcata cggagcgtgc ttcagatgcg gaacagtaac    3720
gctgccacgg gcgaggacta cattaactcc cccgtccgcg acctcaacgg ggtctgcttc    3780
gatagccgct tccagaaccc ggagtggcct atggatgcgg acgcgaacgg ggcctaccac    3840
atcgccctca gggccaact cctgctcaac cacttgaagg aaagcaaaga cctcaaattg     3900
cagaatggca tcagtaacca ggactggctc gcgtacatcc aggaactgag aaacgggtcc    3960
aagaagcggc gtatcaagca agattga                                        3987
```

<210> SEQ ID NO 19
<211> LENGTH: 3987
<212> TYPE: DNA
<213> ORGANISM: Artificial sequence
<220> FEATURE:
<223> OTHER INFORMATION: Synthetic polynucleotide

<400> SEQUENCE: 19

```
atggcgggaa gcaaaaagcg ccggattaag caagacacgc agttcgaggg cttcacgaac     60
ctctaccaag tcagcaagac cctccggttc gagctgatac acagggaaa gacgctcaag     120 cacatccagg aacagggctt catcgaggag acaaggcgc gcaacgacca ctacaaggag     180
ttgaaaccga tcatcgaccg catctacaag acgtacgccg accagtgcct ccagctcgtg    240
cagctcgact gggagaacct ctccgccgcc attgactcgt accggaagga gaagactgag    300
gagacccgca cgccctgat cgaggagcaa gcaacctacc ggaacgccat ccacgactac    360
ttcatcggcc gcaccgacaa cctcaccgac gcgatcaaca gcggcacgc ggagatatac    420
```

```
aaaggctgt tcaaggcgga gctgttcaac ggcaaggtgc tcaagcagct agggacggtg      480
accacgaccg agcacgagaa cgcgctcctc cgcagcttcg acaagttcac cacctacttc      540
agcggcttct accggaaccg caagaatgtg ttcagcgcgg aggacatcag cacggccatc      600
ccgcaccgca tcgtccagga caacttcccg aagttcaagg agaactgcca catcttcacc      660
cgcctgataa ccgccgtccc ctccctgcgg gagcacttcg agaacgtcaa aaaggcaatt      720
gggatcttcg tctcgaccag cattgaggag gtgttcagct tccccttcta caaccagctc      780
ctcacccaga cgcagatcga cctgtacaat cagttgctcg gcgggataag ccgcgaggcg      840
ggaaccgaaa aaatcaaggg gctgaacgaa gtgttgaacc tcgccatcca gaagaacgac      900
gagaccgcgc acatcatcgc ctccctgccc caccggttca tcccgctgtt caagcagatc      960
ctctctgacc ggaacaccct gtccttcatt cttgaggagt tcaagtcgga cgaggaggtc     1020
atccagagct tctgcaagta caagacgctg ctacggaacg agaacgtgct ggagacggcg     1080
gaggcactgt tcaacgagct aaacagcatc gacctcacgc acatcttcat cagtcacaag     1140
aaactggaga ccatctcctc cgcgctgtgc gaccactggg acacgctcag gaacgcgctc     1200
tacgagcgcc gaatcagtga gctgacgggc aagatcacga agtccgcgaa ggagaaggtg     1260
cagcggtccc tcaagcacga ggacatcaac ctccaggaga tcatctcagc ggctgggaaa     1320
gagctgtccg aggcgttcaa gcagaaaacg agcgaaatcc tgtcccacgc gcacgcggcc     1380
ctggatcagc tctgccgac gaccctcaag aaacaagaag aaaggaaat cctcaagtcg     1440 cagctcgact cgctgctggg cctgtaccat ctcctcgact ggttcgccgt ggacgagagc     1500
aacgaggtgg acccccgagtt ctccgcgcgg cttacgggga tcaagctgga gatggagccc     1560
agcctgtcct tctacaacaa ggcgcgcaac tacgccacca agaagcccta cagcgtggag     1620
aagttcaagc tcaacttcca gatgcccact ctcgcacgtg ggtgggacgt caaccgcgaa     1680
aaaaataatg gggcgatcct gttcgtcaag aacggcctgt actacttggg catcatgccg     1740
aaacagaagg gccgctacaa ggccctgagc ttcgaaccga ccgagaaaac gagcgagggg     1800
ttcgacaaga tgtactacga ctacttcccc gacgccgcga agatgattcc aaagtgctcc     1860
acgcagctta aggccgtgac ggcccacttc cagacgcaca cgaccccgat cctcctcagc     1920
aacaacttca tcgagcccct ggagatcacg aaggagatat acgacctgaa caacccggag     1980
aaggagccca gaaattcca gaccgcctac gccaagaaga caggcgacca aaagggttac     2040
agggaggccc tctgcaagtg gatcgacttc actagggact tcctgtccaa gtacaccaag     2100
actacctcta tcgacctgtc cagcctccgc ccgtcgtccc agtacaaaga tttgggcgag     2160
tattacgcgg agctgaaccc actgctctac cacatcagct tccagcgcat cgcggagaag     2220
gagatcatgg acgcagtgga gacgggcaag ctataccatat tcagatatat caacaaagac     2280
ttcgctaagg gacaccacgg caagcctaac ctgcacaccc tctactggac ggggctcttc     2340
agcccggaga acctcgccaa gacctcgatc aagctcaacg gccaggccga gctgttctac     2400
cggcccaagt cccgcatgaa gcggatggcc caccggctcg gggagaaaat gctcaacaag     2460
aaattgaagg accaaaaaac gccgatacco gacaccctat accaggagct gtacgactat     2520
gtgaaccacc gcctgagcca cgacctcagc gacgaggcgc gggccctcct gccgaacgtc     2580
atcacaaagg aggtcagcca cgagatcatc aaggaccggc gcttcacctc cgacaagttt     2640
ttctttcacg tgcccatcac gctcaactac caggccgcca actcgccgtc caagttcaac     2700
cagcgcgtga acgcctacct caaggagcac cccgagaccc cgatcatcgg gattgaccga     2760
```

```
ggggagcgga acctcatcta catcaccgtc atcgacagca ccgggaagat ccttgaacag   2820
cggtcgctca acaccatcca gcagttcgac taccagaaga aactcgacaa ccgggagaag   2880
gagagagtgg cggcccgcca ggcttggtcc gtcgtcggga cgattaagga cttgaaacaa   2940
ggttacctgt cgcaagtgat ccacgagatc gttgacctga tgatccacta ccaagccgtc   3000
gtggtcctgg agaacctcaa cttcggcttc aagagcaaac gaaccggcat cgcggagaag   3060
gccgtgtacc agcagttcga aaaaatgctg atcgacaagc tgaactgcct cgtgctcaag   3120 gactacccccg ctgagaaggt cggcggggtg ctgaacccgt accagctcac tgaccagttc   3180
accagcttcg caaagatggg cacccagtcc ggcttcctgt tctacgtgcc tgcgccatac   3240
acctcgaaga tcgacccgct caccgggttc gtggaccccc tcgtctggaa gaccatcaag   3300
aaccacgaga gccgcaagca cttcctggag ggcttcgact tcctccacta cgacgtcaag   3360 accgggggact tcatcctgca cttcaagatg aaccgcaacc tcagtttcca gcgcggcctg   3420
ccggggttca tgcccgcttg ggatatagtc ttcgagaaga atgagacgca gttcgacgcg   3480
aagggcaccc cgttcatcgc cgggaagcgc atcgtgccgg tcatcgagaa ccaccggttc   3540
accgggcgct accgcgacct ataccgggcg aacgagttga tcgccctcct ggaggagaag   3600
ggcatcgtgt tccgcgacgg ctccaacatc ctcccgaagc tgctcgaaaa cgacgactcc   3660
cacgccatcg acacgatggt cgcgctgatc cggtcggtgc tccagatgcg gaactccaac   3720
gccgcgacgg gcgaggacta catcaacagt ccggtccgcg atctgaacgg cgtctgcttc   3780
gactcccggt tccagaaccc cgagtggccg atggacgcgg acgcgaacgg cgcataccac   3840
atcgccctaa aagggcaatt gctgctcaac caacctcaagg aatccaaaga cctaaagctc   3900
cagaacggca tctccaacca ggactggctg gcgtacatcc aggaactgcg gaacgggagc   3960
aaaaaacgtc ggatcaagca agattga                                       3987

<210> SEQ ID NO 20
<211> LENGTH: 3987
<212> TYPE: DNA
<213> ORGANISM: Artificial sequence
<220> FEATURE:
<223> OTHER INFORMATION: Synthetic polynucleotide

<400> SEQUENCE: 20
atggcgggct ccaagaaacg ccggattaag caagataccc agttcgaggg gttcacgaac     60
ctctaccaag tgagcaagac cctccgattc gaactgattc ctcaggggaa gaccctcaag    120
cacatccagg agcaagggtt catcgaggag gacaaggcgc ggaacgacca ctacaaggaa    180
ctcaaaccca tcatcgaccg catctacaag acctacgccg atcagtgcct ccagctcgtg    240
cagttggact gggagaacct cagcgcggcc attgactcct accggaagga gaaaacggag    300
gagacgcgca acgcgctcat cgaggaacag gcaacctatc gcaacgccat ccacgactac    360
ttcatcggga ggactgacaa cctcactgac gcgattaaca agcgccacgc ggagatatac    420
aagggactct tcaaagcgga gctgtttaac ggcaaggttc tcaagcaact cggcactgtg    480
accacgaccg agcatgagaa cgccctgctc cgctccttcg acaagttcac cacctacttc    540
tccgggttct accgcaaccg caagaatgtc ttcagcgcgg aggacatcag cacggccatt    600
ccacatcgaa tcgtccaaga taacttcccg aagttcaagg agaactgcca catcttcacc    660
cgactcatta ctgctgtacc gtcgttacgc gaacacttcg agaacgtcaa gaaggcaatt    720
ggaatcttcg tctctacgtc aatagaggag gtgttcagct tcccctttcta caaccagctc    780 cttacgcaga cccagataga cctgtacaat cagctcctcg gtgggatcag ccgggaggcg    840
```

```
gggactgaga agattaaagg gctcaacgag gtcttgaacc tggccatcca aaaaaacgat    900
gagacggcgc acatcatcgc ctcgctgccc caccggttca tcccgctgtt caagcagatc    960
ctcagtgaca ggaacacctt gagctttatc ctagaggagt tcaagagcga cgaggaggtg   1020
atccagagct tctgcaagta caaaaccctg ctgaggaacg agaacgtcct ggagacggcg   1080
gaggcgctgt tcaacgagct gaactctatc gacttaactc acatattcat ctcgcacaag   1140
aagctggaga ctattagctc tgcactctgc gaccactggg acaccctccg caacgcgctc   1200
tacgagcgcc gcatctcgga gctgaccggg aagatcacca aatccgcgaa ggaaaaggtc   1260
cagcgttccc tcaaacacga ggatattaac ttacaggaga ttatctcagc ggctgggaag   1320
gagttgtcag aggcgttcaa gcagaaaact tccgagatcc tgagccacgc gcacgcagcg   1380
ctcgaccagc ctctgcccac caccctcaaa agcaggaag aaaaagagat cctcaagagc    1440
cagttggact ccctgctggg gctctatcac cttctcgact ggttcgccgt cgatgagtcg   1500
aacgaggtgg accccgagtt ctccgcccgg ctgaccggca tcaagctaga gatggagccg   1560
tccctcagct tctacaataa ggcccgcaac tacgcgacca aaaaacccta cagcgtggag   1620
aagttcaagc tgaacttcca gatgccgacc ttagcacgcg gttgggacgt aaacagggag   1680
aagaacaatg gagccatcct gttcgtcaag aacgggcttt actacctcgg gataatgccc   1740
aagcagaagg gccgctacaa ggccctttcc ttcgagccga cggagaaaac ctccgagggg   1800
ttcgacaaga tgtactacga ctacttcccc gacgccgcca agatgatccc gaagtgctca   1860
acgcagctaa aagccgtgac cgcccacttc cagacccaca cgacgccgat cctgctgagc   1920
aacaacttca tcgagcccct tgagatcact aaggagatat acgacctgaa caaccccgag   1980
aaggagccca agaagtttca aaccgcctac gccaaaaaaa ctggcgacca aaagggctac   2040
agggaggcgc tgtgtaagtg gatcgacttc acacgcgact tcctttcgaa gtatacgaag   2100
acaacctcta ttgacctgag cagcctgcgt cctagctccc agtacaaaga tttgggcgag   2160
tactacgcgg agcttaatcc actactctac cacatctcat tccagcgcat cgctgagaag   2220
gaaatcatgg acgcggtgga gacaggcaaa ctgtacctct tccagatata caacaaagac   2280
ttcgctaagg ggcaccacgg gaagcccaac cttcatacgc tctactggac gggcctattc   2340
agccccgaaa atctggccaa gacctccatc aagctgaacg ccaagcgga gctgttctac    2400
agacccaaga gccggatgaa gcggatggcc cacaggctcg gcgagaaaat gcttaacaaa   2460
aagttgaagg accagaaaac ccctatcccc gacaccctct accaggaact gtacgactac   2520
gtgaaccaca ggctctcgca cgaccttttc gacgaggccc gtgccctact cccgaacgtc   2580
attaccaaag aggtttcgca cgagatcatc aaggaccggc ggttcacgag cgacaagttt   2640
ttctttcacg tccccatcac ccttaactac caggcggcca actccccatc caagttcaac   2700
cagcgtgtga atgcctacct caaggagcac ccagagaccc cgatcattgg gatcgaccgg   2760
ggcgagcgga acctgatcta catcaccgtc atcgactcga cggcaagat tcttgagcag   2820
agatcgttga ataccataca gcagttcgac taccagaaga aactcgacaa ccgcgagaag   2880
gagcgcgtgg cggcccgcca ggcgtggtcc gtcgttggga cgattaagga cttgaaacaa   2940
ggttatctgt cccaagtcat ccacgagatc gttgatctga tgatccacta tcaggcagtg   3000
gtggtgctgg agaatctcaa cttcggcttc aagagtaagc ggacgggaat cgccgagaag   3060
gccgtgtacc agcagttcga gaagatgctg atcgacaagc tcaactgcct tgtgctgaaa   3120
gactacccgg ccgagaaggt cggcggcgtc ctcaacccgt accaacttac cgaccagttc   3180
```

```
acctccttcg ccaagatggg cactcagtcc gggttcttgt tctacgtccc cgcaccttac   3240
acctctaaga tcgaccctct gactggcttc gtagatccat tcgtgtggaa gaccattaag   3300
aaccacgaga gccgcaagca cttcctggag ggcttcgact tcctgcacta cgacgtgaag   3360
accggggact tcatccttca cttcaagatg aaccggaacc tcagcttcca gcggggcctg   3420
ccggggttca tgcccgcctg ggacatcgtg ttcgagaaga cgagaccca gttcgacgcg   3480 aagggcacgc ccttcatcgc cgggaagcgt atcgtgccgg tgatcgagaa ccatcgtttc   3540
acgggtcgct accgtgacct ctacccggcg aacgagctta tcgcactcct ggaggagaag   3600
ggcatcgtct tccgggacgg ctccaacatc ctcccgaaac tgctggaaaa cgacgactct   3660
cacgccatcg acacgatggt ggccctcatc cggtccgtgc tccaaatgcg gaacagcaac   3720
gccgccaccg gtgaggacta catcaacagc ccggtccggg atctgaacgg ggtgtgcttc   3780
gattcgcggt tccagaatcc tgagtggccg atggacgcg atgcaaacgg ggcgtaccac   3840
atcgcgctca agggccagtt acttctgaac caccttaagg agtctaaaga tttgaaactc   3900
cagaacggga tctcgaacca ggactggctg gcctacatcc aagagttgcg gaacggcagc   3960
aagaagcggc ggattaagca agattag                                       3987

<210> SEQ ID NO 21
<211> LENGTH: 1592
<212> TYPE: DNA
<213> ORGANISM: Medicago truncatula

<400> SEQUENCE: 21
actgttaata attttaaac gtcagcgcac taaaaaaacg aaaagacgga cacgtgaaaa     60
taaaaaacac acactagttt atgacgcaat actattttac ttatgatttg ggtacattag   120
acaaaaccgt gaaagagatg tatcagctat gaaacctgta tacttcaata cagagactta   180
ctcatatcgg atacgtacgc acgaagtatc atattaatta ttttaatttt taataaatat   240
tttatcggat acttatgtga tactctacat atacacaagg atatttctaa gatactttat   300
agatacgtat cctagaaaaa catgaagagt aaaaagtga acaatgttg taaaaattca    360 ttataaatgt atatgattca attttagata tgcatcagta taattgattc tcgatgaaac   420
acttaaaatt atatttcttg tggaagaacg tagcgagaga ggtgattcag ttagacaaca   480
ttaaataaaa ttaatgttaa gttcttttaa tgatgtttct ctcaatatca catcatatga   540
aaatgtaata tgatttataa gaaaattttt aaaaaattta ttttaataat cacatgtact   600
attttttaaa aattgtatct tttataataa taataata aagagtaatc agtgttaatt   660
tttcttcaaa tataagtttt attataaatc attgttaacg tatcataagt cattaccgta   720
tcgtatctta atttttttt aaaaaccgct aattcacgta cccgtattgt attgtacccg   780 caccttgtatc acaatcgatc ttagttagaa gaattgtctc gaggcggtgc aagacagcat   840
ataatagacg tggactctct tataccaaac gttgtcgtat cacaaagggt taggtaacaa   900
gtcacagttt gtccacgtgt cacgttttaa ttggaagagg tgccgttggc gtaatataac   960
agccaatcga ttttgctat aaaagcaaat caggtaaact aaacttcttc attctttct   1020 tccccatcgc tacaaaaccg gttccttttgg aaaagagatt cattcaaacc tagcacccaa   1080
ttccgtttca aggtataatc tactttctat tcttcgatta tttattattatt attagctact   1140 atcgtttaat cgatctttc ttttgatccg tcaaatttaa attcaattag ggttttgttc   1200
ttttctttca tctgattgaa atccttctga attgaaccgt ttacttgatt ttactgttta   1260
ttgtatgatt taatcctttg tttttcaaag acagtcttta gattgtgatt aggggttcat   1320
```

| | |
|---|---:|
| ataaatttt agatttggat ttttgtattg tatgattcaa aaaatacgtc ctttaattag | 1380 |
| attagtacat ggatatttt tacccgattt attgattgtc agggagaatt tgatgagcaa | 1440 |
| gttttttga tgtctgttgt aaattgaatt gattataatt gctgatctgc tgcttccagt | 1500 |
| tttcataacc catattcttt taaccttgtt gtacacacaa tgaaaaattg gtgattgatt | 1560 |
| catttgtttt tctttgtttt ggattataca gg | 1592 |

<210> SEQ ID NO 22
<211> LENGTH: 2000
<212> TYPE: DNA
<213> ORGANISM: Zea mays

<400> SEQUENCE: 22

| | |
|---|---:|
| gtcgtgcccc tctctagaga taaagagcat tgcatgtcta aagtataaaa aattaccaca | 60 |
| tatttttttg tcacacttat ttgaagtgta gtttatctat ctctatacat atatttaaac | 120 |
| ttcactctac aaataatata gtctataata ctaaaataat attagtgttt tagaggatca | 180 |
| tataaataaa ctgctagaca tggtctaaag gataattgaa tattttgaca atctacagtt | 240 |
| ttatctttt agtgtgcatg tgatctctct gttttttttg caaatagctt gacctatata | 300 |
| atacttcatc cattttatta gtacatccat ttaggattta gggttgatgg tttctataga | 360 |
| ctaatttta gtacatccat tttattcttt ttagtctcta aattttttaa aactaaaact | 420 |
| ctattttagt tttttattta ataatttaga tataaaatga aataaaataa attgactaca | 480 |
| aataaaacaa ataccctta agaaataaaa aaactaagca aacattttc ttgtttcgag | 540 |
| tagataatga caggctgttc aacgccgtcg acgagtctaa cggacaccaa ccagcgaacc | 600 |
| agcagcgtcg cgtcgggcca agcgaagcag acggcacggc atctctgtag ctgcctctgg | 660 |
| accctctcg agagttccgc tccaccgttg gacttgctcc gctgtcggca tccagaaatt | 720 |
| gcgtggcgga gcggcagacg tgaggcggca cggcaggcgg cctcttcctc ctctcacggc | 780 |
| accggcagct acggggatt cctttcccac cgctccttcg ctttcccttc ctcgcccgcc | 840 |
| gtaataaata gacaccccct ccacaccctc ttccccaac ctcgtgttcg ttcggagcgc | 900 |
| acacacacgc aaccagatct cccccaaatc cagccgtcgg cacctccgct tcaaggtacg | 960 |
| ccgctcatcc tccccccccc cctctctcta ccttctctag atcggcgatc cggtccatgg | 1020 |
| ttagggcccg gtagttctac ttctgttcat gtttgtgtta gagcaaacat gttcatgttc | 1080 |
| atgtttgtga tgatgtggtc tggttgggcg gtcgttctag atcggagtag gatactgttt | 1140 |
| caagctacct ggtggattta ttaattttgt atctgtatgt gtgtgccata catcttcata | 1200 |
| gttacgagtt taagatgatg gatggaaata tcgatctagg ataggtatac atgttgatgc | 1260 |
| gggtttact gatgcatata cagagatgct tttttctcg cttggttgtg atgatatggt | 1320 |
| ctggttgggc ggtcgttcta gatcggagta gaatactgtt tcaaactacc tggtggattt | 1380 |
| attaaaggat aaagggtcgt tctagatcgg agtagaatac tgtttcaaac tacctggtgg | 1440 |
| atttattaaa ggatctgtat gtatgtgcct acatcttcat agttacgagt taagatgat | 1500 |
| ggatggaaat atcgatctag gataggtata catgttgatg cgggttttac tgatgcatat | 1560 |
| acagagatgc tttttttcgc ttggttgtga tgatgtggtc tggttgggcg gtcgttctag | 1620 |
| atcggagtag aatactgttt caaactacct ggtggattta ttaattttgt atctttatgt | 1680 |
| gtgtgccata catcttcata gttacgagtt taagatgatg gatggaaata ttgatctagg | 1740 |
| ataggtatac atgttgatgt gggttttact gatgcatata catgatggca tatgcggcat | 1800 |

```
ctattcatat gctctaacct tgagtaccta tctattataa taaacaagta tgttttataa    1860 ttatttgat cttgatatac ttggatgatg gcatatgcag cagctatatg tggatttttt     1920
agccctgcct tcatacgcta tttatttgct tggtactgtt tcttttgtcc gatgctcacc    1980
ctgttgtttg gtgatacttc                                                2000

<210> SEQ ID NO 23
<211> LENGTH: 228
<212> TYPE: PRT
<213> ORGANISM: Rattus norvegicus

<400> SEQUENCE: 23

Ser Ser Glu Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
                20                  25                  30

Lys Glu Thr Cys Leu Leu Tyr Glu Ile Asn Trp Gly Gly Arg His Ser
            35                  40                  45

Ile Trp Arg His Thr Ser Gln Asn Thr Asn Lys His Val Glu Val Asn
        50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
            100                 105                 110

Ile Tyr Ile Ala Arg Leu Tyr His His Ala Asp Pro Arg Asn Arg Gln
        115                 120                 125

Gly Leu Arg Asp Leu Ile Ser Ser Gly Val Thr Ile Gln Ile Met Thr
    130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Pro Gln Leu Thr Phe Phe Thr Ile Ala
        195                 200                 205

Leu Gln Ser Cys His Tyr Gln Arg Leu Pro Pro His Ile Leu Trp Ala
    210                 215                 220

Thr Gly Leu Lys
225

<210> SEQ ID NO 24
<211> LENGTH: 199
<212> TYPE: PRT
<213> ORGANISM: Homo sapiens

<400> SEQUENCE: 24

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
```

```
                50                  55                  60
Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                 85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
            115                 120                 125

Ile Tyr Asp Tyr Asp Pro Leu Tyr Lys Glu Ala Leu Gln Met Leu Arg
        130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
                180                 185                 190

Ile Leu Gln Asn Gln Gly Asn
            195

<210> SEQ ID NO 25
<211> LENGTH: 621
<212> TYPE: DNA
<213> ORGANISM: Petromyzon marinus

<400> SEQUENCE: 25
acagatgcag agtatgtgag aattcacgaa aagctggaca tctataccttt caagaagcag     60 ttctttaaca ataagaagtc tgtgagccat aggtgctacg tgctgttcga gctgaagaga    120
aggggtgaaa gaagggcatg ttttttgggg tatgctgtga acaagcccca gtctggaact    180
gagagaggca ttcacgccga aattttcagc atcagaaagg tggaggaata cctgagggat    240
aaccctggac agtttacaat taattggtat tctagctggt ctccatgcgc tgactgtgcc    300
gagaagatcc tggaatggta caaccaggag ctgagaggaa atggccatac cctgaagatt    360
tgggcctgca agctgtacta tgaaaagaac gcaagaaatc agatcggact gtggaacctg    420
agggataatg tgtggggct gaacgtgatg gtgtccgagc actatcagtg ctgtagaaag    480
attttcattc agtcctcaca taatcagctg aacgagaata gatggctgga aaagactctg    540
aagagggctg agaagagaag gtccgaactg tcaattatga tccaggtgaa gatcctgcac    600
accactaagt cacctgccgt g                                              621

<210> SEQ ID NO 26
<211> LENGTH: 160
<212> TYPE: PRT
<213> ORGANISM: Artificial sequence
<220> FEATURE:
<223> OTHER INFORMATION: Synthetic polypeptide

<400> SEQUENCE: 26

Phe Glu Arg Asn Tyr Asp Pro Arg Glu Leu Arg Lys Glu Thr Tyr Leu
  1               5                  10                  15

Leu Tyr Glu Ile Lys Trp Gly Lys Ser Gly Lys Leu Trp Arg His Trp
                 20                  25                  30

Cys Gln Asn Asn Arg Thr Gln His Ala Glu Val Tyr Phe Leu Glu Asn
             35                  40                  45

Ile Phe Asn Ala Arg Arg Phe Asn Pro Ser Thr His Cys Ser Ile Thr
```

```
                    50                  55                  60
Trp Tyr Leu Ser Trp Ser Pro Cys Ala Glu Cys Ser Gln Lys Ile Val
 65                  70                  75                  80

Asp Phe Leu Lys Glu His Pro Asn Val Leu Glu Ile Tyr Val Ala Arg
                     85                  90                  95

Leu Tyr Tyr His Glu Asp Glu Arg Asn Arg Gln Gly Leu Arg Asp Leu
                    100                 105                 110

Val Asn Ser Gly Val Thr Ile Arg Ile Met Asp Leu Pro Asp Tyr Asn
                115                 120                 125

Tyr Cys Trp Lys Thr Phe Val Ser Asp Gln Gly Gly Asp Glu Asp Tyr
            130                 135                 140

Trp Pro Gly His Phe Ala Pro Trp Ile Lys Gln Tyr Ser Leu Lys Leu
145                 150                 155                 160

<210> SEQ ID NO 27
<211> LENGTH: 207
<212> TYPE: PRT
<213> ORGANISM: Artificial sequence
<220> FEATURE:
<223> OTHER INFORMATION: Synthetic polypeptide

<400> SEQUENCE: 27

Thr Asp Ala Glu Tyr Val Arg Ile His Glu Lys Leu Asp Ile Tyr Thr
  1               5                  10                  15

Phe Lys Lys Gln Phe Ser Asn Asn Lys Lys Ser Val Ser His Arg Cys
                 20                  25                  30

Tyr Val Leu Phe Glu Leu Lys Arg Arg Gly Glu Arg Arg Ala Cys Phe
             35                  40                  45

Trp Gly Tyr Ala Val Asn Lys Pro Gln Ser Gly Thr Glu Arg Gly Ile
         50                  55                  60

His Ala Glu Ile Phe Ser Ile Arg Lys Val Glu Glu Tyr Leu Arg Asp
 65                  70                  75                  80

Asn Pro Gly Gln Phe Thr Ile Asn Trp Tyr Ser Ser Trp Ser Pro Cys
                 85                  90                  95

Ala Asp Cys Ala Glu Lys Ile Leu Glu Trp Tyr Asn Gln Glu Leu Arg
            100                 105                 110

Gly Asn Gly His Thr Leu Lys Ile Trp Val Cys Lys Leu Tyr Tyr Glu
        115                 120                 125

Lys Asn Ala Arg Asn Gln Ile Gly Leu Trp Asn Leu Arg Asp Asn Gly
    130                 135                 140

Val Gly Leu Asn Val Met Val Ser Glu His Tyr Gln Cys Cys Arg Lys
145                 150                 155                 160

Ile Phe Ile Gln Ser Ser His Asn Gln Leu Asn Glu Asn Arg Trp Leu
                165                 170                 175

Glu Lys Thr Leu Lys Arg Ala Glu Lys Arg Arg Ser Glu Leu Ser Ile
            180                 185                 190

Met Phe Gln Val Lys Ile Leu His Thr Thr Lys Ser Pro Ala Val
        195                 200                 205

<210> SEQ ID NO 28
<211> LENGTH: 228
<212> TYPE: PRT
<213> ORGANISM: Artificial sequence
<220> FEATURE:
<223> OTHER INFORMATION: Synthetic polypeptide

<400> SEQUENCE: 28
```

Ser Ser Lys Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
                20                  25                  30

Lys Glu Thr Cys Leu Leu Tyr Glu Ile Asn Trp Gly Gly Arg His Ser
            35                  40                  45

Ile Trp Arg His Thr Ser Gln Asn Thr Asn Lys His Val Glu Val Asn
        50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro Asn Val Thr Leu Phe
                100                 105                 110

Ile Tyr Ile Ala Arg Leu Tyr His Leu Ala Asn Pro Arg Asn Arg Gln
            115                 120                 125

Gly Leu Arg Asp Leu Ile Ser Ser Gly Val Thr Ile Gln Ile Met Thr
        130                 135                 140

Glu Gln Glu Ser Gly Tyr Cys Trp His Asn Phe Val Asn Tyr Ser Pro
145                 150                 155                 160

Ser Asn Glu Ser His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
                180                 185                 190

Asn Ile Leu Arg Arg Lys Gln Ser Gln Leu Thr Ser Phe Thr Ile Ala
            195                 200                 205

Leu Gln Ser Cys His Tyr Gln Arg Leu Pro Pro His Ile Leu Trp Ala
        210                 215                 220

Thr Gly Leu Lys
225

<210> SEQ ID NO 29
<211> LENGTH: 162
<212> TYPE: PRT
<213> ORGANISM: Artificial sequence
<220> FEATURE:
<223> OTHER INFORMATION: Synthetic polypeptide

<400> SEQUENCE: 29

Ser Phe Glu Arg Asn Tyr Asp Pro Arg Glu Leu Arg Lys Glu Thr Tyr
1               5                   10                  15

Leu Leu Tyr Glu Ile Lys Trp Gly Lys Ser Gly Lys Leu Trp Arg His
                20                  25                  30

Trp Cys Gln Asn Asn Arg Thr Gln His Ala Glu Val Tyr Phe Leu Glu
            35                  40                  45

Asn Ile Phe Asn Ala Arg Arg Phe Asn Pro Ser Thr His Cys Ser Ile
        50                  55                  60

Thr Trp Tyr Leu Ser Trp Ser Pro Cys Ala Glu Cys Ser Gln Lys Ile
65                  70                  75                  80

Val Asp Phe Leu Lys Glu His Pro Asn Val Asn Leu Glu Ile Tyr Val
                85                  90                  95

Ala Arg Leu Tyr Tyr Pro Glu Asn Glu Arg Asn Arg Gln Gly Leu Arg
            100                 105                 110

Asp Leu Val Asn Ser Gly Val Thr Ile Arg Ile Met Asp Leu Pro Asp
        115                 120                 125

Tyr Asn Tyr Cys Trp Lys Thr Phe Val Ser Asp Gln Gly Gly Asp Glu
130                 135                 140

Asp Tyr Trp Pro Gly His Phe Ala Pro Trp Ile Lys Gln Tyr Ser Leu
145                 150                 155                 160

Lys Leu

<210> SEQ ID NO 30
<211> LENGTH: 166
<212> TYPE: PRT
<213> ORGANISM: Escherichia coli

<400> SEQUENCE: 30

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
                20                  25                  30

Leu Val His Asn Asn Arg Val Ile Gly Glu Gly Trp Asn Arg Pro Ile
            35                  40                  45

Gly Arg His Asp Pro Thr Ala His Ala Glu Ile Met Ala Leu Arg Gln
50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
                100                 105                 110

Ala Gly Ser Leu Met Asp Val Leu His His Pro Gly Met Asn His Arg
            115                 120                 125

Val Glu Ile Thr Glu Gly Ile Leu Ala Asp Glu Cys Ala Ala Leu Leu
130                 135                 140

Ser Asp Phe Phe Arg Met Arg Arg Gln Glu Ile Lys Ala Gln Lys Lys
145                 150                 155                 160

Ala Gln Ser Ser Thr Asp
                165

<210> SEQ ID NO 31
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 31

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
                20                  25                  30

Leu Val Leu Asn Asn Arg Val Ile Gly Glu Gly Trp Asn Arg Ala Ile
            35                  40                  45

Gly Leu His Asp Pro Thr Ala His Ala Glu Ile Met Ala Leu Arg Gln
50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
                100                 105                 110

```
Ala Gly Ser Leu Met Asp Val Leu His Tyr Pro Gly Met Asn His Arg
        115                 120                 125

Val Glu Ile Thr Glu Gly Ile Leu Ala Asp Glu Cys Ala Ala Leu Leu
        130                 135                 140

Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 32
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 32

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val Leu Asn Asn Arg Val Ile Gly Glu Gly Trp Asn Arg Ser Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Ala Ala Leu Leu
        130                 135                 140

Cys Tyr Phe Phe Arg Met Arg Arg Gln Val Phe Asn Ala Gln Lys Lys
145                 150                 155                 160

Ala Gln Ser Ser Thr Asp
                165

<210> SEQ ID NO 33
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 33

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
```

```
                65                  70                  75                  80
Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
               100                 105                 110

Ala Gly Ser Leu Met Asp Val Leu His Tyr Pro Gly Met Asn His Arg
               115                 120                 125

Val Glu Ile Thr Glu Gly Ile Leu Ala Asp Glu Cys Asn Ala Leu Leu
       130                 135                 140

Cys Tyr Phe Phe Arg Met Arg Arg Gln Val Phe Asn Ala Gln Lys Lys
145                 150                 155                 160

Ala Gln Ser Ser Thr Asp
                165

<210> SEQ ID NO 34
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 34

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
                20                  25                  30

Leu Val Leu Asn Asn Arg Val Ile Gly Glu Gly Trp Asn Arg Ala Ile
            35                  40                  45

Gly Leu His Asp Pro Thr Ala His Ala Glu Ile Met Ala Leu Arg Gln
        50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
               100                 105                 110

Ala Gly Ser Leu Met Asp Val Leu His Tyr Pro Gly Met Asn His Arg
               115                 120                 125

Val Glu Ile Thr Glu Gly Ile Leu Ala Asp Glu Cys Asn Ala Leu Leu
       130                 135                 140

Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 35
<211> LENGTH: 1763
<212> TYPE: PRT
<213> ORGANISM: Artificial sequence
<220> FEATURE:
<223> OTHER INFORMATION: Synthetic polypeptide

<400> SEQUENCE: 35

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
                20                  25                  30
```

-continued

Leu Val His Asn Asn Arg Val Ile Gly Glu Gly Trp Asn Arg Pro Ile
    35                  40                  45

Gly Arg His Asp Pro Thr Ala His Ala Glu Ile Met Ala Leu Arg Gln
50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Ser Glu Val Glu Phe Ser His Glu Tyr Trp
        195                 200                 205

Met Arg His Ala Leu Thr Leu Ala Lys Arg Ala Arg Asp Glu Arg Glu
    210                 215                 220

Val Pro Val Gly Ala Val Leu Val Leu Asn Asn Arg Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Met Gln Asn Tyr Arg Leu
            260                 265                 270

Ile Asp Ala Thr Leu Tyr Val Thr Phe Glu Pro Cys Val Met Cys Ala
        275                 280                 285

Gly Ala Met Ile His Ser Arg Ile Gly Arg Val Val Phe Gly Val Arg
    290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Phe Arg Met Pro Arg Gln Val
            340                 345                 350

Phe Asn Ala Gln Lys Lys Ala Gln Ser Ser Thr Asp Ser Gly Gly Ser
        355                 360                 365

Ser Gly Gly Ser Ser Gly Ser Glu Thr Pro Gly Thr Ser Glu Ser Ala
    370                 375                 380

Thr Pro Glu Ser Ser Gly Gly Ser Ser Gly Gly Ser Asp Lys Lys Tyr
385                 390                 395                 400

Ser Ile Gly Leu Ala Ile Gly Thr Asn Ser Val Gly Trp Ala Val Ile
                405                 410                 415

Thr Asp Glu Tyr Lys Val Pro Ser Lys Lys Phe Lys Val Leu Gly Asn
            420                 425                 430

Thr Asp Arg His Ser Ile Lys Lys Asn Leu Ile Gly Ala Leu Leu Phe
        435                 440                 445

Asp Ser Gly Glu Thr Ala Glu Ala Thr Arg Leu Lys Arg Thr Ala Arg

```
            450                 455                 460
Arg Arg Tyr Thr Arg Arg Lys Asn Arg Ile Cys Tyr Leu Gln Glu Ile
465                 470                 475                 480

Phe Ser Asn Glu Met Ala Lys Val Asp Asp Ser Phe Phe His Arg Leu
                    485                 490                 495

Glu Glu Ser Phe Leu Val Glu Glu Asp Lys Lys His Glu Arg His Pro
                500                 505                 510

Ile Phe Gly Asn Ile Val Asp Glu Val Ala Tyr His Glu Lys Tyr Pro
                515                 520                 525

Thr Ile Tyr His Leu Arg Lys Lys Leu Val Asp Ser Thr Asp Lys Ala
                530                 535                 540

Asp Leu Arg Leu Ile Tyr Leu Ala Leu Ala His Met Ile Lys Phe Arg
545                 550                 555                 560

Gly His Phe Leu Ile Glu Gly Asp Leu Asn Pro Asp Asn Ser Asp Val
                565                 570                 575

Asp Lys Leu Phe Ile Gln Leu Val Gln Thr Tyr Asn Gln Leu Phe Glu
                580                 585                 590

Glu Asn Pro Ile Asn Ala Ser Gly Val Asp Ala Lys Ala Ile Leu Ser
                595                 600                 605

Ala Arg Leu Ser Lys Ser Arg Arg Leu Glu Asn Leu Ile Ala Gln Leu
610                 615                 620

Pro Gly Glu Lys Lys Asn Gly Leu Phe Gly Asn Leu Ile Ala Leu Ser
625                 630                 635                 640

Leu Gly Leu Thr Pro Asn Phe Lys Ser Asn Phe Asp Leu Ala Glu Asp
                645                 650                 655

Ala Lys Leu Gln Leu Ser Lys Asp Thr Tyr Asp Asp Asp Leu Asp Asn
                660                 665                 670

Leu Leu Ala Gln Ile Gly Asp Gln Tyr Ala Asp Leu Phe Leu Ala Ala
                675                 680                 685

Lys Asn Leu Ser Asp Ala Ile Leu Leu Ser Asp Ile Leu Arg Val Asn
                690                 695                 700

Thr Glu Ile Thr Lys Ala Pro Leu Ser Ala Ser Met Ile Lys Arg Tyr
705                 710                 715                 720

Asp Glu His His Gln Asp Leu Thr Leu Leu Lys Ala Leu Val Arg Gln
                    725                 730                 735

Gln Leu Pro Glu Lys Tyr Lys Glu Ile Phe Phe Asp Gln Ser Lys Asn
                740                 745                 750

Gly Tyr Ala Gly Tyr Ile Asp Gly Gly Ala Ser Gln Glu Glu Phe Tyr
                755                 760                 765

Lys Phe Ile Lys Pro Ile Leu Glu Lys Met Asp Gly Thr Glu Glu Leu
770                 775                 780

Leu Val Lys Leu Asn Arg Glu Asp Leu Leu Arg Lys Gln Arg Thr Phe
785                 790                 795                 800

Asp Asn Gly Ser Ile Pro His Gln Ile His Leu Gly Glu Leu His Ala
                    805                 810                 815

Ile Leu Arg Arg Gln Glu Asp Phe Tyr Pro Phe Leu Lys Asp Asn Arg
                820                 825                 830

Glu Lys Ile Glu Lys Ile Leu Thr Phe Arg Ile Pro Tyr Tyr Val Gly
                835                 840                 845

Pro Leu Ala Arg Gly Asn Ser Arg Phe Ala Trp Met Thr Arg Lys Ser
                850                 855                 860

Glu Glu Thr Ile Thr Pro Trp Asn Phe Glu Val Val Asp Lys Gly
865                 870                 875                 880
```

-continued

```
Ala Ser Ala Gln Ser Phe Ile Glu Arg Met Thr Asn Phe Asp Lys Asn
            885                 890                 895

Leu Pro Asn Glu Lys Val Leu Pro Lys His Ser Leu Leu Tyr Glu Tyr
        900                 905                 910

Phe Thr Val Tyr Asn Glu Leu Thr Lys Val Lys Tyr Val Thr Glu Gly
        915                 920                 925

Met Arg Lys Pro Ala Phe Leu Ser Gly Glu Gln Lys Lys Ala Ile Val
    930                 935                 940

Asp Leu Leu Phe Lys Thr Asn Arg Lys Val Thr Val Lys Gln Leu Lys
945                 950                 955                 960

Glu Asp Tyr Phe Lys Lys Ile Glu Cys Phe Asp Ser Val Glu Ile Ser
            965                 970                 975

Gly Val Glu Asp Arg Phe Asn Ala Ser Leu Gly Thr Tyr His Asp Leu
        980                 985                 990

Leu Lys Ile Ile Lys Asp Lys Asp Phe Leu Asp Asn Glu Glu Asn Glu
        995                 1000                1005

Asp Ile Leu Glu Asp Ile Val Leu Thr Leu Thr Leu Phe Glu Asp
    1010                1015                1020

Arg Glu Met Ile Glu Glu Arg Leu Lys Thr Tyr Ala His Leu Phe
    1025                1030                1035

Asp Asp Lys Val Met Lys Gln Leu Lys Arg Arg Arg Tyr Thr Gly
    1040                1045                1050

Trp Gly Arg Leu Ser Arg Lys Leu Ile Asn Gly Ile Arg Asp Lys
    1055                1060                1065

Gln Ser Gly Lys Thr Ile Leu Asp Phe Leu Lys Ser Asp Gly Phe
    1070                1075                1080

Ala Asn Arg Asn Phe Met Gln Leu Ile His Asp Asp Ser Leu Thr
    1085                1090                1095

Phe Lys Glu Asp Ile Gln Lys Ala Gln Val Ser Gly Gln Gly Asp
    1100                1105                1110

Ser Leu His Glu His Ile Ala Asn Leu Ala Gly Ser Pro Ala Ile
    1115                1120                1125

Lys Lys Gly Ile Leu Gln Thr Val Lys Val Val Asp Glu Leu Val
    1130                1135                1140

Lys Val Met Gly Arg His Lys Pro Glu Asn Ile Val Ile Glu Met
    1145                1150                1155

Ala Arg Glu Asn Gln Thr Thr Gln Lys Gly Gln Lys Asn Ser Arg
    1160                1165                1170

Glu Arg Met Lys Arg Ile Glu Glu Gly Ile Lys Glu Leu Gly Ser
    1175                1180                1185

Gln Ile Leu Lys Glu His Pro Val Glu Asn Thr Gln Leu Gln Asn
    1190                1195                1200

Glu Lys Leu Tyr Leu Tyr Tyr Leu Gln Asn Gly Arg Asp Met Tyr
    1205                1210                1215

Val Asp Gln Glu Leu Asp Ile Asn Arg Leu Ser Asp Tyr Asp Val
    1220                1225                1230

Asp His Ile Val Pro Gln Ser Phe Leu Lys Asp Asp Ser Ile Asp
    1235                1240                1245

Asn Lys Val Leu Thr Arg Ser Asp Lys Asn Arg Gly Lys Ser Asp
    1250                1255                1260

Asn Val Pro Ser Glu Glu Val Val Lys Lys Met Lys Asn Tyr Trp
    1265                1270                1275
```

-continued

```
Arg Gln Leu Leu Asn Ala Lys Leu Ile Thr Gln Arg Lys Phe Asp
    1280                1285                1290

Asn Leu Thr Lys Ala Glu Arg Gly Gly Leu Ser Glu Leu Asp Lys
    1295                1300                1305

Ala Gly Phe Ile Lys Arg Gln Leu Val Glu Thr Arg Gln Ile Thr
    1310                1315                1320

Lys His Val Ala Gln Ile Leu Asp Ser Arg Met Asn Thr Lys Tyr
    1325                1330                1335

Asp Glu Asn Asp Lys Leu Ile Arg Glu Val Lys Val Ile Thr Leu
    1340                1345                1350

Lys Ser Lys Leu Val Ser Asp Phe Arg Lys Asp Phe Gln Phe Tyr
    1355                1360                1365

Lys Val Arg Glu Ile Asn Asn Tyr His His Ala His Asp Ala Tyr
    1370                1375                1380

Leu Asn Ala Val Val Gly Thr Ala Leu Ile Lys Lys Tyr Pro Lys
    1385                1390                1395

Leu Glu Ser Glu Phe Val Tyr Gly Asp Tyr Lys Val Tyr Asp Val
    1400                1405                1410

Arg Lys Met Ile Ala Lys Ser Glu Gln Glu Ile Gly Lys Ala Thr
    1415                1420                1425

Ala Lys Tyr Phe Phe Tyr Ser Asn Ile Met Asn Phe Phe Lys Thr
    1430                1435                1440

Glu Ile Thr Leu Ala Asn Gly Glu Ile Arg Lys Arg Pro Leu Ile
    1445                1450                1455

Glu Thr Asn Gly Glu Thr Gly Glu Ile Val Trp Asp Lys Gly Arg
    1460                1465                1470

Asp Phe Ala Thr Val Arg Lys Val Leu Ser Met Pro Gln Val Asn
    1475                1480                1485

Ile Val Lys Lys Thr Glu Val Gln Thr Gly Gly Phe Ser Lys Glu
    1490                1495                1500

Ser Ile Leu Pro Lys Arg Asn Ser Asp Lys Leu Ile Ala Arg Lys
    1505                1510                1515

Lys Asp Trp Asp Pro Lys Lys Tyr Gly Gly Phe Asp Ser Pro Thr
    1520                1525                1530

Val Ala Tyr Ser Val Leu Val Ala Lys Val Glu Lys Gly Lys
    1535                1540                1545

Ser Lys Lys Leu Lys Ser Val Lys Glu Leu Leu Gly Ile Thr Ile
    1550                1555                1560

Met Glu Arg Ser Ser Phe Glu Lys Asn Pro Ile Asp Phe Leu Glu
    1565                1570                1575

Ala Lys Gly Tyr Lys Glu Val Lys Lys Asp Leu Ile Ile Lys Leu
    1580                1585                1590

Pro Lys Tyr Ser Leu Phe Glu Leu Glu Asn Gly Arg Lys Arg Met
    1595                1600                1605

Leu Ala Ser Ala Gly Glu Leu Gln Lys Gly Asn Glu Leu Ala Leu
    1610                1615                1620

Pro Ser Lys Tyr Val Asn Phe Leu Tyr Leu Ala Ser His Tyr Glu
    1625                1630                1635

Lys Leu Lys Gly Ser Pro Glu Asp Asn Glu Gln Lys Gln Leu Phe
    1640                1645                1650

Val Glu Gln His Lys His Tyr Leu Asp Glu Ile Ile Glu Gln Ile
    1655                1660                1665

Ser Glu Phe Ser Lys Arg Val Ile Leu Ala Asp Ala Asn Leu Asp
```

```
                     1670                1675                1680

Lys Val Leu Ser Ala Tyr Asn Lys His Arg Asp Lys Pro Ile Arg
            1685                1690                1695

Glu Gln Ala Glu Asn Ile Ile His Leu Phe Thr Leu Thr Asn Leu
        1700                1705                1710

Gly Ala Pro Ala Ala Phe Lys Tyr Phe Asp Thr Thr Ile Asp Arg
        1715                1720                1725

Lys Arg Tyr Thr Ser Thr Lys Glu Val Leu Asp Ala Thr Leu Ile
        1730                1735                1740

His Gln Ser Ile Thr Gly Leu Tyr Glu Thr Arg Ile Asp Leu Ser
        1745                1750                1755

Gln Leu Gly Gly Asp
        1760

<210> SEQ ID NO 36
<211> LENGTH: 1565
<212> TYPE: PRT
<213> ORGANISM: Artificial sequence
<220> FEATURE:
<223> OTHER INFORMATION: Synthetic polypeptide

<400> SEQUENCE: 36

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ser Lys Arg Gly Ala
            100                 105                 110

Ala Gly Ser Leu Met Asn Val Leu Asn Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Asp Phe Tyr Arg Met Pro Arg Gln Val Phe Asn Ala Gln Lys Lys
145                 150                 155                 160

Ala Gln Ser Ser Ile Asn Ser Gly Gly Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Asp Lys Lys Tyr Ser Ile Gly Leu Ala Ile
        195                 200                 205

Gly Thr Asn Ser Val Gly Trp Ala Val Ile Thr Asp Glu Tyr Lys Val
    210                 215                 220

Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
                245                 250                 255

Glu Ala Thr Arg Leu Lys Arg Thr Ala Arg Arg Arg Tyr Thr Arg Arg
```

```
            260                 265                 270
Lys Asn Arg Ile Cys Tyr Leu Gln Glu Ile Phe Ser Asn Glu Met Ala
            275                 280                 285
Lys Val Asp Asp Ser Phe Phe His Arg Leu Glu Glu Ser Phe Leu Val
            290                 295                 300
Glu Glu Asp Lys Lys His Glu Arg His Pro Ile Phe Gly Asn Ile Val
305                 310                 315                 320
Asp Glu Val Ala Tyr His Glu Lys Tyr Pro Thr Ile Tyr His Leu Arg
                    325                 330                 335
Lys Lys Leu Val Asp Ser Thr Asp Lys Ala Asp Leu Arg Leu Ile Tyr
                    340                 345                 350
Leu Ala Leu Ala His Met Ile Lys Phe Arg Gly His Phe Leu Ile Glu
                355                 360                 365
Gly Asp Leu Asn Pro Asp Asn Ser Asp Val Asp Lys Leu Phe Ile Gln
                370                 375                 380
Leu Val Gln Thr Tyr Asn Gln Leu Phe Glu Glu Asn Pro Ile Asn Ala
385                 390                 395                 400
Ser Gly Val Asp Ala Lys Ala Ile Leu Ser Ala Arg Leu Ser Lys Ser
                    405                 410                 415
Arg Arg Leu Glu Asn Leu Ile Ala Gln Leu Pro Gly Glu Lys Lys Asn
                    420                 425                 430
Gly Leu Phe Gly Asn Leu Ile Ala Leu Ser Leu Gly Leu Thr Pro Asn
                435                 440                 445
Phe Lys Ser Asn Phe Asp Leu Ala Glu Asp Ala Lys Leu Gln Leu Ser
            450                 455                 460
Lys Asp Thr Tyr Asp Asp Asp Leu Asp Asn Leu Leu Ala Gln Ile Gly
465                 470                 475                 480
Asp Gln Tyr Ala Asp Leu Phe Leu Ala Ala Lys Asn Leu Ser Asp Ala
                    485                 490                 495
Ile Leu Leu Ser Asp Ile Leu Arg Val Asn Thr Glu Ile Thr Lys Ala
                500                 505                 510
Pro Leu Ser Ala Ser Met Ile Lys Arg Tyr Asp Glu His His Gln Asp
                515                 520                 525
Leu Thr Leu Leu Lys Ala Leu Val Arg Gln Gln Leu Pro Glu Lys Tyr
            530                 535                 540
Lys Glu Ile Phe Phe Asp Gln Ser Lys Asn Gly Tyr Ala Gly Tyr Ile
545                 550                 555                 560
Asp Gly Gly Ala Ser Gln Glu Glu Phe Tyr Lys Phe Ile Lys Pro Ile
                    565                 570                 575
Leu Glu Lys Met Asp Gly Thr Glu Glu Leu Leu Val Lys Leu Asn Arg
                580                 585                 590
Glu Asp Leu Leu Arg Lys Gln Arg Thr Phe Asp Asn Gly Ser Ile Pro
            595                 600                 605
His Gln Ile His Leu Gly Glu Leu His Ala Ile Leu Arg Arg Gln Glu
            610                 615                 620
Asp Phe Tyr Pro Phe Leu Lys Asp Asn Arg Glu Lys Ile Glu Lys Ile
625                 630                 635                 640
Leu Thr Phe Arg Ile Pro Tyr Tyr Val Gly Pro Leu Ala Arg Gly Asn
                    645                 650                 655
Ser Arg Phe Ala Trp Met Thr Arg Lys Ser Glu Glu Thr Ile Thr Pro
                660                 665                 670
Trp Asn Phe Glu Glu Val Val Asp Lys Gly Ala Ser Ala Gln Ser Phe
            675                 680                 685
```

-continued

```
Ile Glu Arg Met Thr Asn Phe Asp Lys Asn Leu Pro Asn Glu Lys Val
690                 695                 700

Leu Pro Lys His Ser Leu Leu Tyr Glu Tyr Phe Thr Val Tyr Asn Glu
705                 710                 715                 720

Leu Thr Lys Val Lys Tyr Val Thr Glu Gly Met Arg Lys Pro Ala Phe
                725                 730                 735

Leu Ser Gly Glu Gln Lys Lys Ala Ile Val Asp Leu Leu Phe Lys Thr
                740                 745                 750

Asn Arg Lys Val Thr Val Lys Gln Leu Lys Glu Asp Tyr Phe Lys Lys
                755                 760                 765

Ile Glu Cys Phe Asp Ser Val Glu Ile Ser Gly Val Glu Asp Arg Phe
770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
                805                 810                 815

Val Leu Thr Leu Thr Leu Phe Glu Asp Arg Glu Met Ile Glu Glu Arg
                820                 825                 830

Leu Lys Thr Tyr Ala His Leu Phe Asp Asp Lys Val Met Lys Gln Leu
                835                 840                 845

Lys Arg Arg Arg Tyr Thr Gly Trp Gly Arg Leu Ser Arg Lys Leu Ile
850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
                885                 890                 895

Asp Ser Leu Thr Phe Lys Glu Asp Ile Gln Lys Ala Gln Val Ser Gly
                900                 905                 910

Gln Gly Asp Ser Leu His Glu His Ile Ala Asn Leu Ala Gly Ser Pro
                915                 920                 925

Ala Ile Lys Lys Gly Ile Leu Gln Thr Val Lys Val Val Asp Glu Leu
930                 935                 940

Val Lys Val Met Gly Arg His Lys Pro Glu Asn Ile Val Ile Glu Met
945                 950                 955                 960

Ala Arg Glu Asn Gln Thr Thr Gln Lys Gly Gln Lys Asn Ser Arg Glu
                965                 970                 975

Arg Met Lys Arg Ile Glu Glu Gly Ile Lys Glu Leu Gly Ser Gln Ile
                980                 985                 990

Leu Lys Glu His Pro Val Glu Asn Thr Gln Leu Gln Asn Glu Lys Leu
                995                 1000                1005

Tyr Leu Tyr Tyr Leu Gln Asn Gly Arg Asp Met Tyr Val Asp Gln
1010                1015                1020

Glu Leu Asp Ile Asn Arg Leu Ser Asp Tyr Asp Val Asp His Ile
1025                1030                1035

Val Pro Gln Ser Phe Leu Lys Asp Asp Ser Ile Asp Asn Lys Val
1040                1045                1050

Leu Thr Arg Ser Asp Lys Asn Arg Gly Lys Ser Asp Asn Val Pro
1055                1060                1065

Ser Glu Glu Val Val Lys Lys Met Lys Asn Tyr Trp Arg Gln Leu
1070                1075                1080

Leu Asn Ala Lys Leu Ile Thr Gln Arg Lys Phe Asp Asn Leu Thr
1085                1090                1095
```

```
Lys Ala Glu Arg Gly Gly Leu Ser Glu Leu Asp Lys Ala Gly Phe
1100                1105                1110

Ile Lys Arg Gln Leu Val Glu Thr Arg Gln Ile Thr Lys His Val
    1115                1120                1125

Ala Gln Ile Leu Asp Ser Arg Met Asn Thr Lys Tyr Asp Glu Asn
    1130                1135                1140

Asp Lys Leu Ile Arg Glu Val Lys Val Ile Thr Leu Lys Ser Lys
    1145                1150                1155

Leu Val Ser Asp Phe Arg Lys Asp Phe Gln Phe Tyr Lys Val Arg
    1160                1165                1170

Glu Ile Asn Asn Tyr His His Ala His Asp Ala Tyr Leu Asn Ala
    1175                1180                1185

Val Val Gly Thr Ala Leu Ile Lys Lys Tyr Pro Lys Leu Glu Ser
    1190                1195                1200

Glu Phe Val Tyr Gly Asp Tyr Lys Val Tyr Asp Val Arg Lys Met
    1205                1210                1215

Ile Ala Lys Ser Glu Gln Glu Ile Gly Lys Ala Thr Ala Lys Tyr
    1220                1225                1230

Phe Phe Tyr Ser Asn Ile Met Asn Phe Phe Lys Thr Glu Ile Thr
    1235                1240                1245

Leu Ala Asn Gly Glu Ile Arg Lys Arg Pro Leu Ile Glu Thr Asn
    1250                1255                1260

Gly Glu Thr Gly Glu Ile Val Trp Asp Lys Gly Arg Asp Phe Ala
    1265                1270                1275

Thr Val Arg Lys Val Leu Ser Met Pro Gln Val Asn Ile Val Lys
    1280                1285                1290

Lys Thr Glu Val Gln Thr Gly Gly Phe Ser Lys Glu Ser Ile Leu
    1295                1300                1305

Pro Lys Arg Asn Ser Asp Lys Leu Ile Ala Arg Lys Lys Asp Trp
    1310                1315                1320

Asp Pro Lys Lys Tyr Gly Gly Phe Asp Ser Pro Thr Val Ala Tyr
    1325                1330                1335

Ser Val Leu Val Val Ala Lys Val Glu Lys Gly Lys Ser Lys Lys
    1340                1345                1350

Leu Lys Ser Val Lys Glu Leu Leu Gly Ile Thr Ile Met Glu Arg
    1355                1360                1365

Ser Ser Phe Glu Lys Asn Pro Ile Asp Phe Leu Glu Ala Lys Gly
    1370                1375                1380

Tyr Lys Glu Val Lys Lys Asp Leu Ile Ile Lys Leu Pro Lys Tyr
    1385                1390                1395

Ser Leu Phe Glu Leu Glu Asn Gly Arg Lys Arg Met Leu Ala Ser
    1400                1405                1410

Ala Gly Glu Leu Gln Lys Gly Asn Glu Leu Ala Leu Pro Ser Lys
    1415                1420                1425

Tyr Val Asn Phe Leu Tyr Leu Ala Ser His Tyr Glu Lys Leu Lys
    1430                1435                1440

Gly Ser Pro Glu Asp Asn Glu Gln Lys Gln Leu Phe Val Glu Gln
    1445                1450                1455

His Lys His Tyr Leu Asp Glu Ile Ile Glu Gln Ile Ser Glu Phe
    1460                1465                1470

Ser Lys Arg Val Ile Leu Ala Asp Ala Asn Leu Asp Lys Val Leu
    1475                1480                1485

Ser Ala Tyr Asn Lys His Arg Asp Lys Pro Ile Arg Glu Gln Ala
```

-continued

```
                1490                1495                1500

Glu Asn Ile Ile His Leu Phe Thr Leu Thr Asn Leu Gly Ala Pro
    1505                1510                1515

Ala Ala Phe Lys Tyr Phe Asp Thr Thr Ile Asp Arg Lys Arg Tyr
    1520                1525                1530

Thr Ser Thr Lys Glu Val Leu Asp Ala Thr Leu Ile His Gln Ser
    1535                1540                1545

Ile Thr Gly Leu Tyr Glu Thr Arg Ile Asp Leu Ser Gln Leu Gly
    1550                1555                1560

Gly Asp
    1565

<210> SEQ ID NO 37
<211> LENGTH: 1565
<212> TYPE: PRT
<213> ORGANISM: Artificial sequence
<220> FEATURE:
<223> OTHER INFORMATION: Synthetic polypeptide

<400> SEQUENCE: 37

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
                20                  25                  30

Leu Val Leu Asn Asn Arg Val Ile Gly Glu Gly Trp Asn Arg Ala Ile
            35                  40                  45

Gly Leu His Asp Pro Thr Ala His Ala Glu Ile Met Ala Leu Arg Gln
        50                  55                  60

Gly Gly Leu Val Met Gln Asn Tyr Arg Leu Tyr Asp Ala Thr Leu Tyr
65                  70                  75                  80

Ser Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
                100                 105                 110

Ala Gly Ser Leu Met Asp Val Leu His His Pro Gly Met Asn His Arg
            115                 120                 125

Val Glu Ile Thr Glu Gly Ile Leu Ala Asp Glu Cys Ala Ala Leu Leu
        130                 135                 140

Cys Arg Phe Phe Arg Met Pro Arg Arg Val Phe Asn Ala Gln Lys Lys
145                 150                 155                 160

Ala Gln Ser Ser Thr Asp Ser Gly Gly Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Asp Lys Lys Tyr Ser Ile Gly Leu Ala Ile
        195                 200                 205

Gly Thr Asn Ser Val Gly Trp Ala Val Ile Thr Asp Glu Tyr Lys Val
    210                 215                 220

Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
                245                 250                 255

Glu Ala Thr Arg Leu Lys Arg Thr Ala Arg Arg Arg Tyr Thr Arg Arg
                260                 265                 270

Lys Asn Arg Ile Cys Tyr Leu Gln Glu Ile Phe Ser Asn Glu Met Ala
```

```
            275                 280                 285
Lys Val Asp Asp Ser Phe Phe His Arg Leu Glu Glu Ser Phe Leu Val
    290                 295                 300
Glu Glu Asp Lys Lys His Glu Arg His Pro Ile Phe Gly Asn Ile Val
305                 310                 315                 320
Asp Glu Val Ala Tyr His Glu Lys Tyr Pro Thr Ile Tyr His Leu Arg
                325                 330                 335
Lys Lys Leu Val Asp Ser Thr Asp Lys Ala Asp Leu Arg Leu Ile Tyr
                340                 345                 350
Leu Ala Leu Ala His Met Ile Lys Phe Arg Gly His Phe Leu Ile Glu
                355                 360                 365
Gly Asp Leu Asn Pro Asp Asn Ser Asp Val Asp Lys Leu Phe Ile Gln
    370                 375                 380
Leu Val Gln Thr Tyr Asn Gln Leu Phe Glu Glu Asn Pro Ile Asn Ala
385                 390                 395                 400
Ser Gly Val Asp Ala Lys Ala Ile Leu Ser Ala Arg Leu Ser Lys Ser
                405                 410                 415
Arg Arg Leu Glu Asn Leu Ile Ala Gln Leu Pro Gly Glu Lys Lys Asn
                420                 425                 430
Gly Leu Phe Gly Asn Leu Ile Ala Leu Ser Leu Gly Leu Thr Pro Asn
                435                 440                 445
Phe Lys Ser Asn Phe Asp Leu Ala Glu Asp Ala Lys Leu Gln Leu Ser
    450                 455                 460
Lys Asp Thr Tyr Asp Asp Asp Leu Asp Asn Leu Leu Ala Gln Ile Gly
465                 470                 475                 480
Asp Gln Tyr Ala Asp Leu Phe Leu Ala Ala Lys Asn Leu Ser Asp Ala
                485                 490                 495
Ile Leu Leu Ser Asp Ile Leu Arg Val Asn Thr Glu Ile Thr Lys Ala
                500                 505                 510
Pro Leu Ser Ala Ser Met Ile Lys Arg Tyr Asp Glu His His Gln Asp
                515                 520                 525
Leu Thr Leu Leu Lys Ala Leu Val Arg Gln Gln Leu Pro Glu Lys Tyr
    530                 535                 540
Lys Glu Ile Phe Phe Asp Gln Ser Lys Asn Gly Tyr Ala Gly Tyr Ile
545                 550                 555                 560
Asp Gly Gly Ala Ser Gln Glu Glu Phe Tyr Lys Phe Ile Lys Pro Ile
                565                 570                 575
Leu Glu Lys Met Asp Gly Thr Glu Glu Leu Leu Val Lys Leu Asn Arg
                580                 585                 590
Glu Asp Leu Leu Arg Lys Gln Arg Thr Phe Asp Asn Gly Ser Ile Pro
                595                 600                 605
His Gln Ile His Leu Gly Glu Leu His Ala Ile Leu Arg Arg Gln Glu
    610                 615                 620
Asp Phe Tyr Pro Phe Leu Lys Asp Asn Arg Glu Lys Ile Glu Lys Ile
625                 630                 635                 640
Leu Thr Phe Arg Ile Pro Tyr Tyr Val Gly Pro Leu Ala Arg Gly Asn
                645                 650                 655
Ser Arg Phe Ala Trp Met Thr Arg Lys Ser Glu Glu Thr Ile Thr Pro
                660                 665                 670
Trp Asn Phe Glu Glu Val Val Asp Lys Gly Ala Ser Ala Gln Ser Phe
                675                 680                 685
Ile Glu Arg Met Thr Asn Phe Asp Lys Asn Leu Pro Asn Glu Lys Val
    690                 695                 700
```

```
Leu Pro Lys His Ser Leu Leu Tyr Glu Tyr Phe Thr Val Tyr Asn Glu
705                 710                 715                 720

Leu Thr Lys Val Lys Tyr Val Thr Glu Gly Met Arg Lys Pro Ala Phe
            725                 730                 735

Leu Ser Gly Glu Gln Lys Lys Ala Ile Val Asp Leu Leu Phe Lys Thr
            740                 745                 750

Asn Arg Lys Val Thr Val Lys Gln Leu Lys Glu Asp Tyr Phe Lys Lys
        755                 760                 765

Ile Glu Cys Phe Asp Ser Val Glu Ile Ser Gly Val Glu Asp Arg Phe
770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
                805                 810                 815

Val Leu Thr Leu Thr Leu Phe Glu Asp Arg Glu Met Ile Glu Glu Arg
                820                 825                 830

Leu Lys Thr Tyr Ala His Leu Phe Asp Asp Lys Val Met Lys Gln Leu
        835                 840                 845

Lys Arg Arg Arg Tyr Thr Gly Trp Gly Arg Leu Ser Arg Lys Leu Ile
850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
                885                 890                 895

Asp Ser Leu Thr Phe Lys Glu Asp Ile Gln Lys Ala Gln Val Ser Gly
                900                 905                 910

Gln Gly Asp Ser Leu His Glu His Ile Ala Asn Leu Ala Gly Ser Pro
            915                 920                 925

Ala Ile Lys Lys Gly Ile Leu Gln Thr Val Lys Val Val Asp Glu Leu
930                 935                 940

Val Lys Val Met Gly Arg His Lys Pro Glu Asn Ile Val Ile Glu Met
945                 950                 955                 960

Ala Arg Glu Asn Gln Thr Thr Gln Lys Gly Gln Lys Asn Ser Arg Glu
                965                 970                 975

Arg Met Lys Arg Ile Glu Glu Gly Ile Lys Glu Leu Gly Ser Gln Ile
            980                 985                 990

Leu Lys Glu His Pro Val Glu Asn Thr Gln Leu Gln Asn Glu Lys Leu
        995                 1000                1005

Tyr Leu Tyr Tyr Leu Gln Asn Gly Arg Asp Met Tyr Val Asp Gln
    1010                1015                1020

Glu Leu Asp Ile Asn Arg Leu Ser Asp Tyr Asp Val Asp His Ile
    1025                1030                1035

Val Pro Gln Ser Phe Leu Lys Asp Asp Ser Ile Asp Asn Lys Val
    1040                1045                1050

Leu Thr Arg Ser Asp Lys Asn Arg Gly Lys Ser Asp Asn Val Pro
    1055                1060                1065

Ser Glu Glu Val Val Lys Lys Met Lys Asn Tyr Trp Arg Gln Leu
    1070                1075                1080

Leu Asn Ala Lys Leu Ile Thr Gln Arg Lys Phe Asp Asn Leu Thr
    1085                1090                1095

Lys Ala Glu Arg Gly Gly Leu Ser Glu Leu Asp Lys Ala Gly Phe
    1100                1105                1110
```

```
Ile Lys Arg Gln Leu Val Glu Thr Arg Gln Ile Thr Lys His Val
1115                1120                1125

Ala Gln Ile Leu Asp Ser Arg Met Asn Thr Lys Tyr Asp Glu Asn
1130                1135                1140

Asp Lys Leu Ile Arg Glu Val Lys Val Ile Thr Leu Lys Ser Lys
1145                1150                1155

Leu Val Ser Asp Phe Arg Lys Asp Phe Gln Phe Tyr Lys Val Arg
1160                1165                1170

Glu Ile Asn Asn Tyr His His Ala His Asp Ala Tyr Leu Asn Ala
1175                1180                1185

Val Val Gly Thr Ala Leu Ile Lys Lys Tyr Pro Lys Leu Glu Ser
1190                1195                1200

Glu Phe Val Tyr Gly Asp Tyr Lys Val Tyr Asp Val Arg Lys Met
1205                1210                1215

Ile Ala Lys Ser Glu Gln Glu Ile Gly Lys Ala Thr Ala Lys Tyr
1220                1225                1230

Phe Phe Tyr Ser Asn Ile Met Asn Phe Phe Lys Thr Glu Ile Thr
1235                1240                1245

Leu Ala Asn Gly Glu Ile Arg Lys Arg Pro Leu Ile Glu Thr Asn
1250                1255                1260

Gly Glu Thr Gly Glu Ile Val Trp Asp Lys Gly Arg Asp Phe Ala
1265                1270                1275

Thr Val Arg Lys Val Leu Ser Met Pro Gln Val Asn Ile Val Lys
1280                1285                1290

Lys Thr Glu Val Gln Thr Gly Gly Phe Ser Lys Glu Ser Ile Leu
1295                1300                1305

Pro Lys Arg Asn Ser Asp Lys Leu Ile Ala Arg Lys Lys Asp Trp
1310                1315                1320

Asp Pro Lys Lys Tyr Gly Gly Phe Asp Ser Pro Thr Val Ala Tyr
1325                1330                1335

Ser Val Leu Val Val Ala Lys Val Glu Lys Gly Lys Ser Lys Lys
1340                1345                1350

Leu Lys Ser Val Lys Glu Leu Leu Gly Ile Thr Ile Met Glu Arg
1355                1360                1365

Ser Ser Phe Glu Lys Asn Pro Ile Asp Phe Leu Glu Ala Lys Gly
1370                1375                1380

Tyr Lys Glu Val Lys Lys Asp Leu Ile Ile Lys Leu Pro Lys Tyr
1385                1390                1395

Ser Leu Phe Glu Leu Glu Asn Gly Arg Lys Arg Met Leu Ala Ser
1400                1405                1410

Ala Gly Glu Leu Gln Lys Gly Asn Glu Leu Ala Leu Pro Ser Lys
1415                1420                1425

Tyr Val Asn Phe Leu Tyr Leu Ala Ser His Tyr Glu Lys Leu Lys
1430                1435                1440

Gly Ser Pro Glu Asp Asn Glu Gln Lys Gln Leu Phe Val Glu Gln
1445                1450                1455

His Lys His Tyr Leu Asp Glu Ile Ile Glu Gln Ile Ser Glu Phe
1460                1465                1470

Ser Lys Arg Val Ile Leu Ala Asp Ala Asn Leu Asp Lys Val Leu
1475                1480                1485

Ser Ala Tyr Asn Lys His Arg Asp Lys Pro Ile Arg Glu Gln Ala
1490                1495                1500

Glu Asn Ile Ile His Leu Phe Thr Leu Thr Asn Leu Gly Ala Pro
```

```
                    1505                1510                1515
Ala Ala Phe Lys Tyr Phe Asp Thr Thr Ile Asp Arg Lys Arg Tyr
        1520                1525                1530

Thr Ser Thr Lys Glu Val Leu Asp Ala Thr Leu Ile His Gln Ser
        1535                1540                1545

Ile Thr Gly Leu Tyr Glu Thr Arg Ile Asp Leu Ser Gln Leu Gly
        1550                1555                1560

Gly Asp
    1565

<210> SEQ ID NO 38
<211> LENGTH: 364
<212> TYPE: PRT
<213> ORGANISM: Artificial sequence
<220> FEATURE:
<223> OTHER INFORMATION: Synthetic polypeptide

<400> SEQUENCE: 38

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val His Asn Asn Arg Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Ser Glu Val Glu Phe Ser His Glu Tyr Trp
        195                 200                 205

Met Arg His Ala Leu Thr Leu Ala Lys Arg Ala Arg Asp Glu Arg Glu
    210                 215                 220

Val Pro Val Gly Ala Val Leu Val Leu Asn Asn Arg Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Met Gln Asn Tyr Arg Leu
            260                 265                 270

Ile Asp Ala Thr Leu Tyr Val Thr Phe Glu Pro Cys Val Met Cys Ala
        275                 280                 285

Gly Ala Met Ile His Ser Arg Ile Gly Arg Val Val Phe Gly Val Arg
```

```
                290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Arg Met Pro Arg Gln Val
                340                 345                 350

Phe Asn Ala Gln Lys Lys Ala Gln Ser Ser Thr Asp
        355                 360

<210> SEQ ID NO 39
<211> LENGTH: 167
<212> TYPE: PRT
<213> ORGANISM: Artificial sequence
<220> FEATURE:
<223> OTHER INFORMATION: Synthetic polypeptide

<400> SEQUENCE: 39

Met Ser Glu Val Glu Phe Ser His Glu Tyr Trp Met Arg His Ala Leu
1               5                   10                  15

Thr Leu Ala Lys Arg Ala Arg Asp Glu Arg Glu Val Pro Val Gly Ala
                20                  25                  30

Val Leu Val Leu Asn Asn Arg Val Ile Gly Glu Gly Trp Asn Arg Ala
        35                  40                  45

Ile Gly Leu His Asp Pro Thr Ala His Ala Glu Ile Met Ala Leu Arg
    50                  55                  60

Gln Gly Gly Leu Val Met Gln Asn Tyr Arg Leu Tyr Asp Ala Thr Leu
65                  70                  75                  80

Tyr Ser Thr Phe Glu Pro Cys Val Met Cys Ala Gly Ala Met Ile His
                85                  90                  95

Ser Arg Ile Gly Arg Val Val Phe Gly Val Arg Asn Ala Lys Thr Gly
                100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
    130                 135                 140

Leu Cys Arg Phe Phe Arg Met Pro Arg Arg Val Phe Asn Ala Gln Lys
145                 150                 155                 160

Lys Ala Gln Ser Ser Thr Asp
            165

<210> SEQ ID NO 40
<211> LENGTH: 167
<212> TYPE: PRT
<213> ORGANISM: Artificial sequence
<220> FEATURE:
<223> OTHER INFORMATION: Synthetic polypeptide

<400> SEQUENCE: 40

Met Ser Glu Val Glu Phe Ser His Glu Tyr Trp Met Arg His Ala Leu
1               5                   10                  15

Thr Leu Ala Lys Arg Ala Arg Asp Glu Arg Glu Val Pro Val Gly Ala
                20                  25                  30

Val Leu Val Leu Asn Asn Arg Val Ile Gly Glu Gly Trp Asn Arg Ala
        35                  40                  45

Ile Gly Leu His Asp Pro Thr Ala His Ala Glu Ile Met Ala Leu Arg
    50                  55                  60
```

```
Gln Gly Gly Leu Val Met Gln Asn Tyr Arg Leu Ile Asp Ala Thr Leu
 65                  70                  75                  80

Tyr Val Thr Phe Glu Pro Cys Val Met Cys Ala Gly Ala Met Ile His
                 85                  90                  95

Ser Arg Ile Gly Arg Val Val Phe Gly Val Arg Asn Ser Lys Arg Gly
            100                 105                 110

Ala Ala Gly Ser Leu Met Asn Val Leu Asn Tyr Pro Gly Met Asn His
        115                 120                 125

Arg Val Glu Ile Thr Glu Gly Ile Leu Ala Asp Glu Cys Ala Ala Leu
    130                 135                 140

Leu Cys Asp Phe Tyr Arg Met Pro Arg Gln Val Phe Asn Ala Gln Lys
145                 150                 155                 160

Lys Ala Gln Ser Ser Ile Asn
                165

<210> SEQ ID NO 41
<211> LENGTH: 83
<212> TYPE: PRT
<213> ORGANISM: Bacillus phage AR9

<400> SEQUENCE: 41

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Glu Asn Lys Ile
65                  70                  75                  80

Lys Met Leu

<210> SEQ ID NO 42
<211> LENGTH: 19
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: n is a, c, g, or u

<400> SEQUENCE: 42 nnnnnnnnn nnnnnnnnn                                                 19

<210> SEQ ID NO 43
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(22)
<223> OTHER INFORMATION: n is a, c, g, or t

<400> SEQUENCE: 43
aaannnnnnn nnnnnnnnnn nn                                            22
```

```
<210> SEQ ID NO 44
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(22)
<223> OTHER INFORMATION: n is a, c, g, or t

<400> SEQUENCE: 44
tttnnnnnnn nnnnnnnnnn nn                                                  22

<210> SEQ ID NO 45
<211> LENGTH: 24
<212> TYPE: PRT
<213> ORGANISM: Artificial sequence
<220> FEATURE:
<223> OTHER INFORMATION: Synthetic peptide

<400> SEQUENCE: 45

Glu Glu Leu Leu Ser Lys Asn Tyr His Leu Glu Asn Glu Val Ala Arg
1               5                   10                  15

Leu Lys Lys Gly Ser Gly Ser Gly
            20

<210> SEQ ID NO 46
<211> LENGTH: 241
<212> TYPE: PRT
<213> ORGANISM: Artificial sequence
<220> FEATURE:
<223> OTHER INFORMATION: Synthetic polypeptide

<400> SEQUENCE: 46

Glu Glu Glu Leu Leu Ser Lys Asn Tyr His Leu Glu Asn Glu Val Ala
1               5                   10                  15

Arg Leu Lys Lys Gly Ser Gly Ser Gly Glu Glu Leu Leu Ser Lys Asn
                20                  25                  30

Tyr His Leu Glu Asn Glu Val Ala Arg Leu Lys Lys Gly Ser Gly Ser
            35                  40                  45

Gly Glu Glu Leu Leu Ser Lys Asn Tyr His Leu Glu Asn Glu Val Ala
    50                  55                  60

Arg Leu Lys Lys Gly Ser Gly Ser Gly Glu Glu Leu Leu Ser Lys Asn
65                  70                  75                  80

Tyr His Leu Glu Asn Glu Val Ala Arg Leu Lys Lys Gly Ser Gly Ser
                85                  90                  95

Gly Glu Glu Leu Leu Ser Lys Asn Tyr His Leu Glu Asn Glu Val Ala
            100                 105                 110

Arg Leu Lys Lys Gly Ser Gly Ser Gly Glu Glu Leu Leu Ser Lys Asn
        115                 120                 125

Tyr His Leu Glu Asn Glu Val Ala Arg Leu Lys Lys Gly Ser Gly Ser
    130                 135                 140

Gly Glu Glu Leu Leu Ser Lys Asn Tyr His Leu Glu Asn Glu Val Ala
145                 150                 155                 160

Arg Leu Lys Lys Gly Ser Gly Ser Gly Glu Glu Leu Leu Ser Lys Asn
                165                 170                 175

Tyr His Leu Glu Asn Glu Val Ala Arg Leu Lys Lys Gly Ser Gly Ser
            180                 185                 190

Gly Glu Glu Leu Leu Ser Lys Asn Tyr His Leu Glu Asn Glu Val Ala
        195                 200                 205
```

Arg Leu Lys Lys Gly Ser Gly Ser Gly Glu Glu Leu Leu Ser Lys Asn
210                 215                 220

Tyr His Leu Glu Asn Glu Val Ala Arg Leu Lys Lys Gly Ser Gly Ser
225                 230                 235                 240

Gly

<210> SEQ ID NO 47
<211> LENGTH: 277
<212> TYPE: PRT
<213> ORGANISM: Artificial sequence
<220> FEATURE:
<223> OTHER INFORMATION: Synthetic polypeptide

<400> SEQUENCE: 47

Met Gly Pro Asp Ile Val Met Thr Gln Ser Pro Ser Ser Leu Ser Ala
1               5                   10                  15

Ser Val Gly Asp Arg Val Thr Ile Thr Cys Arg Ser Ser Thr Gly Ala
                20                  25                  30

Val Thr Thr Ser Asn Tyr Ala Ser Trp Val Gln Glu Lys Pro Gly Lys
            35                  40                  45

Leu Phe Lys Gly Leu Ile Gly Gly Thr Asn Asn Arg Ala Pro Gly Val
    50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
            100                 105                 110

Lys Arg Gly Gly Gly Gly Ser Gly Gly Gly Gly Ser Gly Gly Gly Gly
    115                 120                 125

Ser Ser Gly Gly Gly Ser Glu Val Lys Leu Leu Glu Ser Gly Gly Gly
130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
                165                 170                 175

Arg Gly Leu Glu Trp Ile Gly Val Ile Trp Gly Asp Gly Ile Thr Asp
            180                 185                 190

Tyr Asn Ser Ala Leu Lys Asp Arg Phe Ile Ile Ser Lys Asp Asn Gly
        195                 200                 205

Lys Asn Thr Val Tyr Leu Gln Met Ser Lys Val Arg Ser Asp Asp Thr
    210                 215                 220

Ala Leu Tyr Tyr Cys Val Thr Gly Leu Phe Asp Tyr Trp Gly Gln Gly
225                 230                 235                 240

Thr Leu Val Thr Val Ser Ser Tyr Pro Tyr Asp Val Pro Asp Tyr Ala
                245                 250                 255

Gly Gly Gly Gly Gly Ser Gly Gly Gly Ser Gly Gly Gly Gly Ser
            260                 265                 270

Gly Gly Gly Gly Ser
        275

<210> SEQ ID NO 48
<211> LENGTH: 66
<212> TYPE: DNA
<213> ORGANISM: Saccharomyces bayanus

<400> SEQUENCE: 48

```
ttcttgtcgt acttatagat cgctacgtta tttcaatttt gaaaatctga gtcctgggag    60
tgcgga                                                                66
```

<210> SEQ ID NO 49
<211> LENGTH: 605
<212> TYPE: PRT
<213> ORGANISM: Homo sapiens

<400> SEQUENCE: 49

```
Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
            20                  25                  30

Ser Gly Arg Asp Ser Leu Ile Phe Leu Val Asp Ala Ser Lys Ala Met
        35                  40                  45

Phe Glu Ser Gln Ser Glu Asp Glu Leu Thr Pro Phe Asp Met Ser Ile
    50                  55                  60

Gln Cys Ile Gln Ser Val Tyr Ile Ser Lys Ile Ile Ser Ser Asp Arg
65                  70                  75                  80

Asp Leu Leu Ala Trp Phe Tyr Gly Thr Glu Lys Asp Lys Asn Ser Val
                85                  90                  95

Asn Phe Lys Ile Tyr Val Leu Gln Glu Leu Asp Asn Pro Gly Ala Lys
            100                 105                 110

Arg Ile Leu Glu Leu Asp Gln Phe Lys Gly Gln Gln Gly Gln Lys Arg
        115                 120                 125

Phe Gln Asp Met Met Gly His Gly Ser Asp Tyr Ser Leu Ser Glu Val
    130                 135                 140

Leu Trp Val Cys Ala Asn Leu Phe Ser Asp Val Gln Phe Lys Met Ser
145                 150                 155                 160

His Lys Arg Ile Met Leu Phe Thr Asn Glu Asp Asn Pro His Gly Asn
                165                 170                 175

Asp Ser Ala Lys Ala Ser Arg Ala Arg Thr Lys Ala Gly Asp Leu Arg
            180                 185                 190

Asp Thr Gly Ile Phe Leu Asp Leu His Leu Lys Lys Pro Gly Gly Phe
        195                 200                 205

Asp Ile Ser Leu Phe Tyr Arg Asp Ile Ile Ser Ile Ala Glu Asp Glu
    210                 215                 220

Asp Leu Arg Val His Phe Glu Glu Ser Ser Lys Leu Glu Asp Leu Leu
225                 230                 235                 240

Arg Lys Val Arg Ala Lys Glu Thr Arg Lys Arg Ala Leu Ser Arg Leu
                245                 250                 255

Lys Leu Lys Leu Asn Lys Asp Ile Val Ile Ser Val Gly Ile Tyr Asn
            260                 265                 270

Leu Val Gln Lys Ala Leu Lys Pro Pro Pro Ile Lys Leu Tyr Arg Glu
        275                 280                 285

Thr Asn Glu Pro Val Lys Thr Lys Thr Arg Thr Phe Asn Thr Ser Thr
    290                 295                 300

Gly Gly Leu Leu Leu Pro Ser Asp Thr Lys Arg Ser Gln Ile Tyr Gly
305                 310                 315                 320

Ser Arg Gln Ile Ile Leu Glu Lys Glu Glu Thr Glu Glu Leu Lys Arg
                325                 330                 335

Phe Asp Asp Pro Gly Leu Met Leu Met Gly Phe Lys Pro Leu Val Leu
            340                 345                 350
```

```
Leu Lys Lys His His Tyr Leu Arg Pro Ser Leu Phe Val Tyr Pro Glu
            355                 360                 365

Glu Ser Leu Val Ile Gly Ser Ser Thr Leu Phe Ser Ala Leu Leu Ile
        370                 375                 380

Lys Cys Leu Glu Lys Glu Val Ala Ala Leu Cys Arg Tyr Thr Pro Arg
385                 390                 395                 400

Arg Asn Ile Pro Pro Tyr Phe Val Ala Leu Val Pro Gln Glu Glu
                405                 410                 415

Leu Asp Asp Gln Lys Ile Gln Val Thr Pro Pro Gly Phe Gln Leu Val
            420                 425                 430

Phe Leu Pro Phe Ala Asp Asp Lys Arg Lys Met Pro Phe Thr Glu Lys
            435                 440                 445

Ile Met Ala Thr Pro Glu Gln Val Gly Lys Met Lys Ala Ile Val Glu
            450                 455                 460

Lys Leu Arg Phe Thr Tyr Arg Ser Asp Ser Phe Glu Asn Pro Val Leu
465                 470                 475                 480

Gln Gln His Phe Arg Asn Leu Glu Ala Leu Ala Leu Asp Leu Met Glu
                485                 490                 495

Pro Glu Gln Ala Val Asp Leu Thr Leu Pro Lys Val Glu Ala Met Asn
            500                 505                 510

Lys Arg Leu Gly Ser Leu Val Asp Glu Phe Lys Glu Leu Val Tyr Pro
            515                 520                 525

Pro Asp Tyr Asn Pro Glu Gly Lys Val Thr Lys Arg Lys His Asp Asn
            530                 535                 540

Glu Gly Ser Gly Ser Lys Arg Pro Lys Val Glu Tyr Ser Glu Glu Glu
545                 550                 555                 560

Leu Lys Thr His Ile Ser Lys Gly Thr Leu Gly Lys Phe Thr Val Pro
                565                 570                 575

Leu Lys Glu Ala Cys Arg Ala Tyr Gly Leu Lys Ser Gly Leu Lys Lys
            580                 585                 590

Gln Glu Leu Leu Glu Ala Leu Thr Lys His Phe Gln Asp
            595                 600                 605

<210> SEQ ID NO 50
<211> LENGTH: 482
<212> TYPE: PRT
<213> ORGANISM: Artificial sequence
<220> FEATURE:
<223> OTHER INFORMATION: Synthetic polypeptide

<400> SEQUENCE: 50

Met Val Arg Ser Gly Asn Lys Ala Ala Trp Leu Cys Met Asp Val Gly
1               5                   10                  15

Phe Thr Met Ser Asn Ser Ile Pro Gly Ile Glu Ser Pro Phe Glu Gln
                20                  25                  30

Ala Lys Lys Val Ile Thr Met Phe Val Gln Arg Gln Val Phe Ala Glu
            35                  40                  45

Asn Lys Asp Glu Ile Ala Leu Val Leu Phe Gly Thr Asp Gly Thr Asp
        50                  55                  60

Asn Pro Leu Ser Gly Gly Asp Gln Tyr Gln Asn Ile Thr Val His Arg
65                  70                  75                  80

His Leu Met Leu Pro Asp Phe Asp Leu Leu Glu Asp Ile Glu Ser Lys
                85                  90                  95

Ile Gln Pro Gly Ser Gln Gln Ala Asp Phe Leu Asp Ala Leu Ile Val
            100                 105                 110
```

```
Ser Met Asp Val Ile Gln His Glu Thr Ile Gly Lys Lys Phe Glu Lys
        115                 120                 125

Arg His Ile Glu Ile Phe Thr Asp Leu Ser Ser Arg Phe Ser Lys Ser
        130                 135                 140

Gln Leu Asp Ile Ile His Ser Leu Lys Lys Cys Asp Ile Ser Glu
145                 150                 155                 160

Arg His Ser Ile His Trp Pro Cys Arg Leu Thr Ile Gly Ser Asn Leu
                165                 170                 175

Ser Ile Arg Ile Ala Ala Tyr Lys Ser Ile Leu Gln Glu Arg Val Lys
            180                 185                 190

Lys Thr Thr Trp Asp Ala Lys Thr Leu Lys Lys Glu Asp Ile Gln Lys
        195                 200                 205

Glu Thr Val Tyr Cys Leu Asn Asp Asp Glu Thr Glu Val Leu Lys
210                 215                 220

Glu Asp Ile Ile Gln Gly Phe Arg Tyr Gly Ser Asp Ile Val Pro Phe
225                 230                 235                 240

Ser Lys Val Asp Glu Glu Gln Met Lys Tyr Lys Ser Glu Gly Lys Cys
                245                 250                 255

Phe Ser Val Leu Gly Phe Cys Lys Ser Ser Gln Val Gln Arg Arg Phe
            260                 265                 270

Phe Met Gly Asn Gln Val Leu Lys Val Phe Ala Ala Arg Asp Asp Glu
        275                 280                 285

Ala Ala Val Ala Leu Ser Ser Leu Ile His Ala Leu Asp Asp Leu
290                 295                 300

Asp Ile Trp Ala Ile Val Arg Tyr Ala Tyr Asp Lys Arg Ala Asn Pro
305                 310                 315                 320

Gln Val Gly Val Ala Phe Pro His Ile Lys His Asn Tyr Glu Cys Leu
                325                 330                 335

Val Tyr Val Gln Leu Pro Phe Met Glu Asp Leu Arg Gln Tyr Met Phe
            340                 345                 350

Ser Ser Leu Lys Asn Ser Lys Lys Tyr Ala Pro Thr Glu Ala Gln Leu
        355                 360                 365

Asn Ala Val Asp Ala Leu Ile Asp Ser Met Ser Leu Ala Lys Lys Asp
370                 375                 380

Glu Lys Thr Asp Thr Leu Glu Asp Leu Phe Pro Thr Thr Lys Ile Pro
385                 390                 395                 400

Asn Pro Arg Phe Gln Arg Leu Phe Gln Cys Leu Leu His Arg Ala Leu
                405                 410                 415

His Pro Arg Glu Pro Leu Pro Pro Ile Gln Gln His Ile Trp Asn Met
            420                 425                 430

Leu Asn Pro Pro Ala Glu Val Thr Thr Lys Ser Gln Ile Pro Leu Ser
        435                 440                 445

Lys Ile Lys Thr Leu Phe Pro Leu Ile Glu Ala Lys Lys Asp Gln
450                 455                 460

Val Thr Ala Gln Glu Ile Phe Gln Asp Asn His Glu Asp Gly Pro Thr
465                 470                 475                 480

Ala Lys

<210> SEQ ID NO 51
<211> LENGTH: 10
<212> TYPE: DNA
<213> ORGANISM: Methanobacterium thermoautotrophicum

<400> SEQUENCE: 51
``` aattttttgga    10

<210> SEQ ID NO 52
<211> LENGTH: 83
<212> TYPE: PRT
<213> ORGANISM: Methanobacterium thermoautotrophicum

<400> SEQUENCE: 52

Gly Ser Val Ile Asp Val Ser Ser Gln Arg Val Asn Val Gln Arg Pro
1               5                   10                  15

Leu Asp Ala Leu Gly Asn Ser Leu Asn Ser Pro Val Ile Ile Lys Leu
            20                  25                  30

Lys Gly Asp Arg Glu Phe Arg Gly Val Leu Lys Ser Phe Asp Leu His
        35                  40                  45

Met Asn Leu Val Leu Asn Asp Ala Glu Glu Leu Glu Asp Gly Glu Val
    50                  55                  60

Thr Arg Arg Leu Gly Thr Val Leu Ile Arg Gly Asp Asn Ile Val Tyr
65                  70                  75                  80

Ile Ser Pro

<210> SEQ ID NO 53
<211> LENGTH: 25
<212> TYPE: DNA
<213> ORGANISM: Bacteriophage MS2

<400> SEQUENCE: 53
gcgcacatga ggatcaccca tgtgc    25

<210> SEQ ID NO 54
<211> LENGTH: 116
<212> TYPE: PRT
<213> ORGANISM: Bacteriophage MS2

<400> SEQUENCE: 54

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Gly Ala Trp Arg Ser Tyr Leu Asn Met Glu Leu Thr Ile Pro
65                  70                  75                  80

Ile Phe Ala Thr Asn Ser Asp Cys Glu Leu Ile Val Lys Ala Met Gln
                85                  90                  95

Gly Leu Leu Lys Asp Gly Asn Pro Ile Pro Ser Ala Ile Ala Ala Asn
            100                 105                 110

Ser Gly Ile Tyr
        115

<210> SEQ ID NO 55
<211> LENGTH: 26
<212> TYPE: DNA
<213> ORGANISM: Bacteriophage PP7

<400> SEQUENCE: 55
ataaggagtt tatatggaaa ccctta    26

<210> SEQ ID NO 56
<211> LENGTH: 127
<212> TYPE: PRT
<213> ORGANISM: Bacteriophage PP7

<400> SEQUENCE: 56

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Trp Asp Cys Ser Thr Ser Val Cys Gly Glu Leu Pro Lys Val Arg Tyr
65                  70                  75                  80

Thr Gln Val Trp Ser His Asp Val Thr Ile Val Ala Asn Ser Thr Glu
                85                  90                  95

Ala Ser Arg Lys Ser Leu Tyr Asp Leu Thr Lys Ser Leu Val Ala Thr
            100                 105                 110

Ser Gln Val Glu Asp Leu Val Val Asn Leu Val Pro Leu Gly Arg
        115                 120                 125

<210> SEQ ID NO 57
<211> LENGTH: 19
<212> TYPE: DNA
<213> ORGANISM: Shigella phage

<400> SEQUENCE: 57
ctgaatgcct gcgagcatc                                                  19

<210> SEQ ID NO 58
<211> LENGTH: 62
<212> TYPE: PRT
<213> ORGANISM: Shigella phage

<400> SEQUENCE: 58

Met Lys Ser Ile Arg Cys Lys Asn Cys Asn Lys Leu Leu Phe Lys Ala
1               5                   10                  15

Asp Ser Phe Asp His Ile Glu Ile Arg Cys Pro Arg Cys Lys Arg His
            20                  25                  30

Ile Ile Met Leu Asn Ala Cys Glu His Pro Thr Glu Lys His Cys Gly
        35                  40                  45

Lys Arg Glu Lys Ile Thr His Ser Asp Glu Thr Val Arg Tyr
    50                  55                  60

<210> SEQ ID NO 59
<211> LENGTH: 1367
<212> TYPE: PRT
<213> ORGANISM: Artificial sequence
<220> FEATURE:
<223> OTHER INFORMATION: Synthetic polypeptide

<400> SEQUENCE: 59

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
              35                  40                  45

Ala Leu Leu Phe Asp Ser Gly Glu Thr Ala Glu Ala Thr Arg Leu Lys
 50                  55                  60

Arg Thr Ala Arg Arg Tyr Thr Arg Arg Lys Asn Arg Ile Cys Tyr
 65                  70                  75                  80

Leu Gln Glu Ile Phe Ser Asn Glu Met Ala Lys Val Asp Asp Ser Phe
                 85                  90                  95

Phe His Arg Leu Glu Glu Ser Phe Leu Val Glu Asp Lys Lys His
                100                 105                 110

Glu Arg His Pro Ile Phe Gly Asn Ile Val Asp Glu Val Ala Tyr His
                115                 120                 125

Glu Lys Tyr Pro Thr Ile Tyr His Leu Arg Lys Lys Leu Val Asp Ser
130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
                180                 185                 190

Gln Leu Phe Glu Glu Asn Pro Ile Asn Ala Ser Gly Val Asp Ala Lys
                195                 200                 205

Ala Ile Leu Ser Ala Arg Leu Ser Lys Ser Arg Arg Leu Glu Asn Leu
210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
                260                 265                 270

Asp Leu Asp Asn Leu Leu Ala Gln Ile Gly Asp Gln Tyr Ala Asp Leu
                275                 280                 285

Phe Leu Ala Ala Lys Asn Leu Ser Asp Ala Ile Leu Leu Ser Asp Ile
290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
                340                 345                 350

Gln Ser Lys Asn Gly Tyr Ala Gly Tyr Ile Asp Gly Gly Ala Ser Gln
                355                 360                 365

Glu Glu Phe Tyr Lys Phe Ile Lys Pro Ile Leu Glu Lys Met Asp Gly
                370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
                420                 425                 430

Lys Asp Asn Arg Glu Lys Ile Glu Lys Ile Leu Thr Phe Arg Ile Pro
                435                 440                 445

Tyr Tyr Val Gly Pro Leu Ala Arg Gly Asn Ser Arg Phe Ala Trp Met

-continued

```
            450                 455                 460
Thr Arg Lys Ser Glu Glu Thr Ile Thr Pro Trp Asn Phe Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
                500                 505                 510

Leu Tyr Glu Tyr Phe Thr Val Tyr Asn Glu Leu Thr Lys Val Lys Tyr
                515                 520                 525

Val Thr Glu Gly Met Arg Lys Pro Ala Phe Leu Ser Gly Glu Gln Lys
                530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
                580                 585                 590

Tyr His Asp Leu Leu Lys Ile Ile Lys Asp Lys Asp Phe Leu Asp Asn
                595                 600                 605

Glu Glu Asn Glu Asp Ile Leu Glu Asp Ile Val Leu Thr Leu Thr Leu
610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
                660                 665                 670

Gln Ser Gly Lys Thr Ile Leu Asp Phe Leu Lys Ser Asp Gly Phe Ala
                675                 680                 685

Asn Arg Asn Phe Met Gln Leu Ile His Asp Asp Ser Leu Thr Phe Lys
                690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
                740                 745                 750

His Lys Pro Glu Asn Ile Val Ile Glu Met Ala Arg Glu Asn Gln Thr
                755                 760                 765

Thr Gln Lys Gly Gln Lys Asn Ser Arg Glu Arg Met Lys Arg Ile Glu
                770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Leu Lys Asp
                835                 840                 845

Asp Ser Ile Asp Asn Lys Val Leu Thr Arg Ser Asp Lys Asn Arg Gly
                850                 855                 860

Lys Ser Asp Asn Val Pro Ser Glu Glu Val Val Lys Lys Met Lys Asn
865                 870                 875                 880
```

-continued

```
Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Gln Ile Thr Lys
                915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr  Pro Lys Leu Glu Ser  Glu Phe Val
                995                 1000                 1005

Tyr Gly Asp Tyr Lys Val Tyr  Asp Val Arg Lys Met  Ile Ala Lys
    1010                1015                1020

Ser Glu Gln Glu Ile Gly Lys Ala Thr Ala Lys Tyr  Phe Phe Tyr
    1025                1030                1035

Ser Asn Ile Met Asn Phe Phe  Lys Thr Glu Ile Thr  Leu Ala Asn
    1040                1045                1050

Gly Glu Ile Arg Lys Arg Pro  Leu Ile Glu Thr Asn  Gly Glu Thr
    1055                1060                1065

Gly Glu Ile Val Trp Asp Lys  Gly Arg Asp Phe Ala  Thr Val Arg
    1070                1075                1080

Lys Val Leu Ser Met Pro Gln Val Asn Ile Val Lys  Lys Thr Glu
    1085                1090                1095

Val Gln Thr Gly Gly Phe Ser  Lys Glu Ser Ile Leu  Pro Lys Arg
    1100                1105                1110

Asn Ser Asp Lys Leu Ile Ala  Arg Lys Lys Asp Trp  Asp Pro Lys
    1115                1120                1125

Lys Tyr Gly Gly Phe Asp Ser  Pro Thr Val Ala Tyr  Ser Val Leu
    1130                1135                1140

Val Val Ala Lys Val Glu Lys  Gly Lys Ser Lys Lys  Leu Lys Ser
    1145                1150                1155

Val Lys Glu Leu Leu Gly Ile  Thr Ile Met Glu Arg  Ser Ser Phe
    1160                1165                1170

Glu Lys Asn Pro Ile Asp Phe  Leu Glu Ala Lys Gly  Tyr Lys Glu
    1175                1180                1185

Val Lys Lys Asp Leu Ile Ile  Lys Leu Pro Lys Tyr  Ser Leu Phe
    1190                1195                1200

Glu Leu Glu Asn Gly Arg Lys  Arg Met Leu Ala Ser  Ala Gly Glu
    1205                1210                1215

Leu Gln Lys Gly Asn Glu Leu  Ala Leu Pro Ser Lys  Tyr Val Asn
    1220                1225                1230

Phe Leu Tyr Leu Ala Ser His  Tyr Glu Lys Leu Lys  Gly Ser Pro
    1235                1240                1245

Glu Asp Asn Glu Gln Lys Gln  Leu Phe Val Glu Gln  His Lys His
    1250                1255                1260

Tyr Leu Asp Glu Ile Ile Glu  Gln Ile Ser Glu Phe  Ser Lys Arg
    1265                1270                1275
```

```
Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 60
<211> LENGTH: 1367
<212> TYPE: PRT
<213> ORGANISM: Artificial sequence
<220> FEATURE:
<223> OTHER INFORMATION: Synthetic polypeptide

<400> SEQUENCE: 60

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270
```

```
Asp Leu Asp Asn Leu Leu Ala Gln Ile Gly Asp Gln Tyr Ala Asp Leu
            275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
```

```
            690                 695                 700
Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
                740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
        770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Ala Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Ala Leu Glu Ser Glu Phe Val
        995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Ala Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110
```

Asn Ser Asp Lys Leu Ile Ala Arg Lys Lys Asp Trp Asp Pro Lys
1115                1120                1125

Lys Tyr Gly Gly Phe Asp Ser Pro Thr Val Ala Tyr Ser Val Leu
1130                1135                1140

Val Val Ala Lys Val Glu Lys Gly Lys Ser Lys Lys Leu Lys Ser
1145                1150                1155

Val Lys Glu Leu Leu Gly Ile Thr Ile Met Glu Arg Ser Ser Phe
1160                1165                1170

Glu Lys Asn Pro Ile Asp Phe Leu Glu Ala Lys Gly Tyr Lys Glu
1175                1180                1185

Val Lys Lys Asp Leu Ile Ile Lys Leu Pro Lys Tyr Ser Leu Phe
1190                1195                1200

Glu Leu Glu Asn Gly Arg Lys Arg Met Leu Ala Ser Ala Gly Glu
1205                1210                1215

Leu Gln Lys Gly Asn Glu Leu Ala Leu Pro Ser Lys Tyr Val Asn
1220                1225                1230

Phe Leu Tyr Leu Ala Ser His Tyr Glu Lys Leu Lys Gly Ser Pro
1235                1240                1245

Glu Asp Asn Glu Gln Lys Gln Leu Phe Val Glu Gln His Lys His
1250                1255                1260

Tyr Leu Asp Glu Ile Ile Glu Gln Ile Ser Glu Phe Ser Lys Arg
1265                1270                1275

Val Ile Leu Ala Asp Ala Asn Leu Asp Lys Val Leu Ser Ala Tyr
1280                1285                1290

Asn Lys His Arg Asp Lys Pro Ile Arg Glu Gln Ala Glu Asn Ile
1295                1300                1305

Ile His Leu Phe Thr Leu Thr Asn Leu Gly Ala Pro Ala Ala Phe
1310                1315                1320

Lys Tyr Phe Asp Thr Thr Ile Asp Arg Lys Arg Tyr Thr Ser Thr
1325                1330                1335

Lys Glu Val Leu Asp Ala Thr Leu Ile His Gln Ser Ile Thr Gly
1340                1345                1350

Leu Tyr Glu Thr Arg Ile Asp Leu Ser Gln Leu Gly Gly Asp
1355                1360                1365

<210> SEQ ID NO 61
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 61
gacaagaagt acagcatcgg gctggcgatc gggaccaact ccgtcggctg ggctgtgatt      60
accgacgagt acaaggtgcc atccaagaag ttcaaggtcc tcggcaacac tgaccggcac     120
agcattaaga gaacctgat tggggcgctg ctgttcgatt cggggagac tgcggaggcg      180 accaggctga agcggactgc gcgccggagg tacaccagga ggaagaatcg gatctgctac     240
ctccaggaga ttttctcgaa tgagatggcc aaggtggacg attccttctt ccatcgcctg     300
gaggagtcgt tcctcgttga ggaggacaag aagcatgaga ggcatcccat tttcgggaat     360
atcgttgacg aggtggctta ccatgagaag tacccgacca tctaccatct gcggaagaag     420
ctcgtcgatt cgaccgataa ggccgacctg cggctgatct acctggccct cgcgcacatg     480
attaagttcc ggggccattt cctcatcgag ggcgacctca cccggacaa ctcggacgtg     540

```
gataagctct tcattcagct cgtgcagaca tacaaccagc tcttcgagga gaatcccatt    600
aacgcctcgg gggtcgacgc taaggctatt ctctcggctc ggctgtcgaa gtcgcgccgg    660
ctggagaatc tcattgccca gctcccaggc gagaagaaga acggcctctt cggcaacctg    720
attgccctgt cgctggggct cacaccgaat ttcaagtcga acttcgacct cgccgaggac    780
gctaagctcc agctcagcaa ggatacttac gatgatgacc tcgataacct gctcgcccag    840
attggggatc agtacgcgga tctgttcctc gcggccaaga atctcagcga tgctattctc    900
ctgtcggaca ttctccgcgt caacacagag attactaagg ccccactgtc ggcgagcatg    960
attaagaggt acgatgagca tcatcaggac ctgacactgc tcaaggcgct ggtccggcag   1020
cagctccccg agaagtacaa ggagattttc ttcgatcagt caaagaatgg gtacgcgggc   1080
tacattgatg gcggcgcgtc ccaggaggag ttctacaagt tcattaagcc catcctggag   1140
aagatggacg ggaccgagga gctgctggtg aagctcaatc gggaggacct gctccggaag   1200
cagcgcacat tcgacaatgg ctcgattcct caccagattc acctgggcga gctgcacgcc   1260
attctccgca ggcaggagga cttctacccg ttcctcaagg acaaccgcga agatcgag    1320
aagatcctga ccttccggat tccatactac gtggggccgc tcgcgcgggg gaactcccgg   1380
ttcgcgtgga tgactcgcaa gtccgaagaa acgattacac cgtggaattt cgaggaggtc   1440
gtcgacaagg cgctagtgc gcagtcattc attgagagga tgaccaattt cgataagaac   1500
ctgcctaacg agaaggtgct gccgaagcat tcgctgctct acgagtactt caccgtttac   1560
aatgagctga ccaaggtgaa gtatgtgact gagggcatga ggaagccagc gttcctgagc   1620
ggcgagcaga agaaggctat cgtggacctg ctcttcaaga ctaaccggaa ggtgactgtg   1680
aagcagctca aggaggacta cttcaagaag attgagtgct tcgattccgt tgagattagc   1740
ggggtggagg atcggttcaa tgcttcgctc gggacatacc acgatctcct gaagatcatt   1800
aaggataagg acttcctcga caacgaggag aacgaggaca ttctcgaaga tattgtcctg   1860
accctcaccc tcttcgagga tcgggagatg atcgaggaga ggctcaagac atacgctcat   1920
ctgttcgatg ataaggtcat gaagcagctg aagcgcaggc ggtacacagg gtgggggcgg   1980
ctgagccgga agctgatcaa cgggattcgg gataagcagt ccgggaagac aattctcgac   2040
ttcctcaagt ccgacgggtt cgctaaccgg aacttcatgc agctcattca tgatgactcg   2100
ctgacattca aggaggatat tcagaaggcg caggtttcgg ggcagggcga ctcgctccac   2160
gagcatattg cgaatctggc gggctccccc gcgattaaga agggcattct gcaaaccgtc   2220
aaggtggttg atgagctggt caaggtcatg gggcggcata agccagagaa tattgtcatc   2280
gagatggcgc gggagaatca gaccacacag aaggggcaga agaactcacg ggagcggatg   2340
aagcgcatcg aggagggcat caaggagctg gggtcgcaga tcctgaagga gcatcccgtg   2400
gagaacactc agctgcaaaa tgagaagctg tacctctact acctccagaa cgggagggac   2460
atgtatgtgg atcaggagct ggatattaat aggctgagcg attacgatgt cgaccacatt   2520
gtcccacagt cgttcctgaa ggacgacagc attgacaaca aggtgctgac ccgctcggat   2580
aagaacaggg gcaagagcga taatgttcca agcgaggagg ttgtgaagaa gatgaagaac   2640
tactggcggc agctcctgaa cgcgaagctc atcacacagg gaagttcga caacctcacc   2700
aaggctgagc gcggggggcct gagcgagctg gacaaggcgg ggttcattaa gaggcagctg   2760
gtcgagacac ggcagattac aaagcatgtt gcgcagattc tcgattcccg gatgaacacc   2820
aagtacgatg agaacgataa gctgattcgg gaggtcaagg taattaccct gaagtccaag   2880
```

```
ctggtgtccg acttcaggaa ggacttccag ttctacaagg ttcgggagat caacaactac    2940
caccacgcgc atgatgccta cctcaacgcg gtcgtgggga ccgctctcat caagaagtac    3000
ccaaagctgg agtcagagtt cgtctacggg gattacaagg tttacgacgt gcggaagatg    3060
atcgctaaga gcgagcagga gattggcaag gctaccgcta agtacttctt ctactccaac    3120
atcatgaact tcttcaagac agagattacc ctcgcgaatg gcgagatccg aagaggccc     3180 ctcatcgaga caaatgggga gacagggag attgtctggg ataaggggcg ggatttcgcg     3240
accgtccgga aggtcctgtc gatgccccag gttaatattg tcaagaagac tgaggtccag    3300
actggcggct tctcaaagga gtcgattctc ccaaagagga actccgataa gctcattgct    3360
cggaagaagg attgggaccc caagaagtac ggggggattcg actccccac tgttgcttac    3420 tctgttctgg ttgttgctaa ggtggagaag ggaagtcga agaagctgaa gagcgtgaag    3480
gagctgctcg ggattacaat tatggagagg tcatccttcg agaagaatcc catcgacttc    3540
ctggaggcca agggctacaa ggaggtgaag aaggacctga ttattaagct gcccaagtac    3600
tcgctcttcg agctggagaa tgggcggaag cggatgctgg cgtccgcggg ggagctgcaa    3660
aaggggaacg agctggcgct cccctccaag tatgtgaact tcctctacct ggcgtcgcac    3720
tacgagaagc tgaaggggtc cccagaggat aatgagcaga agcagctctt cgtcgagcag    3780
cataagcact acctggacga gattatcgag cagattagcg agttctcgaa gcgggtcatc    3840
ctcgcggatg cgaacctgga taaggtgctc agcgcctaca ataagcaccg ggacaagccg    3900
attcgggagc aggcggagaa tattattcac ctcttcacac tcaccaacct cggggcacca    3960
gctgcgttca gtacttcga cactactatc gaccggaagc ggtacacctc gacgaaggag    4020
gtgctcgacg ccaccctcat tcaccagtcg atcacaggcc tgtacgagac acggattgac    4080
ctgtcccagc tcgggggcga c                                             4101
```

<210> SEQ ID NO 62
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 62

```
gacaagaagt actccattgg cctggcgatt gggacaaact cggtgggtg ggccgtgatt     60 acggatgagt acaaggttcc aagcaagaag ttcaaggtcc tcgggaacac agatcggcat    120
tcgattaaga gaatctcat tggggcgctc ctcttcgact cggggggagac agcggaggct    180 accaggctca gcggacagc caggcggcgg tacacaaggc ggaagaatcg catctgctac    240
ctccaggaga ttttctcgaa tgagatggcg aaggtggacg acagcttctt ccatcggctg    300
gaggagtcct tcctggtgga ggaggataag aagcacgaga ggcatccaat tttcgggaac    360
atcgtggacg aggttgcgta ccatgagaag taccctacaa tctaccatct gcggaagaag    420
ctggttgact ccacagacaa ggcggacctg aggctgatct acctcgctct ggcccacatg    480
attaagttcc gcgggcattt cctgatcgag ggggacctga tcccgacaa ttcggatgtg    540 gacaagctct tcatccagct ggtgcagacc tacaaccagc tgttcgagga gaatcccatc    600
aatgcgtcgg gcgttgacgc taaggccatt ctgtccgcta ggctgtcgaa gagcaggagg    660
ctggagaacc tgatcgccca gctgccaggc gagaagaaga tgggctctt cgggaatctg    720 attgcgctct ccctggggct gacaccgaac ttcaagagca atttcgatct ggctgaggac    780
gcgaagctcc agctctcgaa ggacacttac gacgatgacc tcgataacct cctcgcgcag    840
```

```
atcggggacc agtacgctga tctcttcctc gccgctaaga acctctcgga tgctatcctg    900
ctctccgaca ttctccgggt taataccgag attacaaagg ccccactgtc ggcgtccatg    960
atcaagcggt acgatgagca tcatcaggat ctcaccctgc tcaaggccct cgtgcggcag   1020
cagctgcccg agaagtacaa ggagattttc ttcgaccaga gcaagaatgg gtacgctggc   1080
tacattgacg gcggggcctc acaggaggag ttctacaagt tcatcaagcc aatcctggag   1140
aagatggatg gacagagga gctgctggtg aagctcaacc gggaggatct gctcaggaag   1200
cagcggacgt tcgacaacgg gtcgattccc catcagatcc acctggggga gctgcacgcg   1260
atcctgcgcc ggcaggagga tttctaccct ttcctgaagg ataatcggga gaagatcgag   1320
aagattctca ccttccggat tccctactac gtcgggccac tcgcgcgggg caatagcagg   1380
ttcgcctgga tgacacggaa gagcgaggag acaatcaccc cctggaactt cgaggaggtt   1440
gtcgacaagg gggcgtccgc ccagtcattc attgagcgga tgaccaattt cgacaagaat   1500
ctgccaaatg agaaggttct cccaaagcat agcctcctct acgagtactt cactgtttac   1560
aacgagctga ccaaggtgaa gtatgtgacc gagggcatgc ggaagcccgc gttcctgtcc   1620
ggcgagcaga agaaggccat tgtggacctc ctgttcaaga ccaatcgcaa ggtcacagtc   1680
aagcagctca aggaggatta cttcaagaag atcgagtgct cgactcggt tgagattagc   1740 ggggtggaga tcggttcaa cgcgagcctc ggcacttacc acgacctcct gaagatcatc   1800
aaggataagg acttcctcga caacgaggag aacgaggata ttctggagga catcgtgctc   1860
accctgacgc tgttcgagga tcgggagatg atcgaggagc gcctgaagac ctacgctcat   1920
ctcttcgatg ataaggtcat gaagcagctg aagaggaggc ggtacaccgg gtggggccgc   1980
ctgagcagga agctcattaa cgggatcagg gacaagcaga gcggcaagac catcctggac   2040
ttcctcaaga gcgatggctt cgccaaccgg aatttcatgc agctcatcca cgacgactcc   2100
ctcaccttca aggaggacat tcagaaggct caggtcagcg gccagggcga ctcgctgcat   2160
gagcacatcg ctaacctggc gggcagccca gccatcaaga agggcatcct ccagacagtg   2220
aaggtcgtgg atgagctggt gaaggtcatg ggccggcata agcccgagaa tattgtgatt   2280
gagatggcgc gggagaatca gaccactcag aagggccaga agaactcgcg ggagcgcatg   2340
aagaggatcg aggagggggat taaggagctg ggcagccaga ttctcaagga gcaccccgtg   2400
gagaataccc agctccagaa cgagaagctg tacctctact acctcagaa tgggcgggac   2460 atgtatgttg atcaggagct ggacatcaat cgcctctcgg attacgacgt ggaccacatc   2520
gtgccccaga gcttcctgaa ggatgatagc atcgacaata aggtcctgac ccgctccgac   2580
aagaatcgcg gcaagagcga caacgtgccg agcgaggagg tcgtgaagaa gatgaagaac   2640
tactggcgga gctgctgaa cgcgaagctc attacacagc ggaagttcga taacctgacg   2700
aaggcggaga ggggcggcct ctccgagctg gacaaggcgg gcttcattaa gaggcagctc   2760
gtggagactc gccagatcac caagcacgtg gctcagatcc tcgatagccg gatgaatacg   2820
aagtacgatg agaatgacaa gctcatccgg gaggtgaagg taatcaccct gaagtcaaag   2880
ctcgttagcg atttccggaa ggacttccag ttctacaagg tgcgggagat taacaactac   2940
catcatcgcg acgatgcgta cctcaatgcg gtggtgggca cagccctgat taagaagtac   3000
cccaagctgg agagcgagtt cgtctacggg gactacaagg tgtacgatgt tcggaagatg   3060
atcgccaaga gcgagcagga gattgggaag gccaccgcta agtacttctt ctactcgaat   3120
attatgaatt tcttcaagac cgagatcaca ctcgctaatg gggagattcg gaagcggccc   3180
```

```
ctcatcgaga ctaacgggga gactggcgag attgtgtggg acaaggggcg cgacttcgct    3240
accgtgcgca aggtcctctc gatgccccag gttaatattg ttaagaagac agaggtgcag    3300
acgggcgggt tctccaagga gtctatcctg ccgaagcgga actcggacaa gctgatcgcc    3360
cgcaagaagg attgggaccc caagaagtac gggggattcg atagcccaac cgtggcttac    3420
agcgtcctgg tggtcgccaa ggttgagaag gggaagtcga agaagctcaa gagcgttaag    3480
gagctgctgg gcatcaccat catggagcgg tccagcttcg agaagaatcc tatcgacttc    3540
ctggaggcta aggggtacaa ggaggtcaag aaggacctga tcattaagct gcccaagtac    3600
tctctgttcg agctggagaa cgggaggaag cggatgctgg cgtctgctgg cgagctacag    3660
aagggcaatg agctggcgct ccccctcgaag tatgtcaact tcctctacct ggcttcccat    3720
tacgagaagc tgaagggctc gcccgaggat aatgagcaga agcagctctt cgtggagcag    3780
cacaagcact acctcgacga gatcattgag cagatttcgg agttctcgaa gcgggtcatt    3840
ctcgcggacg cgaacctcga caaggtcctc tcggcgtaca acaagcaccg ggacaagccc    3900
atccgggagc aggccgagaa cattatccac ctcttcacac tgaccaacct cggcgctccc    3960
gccgcgttca gtacttcga caccaccatt gaccgcaaga gatacacatc caccaaggag    4020
gtgctggacg cgaccctcat ccaccagagc atcacaggcc tctacgagac acggatcgac    4080
ctctcgcagc tcggggcga t                                              4101

<210> SEQ ID NO 63
<211> LENGTH: 4092
<212> TYPE: DNA
<213> ORGANISM: Artificial sequence
<220> FEATURE:
<223> OTHER INFORMATION: Synthetic polynucleotide

<400> SEQUENCE: 63
gacaagaagt actcgatcgg cctggcgatt ggcacaaaca gcgtggggtg ggctgtgatc      60
actgatgagt acaaggtgcc atcgaagaag ttcaaggtgc tggggaatac agaccggcat     120
tcgatcaaga agaatctcat tggcgctctc ctcttcgatt ccggcgagac tgctgaggcg     180
acccgcctga gcgcaccgc ccggcggcgc tacactcggc ggaagaatag gatttgctac     240
ctccaggaga tttttctcga atgagatggcc aaggtggatg acagcttctt ccaccgcctg     300
gaggagtcgt tcctggtcga ggaggacaag aagcatgagc ggcacccctat cttcgggaat     360 atcgttgatg aggtcgccta ccacgagaag taccccacta tctaccatct ccgcaagaag     420
ctcgtggaca gcacagataa ggccgacctc cgcctgatct acctcgccct cgcgcacatg     480
attaagttcc gggggcactt cctcattgag ggggatctga atcccgataa ctccgacgtg     540
gacaagctgt tcatccagct ggtgcagaca taccaaccagc tgttcgagga gaatcccatc     600
aacgcgagcg gcgtggacgc taaggccatt ctgtcggcta ggctctcgaa gtcgaggcgg     660
ctggagaacc tgattgcgca gctccccggc gagaagaaga cgggctgtt cgggaatctc     720 atcgccctct ccctcggcct cacaccaaac ttcaagagca atttcgacct ggctgaggac     780
gctaagctgc aactctcaaa ggatacatac gatgacgacc tggacaatct cctggctcag     840
atcggcgacc agtacgctga cctgttcctc gcggccaaga tctgtcgga cgcgattctc     900 ctcagcgaca tcctgcgcgt caataccgag attacgaagg ctccactgtc tgcgtcaatg     960
attaagcggt acgatgagca tcaccaggat ctgaccctcc tgaaggcgct cgtgcggcag    1020
cagctgcccg agaagtacaa ggagattttc ttcgatcaga gcaagaatgg ctacgccggc    1080
tacatcgacg ggggcgcgag ccaggaggag ttctacaagt tcatcaagcc catcctggag    1140
```

-continued

```
aagatggacg gcaccgagga gctactcgtg aagctcaatc gggaggatct cctccggaag    1200
cagcggacat tcgataacgg gtctatccca caccagatcc acctcggcga gctgcatgcg    1260
attctgcggc ggcaggagga tttctaccct ttcctgaagg acaaccggga gaagatcgag    1320
aagatcctca cattccggat tccatactac gtcggccccc tggcgagggg caatagccgg    1380
ttcgcgtgga tgacaaggaa gtccgaggag actattaccc cgtggaattt cgaggaggtg    1440
gttgacaagg gcgcttccgc gcagagcttc attgagcgga tgacaaactt cgacaagaat    1500
ctccccaacg agaaggtcct gccgaagcat agcctcctgt acgagtactt caccgtctac    1560
aatgagctaa ctaaggtcaa gtatgtgaca gagggcatga ggaagccagc cttcctctca    1620
ggcgagcaga agaaggccat tgtggacctc ctgttcaaga caaaccgcaa ggtgacagtg    1680
aagcagctga aggaggatta cttcaagaag attgagtgct tcgactcagt ggagatttca    1740
ggcgtggagg atcggttcaa cgcgagcctg ggacttacc acgacctgct gaagattatt    1800
aaggacaagg acttcctgga taacgaggag aatgaggaca tcctggagga tattgtgctc    1860
accctcaccc tgttcgagga cagggagatg attgaggaga ggctcaagac ctacgcgcac    1920
ctgttcgatg acaaggtcat gaagcagctg aagaggcggc gctacactgg gtggggccgc    1980
ctgtcgcgga agctgatcaa cggcattcgg gataagcagt ccgggaagac cattctggat    2040
ttcctgaagt cggacggctt cgccaacagg aatttcatgc agctgatcca cgacgactcc    2100
ctcaccttca aggaggacat tcagaaggcc caggttagcg gccaggggga ctcactccac    2160
gagcatattg ccaatctggc cggctctcca gctatcaaga agggcatcct gcaaacagtt    2220
aaggttgttg acgagctggt taaggtcatg gggcggcata agcccgagaa cattgtcatc    2280
gagatggctc gggagaacca gacaactcag aagggccaga agaactccag ggagcgcatg    2340
aagcggattg aggagggcat taaggagctg gggtcccaga tcctcaagga gcaccctgtc    2400
gagaacactc agctgcaaaa cgagaagctc tacctgtact acctccagaa cgggcgggat    2460
atgtatgtgg atcaggagct ggacatcaac aggctctccg actacgacgt ggatcacatt    2520
gtcccacagt cttcctcaa ggatgattcc atcgacaaca aggtgctgac gcgcagcgac    2580
aagaataggg ggaagtcgga caacgttccg agcgaggagg tcgtgaagaa gatgaagaat    2640
tactggaggc agctcctgaa tgcgaagctg atcactcaga ggaagttcga caatctgaca    2700
aaggcggaga ggggcgggct ctcggagctg gataaggcgg gcttcatcaa gcggcagctc    2760
gttgaaaccc ggcagatcac caagcatgtc gcccagatcc tcgatagccg catgaacacc    2820
aagtacgatg agaacgacaa gctcattcgg gaggttaagg tcattacgct gaagtccaag    2880
ctcgtcagcg acttcaggaa ggatttccag ttctacaagg ttcgggagat taacaactac    2940
caccacgcgc atgatgcgta cctgaacgct gttgtcggca ctgctctcat caagaagtac    3000
ccaaagctgg agtccgagtt cgtctacggg gactacaagg tctacgatgt ccggaagatg    3060
atcgccaagt cggagcagga gatcgggaag gctactgcga gtacttctt ctacagcaac    3120 attatgaatt tcttcaagac ggagattacg ctggcgaacg gggagattag gaagaggccc    3180
ctcattgaga ctaatgggga gacaggcgag attgtttggg acaagggccg cgacttcgcg    3240
actgtgcgga aggtcctgtc catgccacag gtgaatattt taagaagac agaggtgcag    3300 actgggggct ctctcgaagga gagcattctc ccaaagcgga acagcgataa gctcatcgcg    3360
cgcaagaagt attgggaccc taagaagtac ggcggcttcg attctcccac tgtggcctac    3420
tccgttctcg tggttgccaa ggttgagaag gggaagtcga agaagctgaa gtcggtcaag    3480
```

```
gagctgctcg ggattacaat catggagcgg agcagcttcg agaagaaccc tattgatttc    3540
ctggaggcca agggctacaa ggaggttaag aaggatctca ttatcaagct ccctaagtac    3600
tctctgttcg agctggagaa tggccggaag aggatgctgg cctcggctgg cgagctacag    3660
aaggggaatg agctggccct cccgtcgaag tatgtgaatt tcctgtacct cgcgtcgcac    3720
tacgagaagc tcaagggcag cccggaggat aatgagcaga agcagctctt cgtggagcag    3780
cataagcact acctggacga gatcattgag cagatcagcg agttctcgaa gcgggttatt    3840
ctggctgatg ctaacctgga caaggttctg agcgcctaca ataagcatcg cgacaagccg    3900
attcgcgagc aggcggagaa tattatccac ctgttcaccc tcactaacct cggggctccc    3960
gcggccttca agtacttcga taccacaata gataggaagc ggtacacctc gacgaaggag    4020
gtcctcgacg ccacactcat ccatcagtcg attacaggcc tgtacgagac acggattgac    4080
ctctcgcagc tg                                                        4092

<210> SEQ ID NO 64
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 64
gacaagaagt attccatagg cctggctatc ggcaccaaca gcgtgggctg ggccgtcatc      60
accgacgagt acaaagtgcc gagtaaaaag ttcaaagtgc tcggcaacac cgaccgccac     120
tccataaaga aaaacctgat cggggcgctc ctgttcgaca cgggcgagac ggcggaggcc     180
acccgcttga acgcacggc ccgacggcgc tacacgcggc gcaagaaccg gatctgttac     240
ctacaggaga ttttctctaa cgagatggcg aaggtggacg actcgttctt tcaccgcctc     300
gaagagtcct tctcgtgga ggaggacaag aaacacgagc gccacccgat cttcggcaac     360
atcgtggacg aggtggccta ccacgagaag tacccgacca tctaccacct ccggaagaaa     420
ctcgtggaca gcacggacaa ggccgacctg aggctcatct acctcgccct ggcgcacatg     480
attaagttcc ggggccactt cctgatcgag ggcgacctga accgggacaa cagcgacgtg     540
gacaagctgt tcatccagct agtccagacc tacaaccagc ttttcgagga aaaccccatc     600
aacgccagcg gggtggacgc gaaggcgatc ctgtccgccc ggctgagcaa gtcccggcgg     660
ctggagaacc tcatcgcgca gttgcccggc gagaagaaga cgggctgtt cgggaacctg     720 atcgccctct ccctggggct caccccgaac ttcaagtcca acttcgacct cgccgaggac     780
gccaaactac agctgagcaa ggacacctac gacgacgacc tcgacaacct gctggcccag     840
atcggggacc agtacgcaga cctgttcctc gccgccaaga acctctccga cgccatcctg     900
ctgtcggaca tcctgcgggt gaacacgag atcacgaagg cccgctctc ggcctcgatg     960 attaaacgct acgacgagca ccaccaggac ttgaccctcc tcaaggcgct ggtccgccag    1020
cagcttcccg agaagtacaa ggaaatcttt ttcgatcaga gcaagaacgg gtacgccggg    1080
tacatcgacg gcggggcgtc ccaggaggag ttctacaagt tcatcaagcc catcctggag    1140
aaaatggacg gaaccgagga gctgctcgtg aagctcaacc gcgaagattt gctccgcaag    1200
cagcgcacgt tcgacaacgg gtcgatcccg caccagatcc acctgggcga gctgcacgcg    1260
atcctccagg gtcaggaaga cttctacccc ttcctcaagg acaaccgcga agatagag     1320 aagattctga cctcagaat tccttattac gtgggcccgc tggctcgggg caactcgcgc    1380
ttcgcctgga tgacgcgcaa gtccgaggag accatcaccc cgtggaactt cgaggaggtg    1440
```

```
gtggataagg gtgcctcggc ccagtccttc atcgagcgga tgaccaactt cgacaagaac   1500
ctgccgaacg agaaggtgct cccccaagcac agcctgctct acgaatattt cacggtgtac   1560
aacgagctga cgaaggtcaa gtacgtgacc gagggaatga ggaaacctgc attcctctcc   1620
ggggagcaga agaaagccat agtcgacctc ctgttcaaga ccaaccggaa ggtcaccgtc   1680
aagcagctca aggaggacta cttcaagaag atcgagtgct tcgattcagt ggagatcagc   1740
ggcgtcgagg accggttcaa cgccagcctg ggcacctacc acgacctgct caagatcatc   1800
aaggacaagg acttcctcga caacgaggag aacgaggaca tcctggagga catcgtgctg   1860
accctgacgc tcttcgagga ccgcgagatg atcgaggagc cctcaagac ctacgcccac   1920 ctgttcgacg acaaggtgat gaagcagctc aagcggcgga gatatactgg gtggggccgc   1980
ctctcccgga agctcattaa cggtatcagg gataagcagt ccgggaagac gatcctcgac   2040
ttcctcaagt cggacgggtt cgccaaccgc aacttcatgc agctcatcca cgacgactcc   2100
ctgacgttca aggaggacat ccagaaggcc caagtgtctg gtcaaggtga ctcgctccac   2160
gagcacatcg ccaacctcgc gggcagcccg gccatcaaga agggaatact ccagaccgtc   2220
aaggtggtgg acgagctggt gaaggtcatg gccgccaca agccggagaa catcgtcatc   2280
gagatggcgc gggagaacca gaccacgcag aagggcaga aaaatagccg tgagcgcatg   2340
aagcgcatcg aggaggggat taaggagttg ggcagcaga tcctcaagga gcaccctgtg   2400
gagaacacgc agttgcaaaa cgagaagctc tacctgtact acctccagaa cgggagggat   2460
atgtacgtgg accaagaact ggacatcaac cgcctgtccg actacgacgt ggaccacatc   2520
gtgccgcaga gcttcctcaa ggacgacagc atcgacaaca aggtgctcac ccggtccgac   2580
aagaatcggg gcaagtccga caacgtgccc agcgaggagg tcgtcaaaaa gatgaaaaac   2640
tactggcgac aactactgaa cgccaagctc atcacccagc gcaagttcga caacctcaca   2700
aaagccgagc gcggcgggtt gagcgagctg gacaaggccg ggttcatcaa gcgccagctc   2760
gtcgagacgc gccagatcac gaagcacgtc gcgcagatac tcgacagccg gatgaacacc   2820
aagtacgacg agaacgacaa gctcatccgg gaggtgaagg tcatcaccct caagtcgaag   2880
ctcgtgagcg acttccgcaa ggacttccag ttctacaagg tccgggagat caacaactac   2940
caccacgccc acgatgctta tcttaacgcc gtggtgggga cggccctcat taagaaatac   3000
ccgaagctgg agtcggagtt cgtgtacggc gactacaagg tgtacgacgt caggaagatg   3060
atcgccaagt ccgaacagga gatcgggaag gccacggcga atacttctt ctacagcaac   3120 atcatgaact tcttcaagac cgagatcacc ctcgccaacg gcgagatccg caagcgcccg   3180
ctcatcgaga cgaacgggga gaccggcgag atcgtctggg acaaggggcg cgacttcgcc   3240
actgtgcgga aggtgctgtc gatgcccag gtcaacatcg tcaagaagac ggaggtccag   3300
acgggcgggt tcagcaagga gagcatcctg ccgaagcgca acagcgacaa gctgatcgcc   3360
cgcaaaaagg actgggatcc aaaaaagtac ggcggcttcg acagcccac cgtcgcctac   3420 agcgtcctcg tcgtcgctaa agtcgagaag ggcaagtcca aaaagctcaa gagcgtcaag   3480
gagctgctcg gatcaccat catggagcgg tccagcttcg agaagaaccc aattgatttc   3540
ctggaggcga agggctacaa ggaggtcaag aaagacctca tcataaagct gccgaagtac   3600
tcactcttcg agctggagaa cgggcgcaag cggatgctgg cgtcggccgg agagctccaa   3660
aagggcaacg agctggcgct gccgagcaag tacgtgaact tcctctacct ggcgtcccac   3720
tacgagaagc tcaagggcag tccagaggat aacgagcaga agcagctatt cgtggagcag   3780
```

-continued

| | |
|---|---|
| cacaagcact acctggacga gatcatcgag cagatcagcg agttctccaa gcgcgtcatc | 3840 |
| ctggcggacg ccaacctgga caaggtgctg tccgcgtaca acaagcaccg cgacaagccg | 3900 |
| atccgcgagc aagccgagaa catcatccac ctgttcaccc tcacgaacct cggggcaccc | 3960 |
| gccgccttca atatttcga cacgaccatc gaccgcaagc gctacaccag cacgaaggag | 4020 |
| gtgctcgacg ccaccctgat ccaccagagc atcaccgggc tgtacgagac ccgcatcgac | 4080 |
| ctctcgcagc tcggcgggga c | 4101 |

<210> SEQ ID NO 65
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 65

| | |
|---|---|
| gacaagaagt acagtattgg attggccatc gggacgaaca gcgtgggctg ggccgtcatc | 60 |
| accgacgagt acaaggtgcc atccaagaag tttaaggttc tggggaatac cgaccgccac | 120 |
| tcgatcaaga aaatctcat cggggcgctg cttttcgaca gcggcgagac ggcggaagcg | 180 |
| acgcggctca gcggacggc tcgtcgccgt acacccggc gtaagaaccg catctgttac | 240 |
| ctccaggaga tattcagcaa cgagatggcg aaggtggacg actcctttt ccaccgtctt | 300 |
| gaggagtcct tcctggtcga ggaggacaag aagcacgagc gccacccgat cttcgggaac | 360 |
| atcgtggacg aggtggccta ccacgagaag taccccacga tctaccacct ccgcaaaaaa | 420 |
| ctcgtggact caactgacaa ggccgatttg aggcttatct acctcgccct cgcccacatg | 480 |
| attaagttcc gtgggcactt cctaatcgag ggtgacctca ccccgacaa ctctgacgtg | 540 |
| gacaagctgt tcatccagct tgtgcagacc tacaatcagc tctttgagga gaatccgatc | 600 |
| aacgcatctg gtgtggacgc aaaggccatc ctcagcgcgc ggctgagcaa gtctaggcgg | 660 |
| ttggagaacc tgatcgccca actgcccggc gagaagaaaa atggcctctt cggcaacctg | 720 |
| atcgccctgt cgctggggct cacgccgaac ttcaagagta actttgacct ggcggaggac | 780 |
| gctaagctcc agctatctaa ggacacatac gacgacgacc tggacaacct gctggcccag | 840 |
| atcggcgacc agtacgccga cctcttccta gccgccaaga acctgtccga cgccatcctc | 900 |
| ctcagcgaca tcctgcgcgt gaacacggag atcacgaagg ctccgctcag cgcctccatg | 960 |
| attaagcggt acgacgagca ccaccaagac ctaactttac tcaaagccct cgtgcggcag | 1020 |
| cagcttcccg agaagtacaa agagatattt tttgatcagt ccaagaacgg ttatgcgggc | 1080 |
| tacatcgacg gcggcgcgag ccaggaggag ttctacaagt tcatcaagcc catcctggag | 1140 |
| aagatggacg gcacggagga gctgctcgtg aagctcaacc gtgaagacct cctgcgaaag | 1200 |
| cagcgaacct tcgacaacgg ttcgatcccg caccagatcc acctcgggga gctgcacgcc | 1260 |
| atcctgaggc gacaggagga cttctaccct ttcctaaagg acaaccgcga gaagattgaa | 1320 |
| aaaatcctga cgtttcgcat accctactac gtcggcccgc tggcgcgcgg caactcccgg | 1380 |
| ttcgcctgga tgacccgtaa gagcgaggag acgatcaccc cgtggaactt cgaggaggtc | 1440 |
| gtggacaagg cgcgagcgc gcagagcttc atcgagcgca tgaccaactt cgacaagaac | 1500 |
| ctcccgaacg agaaggtgct cccaaagcac tccctcctgt acgagtattt caccgtgtac | 1560 |
| aacgagttga caaaggtgaa gtacgtgacg gagggaatgc ggaagccctg gttcctctcg | 1620 |
| ggcgagcaga agaaggcaat cgtggacctg ctcttcaaga ccaaccggaa ggtgacggtg | 1680 |
| aagcagctca aggaggacta cttcaaaaaa atcgagtgct tcgactccgt ggagataagc | 1740 |

-continued

```
ggcgtggagg accgattcaa cgcctccctc ggcacctacc acgacctcct taagatcatc    1800
aaggacaagg acttcctgga caacgaggag aacgaggaca tcctggagga catcgtgctc    1860
accctgaccc tcttcgagga ccgggagatg atcgaggagc gcctcaagac gtacgcccac    1920
ttgttcgacg acaaggtgat gaagcagctc aagcggcggc gatacaccgg gtggggccgc    1980
ctatcccgca aacttatcaa cggcatccgc gacaagcagt ccggcaagac gatcctggat    2040
ttcctcaagt cggacgggtt cgccaaccgg aacttcatgc agctcatcca cgacgacagc    2100
ctcacgttca aggaggacat ccagaaggcc caagtgagcg gtcaagggga cagcctccac    2160
gagcacattg cgaaccttgc tgggagccct gcgatcaaga aggggatatt gcaaaccgtg    2220
aaggtcgtgg acgagttggt gaaggtcatg gggcgacaca gcccgagaa catcgtgatc     2280
gagatggcca gggaaaatca gaccacgcag aagggccaaa aaaacagccg cgagcggatg    2340
aagcggatcg aggagggcat caaggagctg gggtcgcaga tcctcaagga gcacccggtg    2400
gagaacacgc agctccagaa cgagaagctg tacctctatt acctacagaa cgggcgggat    2460
atgtacgtgg accaggagct agacatcaac cgcctgtccg actacgacgt ggaccatatc    2520
gtcccgcagt cgttcttgaa ggacgacagc atcgacaaca aggtgctcac aagatcggat    2580
aagaatcgag gcaagtccga caacgtgccc tcggaggagg tggtcaagaa atgaaaaac    2640
tactggcggc agttgctgaa cgccaagctc attacgcagc ggaagttcga caacctgacg    2700
aaggctgaac gtggtgggct cagcgagcta gacaaggcgg ggttcatcaa gcggcagctc    2760
gtcgagaccc ggcagatcac caagcacgtg gcgcagatcc tggactcgcg catgaacacc    2820
aagtacgacg agaacgacaa gctcatccgt gaggtgaagg tcatcaccct taagtctaag    2880
ctggtcagtg acttccgcaa ggacttccag ttctacaagg tccgggagat caacaactac    2940
caccacgcgc acgacgccta cctcaacgcg gtggtgggga cggcgcttat taagaaatat    3000
cccaagctgg aaagcgagtt cgtttacggc gactacaagg tgtacgacgt ccgcaagatg    3060
atcgcaaagt cggaacagga atcggaaag gcgacggcca atatttctt ttactccaac      3120
atcatgaatt tttttaagac ggagatcacc ctggcgaacg gggagatccg caagcggccc    3180
ctcatcgaga ccaacgggga cagggcgag atcgtctggg acaagggccg ggacttcgcc     3240
accgtgcgga aggtgctttc tatgcctcaa gtcaatatcg tcaaaaagac agaggtgcag    3300
accggcgggt tcagcaagga gtctatcctg ccgaagcgca actcggacaa gctcatcgcg    3360
cgcaagaaag actgggaccc caaaaaatat ggcgggttcg actcgccgac cgtcgcctac    3420
agcgtcctcg tggtggctaa ggtcgagaag ggcaagagca aaaagctaaa gtcggtgaag    3480
gagctgctgg gcatcaccat catggagcgc tcgtctttcg agaagaatcc aatcgacttc    3540
ctagaggcga aggggtacaa ggaggtcaaa aaggatctta tcatcaaact gccgaagtac    3600
agtctgttcg agctggagaa cgggcggaag cggatgctgg ctagtgcggg cgagttgcag    3660
aagggcaacg agttggcact gccctccaag tacgtgaact tcctgtacct ggcctcccac    3720
tacgagaagc tcaaggggag ccccgaggac aacgagcaga agcagctatt cgtcgagcag    3780
cacaagcact acctggacga gatcatcgag cagatcagtg agttctccaa gcgggtcatc    3840
ctcgcggacg ccaacctgga caaggtgctg agcgcgtaca acaagcacag ggacaagcca    3900
atcagggaac aggccgagaa catcatccac ctgttcaccc tgaccaacct gggtgcaccg    3960
gctgccttca gtactttgga cacgaccatc gaccggaagc gctacacctc cacgaaggag    4020
gtgctggacg ccacgctgat ccaccagagc atcaccgggc tctacgagac acggatcgac    4080
```

```
ctgagccagc ttggcgggga c                                          4101
```

<210> SEQ ID NO 66
<211> LENGTH: 4092
<212> TYPE: DNA
<213> ORGANISM: Artificial sequence
<220> FEATURE:
<223> OTHER INFORMATION: Synthetic polynucleotide

<400> SEQUENCE: 66

```
gacaaaaagt attccattgg actcgctatc ggcacgaaca gcgtcgggtg ggcggtcatc    60
actgacgagt acaaggtgcc gagcaagaag tttaaggtgc tgggaaacac cgacaggcac   120
tcgatcaaga aaatcttat cggggcccta ctcttcgact ccggagaaac cgccgaggcc    180
acccggttga agcgcacggc ccgccgtcgc tacaccaggc gcaagaaccg gatctgctac   240
ctccaggaga tattcagcaa tgagatggcg aaggtggacg actcgttttt tcacaggcta   300
gaggagtctt cctcgtgga ggaggacaag aaacacgagc gccacccat cttcggcaac     360
atcgtggatg aggtggcata tcacgagaag tacccaacca tctaccacct ccgcaaaaag   420
ctcgtggact ctaccgacaa ggccgacctc cgtctgatct acctcgcgct ggcccacatg   480
attaagttcc gaggacactt tctgatcgag ggcgacctga cccagacaa cagcgacgtg    540
gacaagctgt tcatccaact tgtccagacc tacaatcagc tcttcgagga gaaccctatc   600
aacgcctcgg gcgtggacgc gaaggccatc ctgtccgccc gctgagcaa gtcgcggcgg    660
ctggagaacc tgatcgccca gctccccggc gaaaaaaga acggcctctt cggcaacctc   720
atcgcgttgt cgctgggggct cacccccgaac ttcaagtcca acttcgacct ggccgaggac  780
gctaaactcc agctctcgaa ggataccctac gacgacgacc tcgacaacct gctggcccag  840
atcggcgacc agtacgcgga cctttttcctg gcggccaaga acctgagcga gcgatcctc   900
cttagcgaca tactccgtgt gaacaccgag atcacgaagg ccccgctctc cgcgtccatg   960
attaagcgct acgacgagca ccaccaagac cttaccctgc ttaaggcgct ggtcaggcag  1020
cagttaccgg agaagtacaa ggagatcttt tttgatcaat ctaagaacgg ttacgccggg  1080
tacatcgacg gcggcgcgtc ccaggaggag ttctacaagt tcatcaagcc gatcttggag  1140
aaaatggacg ggaccgagga gctgctcgtg aagctcaacc gcgaagacct cctccgcaag  1200
cagcgcacct tcgacaacgg gagcatcccg caccagatcc acctgggaga gctgcacgcg  1260
atcctgcgga gacaagagga cttctacccc ttcctcaagg acaaccggga gaagattgaa  1320
aaaatactta cttttcgtat cccgtactac gtcgggcccc ttgcgagggg caactccaga  1380
ttcgcgtgga tgacccgcaa gtccgaggag accatcaccc cgtggaactt cgaggaggtg  1440
gtggacaagg gcgcgtcggc ccagtcgttc atcgagcgca tgaccaactt cgacaagaac  1500
cttccgaacg agaaggtgct cccgaagcac agcctgctct acgaatattt tactgtgtac  1560
aacgagctga cgaaggtcaa gtacgttacg gaggggatga ggaagcccgc cttcctctcc  1620
ggcgagcaga agaaagccat tgtggatctc ctgttcaaga ccaaccgcaa ggtgacggtg  1680
aaacagctca agaggactac cttcaagaag atcgagtgct cgactccgt agagatcagc   1740
ggggtcgagg accgcttcaa cgcctcgctg ggcacgtacc acgacctgct aaagattatc  1800
aaggacaaag acttcctaga caatgaggag aacgaggaca ttctggagga catcgtgctg  1860
actctgacgc tgttcgaaga ccgcgagatg atcgaggagc ggcttaagac gtacgcccac  1920
ctgttcgacg acaaggtgat gaagcagttg aaacggcggc gctacaccgg gtggggccgc  1980
ctctcccgca agctcatcaa cggcatccgc gacaagcagt cggggaagac gatcctggac  2040
```

```
ttcctcaaga gcgacggctt cgccaaccga aacttcatgc agctaatcca cgacgacagc    2100
ctgacgttca aggaggacat ccagaaggcc aagtgagcg gccagggaga ctcgctacac    2160
gagcatatcg ccaacctggc tggcagcccg gcgattaaga aaggaatcct ccaaaccgtc    2220
aaagtggtgg acgagctggt gaaggtgatg ggccgccaca agcccgagaa cattgtgatc    2280
gagatggcgc gggagaacca gacgacgcag aagggccaaa aaatagcag ggaaaggatg    2340 aagcgaatag aggaggggat caaggagctg ggagccaga ttctcaaaga gcacccggtc    2400
gagaacacac agctccagaa cgagaagctg tacctctact acctccaaaa cggccgcgat    2460
atgtacgtgg accaggaact agacatcaac cggctgagcg actatgacgt ggaccacatc    2520
gtgccgcagt ccttcctcaa ggacgactcg attgacaaca aagtgctcac tagatccgac    2580
aagaacagag gcaagagcga taacgtcccg tcggaggagg tcgtcaagaa aatgaaaaac    2640
tactggcggc agctcctaaa cgccaagctc atcacgcagc gtaagttcga caacctgacg    2700
aaggcggagc ggggcgggct gagcgagctg gacaaagcgg ggttcatcaa gcggcagctc    2760
gttgagacgc ggcagatcac aaagcacgtc gcgcaaatcc tcgactcccg catgaacacc    2820
aagtacgacg agaacgacaa gctcatccgg gaggtgaagg tcattaccct taaatcgaag    2880
ctcgtcagcg actttcgtaa ggacttccag ttctacaagg tcagagagat caacaactac    2940
caccacgccc acgacgccta tctgaacgcc gtggtgggca ccgcgcttat taagaagtac    3000
cccaagctgg agtccgagtt cgtgtacggc gactacaagg tttatgacgt caggaagatg    3060
atcgccaagt cggaacagga gatcggaaaa gctaccgcca aatatttctt ctatagcaac    3120
atcatgaact tcttcaaaac cgagatcacc ctcgccaacg gcgagatccg gaagcgcccg    3180
ctcatcgaga ccaacgggga gaccggggag atcgtctggg acaaggggcg ggacttcgct    3240
actgtccgaa aggtgctctc catgccacaa gtgaatatcg tcaagaaaac agaggtgcag    3300
accggagggt tcagtaagga gtccatcctg cccaagcgga actccgacaa gctaattgct    3360
cgcaaaaagg attgggatcc taaaaaatat ggcggcttcg actcgcccac ggtcgcctac    3420
tctgtgctgg tcgtggcgaa ggtggagaag ggcaagtcca agaagctcaa gagcgtcaag    3480
gagctgctgg ggatcacgat catggagcgt agttcgtttg agaagaatcc catcgacttc    3540
ctggaggcta agggctacaa ggaggtcaaa aaggacctca tcattaagct gccgaagtac    3600
agcctcttcg agctggagaa cgggcggaag cgtatgctcg cctccgctgg ggagttacaa    3660
aaggggaacg agctggcgct gccgtctaag tacgtcaact tcctgtacct ggcctcccac    3720
tacgagaagc tcaaggggtc gccggaggac aacgagcaga agcagctctt cgtagagcag    3780
cacaagcact acctggacga gatcatcgag cagatttcag agttctcaaa gcgggtcatc    3840
ctcgccgacg ccaacctgga caaggtgctc tcggcctaca acaagcaccg ggacaagccg    3900
atccgcgaac aggccgaaaa catcatccac ctgttcacgc tcaccaacct cggtgccccg    3960
gcggccttca gtactttga cacgaccatc gaccggaagc gctataccct gacgaaggag    4020
gtgctggacg ccacccttgat ccaccagtcc atcaccgggc tttacgagac ccggatcgac    4080
ctctcgcagc ta                                                        4092
```

<210> SEQ ID NO 67
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 67

```
gacaagaagt atagtattgg actcgccatc ggaaccaact ctgtggggtg ggctgttatt      60
acagatgaat ataaggtgcc atccaaaaag tttaaagttc tgggcaatac tgatagacac     120
tcaatcaaga agaatctgat aggtgcactt ctgtttgata gtggagagac tgccgaggca     180
accagactta aaaggactgc aagaagaaga tataccagaa gaaagaatag gatttgctat     240
ttgcaggaaa tcttcagcaa cgaaatggcc aaggttgatg actcattttt ccataggttg     300
gaggagagtt ttcttgtgga ggaagataag aagcacgaaa gacacccaat tttcgggaat     360
atagtggacg aggtggctta tcatgagaag tatcccacta tctaccacct gagaaagaaa     420
cttgtggact caaccgataa ggctgatctt aggcttatat acttggccct tgcacatatg     480
atcaaattca ggggccattt tcttatcgaa ggcgatctta atcccgataa ctcagatgtg     540
gacaagctgt ttatacaact tgtgcaaacc tacaatcaac tcttcgagga gaatcccatt     600
aacgcctccg gcgtggatgc aaaagccata ctgtcagcca gactgagcaa agtaggaga      660
ctggagaatc ttatagccca actgcccggt gaaaagaaga atgggctctt cggaaatctg     720
atcgctcttt cattggggtt gacacccaac tttaagagta actttgactt ggcagaagat     780
gcaaagttgc agctcagtaa agacacatat gacgatgacc ttgacaatct cttggcacaa     840
ataggggatc aatacgctga ccttttcctc gctgccaaga acctcagcga cgctatactg     900
ttgtccgaca ttcttagggt taataccgaa attacaaagg cccctcttag tgcaagtatg     960
atcaaaaggt atgatgagca tcaccaagac cttacactgc tgaaggctct ggttagacag    1020
caactccctg aaaagtataa ggaaatattc ttcgaccaaa gtaagaacgg gtacgccggt    1080
tatattgatg ggggcgcaag tcaagaagaa ttttacaaat tcatcaagcc aattcttgaa    1140
aagatggacg ggactgagga attgctggtg aaactgaata gagaggacct tcttagaaaa    1200
cagaggacat ttgacaatgg gtccatccca caccagattc atctggggga actccacgca    1260
atattgagga gacaagaaga cttttaccca ttccttaagg ataatagaga gaaaatcgaa    1320
aaaatcctga ctttcaggat tccttactat gttgggccac tggccagggg gaactcaaga    1380
ttcgcttgga tgacaaggaa gtcagaagaa accataaccc cttggaattt tgaagaggtg    1440
gttgataagg gggcatcagc ccagtctttc atagagagga tgaccaactt tgataaaaat    1500
cttccaaatg agaaggtttt gccaaaacat agtcttttgt acgagtactt tactgtttat    1560
aacgaattga ccaaggtgaa gtatgtgacc gagggaatga ggaagccagc attttttgtcc   1620
ggggagcaaa agaaagcaat cgttgatctt ctcttcaaga ccaacagaaa agtgaccgtg    1680
aaacaactga aggaagacta cttcaaaaag atagaatgtt tcgattcagt ggaaattagc    1740
ggtgttgaag acaggttcaa tgcttcattg ggtacttacc acgacctgtt gaagataatc    1800
aaagacaagg actttctcga taatgaggag aacgaagaca tcttggaaga cattgtgctt    1860
acactcactt tgtttgagga cagggaaatg attgaggaaa gactcaaaac ttacgctcat    1920
ttgtttgatg ataaggttat gaaacaacta aaaagaagaa ggtacaccgg ctggggaaga    1980
ttgagtagga aactgatcaa cggtattaga gataaacaat ccggaaagac tatcctcgat    2040
ttccttaaga gtgatggctt tgcaataggg aattttatgc agctgattca tgacgactca    2100
cttaccttca agaagacat ccaaaaagct caggtgtctg gcaaggcga cagtctgcat      2160
gaacatatag ctaacttggc tgggagtccc gccatcaaga agggatact tcaaacagtt     2220
aaagttgtgg acgaattggt gaaggtaatg ggaaggcaca agcctgaaaa tatagtgata    2280
gaaatggcaa gggaaaatca acaacccag aagggacaga agaacagtag ggaaaggatg     2340
```

```
aaaaggatag aagagggat caaagagctt ggtagccaga tcctcaagga acatccagtg   2400
gagaataccc aacttcaaaa cgagaaactc tatttgtact acttgcagaa cggaagagat   2460
atgtatgtgg accaagagct tgatattaac aggctgagcg attatgacgt tgaccacata   2520
gtgccccaat cattcctcaa ggatgactct attgataata aggtgctgac aaggagtgac   2580
aagaatagag ggaaatccga caacgttcca tccgaggaag ttgtgaagaa gatgaagaac   2640
tactggaggc agttgctgaa cgctaagctc attacccaga ggaaattcga taacctgacc   2700
aaagcagaga gaggcgggct gagcgaactc gataaagcag gtttcatcaa gagacaactc   2760
gtggagacta ggcaaattac taagcacgtg gctcaaatac tcgacagcag gatgaacaca   2820
aagtacgacg agaacgacaa gctcattaga gaggttaagg ttattactct gaaaagtaaa   2880
ttggttagcg atttcagaaa ggatttccaa ttctataagg ttagagagat caacaattat   2940
catcatgcac atgatgccta tctgaatgct gtggttggta cagcccttat caagaagtac   3000
cctaagctag agcgagtt tgtgtacgga gattataagg tgtatgatgt gaggaaaatg   3060
atcgctaaaa gtgagcaaga gattggaaag gctaccgcca aatacttctt ttattccaat   3120
attatgaatt tcttcaagac agaaatcacc ctggctaacg gcgagataag gaagaggccg   3180
cttatcgaaa ctaatgggga gacaggcgaa atagtgtggg acaaagggag ggatttcgca   3240
actgtgagga aggttttgag catgcctcag gtgaatatcg ttaagaaaac cgaagttcaa   3300
actggagggt tctctaagga aagcattctc cccaagagga actccgacaa gctgattgct   3360
agaaagaaag actgggaccc caagaagtat ggcggattcg actcacccac tgtggcatat   3420
agcgttctcg tggtggcaaa ggttgaaaag ggtaaatcca aaaaactcaa atccgtgaag   3480
gaactccttg gcataactat tatggaaagg agtagctttg aaaagaatcc catcgacttt   3540
ctcgaagcta agggctataa ggaagttaag aaggacctta taatcaaaact tccaaaatac   3600 tcccttttg agttggaaaa cggcagaaag agaatgttgg ccagtgccgg ggagcttcaa   3660
aagggcaacg aactggctct gcctagcaaa tatgtgaact ttttgtatct ggcatcacac   3720
tacgagaaac ttaaaggctc tcctgaggac aacgagcaaa aacagctctt tgttgaacag   3780
cataagcact acctcgacga gattattgag cagatcagcg agttctcaaa gagagttatt   3840
ctggctgacg ctaatcttga caaggttttg tccgcttaca caaacacag ggataagcca   3900 atcagggagc aggcagaaaa cataatccat ctctttaccc tgacaaacct cggtgccccc   3960
gctgctttca gtattttga tactaccatt gacaggaaga gatatacttc cactaaggaa   4020
gtgctcgacg caaccctcat acaccaaagt atcacaggcc tctatgaaac taggatagat   4080
ttgtctcaac ttgggggcga t                                             4101
```

<210> SEQ ID NO 68
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 68

```
gacaaaaagt attccatcgg gcttgctatc ggaaccaact ctgtggggtg ggcagttatt     60
accgacgaat acaaggtgcc cagcaagaag tttaaggttc tggggaacac agatagacat    120
agcataaaga aaaaccctgat aggcgcactg ttgttcgact ccggggaaac agccgaagct    180
accaggctga agagaactgc aagaagaagg tacaccagaa gaaaaaacag aatatgttat    240
```

```
ctccaagaga ttttctctaa cgagatggcc aaggtggacg actcattctt tcacagactg    300
gaagaatctt tccttgtgga agaagataag aaacacgaga ggcaccctat ttttggcaat    360
atcgtggatg aggtggctta ccacgaaaaa taccctacaa tataccacct caggaaaaaa    420
ttggttgata gtacagacaa ggccgacctc aggctcatct atttggccct ggcccatatg    480
attaaattca gggggcactt tctcatcgag ggagatttga accccgacaa cagtgatgtt    540
gataagctct ttattcagct cgtgcagact tacaatcagt tgtttgagga aaaccccatt    600
aatgcttccg gggtggacgc caaggcaatc ctttctgcaa gactctcaaa gtcaaggaga    660
ctcgaaaatc tgatagcaca gcttccagga gagaagaaga acgggctctt tggaaacctg    720
atcgctctgt cactcggact cacacccaat ttcaaaagca attttgattt ggcagaggac    780
gctaagctgc aactcagtaa ggatacctac gacgatgact tggataatct gctcgcacaa    840
attggggacc agtatgcaga cctgtttctc gcagctaaga acttgagtga cgccatattg    900
ctcagtgaca tcctcagggt taataccgag attacaaaag ctccactctc tgcaagcatg    960
atcaagaggt atgacgagca ccatcaagac ctgacactcc ttaaggcgtt ggttaggcag   1020
caacttcctg aaaagtataa ggaaatcttc ttcgatcaaa gcaaaaacgg ctacgccggc   1080
tatatagacg ggggagcatc ccaagaagaa ttttataagt tcataaaacc tatattggag   1140
aagatggacg ggacagagga attgctcgtg aaactgaaca gggaggatct cctcaggaag   1200
caaaggacct tcgacaatgg ctccatccca catcagattc acctcggcga actgcacgca   1260
atactgagaa acaagagga cttttatcct ttcctgaagg acaacaggga gaaaatcgag   1320
aaaatcttga cattcagaat cccatactac gttgggcctc tggccagagg taacagtagg   1380
ttcgcctgga tgactaggaa atcagaggag actattacac cctggaactt gaagaagtt    1440 gttgataagg gagcttcagc acaatcattc atcgaaagaa tgacaaactt gacaaaaat    1500 ctgcctaatg agaaagtgct cccaaaacat ccctgctgt atgagtattt taccgtttat    1560
aacgagctta ccaaggtgaa atacgttact gaaggtatga aaagccagc ttttctttca    1620 ggggagcaaa agaaggctat cgtggatctt ctctttaaga ccaacagaaa ggttaccgtg   1680
aagcagctta aggaagacta ctttaaaaag atcgagtgtt ttgactcagt ggaaataagc   1740
ggtgttgaag atagattcaa cgcatccttg gaacttatc atgatcttct taagataatc   1800
aaggataaag actttctcga caacgaggaa aacgaagata tactggagga catagttctg   1860
acacttactt tgttcgagga tagggagatg atcgaggaaa gactgaaaac atatgctcac   1920
cttttcgacg acaaagttat gaaacaactc aagagaagga gatatacagg gtgggggaga   1980
ttgagcagga aactgattaa tggtatcaga gacaaacagt caggaaaaac aatactcgac   2040
tttttgaaat cagacgggtt cgcaaatagg aatttcatgc agcttataca cgacgattca   2100
cttactttta agaggacat tcaaaaggct caagttagtg gacaaggtga ctccctccac   2160
gaacacatcg caaatctcgc tggcagccct gcaattaaga agggtatact ccagacagtt   2220
aaggttgttg acgagctggt aaagtgatg gaagacaca acccgagaa catagtgata   2280 gagatggcca gggaaaacca aaccactcaa aaagggcaga aaattccag agagaggatg   2340 aaaaggattg aagaaggtat caaggagctg gtagccaaa ttctgaaaga acatcctgtg   2400
gaaaacactc aactccagaa tgagaaactc tatctgtact atctgcaaaa tgggagagat   2460
atgtatgtgg accaggaact ggacataaac aggctctcag attacgatgt ggatcatatc   2520
gtgccacagt ccttttctta aggatgatagc atcgacaata aggtgcttac caggtccgac   2580
aagaacaggg gaaagtcaga taacgtgcct tctgaagaag ttgttaaaaa gatgaagaac   2640
```

```
tactggagac agctgcttaa cgctaagctc ataacacaga ggaagtttga caacttgacc    2700
aaggccgaga gaggcggact ctcagaattg gataaggcag ggttcataaa aaggcagctg    2760
gtggaaacaa ggcagataac taaacatgtg gctcagatcc tcgatagtag gatgaataca    2820
aaatacgatg agaacgacaa gctcataagg gaggttaaag tgataactct gaaatccaaa    2880
ctggttagcg attttaggaa ggatttccag ttttacaaag ttagggagat caacaattat    2940
catcacgccc acgatgccta cttgaacgca gttgtgggta ctgcacttat caaaaagtac    3000
cctaagctgg aatccgagtt tgtttatgga gactataagg tgtacgacgt tagaaaaatg    3060
attgcaaagt cagagcagga gatagggaaa gccactgcaa atatttctt ttatagcaat     3120 atcatgaatt tctttaagac agaaatcaca ctggccaatg gggaaataag gaagaggccc    3180
ctgatcgaaa ctaatggcga gacagggag attgtgtggg ataaaggtag ggactttgca     3240
acagtgagga aagtgctgag catgccccaa gttaatatcg ttaaaaagac cgaggttcaa    3300 acaggggggct ttagtaagga aagcattttg cccaagagga atagtgacaa attgattgct   3360
aggaaaaaag attgggaccc caaaaagtat ggcggatttg atagccccac tgttgcttac    3420
tccgtgctcg tggttgcaaa ggtggagaag ggaaagagca agaaactgaa gtcagttaag    3480
gaactccttg gtatcactat catggaaaga agctcctttg agaagaaccc tattgacttc    3540
ctggaggcta aagggtacaa agaggttaag aaagaccta tcattaaatt gcccaaatat     3600
agtcttttcg agcttgaaaa cggaagaaag aggatgcttg catccgctgg cgaattgcaa    3660
aagggcaatg agcttgctct cccttccaag tatgtgaact tcctttatct tgcctcacac    3720
tatgaaaaac tcaaaggttc acccgaagac aacgaacaaa agcaactatt tgtggaacaa    3780
cacaagcact acctggacga aatcattgag caaatttctg agttttcaaa aagggtaatc    3840
ttggctgacg caaatctcga caaagttttg tcagcttaca caaacatag agataagcca    3900 attagagagc aagctgagaa tatcatccat ctgtttaccc tgactaacct tggagcgcct    3960 gctgcttta aatatttcga caccacaatc gacaggaaga ggtacactag cactaaggaa    4020
gttctcgacg ccaccctcat ccaccagagt attacaggcc tgtacgagac aagaattgat    4080
ctttctcaac ttggtggtga c                                              4101
```

<210> SEQ ID NO 69
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 69

```
gataagaagt actcaatcgg tctggcaatc ggaaccaact ctgtgggttg ggcagtgatt      60
acagatgagt ataaggtgcc aagcaaaaaa ttcaaggtgc tgggtaatac cgacagacac     120
agcattaaga gaatttgat tggagcactc ctctttgact caggggaaac agcagaggca     180
acaaggctga agaggacagc aaggcggagg tacacaaggc ggaaaaacag gatatgctac     240
ctccaggaaa tctttagcaa cgagatggct aaagtggatg atagctttt ccatagactc     300 gaagaatcct tccttgttga gaggacaaa agcatgaaa ggcatccat cttcggcaat       360 atagttgatg aggttgcata ccatgagaag taccccacaa tctaccacct cagaaagaaa    420
cttgtggact ccacagataa agcagacctg aggctcatat acctcgcact cgcacacatg    480
atcaagttca gagggcactt tctcatcgaa ggtgacctga atccagataa ttcagatgtg    540
```

-continued

```
gataaactgt ttatacagct ggtgcaaaca tacaaccaac ttttcgagga aaacccaatc    600
aatgcctccg gtgttgatgc aaaggccatc ctgtcagcaa gactcagcaa aagcaggcgg    660
ctcgaaaacc tcatcgccca gcttcccggt gaaaagaaga acgggctctt tggtaatctc    720
atcgcattga gccttggtct tactccaaac ttcaagagca attttgatct ggcagaggat    780
gctaaactgc aactctcaaa ggacacatat gacgatgacc ttgacaatct gttggcccag    840
atcggggacc aatatgcaga cctcttcctg gccgcaaaga atctgtcaga tgcaatcctc    900
ttgtccgaca tactgagagt taacactgag atcacaaagg cacctctgtc cgcctccatg    960
attaagagat acgatgagca tcaccaggat ctgactttgc tcaaagcccct cgttagacag   1020 cagttgccag aaaagtacaa agaaatattc tttgatcaat caaaaaacgg atatgcaggg   1080
tacatcgacg gtggggcaag ccaggaagag ttctacaaat tcatcaaacc tatcctggaa   1140
aagatggatg ggacagaaga gctgctggtt aagctgaata gggaagacct cctcagaaag   1200
cagaggacat ttgataacgg gagcatccct catcaaatcc acctcggtga actccatgct   1260
atcctgagaa ggcaggaaga cttttatcca ttttttgaagg acaatagga gaaaatcgaa   1320 aaaatcctga cattcagaat cccatactac gttggtcctc tggcaagagg taacagtagg   1380
ttcgcatgga tgacaaggaa aagcgaggag acaatcacac cctggaattt tgaggaagtt   1440
gttgacaagg gtgccagcgc acaatccttt atcgaaagaa tgacaaattt cgacaagaat   1500
ctgcctaacg aaaaggttct cccaaagcat tcactcctgt acgaatattt tacagtttat   1560
aacgaactga ctaaagttaa atacgttacc gagggtatga ggaagccagc attccttttcc   1620 ggggaacaga agaaagctat tgtggacctc ctgttcaaga caaatagaaa agtgacagtt   1680
aagcaactca agaggattta cttcaaaaag atcgaatgtt ttgactctgt ggagatcagc   1740
ggggtggagg atagattcaa cgccagcctg ggtacatatc atgatctcct gaaaatcatt   1800
aaagacaagg acttccttga caacgaggag aacgaggaca ttctggaaga cattgttctg   1860
accctcacac tctttgagga tagggagatg attgaggaaa gactgaagac ctacgcccac   1920
ctctttgacg ataaagtgat gaaacagctc aagagaagaa ggtatacagg ttgggggaga   1980
ctgagcagga agttgatcaa tgggattagg gacaaacagt ccgggaaaac aatcctcgat   2040
tttctgaagt cagacggttt cgcaaacaga aattttatgc agctcattca cgatgacagc   2100
ttgacattca aggaagacat ccaaaaggct caagtgagcg ccaagggga tagcctccac   2160 gagcatattg caaatctggc aggttcacca gccatcaaaa agggcatact tcagacagtt   2220
aaggttgtgg acgaattggt taaagttatg ggcaggcata agccagagaa tatcgttatc   2280
gaaatggcaa gggagaacca acaactcaa aaagggcaga aaaatagcag agagaggatg   2340
aaaagaatcg aggaagggat caaggaactt gggtcccaaa tcctcaagga gcacccagtt   2400
gaaaatactc aactgcaaaa cgagaagctc tatctctact atctccaaaa cgggagggat   2460
atgtatgttg accaggagct ggatattaac agactgtcag attatgatgt tgatcatatc   2520 gtgcccagt cattcctgaa ggacgattcc atcgacaaca aagttctcac aaggtccgat   2580
aaaaacaggg gcaagtccga taacgttcca agcgaagaag tggtgaaaaa gatgaaaaac   2640
tattggagac aacttctgaa tgcaaagttg attactcaga gaaagtttga caacctcaca   2700
aaagcagaaa gaggcgggct tagcgaactc gataaggcag ggttatcaa aagacagctg   2760 gttgagacaa ggcagatcac aaaacatgtg gcacagatcc ttgactcaag gatgaatacc   2820
aagtatgatg agaatgataa gttgatcagg gaggttaaag ttatcacact caaatccaaa   2880
ctggtgtcag acttcaggaa agactttcaa ttttataagg tgagggagat caataactac   2940
```

```
caccatgcac atgacgccta cctgaacgca gtggtgggta cagcattgat taaaaaatac   3000
cctaagctgg agtctgagtt tgtgtacggg gactacaagg tgtacgacgt gaggaaaatg   3060
atagccaagt ccgagcagga gatcgggaaa gcaacagcta agtatttctt ttacagtaat   3120
atcatgaatt tctttaaaac tgagattact ctggcaaacg gggagatcag gaaaagaccc   3180
ctcatcgaga ctaatggtga aacaggtgag atcgtttggg acaaggggag ggattttgct   3240
actgttagaa aagttctgag tatgccacaa gtgaatattg tgaaaaagac agaagttcag   3300
acaggtgggt tctccaaaga atccatcctg cccaagagaa attcagacaa gctcatcgca   3360
agaaagaagg actgggaccc taagaagtac ggaggatttg acagccccac cgtggcctat   3420
tccgtgcttg ttgtggcaaa ggtggagaaa gggaagagca aaaaactgaa atccgtgaaa   3480
gaactgctgg gaattaccat catggaaaga agctcctttg agaagaaccc aatcgacttc   3540
ctggaagcaa aaggatataa ggaagtgaaa aaggacctca ttatcaagct cccaaaatac   3600
tcacttttcg agttggagaa cggtagaaag aggatgctgg caagcgcagg gaacttcag    3660
aaaggcaatg agctggcatt gccatcaaag tatgtgaact tcctctactt ggccagccat   3720
tacgagaaac ttaaaggtag cccagaagat aacgagcaaa aacagctctt tgtggaacag   3780
cataagcatt atctggatga gatcatagaa caaatctcag agttttccaa gagagttatc   3840
ctcgcagatg caaacctgga taaggttctc tcagcctata ataagcatag agacaagcca   3900
attagagagc aagcagagaa cattatccac ttgttcactc ttacaaacct ggggggcacca   3960
gccgccttca aatatttcga tacaacaata gacagaaaga ggtataccag caccaaagaa   4020
gttctcgacg ccacactgat ccatcaatca atcacaggcc tttacgaaac taggatcgac   4080
ttgtcacaac tgggtgggga t                                             4101

<210> SEQ ID NO 70
<211> LENGTH: 3307
<212> TYPE: DNA
<213> ORGANISM: Artificial sequence
<220> FEATURE:
<223> OTHER INFORMATION: Synthetic polynucleotide

<400> SEQUENCE: 70
gagcaaggac acctacgacg acgacttgga caacctattg gcccagatag gtgaccagta     60
tgcagacctc ttccttgcgg ccaagaactt gagtgacgct atactgctca gtgacatcct    120
gagggtgaac actgagatca ctaaggcccc tctctctgcc tcaatgatta agcgttacga    180
cgagcatcac caggatctca ccctgcttaa ggcccttgtt cggcagcagc tcctgagaa     240
gtacaaggag atatttttg accagtctaa gaacggctac gccggttaca ttgacggtgg    300
ggcaagccag gaggagttct acaagttcat caagccgatc cttgagaaga tggacggcac    360
cgaggagcta cttgtcaagt tgaaccggga agacctgctc cggaaacagc gtacattcga    420
caacggcagc atccctcacc agatccacct gggcgaacta cacgccatcc tccgacgtca    480
ggaggacttc tatccattct tgaaagataa cagggaaaaa atcgaaaaaa tacttacgtt    540
tcgaatacct tactacgtgg ggccccttgc tcggggaaac tccagattcg catggatgac    600
caggaagtca gaggagacca tcacaccctg gaactttgag gaggtggttg acaaaggtgc    660
ttctgcccag tccttcattg agcggatgac taacttcgac aagaacctgc ccaacgagaa    720
ggtgctgcca agcacagcc tgctctacga atactttact gtgtacaatg agctgacgaa    780
ggtgaagtac gtgacagagg ggatgcggaa gcccgctttc ctgagcggcg agcaaaaaaa    840
```

```
agcaatcgtg gacctactgt tcaagaccaa ccgaaaggtg acagtgaagc agctcaagga    900
ggactacttc aaaaaaatcg agtgcttcga ctctgttgag ataagcggcg tggaggaccg    960
attcaacgcc tcattgggaa cctatcacga cctgctcaag atcattaagg acaaggactt   1020
cctggataat gaggagaatg aggacatcct ggaggatatt gtgctgaccc ttactctatt   1080
cgaggacagg gagatgatcg aggagcgact caagacctac gctcacctgt tcgacgacaa   1140
ggttatgaag caattgaagc gtaggcgata cacggggtgg ggaagactct cccgaaaact   1200
gataaacggc atcagggaca agcagtcagg gaagacgatc ttggacttcc tgaaatccga   1260
cgggttcgcc aaccgcaact tcatgcagct cattcacgac gactcactaa cgttcaaaga   1320
ggacattcag aaggctcaag tcagtggaca aggcgactcc ctgcacgagc acattgcaaa   1380
ccttgcgggc tccccggcga ttaaaaaggg cattctccaa acggttaagg tggtggacga   1440
gctggtgaag gtgatgggcc gacacaagcc tgagaacatc gtgatcgaga tggccaggga   1500
gaaccagact acccagaagg gtcagaagaa ctctcgggaa cgtatgaagc gtattgagga   1560
ggggattaag gagttgggct ctcaaatcct caaggagcac cctgtggaga acactcagct   1620
ccaaaacgag aagctgtacc tgtactacct gcaaaacggg cgcgatatgt acgtggatca   1680
ggagttggac atcaacaggc ttagcgatta cgacgtggac cacatcgtgc cacagtcatt   1740
cttaaaggac gacagcatcg acaacaaggt tctgacgagg agcgacaaga atcgagggaa   1800
aagtgacaat gttccatccg aggaggtggt caagaaaatg aagaactatt ggcgtcagct   1860
tctgaacgcc aagctcatca cccagcggaa attcgacaac ctgactaagg ctgagcgagg   1920
cggactctcc gagcttgaca aggctggctt catcaagcgg cagttggtcg aaacccgaca   1980
gataacgaag cacgttgccc agatacttga ctcccgtatg aacaccaagt acgacgagaa   2040
cgacaagctc atcagggagg tgaaggtcat tacccttaag tccaaactcg tcagcgactt   2100
tcgtaaggac ttccagttct acaaggtgcg cgagatcaat aactaccacc acgcacacga   2160
cgcctacctg aacgcagtgg ttggaaccgc gttgattaaa aagtacccca agttggagtc   2220
ggagttcgtt tacggggact acaaggtgta cgacgttcgg aagatgatcg ccaagtctga   2280
acaggagatc gggaaagcaa ccgccaagta tttcttctat agcaacatca tgaacttctt   2340
taaaaccgag atcacacttg ccaatggcga gatccgtaag aggccgctga tcgagacaaa   2400
tggggagact ggcgagatcg tgtgggacaa gggccgcgac ttcgcaaccg ttcggaaagt   2460
cttgtccatg cctcaagtca acatcgtcaa gaagactgag gtgcaaacag gcgggttctc   2520
gaaggagtcc atactgccca agaggaactc agacaagctc atagcacgca aaaaagactg   2580
ggatccaaag aaatacggcg ggttcgactc gccgacagtc gcatactccg tgttagtggt   2640
ggctaaagtg gaaaaggga agtccaagaa gctcaagtcc gtcaaggagt tgctcgggat   2700
caccattatg gaacggtcct cattcgagaa gaatcccatt gacttcctag aggcgaaggg   2760
ctacaaagag gtcaaaaagg acctaattat taagctcccc aagtattcac tcttcgaact   2820
tgaaaatggt cgtaagcgga tgttggcaag cgctggagag cttcagaagg gaacgagct   2880
tgcactgcct tccaagtacg tgaacttcct gtacctcgcc tctcattacg agaagttgaa   2940
gggctcaccg gaggacaacg agcagaagca gttgttcgtg gagcagcaca gcactacct   3000
cgacgagatc attgagcaga taagtgagtt cagcaaacgg gtgatccttg ccgacgctaa   3060
cctggacaag gtgctgagcg cctacaacaa gcacagagac aagccgatcc gagagcaagc   3120
ggagaacatc atacacctgt tcaccctcac gaacctcggg gctcccgcag ccttcaaata   3180
ttttgacacg accatcgacc gtaaacgcta cactagcacg aaggaggtgc tggacgctac   3240
```

| | |
|---|---|
| ccttatccac cagtccatca ccggcctgta cgagacgaga atcgacttgt cgcagctcgg | 3300 |
| tggtgac | 3307 |

<210> SEQ ID NO 71
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 71

| | |
|---|---|
| gacaaaaaat actcaattgg tctggcaatt gggaccaaca gtgtcggatg ggccgtgatt | 60 |
| accgacgagt acaaggtgcc gtccaaaaaa ttcaaggtgc ttgggaacac cgaccgccac | 120 |
| tcgatcaaga aaaacctaat cggtgcgttg cttttcgaca gtggggagac cgccgaggca | 180 |
| acacgcttaa aacgcacagc taggaggaga tatacacggc gcaagaaccg aatatgctac | 240 |
| ttacaggaga tattctccaa tgagatggcg aaggtggacg actctttctt ccatcggctt | 300 |
| gaggaatcct tcctggtcga ggaggacaag aagcacgagc gacacccgat attcgggaac | 360 |
| atcgttgatg aggtggcgta ccacgagaag tacccaacga tataccactt acgcaagaag | 420 |
| ctcgtggact ctacggacaa ggccgacttg cgccttatct acttggcact ggcccacatg | 480 |
| attaagttcc gaggccactt ccttatcgag ggtgacctga ccccgataa ctccgacgtg | 540 |
| gacaagctct tcatccaact cgtccagaca tacaaccagc tattcgagga aatcctatc | 600 |
| aacgcctctg ggtggacgc taaagctatc ctctcagccc gcctgtcaaa gtcgaggagg | 660 |
| ttggagaacc taatcgccca gcttccaggc gagaagaaaa atgggctgtt cggaaacctt | 720 |
| atcgcactct cactgggcct aaccccgaac ttcaagtcca acttcgacct ggcagaggac | 780 |
| gcgaaattgc agttgtcgaa agacacctat gacgatgacc tggacaacct gttggcccag | 840 |
| atagggggacc agtacgccga cctgttccta gcggccaaga acctgtccga cgccatcttg | 900 |
| ctgtcggata tactgcgggt gaacaccgag atcactaaag cacctctctc cgccagcatg | 960 |
| attaagcgtt acgacgagca ccaccaagat ttgaccctgc taaaggcact tgtacggcag | 1020 |
| cagcttcccg agaagtacaa ggagatcttt ttcgaccaaa gcaagaacgg ctacgccggg | 1080 |
| tacatcgacg gaggtgccag ccaggaggag ttctacaagt tcattaagcc catcctggag | 1140 |
| aagatggacg ggactgagga actacttgtg aagctgaacc gggaagactt actacggaag | 1200 |
| cagcgtacct tcgacaacgg ttctatccca catcagatcc atcttgggga gttgcacgcg | 1260 |
| atcctgcgac gccaggagga cttttacccc ttcctgaaag acaaccgcga gaaaatcgag | 1320 |
| aagatactga ccttcagaat accttactac gtcggacccc ttgcgcgagg caactcaaga | 1380 |
| ttcgcgtgga tgaccaggaa atcagaggag accatcacac cctggaattt cgaggaggtg | 1440 |
| gttgacaagg gtgcctccgc ccagtccttt atcgaacgaa tgaccaactt cgacaagaac | 1500 |
| ttgcccaacg agaaggtgct ccccaaacac agcctcctct acgaatattt cacagtgtac | 1560 |
| aacgagctta ctaaagttaa gtatgttact gagggcatga ggaaaccgc cttcctgtca | 1620 |
| ggcgagcaga gaaagctat tgtggacctc cttttcaaga ccaaccggaa ggtgacagtg | 1680 |
| aagcagctca aggaggacta cttcaagaag atagagtgct cgacagcgt ggagatcagc | 1740 |
| ggggtggagg acagattcaa tgcctctctc ggaacatacc acgacttgct taagatcatc | 1800 |
| aaggacaagg acttcctcga caacgaggaa aacgaggata ttctggagga tattgttctg | 1860 |
| actcttaccc tgttcgagga ccgggagatg atcgaggagc gtctcaagac ctacgcccac | 1920 |

```
ctgttcgacg acaaagttat gaagcagctc aagcgtcgga gatataccgg atggggccgt    1980
ctgtctcgga agctcatcaa cgggatcagg gacaagcagt cagggaagac gatcttagac    2040
ttccttaagt ctgacggctt cgccaacagg aacttcatgc agttgatcca cgacgacagc    2100
cttaccttca aggaggacat ccagaaggcc caagtgagtg gccagggtga cagcctccac    2160
gagcatattg ctaatcttgc gggttcccca gcgattaaaa agggcatact tcaaaccgtt    2220
aaggtggtgg acgagcttgt caaggtgatg gggcgacaca gcccgagaa catcgtgatc     2280
gagatggcca gggagaacca gaccacccag aaggggcaga agaatagccg agaacgcatg    2340
aagcgcatcg aggagggggat taaggagcta gggagccaga tcctcaagga acatcccgtc   2400
gagaacaccc agctccagaa cgagaagcta tacctctact acttgcaaaa cgggagggat    2460
atgtacgtgg atcaggagtt ggacattaac cgcctaagcg actacgacgt agatcacatc    2520
gtgcctcagt cattcctcaa agacgacagc attgacaaca aagtcttgac ccgatccgac    2580
aagaaccgag gaaaatccga caatgtgccc tcagaggagg tcgtcaagaa aatgaagaac    2640
tattggaggc agctacttaa cgccaaactc ataacccagc ggaagttcga caacctgaca    2700
aaggctgagc ggggtgggct cagcgagctt gacaaggctg gcttcatcaa gcggcagttg    2760
gtggagacaa gacagataac gaagcacgtg gctcagatcc tggactctcg catgaacacg    2820
aagtacgacg agaacgacaa attgatccgc gaggtcaagg ttattacgct caagagcaaa    2880
cttgtcagcg atttccgcaa ggacttccag ttctacaagg tgaggagat taacaactac     2940
caccatgcac atgatgccta cttgaacgca gtggtgggga ccgcgcttat taaaaagtac    3000
cctaagttgg agtcagagtt cgtttatggg gactacaagg tgtacgacgt ccggaagatg    3060
attgcaaagt ctgaacagga aatcgggaag gccaccgcca aatatttctt ctacagtaac    3120
attatgaatt tttttaagac tgaaattact ctcgcaaacg gcgagatcag gaagcgtccc    3180
ctcatcgaga caaacgggga gaccggggag atagtctggg acaaggggcg ggacttcgct    3240
acggtgagga aggtgctctc gatgccacaa gtgaacatcg tcaaaaagac agaggtgcag    3300
accggtggct tctcaaagga gtcaatcctg ccaaaacgta acagcgacaa gctcatcgcc    3360
cgcaagaaag actgggaccc taagaagtat ggtgggttcg actcaccgac ggtcgcatac    3420
tccgttctgg tcgtggcaaa ggtggaaaag ggcaagtcca aaaaactgaa atccgtgaag    3480
gagttgcttg gcattaccat catggaacgc agcagcttcg agaagaaccc cattgacttc    3540
ctggaggcta aagggtacaa ggaggtcaag aaagatttaa ttattaagct acctaagtac    3600
agcttgttcg agctggagaa cggccgaaaa cgaatgctcg catccgccgg ggaacttcaa    3660
aagggcaacg agcttgcgct gccctccaag tacgtgaact tcctgtactt ggcatccac    3720
tacgagaaac tcaagggtag cccagaggac aacgagcaga agcagctatt cgtggagcag    3780
cacaagcact acctcgacga gataatcgag cagatcagtg agttcagtaa gcgggtgata    3840
ctcgcggacg ccaacttgga caaggtgctt agtgcctaca acaagcaccg tgacaagccc    3900
atccgagaac aggctgagaa catcatccac ctttcactc tgacaaacct cggtgctccc     3960
gccgccttca aatacttcga cactaccatc gacaggaagc gctacacatc tacgaaggaa    4020
gttcttgacg ctacgcttat tcatcagtct atcacagggc tgtacgagac aaggatcgac    4080
cttagccaac tcggcgggga t                                              4101
```

<210> SEQ ID NO 72
<211> LENGTH: 427
<212> TYPE: PRT
<213> ORGANISM: Triticum aestivum

<400> SEQUENCE: 72

```
Met Ala Pro Gly Ala Gly Thr Ala Ala Thr Lys Asn Pro Thr Lys
1               5                   10                  15

Thr Leu Ala Ala Ile Leu Leu Val Leu Leu Ala Asp Leu Pro
                20                  25                  30

Leu Cys Ala Ser Gln Pro Leu His Ser Gln Pro Leu Pro Ala Thr
            35                  40                  45

Gln Ser Pro Ala Ala Pro Leu Pro Pro Gln Pro Ser Ala Pro His
    50                  55                  60

Ala Arg Ala Gly Gly Ala Ala Arg Leu Arg Ile Ala Leu Gly Val
65                  70                  75                  80

Leu Leu Gly Ser Leu Ala Gly Phe Leu Leu Ser Leu Ala Phe Leu Tyr
                85                  90                  95

Ala Ile Arg Val Ala Val Leu His Ala Gly Asn Ala Pro Ala Val Ala
                100                 105                 110

Arg Gly Pro Val Ser Phe Thr Pro Gln Ile Ser Pro Lys Ser Leu Gln
            115                 120                 125

Gly Ala Leu Pro Ser Ala Arg Pro Leu Ala Arg Gly Pro Arg Gly Thr
130                 135                 140

Tyr His Lys Leu Asp Leu Asp Gly Asp Leu Thr Val Ala Val Lys Val
145                 150                 155                 160

Leu Asp Leu Ala Ala Ala Ser Arg Ala Glu Ala Ser Pro Ser Pro Ser
                165                 170                 175

Arg Pro Ala Asn Gly Ser Asn Ser Lys Ser Asp Met Arg Arg Val Gln
            180                 185                 190

Arg Gln Leu Glu Leu Leu Ala Arg Val Arg His Leu Asn Val Met Ser
        195                 200                 205

Leu Lys Ala Tyr Val Arg Asp Ala Asp Arg Leu Ser Leu Val Tyr Asp
210                 215                 220

Phe Val Pro Gly Gly Ser Leu Glu Asp Val Met Lys Arg Val Arg Ser
225                 230                 235                 240

Gln Gln Val Ser Leu Ser Trp Asp Thr Arg Asn Arg Ile Ala Ala Gly
                245                 250                 255

Val Ala Lys Gly Leu Arg His Leu His Phe Glu Cys Asn Pro Arg Ile
            260                 265                 270

Leu His Cys Asn Leu Lys Pro Ser Asn Val Met Leu Glu Glu Gly Phe
        275                 280                 285

Glu Pro Val Leu Ala Asp Cys Gly Val Ala Arg Leu Ile Asp Ser Gly
    290                 295                 300

Ser Pro Asp Pro Gln Ser Ser Gly Ser Leu Tyr Thr Ala Pro Glu Cys
305                 310                 315                 320

Tyr Gln Ser Ser Arg Tyr Thr Asp Lys Cys Asp Val Tyr Ala Phe Gly
                325                 330                 335

Met Ile Leu Gly Val Leu Leu Thr Gly Lys Asp Pro Ser Asp Pro Phe
            340                 345                 350

Phe Ser Gly Glu Ser Gly Arg Gly Ser Leu Ala Arg Trp Leu Arg His
        355                 360                 365

Met Gln His Ser Gly Asp Met Lys Glu Ala Leu Asp Ser Ser Ile Val
    370                 375                 380

Gly Glu Glu Val Asp Glu Glu Met Val Met Ala Ile Arg Ile Ala
385                 390                 395                 400

Ile Val Cys Leu Ser Glu Leu Pro Ala Asp Arg Pro Ser Ser Asp Glu
```

```
                            405                 410                 415
Leu Val Ala Met Leu Ala Gln Leu His Ser Phe
                420                 425

<210> SEQ ID NO 73
<211> LENGTH: 427
<212> TYPE: PRT
<213> ORGANISM: Triticum dicoccoides

<400> SEQUENCE: 73

Met Ala Pro Gly Ala Gly Thr Ala Ala Thr Lys Asn Pro Thr Lys
1               5                   10                  15

Thr Leu Ala Ala Ile Leu Leu Val Leu Leu Ala Asp Leu Pro
                20                  25                  30

Leu Cys Ala Ser Gln Pro Pro Leu His Ser Gln Pro Leu Ala Thr
            35                  40                  45

Gln Ser Pro Ala Ala Pro Leu Pro Pro Gln Pro Ser Ala Pro His
    50                  55                  60

Ala Arg Ala Gly Gly Ala Ala Arg Leu Arg Arg Ile Ala Leu Gly Val
65                  70                  75                  80

Leu Leu Gly Ser Leu Ala Gly Phe Leu Leu Ser Leu Ala Phe Leu Tyr
                85                  90                  95

Ala Ile Arg Val Ala Val Leu His Ala Gly Asn Ala Pro Ala Val Ala
                100                 105                 110

Arg Gly Pro Val Ser Phe Thr Pro Gln Ile Ser Pro Lys Ser Leu Gln
            115                 120                 125

Cys Ala Leu Pro Ser Ala Arg Pro Leu Ala Arg Gly Pro Arg Gly Thr
130                 135                 140

Tyr His Lys Leu Asp Leu Asp Gly Asp Leu Thr Val Ala Val Lys Val
145                 150                 155                 160

Leu Asp Leu Ala Ala Ala Ser Arg Ala Glu Ala Ser Pro Ser Pro Ser
                165                 170                 175

Arg Pro Ala Asn Gly Ser Asn Ser Lys Ser Asp Met Arg Arg Val Gln
            180                 185                 190

Arg Gln Leu Glu Leu Leu Ala Arg Val Arg His Leu Asn Val Met Ser
        195                 200                 205

Leu Lys Ala Tyr Val Arg Asp Ala Asp Arg Leu Ser Leu Val Tyr Asp
210                 215                 220

Phe Val Pro Gly Gly Ser Leu Glu Asp Val Met Lys Arg Val Arg Ser
225                 230                 235                 240

Gln Gln Val Ser Leu Ser Trp Asp Thr Arg Asn Arg Ile Ala Ala Gly
                245                 250                 255

Val Ala Lys Gly Leu Arg His Leu His Phe Glu Cys Asn Pro Arg Ile
            260                 265                 270

Leu His Cys Asn Leu Lys Pro Ser Asn Val Met Leu Glu Glu Gly Phe
        275                 280                 285

Glu Pro Val Leu Ala Asp Cys Gly Val Ala Arg Leu Ile Asp Ser Gly
    290                 295                 300

Ser Pro Asp Pro Glu Ser Ser Gly Ser Leu Tyr Thr Ala Pro Glu Cys
305                 310                 315                 320

Tyr Gln Ser Ser Arg Tyr Thr Asp Lys Cys Asp Val Tyr Ala Phe Gly
                325                 330                 335

Met Ile Leu Gly Val Leu Leu Thr Gly Lys Asp Pro Ser Asp Pro Phe
            340                 345                 350
```

```
Phe Ser Gly Glu Ser Gly Arg Gly Ser Leu Ala Arg Trp Leu Arg His
            355                 360                 365

Met Gln His Ser Gly Asp Met Lys Glu Ala Leu Asp Ser Ser Ile Val
    370                 375                 380

Gly Glu Glu Val Asp Glu Glu Met Val Met Ala Val Arg Ile Ala
385                 390                 395                 400

Ile Val Cys Leu Ser Glu Leu Pro Ala Asp Arg Pro Ser Ser Asp Glu
                405                 410                 415

Leu Val Ala Met Leu Ala Gln Leu His Ser Phe
            420                 425

<210> SEQ ID NO 74
<211> LENGTH: 427
<212> TYPE: PRT
<213> ORGANISM: Triticum aestivum

<400> SEQUENCE: 74

Met Ala Pro Gly Ala Gly Thr Ala Ala Ala Lys Asn Pro Thr Lys
1               5                   10                  15

Thr Leu Ala Ala Thr Leu Leu Val Leu Leu Ala Asp Leu Pro
            20                  25                  30

Leu Cys Ala Ser Gln Pro Pro Leu His Ser Gln Pro Leu Pro Ala Thr
            35                  40                  45

Gln Ser Pro Ala Ala Pro Leu Pro Pro Gln Pro Arg Ala Pro His
    50                  55                  60

Ala Arg Ala Gly Gly Ala Ala Arg Leu Arg Arg Ile Ala Leu Gly Val
65                  70                  75                  80

Leu Leu Gly Ser Leu Ala Gly Phe Leu Leu Ser Leu Ala Phe Leu Tyr
                85                  90                  95

Ala Ile Arg Val Ala Val Leu His Ala Gly Asn Ala Pro Ala Val Ala
            100                 105                 110

Arg Gly Pro Val Ser Phe Thr Pro Gln Ile Ser Pro Lys Ser Leu Gln
            115                 120                 125

Cys Ala Leu Pro Ser Ala Arg Pro Leu Ala Arg Gly Pro Arg Gly Thr
    130                 135                 140

Tyr His Lys Leu Asp Leu Asp Gly Asp Val Thr Val Ala Val Lys Val
145                 150                 155                 160

Leu Asp Leu Ala Ala Ala Ser Arg Ala Ser Pro Ser Pro Ser Pro Ser
                165                 170                 175

Pro Ser Arg Pro Ala Ser Gly Ser Lys Ser Asp Met Arg Arg Val Gln
            180                 185                 190

Arg Gln Leu Glu Leu Leu Ala Arg Val Arg His Leu Asn Val Met Ser
    195                 200                 205

Leu Lys Ala Tyr Val Arg Asp Ala Asp Arg Leu Ser Leu Val Tyr Asp
            210                 215                 220

Phe Val Pro Gly Gly Ser Leu Glu Asp Val Met Lys Arg Val Arg Ser
225                 230                 235                 240

Gln Gln Val Ser Leu Ser Trp Asp Thr Arg Asn Arg Ile Ala Gly
                245                 250                 255

Val Ala Lys Gly Leu Arg His Leu His Phe Glu Cys Asn Pro Arg Ile
            260                 265                 270

Leu His Cys Asn Leu Lys Pro Ser Asn Val Met Leu Glu Glu Gly Phe
            275                 280                 285

Glu Pro Val Leu Ala Asp Cys Gly Val Ala Arg Leu Leu Asp Ser Gly
    290                 295                 300
```

```
Ser Pro Asp Pro Glu Ser Ser Gly Ser Leu Tyr Thr Ala Pro Glu Cys
305                 310                 315                 320

Tyr Gln Ser Ser Arg Tyr Thr Asp Lys Cys Asp Val Tyr Ala Phe Gly
            325                 330                 335

Met Ile Leu Gly Val Leu Leu Thr Gly Lys Asp Pro Ala Asp Leu Phe
            340                 345                 350

Phe Ser Gly Glu Ser Gly Arg Gly Ser Leu Ala Arg Trp Leu Arg His
            355                 360                 365

Met Gln His Ser Gly Asp Met Lys Glu Ala Leu Asp Ser Ser Ile Val
            370                 375                 380

Gly Glu Glu Val Asp Glu Glu Met Val Met Ala Val Arg Val Ala
385                 390                 395                 400

Ile Val Cys Leu Ser Glu Leu Pro Ala Asp Arg Pro Ser Ser Asp Glu
            405                 410                 415

Leu Val Ala Met Leu Ala Gln Leu His Ser Phe
            420                 425

<210> SEQ ID NO 75
<211> LENGTH: 429
<212> TYPE: PRT
<213> ORGANISM: Aegilops tauschii

<400> SEQUENCE: 75

Met Ala Pro Gly Ala Gly Thr Ala Ala Ala Lys Asn Pro Thr Lys
1               5                   10                  15

Thr Leu Ala Ala Thr Leu Leu Val Leu Leu Ala Asp Leu Pro
            20                  25                  30

Leu Cys Ala Ser Gln Pro Pro Leu His Ser Gln Pro Leu Pro Ala Thr
            35                  40                  45

Gln Ser Pro Ala Ala Pro Leu Pro Pro Gln Pro Arg Ala Pro His
    50                  55                  60

Ala Arg Ala Gly Gly Ala Ala Arg Leu Arg Ile Ala Leu Gly Val
65                  70                  75                  80

Leu Leu Gly Ser Leu Ala Gly Phe Leu Leu Ser Leu Ala Phe Leu Tyr
            85                  90                  95

Ala Ile Arg Val Ala Val Leu His Ala Gly Asn Ala Pro Ala Val Ala
            100                 105                 110

Arg Gly Pro Val Ser Phe Thr Pro Gln Ile Ser Pro Lys Ser Leu Gln
            115                 120                 125

Cys Ala Leu Pro Ser Ala Arg Pro Leu Ala Arg Gly Pro Arg Gly Thr
130                 135                 140

Tyr His Lys Leu Asp Leu Asp Gly Asp Val Thr Val Ala Val Lys Val
145                 150                 155                 160

Leu Asp Leu Ala Ala Ala Ser Arg Ala Ser Pro Ser Pro Ser Pro Ser
            165                 170                 175

Pro Ser Pro Ser Arg Pro Ala Ser Gly Ser Lys Ser Asp Met Arg Arg
            180                 185                 190

Val Gln Arg Gln Leu Glu Leu Leu Ala Arg Val Arg His Leu Asn Val
            195                 200                 205

Met Ser Leu Lys Ala Tyr Val Arg Asp Ala Asp Arg Leu Ser Leu Val
            210                 215                 220

Tyr Asp Phe Val Pro Gly Gly Ser Leu Glu Asp Val Met Lys Arg Val
225                 230                 235                 240

Arg Ser Gln Gln Val Ser Leu Ser Trp Asp Thr Arg Asn Arg Ile Ala
```

-continued

```
                  245                 250                 255
Ala Gly Val Ala Lys Gly Leu Arg His Leu His Phe Glu Cys Asn Pro
            260                 265                 270

Arg Ile Leu His Cys Asn Leu Lys Pro Ser Asn Val Met Leu Glu Glu
        275                 280                 285

Gly Phe Glu Pro Val Leu Ala Asp Cys Gly Val Ala Arg Leu Leu Asp
    290                 295                 300

Ser Gly Ser Pro Asp Pro Glu Ser Ser Gly Ser Leu Tyr Thr Ala Pro
305                 310                 315                 320

Glu Cys Tyr Gln Ser Ser Arg Tyr Thr Asp Lys Cys Asp Val Tyr Ala
                325                 330                 335

Phe Gly Met Ile Leu Gly Val Leu Leu Thr Gly Lys Asp Pro Ala Asp
            340                 345                 350

Leu Phe Phe Ser Gly Glu Ser Gly Arg Gly Ser Leu Ala Arg Trp Leu
        355                 360                 365

Arg His Met Gln His Ser Gly Asp Met Lys Glu Ala Leu Asp Ser Ser
    370                 375                 380

Ile Val Gly Glu Glu Val Asp Glu Glu Met Val Met Ala Val Arg
385                 390                 395                 400

Val Ala Ile Val Cys Leu Ser Glu Leu Pro Ala Asp Arg Pro Ser Ser
                405                 410                 415

Asp Glu Leu Val Ala Met Leu Ala Gln Leu His Ser Phe
            420                 425

<210> SEQ ID NO 76
<211> LENGTH: 428
<212> TYPE: PRT
<213> ORGANISM: Triticum aestivum

<400> SEQUENCE: 76

Met Ala Thr Gly Ala Gly Thr Ala Ala Ala Ala Lys Asn Pro Thr
1               5                   10                  15

Lys Thr Leu Ala Thr Leu Leu Leu Val Leu Leu Leu Ala Asp Leu
            20                  25                  30

Pro Leu Cys Ala Ser Gln Pro Leu His Ser Gln Pro Leu Pro Ala
        35                  40                  45

Thr Gln Ser Pro Ala Ala Pro Leu Pro Pro Gln Pro Arg Gly Pro
    50                  55                  60

Arg Ala Gln Ala Gly Gly Ala Ala Arg Leu Arg Arg Ile Ala Leu Gly
65                  70                  75                  80

Val Leu Leu Gly Ser Leu Ala Gly Phe Ile Leu Ser Leu Ala Phe Leu
                85                  90                  95

Tyr Ala Ile Arg Val Ala Val Leu His Ala Gly Asn Ala Pro Ala Val
            100                 105                 110

Ala Arg Gly Pro Val Ser Phe Thr Pro Gln Ile Ser Pro Lys Ser Leu
        115                 120                 125

Gln Cys Ala Leu Pro Ser Ala Arg Pro Leu Ala Arg Gly Pro Arg Gly
    130                 135                 140

Thr Tyr His Lys Leu Asp Leu Asp Gly Asp Leu Thr Val Ala Val Lys
145                 150                 155                 160

Val Leu Asp Leu Ala Ala Ala Gly Ala Ser Pro Ser Pro Ser Pro
                165                 170                 175

Ser Pro Ser Arg Pro Ala Ser Gly Ser Lys Ser Asp Met Arg Arg Val
            180                 185                 190
```

Gln Arg Gln Leu Glu Leu Leu Ala Arg Val Arg His Leu Asn Val Met
            195                 200                 205

Ser Leu Lys Ala Tyr Val Arg Asp Ala Asp Arg Leu Ser Leu Val Tyr
210                 215                 220

Asp Phe Val Pro Gly Gly Ser Leu Glu Asp Val Met Lys Arg Val Arg
225                 230                 235                 240

Ser Gln Gln Val Ser Leu Ser Trp Asp Thr Arg Asn Arg Ile Ala Ala
            245                 250                 255

Gly Val Ala Lys Gly Leu Arg His Leu His Phe Glu Cys Asn Pro Arg
            260                 265                 270

Ile Leu His Cys Asn Leu Lys Pro Ser Asn Val Met Leu Glu Glu Gly
            275                 280                 285

Phe Glu Pro Val Leu Ala Asp Cys Gly Val Ala Arg Leu Leu Asp Ser
            290                 295                 300

Gly Ser Pro Asp Pro Glu Ser Ser Gly Ser Leu Tyr Ala Ala Pro Glu
305                 310                 315                 320

Cys Tyr Gln Ser Ser Arg Tyr Thr Asp Lys Cys Asp Val Tyr Ala Phe
            325                 330                 335

Gly Met Ile Leu Gly Val Leu Leu Thr Gly Lys Asp Pro Ala Asp Pro
            340                 345                 350

Phe Phe Ser Gly Glu Ser Gly Arg Gly Ser Leu Ala Arg Trp Leu Arg
            355                 360                 365

His Met Gln His Ser Gly Asp Thr Lys Glu Ala Leu Asp Ser Ser Ile
            370                 375                 380

Val Gly Glu Glu Val Asp Glu Glu Met Val Met Ala Val Arg Val
385                 390                 395                 400

Ala Ile Val Cys Leu Ser Glu Leu Pro Ala Asp Arg Pro Ser Ser Asp
            405                 410                 415

Glu Leu Val Ala Met Leu Ala Gln Leu His Ser Phe
            420                 425

<210> SEQ ID NO 77
<211> LENGTH: 428
<212> TYPE: PRT
<213> ORGANISM: Triticum dicoccoides

<400> SEQUENCE: 77

Met Ala Pro Gly Ala Gly Thr Ala Ala Ala Ala Lys Asn Pro Thr
1               5                   10                  15

Lys Thr Leu Ala Thr Leu Leu Leu Val Leu Leu Leu Ala Asp Leu
                20                  25                  30

Pro Leu Cys Ala Ser Gln Pro Leu His Ser Gln Pro Leu Ser Ala
                35                  40                  45

Thr Gln Ser Pro Ala Ala Pro Leu Pro Pro Gln Pro Arg Pro Pro
            50                  55                  60

Arg Ala Gln Ala Gly Gly Ala Ala His Leu Arg Arg Ile Ala Leu Gly
65                  70                  75                  80

Val Leu Leu Gly Ser Leu Ala Gly Phe Leu Leu Ser Leu Ala Phe Leu
                85                  90                  95

Tyr Ala Ile Arg Val Ala Val Leu His Ala Gly Asn Ala Pro Ala Val
                100                 105                 110

Ala Arg Gly Pro Val Ser Phe Thr Pro Gln Ile Ser Pro Lys Ser Leu
            115                 120                 125

Gln Cys Ala Leu Pro Ser Ala Arg Pro Leu Ala Arg Gly Pro Arg Gly
            130                 135                 140

Thr Tyr His Lys Leu Asp Leu Asp Gly Asp Leu Thr Val Ala Val Lys
145                 150                 155                 160

Val Leu Asp Leu Ala Ala Ala Arg Ala Ser Pro Ser Pro Ser Pro
            165                 170                 175

Ser Pro Ser Arg Pro Ala Ser Gly Ser Lys Ser Asp Met Arg Arg Val
        180                 185                 190

Gln Arg Gln Leu Glu Leu Leu Ala Arg Val Arg His Leu Asn Val Met
        195                 200                 205

Ser Leu Lys Ala Tyr Val Arg Asp Ala Asp Arg Leu Ser Leu Val Tyr
        210                 215                 220

Asp Phe Val Pro Gly Gly Ser Leu Glu Asp Val Met Lys Arg Val Arg
225                 230                 235                 240

Ser Gln Gln Val Ser Leu Ser Trp Asp Thr Arg Asn Arg Ile Ala Ala
                245                 250                 255

Gly Val Ala Lys Gly Leu Arg His Leu His Phe Glu Cys Asn Pro Arg
            260                 265                 270

Ile Leu His Cys Asn Leu Lys Pro Ser Asn Val Met Leu Glu Glu Gly
        275                 280                 285

Phe Glu Pro Val Leu Ala Asp Cys Gly Val Ala Arg Leu Ile Asp Ser
290                 295                 300

Gly Leu Pro Asp Pro Glu Ser Ser Gly Ser Leu Tyr Ala Ala Pro Glu
305                 310                 315                 320

Cys Tyr Gln Ser Asn Arg Tyr Thr Asp Lys Cys Asp Val Tyr Ala Phe
                325                 330                 335

Gly Met Ile Leu Gly Val Leu Leu Thr Gly Lys Asp Pro Ala Asp Pro
            340                 345                 350

Phe Phe Ser Gly Glu Ser Gly Arg Gly Ser Leu Ala Arg Trp Leu Arg
        355                 360                 365

His Met Gln His Ser Gly Asp Thr Lys Glu Ala Leu Asp Ser Ser Ile
        370                 375                 380

Val Gly Glu Glu Val Asp Glu Glu Met Val Met Ala Val Arg Val
385                 390                 395                 400

Ala Ile Val Cys Leu Ser Glu Leu Pro Ala Asp Arg Pro Ser Ser Asp
                405                 410                 415

Glu Leu Val Ala Met Leu Ala Gln His His Ser Phe
            420                 425

<210> SEQ ID NO 78
<211> LENGTH: 420
<212> TYPE: PRT
<213> ORGANISM: Brachypodium distachyon

<400> SEQUENCE: 78

Met Ala Arg Gly Gly Val Val Gly Lys Lys Asn Pro Thr Lys
1               5                   10                  15

Thr Leu Ala Ala Ile Leu Leu Leu Leu Leu Ala Val Phe Pro
            20                  25                  30

Arg Pro Ala Ala Ser Gln Pro Leu His Ser Glu Pro Met Ser Thr Gln
        35                  40                  45

Gln Ser Pro Pro Pro Gln Gln Gln Ser Lys Ile Pro His Ala Gln
        50                  55                  60

Pro Gly Gly Gly Ala Ala Arg Leu Arg Arg Ile Ala Leu Gly Val Leu
65                  70                  75                  80

Phe Gly Ser Leu Thr Gly Phe Leu Leu Ser Leu Ala Leu Leu Tyr Ala 85                  90                  95
Ile Arg Leu Thr Val Leu His Ala Arg Asp Ala Pro Ala Ile Ala Lys
            100                 105                 110

Gly Pro Val Ser Phe Thr Pro Gln Ile Ser Pro Lys Asn Leu Leu Cys
            115                 120                 125

Ala Leu Pro Ala Ala Gln Pro Leu Ala His Gly Thr Tyr His Lys Leu
        130                 135                 140

Ala Leu Asp Gly Gly Leu Thr Val Ala Val Lys Arg Leu Glu Ser Val
145                 150                 155                 160

Ala Ala Asn Arg Pro Glu Ala Ser Pro Ser Ala Pro Pro Asn Gly
                165                 170                 175

Ser Lys Ser Asp Met Arg Arg Val Gln Arg Gln Leu Glu Val Leu Ala
            180                 185                 190

Arg Val Arg His Gln Ser Val Met Ser Leu Lys Ala Tyr Val Arg Glu
            195                 200                 205

Val Asp Arg Leu Ser Leu Val Tyr Asn Phe Val Pro Gly Gly Ser Leu
        210                 215                 220

Glu Asp Val Met Lys Arg Val Arg Ser Gln Gln Leu Ser Leu Asp Trp
225                 230                 235                 240

Asp Thr Arg Ser Arg Ile Ala Ala Gly Val Ala Lys Gly Leu Arg Tyr
                245                 250                 255

Leu His Phe Glu Cys Cys Pro Ser Ile Leu His Cys Asn Leu Lys Pro
            260                 265                 270

Ser Asn Val Met Leu Asp Glu Gly Phe Glu Pro Ile Leu Ala Asp Cys
            275                 280                 285

Gly Val Ala Ser Leu Ile Asp Ser Gly Pro Ala Asp Pro Glu Ser Phe
        290                 295                 300

Gly Ser Val Tyr Ala Ala Pro Glu Phe Tyr Gln Asn Ser Arg Tyr Thr
305                 310                 315                 320

Asp Lys Cys Asp Val Tyr Ala Phe Gly Met Ile Leu Gly Val Leu Leu
                325                 330                 335

Thr Gly Arg Asp Pro Lys Asp Pro Phe Phe Ser Gly Glu Ala Gly Arg
            340                 345                 350

Gly Gly Leu Ala Arg Trp Leu Arg His Met Gln His Ser Gly Glu Ala
            355                 360                 365

Lys Glu Ala Leu Asp Ser Ser Ile Leu Gly Glu Val Cys Glu Glu
        370                 375                 380

Glu Met Leu Met Ala Ile Arg Val Ala Ile Val Cys Leu Ser Asp Leu
385                 390                 395                 400

Pro Ala Asp Arg Pro Ser Ser Asp Glu Leu Val Ala Met Leu Ala Gln
                405                 410                 415

Leu His Ser Leu
            420

<210> SEQ ID NO 79
<211> LENGTH: 421
<212> TYPE: PRT
<213> ORGANISM: Oryza brachyantha

<400> SEQUENCE: 79

Met Glu Glu Gly Gly Gly Met Met Ala Ser Lys Asn Pro Thr Lys Thr
1               5                   10                  15

Leu Ala Ile Leu Leu Leu Val Leu Val Phe Phe Leu Leu Ser Leu Cys
            20                  25                  30

Ser Leu Ala Ala Ser Gln Pro Leu His Ser Glu Pro Met Ser Thr Ala
            35                  40                  45

Glu Tyr Ser Pro Pro Pro Ser Pro Pro Pro Gln Ser Lys Ile Pro
 50                  55                  60

His Ala Gln Ala Gly Gly Ala Ala Arg Leu Arg Arg Ile Val Leu Gly
 65                  70                  75                  80

Val Leu Phe Gly Ser Leu Thr Gly Phe Leu Leu Ala Leu Ala Phe Leu
                 85                  90                  95

Tyr Ala Ile Arg Val Ala Ile Leu His Ala Lys Tyr Ala Pro Ala Ile
                100                 105                 110

Ile Lys Gly Pro Val Ser Phe Thr Pro Gln Ile Ser Pro Lys Asn Leu
            115                 120                 125

Gln Ser Ala Leu Pro Ser Ala Gln Pro Leu Thr His Gly Pro Asn Gly
130                 135                 140

Lys Tyr Tyr Lys Leu Val Leu Asp Asn Asp Val Thr Val Ala Val Lys
145                 150                 155                 160

Arg Leu Glu Ala Ala Ser Arg Pro Glu Ala Ser Pro Ser Met Pro Asn
                165                 170                 175

Val Ser Lys Ser Asp Met Arg Arg Val Gln Arg Gln Leu Glu Leu Leu
            180                 185                 190

Ala Arg Val Arg His Gln Asn Val Met Ala Leu Lys Ala Tyr Val Arg
            195                 200                 205

Glu Ala Asp Arg Leu Ser Leu Ala Tyr Asp Phe Val Pro Gly Gly Ser
        210                 215                 220

Leu Glu Asp Met Met Lys Arg Val Arg Ser Gln Gln Val Asn Leu Asn
225                 230                 235                 240

Trp Asp Ala Arg Asn Arg Ile Ala Ile Gly Val Ala Lys Gly Leu Arg
                245                 250                 255

Tyr Leu His Phe Glu Cys Asn Pro Arg Ile Leu His Ser Asn Leu Lys
                260                 265                 270

Pro Ser Asn Val Met Leu Asp Glu Gly Phe Glu Pro Ser Leu Ala Asp
        275                 280                 285

Cys Gly Val Ser Arg Leu Ile Ala Ser Gly Ser Ala Asp Pro Glu Leu
290                 295                 300

Ala Asn Ser Leu Tyr Ser Ala Pro Glu Cys Tyr Gln Ser Ser Arg Tyr
305                 310                 315                 320

Thr Asp Lys Ser Asp Val Tyr Ser Phe Gly Met Ile Leu Gly Val Leu
                325                 330                 335

Leu Thr Gly Arg Asp Pro Ala Asp Gln Phe Phe Ser Gly Glu Thr Gly
            340                 345                 350

Arg Gly Gly Leu Ala Arg Trp Leu Arg His Met Gln Gln Ser Gly Asp
        355                 360                 365

Ala Lys Asp Ala Leu Asp Ser Ser Ile Leu Gly Glu Glu Gly Glu Glu
370                 375                 380

Asp Glu Met Val Met Ala Val Arg Val Ala Ile Ile Cys Leu Ser Asp
385                 390                 395                 400

Leu Pro Ala Asp Arg Pro Ser Ser Asp Glu Leu Val Ala Met Leu Ile
                405                 410                 415

Gln Leu His Ser Phe
                420

<210> SEQ ID NO 80
<211> LENGTH: 414
<212> TYPE: PRT

<213> ORGANISM: Oryza punctata

<400> SEQUENCE: 80

| | | | | | | | | | | | | | | |
|---|---|---|---|---|---|---|---|---|---|---|---|---|---|---|
| Met | Glu | Met | Met | Ala | Ser | Lys | Asn | Pro | Thr | Lys | Thr | Leu | Ala | Val | His |
| 1 | | | | 5 | | | | | 10 | | | | | 15 | |

Met Glu Met Met Ala Ser Lys Asn Pro Thr Lys Thr Leu Ala Val His
1               5                   10                  15

Leu Leu Leu Leu Leu Val Phe Phe Leu Ser Leu Ala Ser Ser Gln Pro
            20                  25                  30

Leu His Ser Glu Pro Met Ser Thr Thr Thr Gln Ser Pro Pro Pro Pro
            35                  40                  45

Gln Ser Lys Ile Pro His Ala Gln Ala Gly Gly Ala Ala Arg Leu Arg
            50                  55                  60

Arg Ile Val Leu Gly Val Leu Phe Gly Ser Leu Thr Gly Phe Leu Leu
65                  70                  75                  80

Ser Leu Ala Phe Leu Tyr Ala Ile Arg Val Ala Ile Leu His Ala Lys
                85                  90                  95

Tyr Ala Pro Ala Ile Val Lys Gly Pro Val Ser Phe Thr Pro Gln Ile
                100                 105                 110

Ser Pro Lys Asn Leu His Ser Ala Leu Pro Ser Ala Gln Pro Leu Ala
                115                 120                 125

His Gly Pro Asn Gly Lys Tyr Tyr Lys Leu Val Leu Asp Asn Asp Val
130                 135                 140

Thr Val Ala Val Lys Arg Leu Glu Gly Val Ala Ala Ala Ser Arg
145                 150                 155                 160

Pro Glu Ala Ser Pro Ser Met Ser Asn Val Ser Lys Ser Asp Met Arg
                165                 170                 175

Arg Leu Gln Arg Gln Leu Glu Leu Leu Ala Arg Val Arg His Gln Asn
                180                 185                 190

Val Met Gly Leu Lys Ala Tyr Val Arg Glu Ala Asp Arg Leu Ser Leu
                195                 200                 205

Ala Tyr Asp Phe Val Pro Gly Gly Ser Leu Glu Asp Val Met Lys Arg
                210                 215                 220

Val Arg Ser Gln Gln Val Asn Leu Asn Trp Asp Ala Arg Asn Arg Ile
225                 230                 235                 240

Ala Ile Gly Val Ala Lys Gly Leu Arg Tyr Leu His Phe Glu Cys Ser
                245                 250                 255

Pro Arg Ile Leu His Cys Asn Leu Lys Pro Ser Asn Val Met Leu Asp
                260                 265                 270

Glu Gly Phe Glu Pro Arg Leu Ala Asp Cys Gly Val Ser Arg Leu Ile
                275                 280                 285

Ala Ser Gly Ser Ala Asp Arg Glu Leu Ala Ser Ser Leu Tyr Ser Ala
                290                 295                 300

Pro Glu Cys Tyr Gln Thr Ser Arg Tyr Thr Asp Lys Ser Asp Val Tyr
305                 310                 315                 320

Ser Phe Gly Met Ile Leu Gly Val Leu Leu Ser Gly Arg Asp Pro Thr
                325                 330                 335

Asp Gln Phe Phe Ser Gly Glu Thr Gly Arg Gly Leu Ala Arg Trp
                340                 345                 350

Leu Arg His Met Gln Gln Ser Gly Asp Ala Lys Asp Ala Leu Asp Ser
                355                 360                 365

Ser Ile Leu Gly Glu Glu Gly Glu Glu Asp Glu Met Val Met Ala Val
                370                 375                 380

Arg Val Ala Ile Ile Cys Leu Ser Asp Leu Pro Ala Asp Arg Pro Ser
385                 390                 395                 400

```
Ser Asp Glu Leu Val Ala Met Leu Thr Gln Leu His Ser Leu
            405                 410

<210> SEQ ID NO 81
<211> LENGTH: 413
<212> TYPE: PRT
<213> ORGANISM: Oryza meridionalis

<400> SEQUENCE: 81

Met Glu Met Met Ala Ser Lys Asn Pro Thr Lys Thr Leu Leu Leu
1               5                   10                  15

Leu Leu Leu Val Phe Phe Leu Ser Leu Ala Cys Ser Gln Pro Leu His
                20                  25                  30

Ser Glu Pro Met Ser Thr Thr Ala Thr Thr Gln Ser Ala Pro Pro
            35                  40                  45

Pro Pro Pro Gln Ser Lys Ile Pro His Ala Glu Ala Gly Gly Ala Ala
        50                  55                  60

Arg Leu Arg Arg Ile Val Leu Gly Val Leu Phe Gly Ser Leu Thr Gly
65                  70                  75                  80

Phe Leu Leu Ser Leu Ala Phe Leu Tyr Ala Ile Arg Val Ala Ile Leu
                85                  90                  95

His Ala Lys Tyr Ala Pro Ala Ile Val Arg Gly Pro Val Ser Phe Thr
                100                 105                 110

Pro Gln Ile Ser Pro Lys Asn Leu His Ser Ala Leu Pro Ser Ala Gln
            115                 120                 125

Pro Leu Ala His Gly Pro Asn Gly Lys Tyr Tyr Lys Leu Val Leu Asp
        130                 135                 140

Asn Asp Val Thr Val Ala Val Lys Arg Leu Glu Ala Ser Arg Pro Glu
145                 150                 155                 160

Ala Ser Pro Ser Ser Met Pro Asn Val Ser Lys Ser Asp Met Arg Arg
                165                 170                 175

Val Gln Arg Gln Leu Glu Leu Leu Ala Arg Val Arg His Gln Asn Val
            180                 185                 190

Met Gly Leu Lys Ala Tyr Val Arg Glu Ala Asp Arg Leu Ser Leu Ala
        195                 200                 205

Tyr Asp Phe Val Pro Gly Gly Ser Leu Glu Asp Val Met Lys Arg Val
210                 215                 220

Arg Ser Gln Gln Val Asn Leu Asn Trp Asp Ala Arg Asn Arg Ile Ala
225                 230                 235                 240

Ile Gly Val Ala Lys Gly Leu Arg His Leu His Phe Glu Cys Thr Pro
                245                 250                 255

Arg Ile Leu His Cys Ser Leu Lys Pro Ser Asn Val Met Leu Asp Glu
            260                 265                 270

Gly Phe Glu Pro Arg Leu Ala Asp Cys Gly Val Ser Arg Leu Ile Ala
        275                 280                 285

Ser Gly Ser Thr Asp Pro Glu Leu Ala Ser Ser Leu Tyr Ser Ala Pro
        290                 295                 300

Glu Cys Tyr Gln Ser Ser Arg Tyr Thr Asp Lys Ser Asp Val Tyr Ser
305                 310                 315                 320

Phe Gly Met Ile Leu Gly Val Leu Leu Thr Gly Arg Asp Pro Thr Asp
                325                 330                 335

His Phe Phe Ser Gly Glu Thr Gly Gly Leu Ala Arg Trp Leu
            340                 345                 350

Arg His Met Gln Gln Ser Gly Asp Ala Lys Asp Ala Leu Asp Ser Ser
            355                 360                 365
```

```
Val Leu Gly Glu Glu Gly Glu Asp Glu Met Val Met Ala Val Arg
    370             375                 380

Val Ala Ile Ile Cys Leu Ser Asp Leu Pro Ala Asp Arg Pro Ser Ser
385                 390                 395                 400

Asp Glu Leu Val Ala Met Leu Thr Gln Leu His Ser Leu
            405                 410

<210> SEQ ID NO 82
<211> LENGTH: 410
<212> TYPE: PRT
<213> ORGANISM: Oryza sativa Indica Group

<400> SEQUENCE: 82

Met Ala Ser Lys Asn Pro Thr Lys Thr Leu Leu Leu Leu Leu Leu Val
1               5                   10                  15

Phe Phe Leu Ser Leu Ala Cys Ser Gln Pro Leu His Ser Glu Pro Met
            20                  25                  30

Ser Thr Thr Thr Thr Ala Thr Gln Pro Ala Pro Pro Pro Pro Pro Pro
        35                  40                  45

Gln Ser Lys Ile Pro His Ala Glu Ala Gly Ala Ala Arg Leu Arg
    50                  55                  60

Arg Ile Val Leu Gly Val Leu Phe Gly Ser Leu Thr Gly Phe Leu Leu
65                  70                  75                  80

Ser Leu Ala Phe Leu Tyr Ala Ile Arg Val Ala Ile Leu His Ala Lys
                85                  90                  95

Tyr Ser Pro Ala Ile Val Arg Gly Pro Val Ser Phe Thr Pro Gln Ile
            100                 105                 110

Ser Pro Lys Asn Leu His Ser Ala Leu Pro Ser Ala Gln Pro Leu Ala
        115                 120                 125

His Gly Pro Asn Gly Lys Tyr Tyr Lys Leu Val Leu Asp Asn Asp Val
130                 135                 140

Thr Val Ala Val Lys Arg Leu Glu Ala Ser Arg Pro Glu Ala Ser Pro
145                 150                 155                 160

Ser Ser Met Pro Asn Val Ser Lys Ser Asp Met Arg Arg Val Gln Arg
                165                 170                 175

Gln Leu Glu Leu Leu Ala Arg Val Arg His Gln Asn Val Met Gly Leu
            180                 185                 190

Lys Ala Tyr Val Arg Glu Ala Asp Arg Leu Ser Leu Ala Tyr Asp Phe
        195                 200                 205

Val Pro Gly Gly Ser Leu Glu Asp Val Met Lys Arg Val Arg Ser Leu
    210                 215                 220

Gln Val Asn Leu Asn Trp Asp Ala Arg Asn Arg Ile Ala Ile Gly Val
225                 230                 235                 240

Ala Lys Gly Leu Arg Tyr Leu His Phe Glu Cys Thr Pro Arg Ile Leu
                245                 250                 255

His Cys Ser Leu Lys Pro Ser Asn Val Met Leu Asp Glu Gly Phe Glu
            260                 265                 270

Pro Arg Leu Ala Asp Cys Gly Val Ser Arg Leu Ile Ala Ser Gly Ser
        275                 280                 285

Ala Asp Pro Glu Leu Ala Ser Ser Leu Tyr Ser Ala Pro Glu Cys Tyr
    290                 295                 300

Gln Ser Ser Arg Tyr Thr Asp Lys Ser Asp Val Tyr Ser Phe Gly Met
305                 310                 315                 320

Ile Leu Gly Val Leu Leu Thr Gly Arg Asp Pro Thr Asp His Phe Phe
```

```
                    325                 330                 335
Ser Gly Glu Thr Gly Arg Gly Leu Ala Arg Trp Leu Arg His Met
            340                 345                 350

Gln Gln Ser Gly Asp Ala Lys Asp Ala Leu Asp Ser Ser Val Leu Gly
            355                 360                 365

Glu Glu Gly Glu Glu Asp Glu Met Val Met Ala Val Arg Val Ala Ile
            370                 375                 380

Ile Cys Leu Ser Asp Leu Pro Ala Asp Arg Pro Ser Ser Asp Glu Leu
385                 390                 395                 400

Val Pro Met Leu Thr Gln Leu His Ser Leu
            405                 410

<210> SEQ ID NO 83
<211> LENGTH: 414
<212> TYPE: PRT
<213> ORGANISM: Oryza nivara

<400> SEQUENCE: 83

Met Glu Met Met Ala Ser Lys Asn Pro Thr Lys Thr Leu Leu Leu Leu
1               5                   10                  15

Leu Leu Leu Val Phe Phe Leu Ser Leu Ala Cys Ser Gln Pro Leu His
            20                  25                  30

Ser Glu Pro Met Ser Thr Thr Thr Thr Ala Thr Gln Pro Ala Pro Pro
        35                  40                  45

Pro Pro Pro Pro Gln Ser Lys Ile Pro His Ala Glu Ala Gly Gly Ala
    50                  55                  60

Ala Arg Leu Arg Arg Ile Val Leu Gly Val Leu Phe Gly Ser Leu Thr
65                  70                  75                  80

Gly Phe Leu Leu Ser Leu Ala Phe Leu Tyr Ala Ile Arg Val Ala Ile
                85                  90                  95

Leu His Ala Lys Tyr Ser Pro Ala Ile Val Arg Gly Pro Val Ser Phe
            100                 105                 110

Thr Pro Gln Ile Ser Pro Lys Asn Leu His Ser Ala Leu Pro Ser Ala
        115                 120                 125

Gln Pro Leu Ala His Gly Pro Asn Gly Lys Tyr Tyr Lys Leu Val Leu
    130                 135                 140

Asp Asn Asp Val Thr Val Ala Val Lys Arg Leu Glu Ala Ser Arg Pro
145                 150                 155                 160

Glu Ala Ser Pro Ser Ser Met Pro Asn Val Ser Lys Ser Asp Met Arg
                165                 170                 175

Arg Val Gln Arg Gln Leu Glu Leu Leu Ala Arg Val Arg His Gln Asn
            180                 185                 190

Val Met Gly Leu Lys Ala Tyr Val Arg Glu Ala Asp Arg Leu Ser Leu
        195                 200                 205

Ala Tyr Asp Phe Val Pro Gly Gly Ser Leu Glu Asp Val Met Lys Arg
    210                 215                 220

Val Arg Ser Leu Gln Val Asn Leu Asn Trp Asp Ala Arg Asn Arg Ile
225                 230                 235                 240

Ala Ile Gly Val Ala Lys Gly Leu Arg Tyr Leu His Phe Glu Cys Thr
                245                 250                 255

Pro Arg Ile Leu His Cys Ser Leu Lys Pro Ser Asn Val Met Leu Asp
            260                 265                 270

Glu Gly Phe Glu Pro Arg Leu Ala Asp Cys Gly Val Ser Arg Leu Ile
        275                 280                 285
```

```
Ala Ser Gly Ser Ala Asp Pro Glu Leu Ala Ser Ser Leu Tyr Ser Ala
    290                 295                 300

Pro Glu Cys Tyr Gln Ser Ser Arg Tyr Thr Asp Lys Ser Asp Val Tyr
305                 310                 315                 320

Ser Phe Gly Met Ile Leu Gly Val Leu Thr Gly Arg Asp Pro Thr
                325                 330                 335

Asp His Phe Phe Ser Glu Thr Gly Arg Gly Leu Ala Arg Trp
                340                 345                 350

Leu Arg His Met Gln Gln Ser Gly Asp Ala Lys Asp Leu Asp Ser
                355                 360                 365

Ser Val Leu Gly Glu Glu Gly Glu Glu Asp Glu Met Val Met Ala Val
    370                 375                 380

Arg Val Ala Ile Ile Cys Leu Ser Asp Leu Pro Ala Asp Arg Pro Ser
385                 390                 395                 400

Ser Asp Glu Leu Val Pro Met Leu Thr Gln Leu His Ser Leu
                405                 410
```

<210> SEQ ID NO 84
<211> LENGTH: 442
<212> TYPE: PRT
<213> ORGANISM: Oryza rufipogon

<400> SEQUENCE: 84

```
Met Pro Thr Leu Ala Ala Val Ala Pro Leu Leu Ser Ser Pro Leu
1               5                   10                  15

Leu Cys Ser Pro Arg Ala Ile Ala Ser Pro Leu Ser Met Glu Met Met
                20                  25                  30

Ala Ser Lys Asn Pro Thr Lys Thr Leu Leu Leu Leu Leu Leu Val
            35                  40                  45

Phe Phe Leu Ser Leu Ala Cys Ser Gln Pro Leu His Ser Glu Pro Met
    50                  55                  60

Ser Thr Thr Thr Thr Ala Thr Gln Pro Ala Pro Pro Pro Pro Pro
65                  70                  75                  80

Gln Ser Lys Ile Pro His Ala Glu Ala Gly Gly Ala Ala Arg Leu Arg
                85                  90                  95

Arg Ile Val Leu Gly Val Leu Phe Gly Ser Leu Thr Gly Phe Leu Leu
                100                 105                 110

Ser Leu Ala Phe Leu Tyr Ala Ile Arg Val Ala Ile Leu His Ala Lys
            115                 120                 125

Tyr Ala Pro Ala Ile Val Arg Gly Pro Val Ser Phe Thr Pro Gln Ile
    130                 135                 140

Ser Pro Lys Asn Leu His Ser Ala Leu Pro Ser Ala Gln Pro Leu Ala
145                 150                 155                 160

His Gly Pro Asn Gly Lys Tyr Tyr Lys Leu Val Leu Asp Asn Asp Val
                165                 170                 175

Thr Val Ala Val Lys Arg Leu Glu Ala Ser Arg Pro Glu Ala Ser Pro
            180                 185                 190

Ser Ser Met Pro Asn Val Ser Lys Ser Asp Met Arg Arg Val Gln Arg
    195                 200                 205

Gln Leu Glu Leu Leu Ala Arg Val Arg His Gln Asn Val Met Gly Leu
    210                 215                 220

Lys Ala Tyr Val Arg Glu Ala Asp Arg Leu Ser Leu Ala Tyr Asp Phe
225                 230                 235                 240

Val Pro Gly Gly Ser Leu Glu Asp Val Met Lys Arg Val Arg Ser Leu
                245                 250                 255
```

```
Gln Val Asn Leu Asn Trp Asp Ala Arg Asn Arg Ile Ala Ile Gly Val
            260                 265                 270

Ala Lys Gly Leu Arg Tyr Leu His Phe Glu Cys Thr Pro Arg Ile Leu
            275                 280                 285

His Cys Ser Leu Lys Pro Ser Asn Val Met Leu Asp Glu Gly Phe Glu
            290                 295                 300

Pro Arg Leu Ala Asp Cys Gly Val Ser Arg Leu Ile Ala Ser Gly Ser
305                 310                 315                 320

Ala Asp Pro Glu Leu Ala Ser Ser Leu Tyr Ser Ala Pro Glu Cys Tyr
                325                 330                 335

Gln Ser Ser Arg Tyr Thr Asp Lys Ser Asp Val Tyr Ser Phe Gly Met
            340                 345                 350

Ile Leu Gly Val Leu Leu Thr Gly Arg Asp Pro Thr Asp His Phe Phe
            355                 360                 365

Ser Gly Glu Thr Gly Arg Gly Gly Leu Ala Arg Trp Leu Arg His Met
370                 375                 380

Gln Gln Ser Gly Asp Ala Lys Asp Ala Leu Asp Ser Ser Val Leu Gly
385                 390                 395                 400

Glu Glu Gly Glu Glu Asp Glu Met Val Met Ala Val Arg Val Ala Ile
                405                 410                 415

Ile Cys Leu Ser Asp Leu Pro Ala Asp Arg Pro Ser Ser Asp Glu Leu
            420                 425                 430

Val Pro Met Leu Thr Gln Leu His Ser Leu
            435                 440

<210> SEQ ID NO 85
<211> LENGTH: 416
<212> TYPE: PRT
<213> ORGANISM: Oryza barthii

<400> SEQUENCE: 85

Met Glu Met Met Ala Ser Lys Asn Pro Thr Lys Thr His Leu Leu Leu
1               5                   10                  15

Leu Leu Leu Leu Val Phe Phe Leu Ser Leu Ala Cys Ser Gln Pro Leu
            20                  25                  30

His Ser Glu Pro Met Ser Thr Thr Thr Thr Ala Thr Gln Pro Thr
            35                  40                  45

Pro Pro Pro Pro Pro Gln Ser Lys Ile Pro His Ala Glu Ala Gly
50                  55                  60

Gly Ala Ala Arg Leu Arg Arg Ile Val Leu Gly Val Leu Phe Gly Ser
65                  70                  75                  80

Leu Thr Gly Phe Leu Leu Ser Leu Ala Phe Leu Tyr Ala Ile Arg Val
                85                  90                  95

Ala Ile Leu His Ala Lys Tyr Ala Pro Ala Ile Val Arg Gly Pro Val
            100                 105                 110

Ser Phe Thr Pro Gln Ile Ser Pro Lys Asn Leu His Ser Ala Leu Pro
            115                 120                 125

Ser Ala Gln Pro Leu Ala His Gly Pro Asn Gly Lys Tyr Tyr Lys Leu
130                 135                 140

Val Leu Asp Asn Asp Val Thr Val Ala Val Lys Arg Leu Glu Ala Ser
145                 150                 155                 160

Arg Pro Glu Ala Ser Pro Ser Met Pro Asn Val Ser Lys Ser Asp
            165                 170                 175

Met Arg Arg Val Gln Arg Gln Leu Glu Leu Leu Ala Arg Val Arg His
```

```
                180                 185                 190
Gln Asn Val Met Gly Leu Lys Ala Tyr Val Arg Glu Ala Asp Arg Leu
            195                 200                 205
Ser Leu Ala Tyr Asp Phe Val Pro Gly Gly Ser Leu Glu Asp Val Met
        210                 215                 220
Lys Arg Val Arg Ser Leu Gln Val Asn Leu Asn Trp Asp Ala Arg Asn
225                 230                 235                 240
Arg Ile Ala Ile Gly Val Ala Lys Gly Leu Arg Tyr Leu His Phe Glu
                245                 250                 255
Cys Thr Pro Arg Ile Leu His Cys Ser Leu Lys Pro Ser Asn Val Met
            260                 265                 270
Leu Asp Glu Gly Phe Glu Pro Arg Leu Ala Asp Cys Gly Val Ser Arg
        275                 280                 285
Leu Ile Ala Ser Gly Ser Ala Asp Pro Glu Leu Ala Ser Ser Leu Tyr
    290                 295                 300
Ser Ala Pro Glu Cys Tyr Gln Ser Ser Arg Tyr Thr Asp Lys Ser Asp
305                 310                 315                 320
Val Tyr Ser Phe Gly Met Ile Leu Gly Val Leu Leu Thr Gly Arg Asp
                325                 330                 335
Pro Thr Asp His Phe Phe Ser Gly Glu Thr Gly Arg Gly Leu Ala
            340                 345                 350
Arg Trp Leu Arg His Met Gln Gln Ser Gly Asp Ala Lys Asp Ala Leu
        355                 360                 365
Asp Ser Ser Val Leu Gly Glu Glu Gly Glu Asp Glu Met Val Met
    370                 375                 380
Ala Val Arg Val Ala Ile Ile Cys Leu Ser Asp Leu Pro Ala Asp Arg
385                 390                 395                 400
Pro Ser Ser Asp Glu Leu Val Pro Met Leu Thr Gln Leu His Ser Leu
                405                 410                 415

<210> SEQ ID NO 86
<211> LENGTH: 414
<212> TYPE: PRT
<213> ORGANISM: Oryza sativa Japonica Group

<400> SEQUENCE: 86

Met Glu Met Met Ala Ser Lys Asn Pro Thr Lys Thr Leu Leu Leu Leu
1               5                   10                  15
Leu Leu Leu Val Phe Phe Leu Ser Leu Ala Cys Ser Gln Pro Leu His
            20                  25                  30
Ser Glu Pro Met Ser Thr Thr Thr Ala Thr Gln Pro Ala Pro Pro
        35                  40                  45
Pro Pro Pro Pro Gln Ser Lys Ile Pro His Ala Glu Ala Gly Gly Ala
    50                  55                  60
Ala Arg Leu Arg Arg Ile Val Leu Gly Val Leu Phe Gly Ser Leu Thr
65                  70                  75                  80
Gly Phe Leu Leu Ser Leu Ala Phe Leu Tyr Ala Ile Arg Val Ala Ile
                85                  90                  95
Leu His Ala Lys Tyr Ala Pro Ala Ile Val Arg Gly Pro Val Ser Phe
            100                 105                 110
Thr Pro Gln Ile Ser Pro Lys Asn Leu His Ser Ala Leu Pro Ser Ala
        115                 120                 125
Gln Pro Leu Ala His Gly Pro Asn Gly Lys Tyr Tyr Lys Leu Val Leu
    130                 135                 140
```

Asp Asn Asp Val Thr Val Ala Val Lys Arg Leu Glu Ala Ser Arg Pro
145                 150                 155                 160

Glu Ala Ser Pro Ser Ser Met Pro Asn Val Ser Lys Ser Asp Met Arg
            165                 170                 175

Arg Val Gln Arg Gln Leu Glu Leu Leu Ala Arg Val Arg His Gln Asn
            180                 185                 190

Val Met Gly Leu Lys Ala Tyr Val Arg Glu Ala Asp Arg Leu Ser Leu
        195                 200                 205

Ala Tyr Asp Phe Val Pro Gly Gly Ser Leu Glu Asp Val Met Lys Arg
    210                 215                 220

Val Arg Ser Leu Gln Val Asn Leu Asn Trp Asp Ala Arg Asn Arg Ile
225                 230                 235                 240

Ala Ile Gly Val Ala Lys Gly Leu Arg Tyr Leu His Phe Glu Cys Thr
                245                 250                 255

Pro Arg Ile Leu His Cys Ser Leu Lys Pro Ser Asn Val Met Leu Asp
            260                 265                 270

Glu Asp Phe Glu Pro Arg Leu Ala Asp Cys Gly Val Ser Arg Leu Ile
        275                 280                 285

Ala Ser Gly Ser Ala Asp Pro Glu Leu Ala Ser Ser Leu Tyr Ser Ala
    290                 295                 300

Pro Glu Cys Tyr Gln Ser Ser Arg Tyr Thr Asp Lys Ser Asp Val Tyr
305                 310                 315                 320

Ser Phe Gly Met Ile Leu Gly Val Leu Leu Thr Gly Arg Asp Pro Thr
                325                 330                 335

Asp His Phe Phe Ser Gly Glu Thr Gly Arg Gly Gly Leu Ala Arg Trp
            340                 345                 350

Leu Arg His Met Gln Gln Ser Gly Asp Ala Lys Asp Ala Leu Asp Ser
        355                 360                 365

Ser Val Leu Gly Glu Glu Gly Glu Asp Glu Met Val Met Ala Val
    370                 375                 380

Arg Val Ala Ile Ile Cys Leu Ser Asp Leu Pro Ala Asp Arg Pro Ser
385                 390                 395                 400

Ser Asp Glu Leu Val Pro Met Leu Thr Gln Leu His Ser Leu
                405                 410

<210> SEQ ID NO 87
<211> LENGTH: 414
<212> TYPE: PRT
<213> ORGANISM: Oryza glumipatula

<400> SEQUENCE: 87

Met Glu Met Met Ala Ser Lys Asn Pro Thr Lys Thr Leu Leu Leu Leu
1               5                   10                  15

Leu Leu Leu Val Phe Phe Leu Ser Leu Ala Cys Ser Gln Pro Leu His
                20                  25                  30

Ser Glu Pro Met Ser Thr Thr Thr Thr Ala Thr Gln Pro Ala Pro Pro
            35                  40                  45

Pro Pro Pro Pro Gln Ser Lys Ile Pro His Ala Glu Ala Gly Gly Ala
    50                  55                  60

Ala Arg Leu Arg Arg Ile Val Leu Gly Val Leu Phe Gly Ser Leu Thr
65                  70                  75                  80

Gly Phe Leu Leu Ser Leu Ala Phe Leu Tyr Ala Ile Arg Val Ala Ile
                85                  90                  95

Leu His Ala Lys Tyr Ala Pro Ala Ile Val Arg Gly Pro Val Ser Phe
                100                 105                 110

Thr Pro Gln Ile Ser Pro Lys Asn Leu His Ser Ala Leu Pro Ser Ala
            115                 120                 125

Gln Pro Leu Ala His Gly Pro Asn Gly Lys Tyr Tyr Lys Leu Val Leu
        130                 135                 140

Asp Asn Asp Val Thr Val Ala Val Lys Arg Leu Glu Ala Ser Arg Pro
145                 150                 155                 160

Glu Ala Ser Pro Ser Ser Met Pro Asn Val Ser Lys Ser Asp Met Arg
                165                 170                 175

Arg Val Gln Arg Gln Leu Glu Leu Leu Ala Arg Val Arg His Gln Asn
            180                 185                 190

Val Met Gly Leu Lys Ala Tyr Val Arg Glu Ala Asp Arg Leu Ser Leu
        195                 200                 205

Ala Tyr Asp Phe Val Pro Gly Gly Ser Leu Glu Asp Val Met Lys Arg
    210                 215                 220

Val Arg Ser Leu Gln Val Asn Leu Asn Trp Asp Ala Arg Asn Arg Ile
225                 230                 235                 240

Ala Ile Gly Val Ala Lys Gly Leu Arg Tyr Leu His Phe Glu Cys Thr
                245                 250                 255

Pro Arg Ile Leu His Cys Ser Leu Lys Pro Ser Asn Val Met Leu Asp
            260                 265                 270

Glu Gly Phe Glu Pro Arg Leu Ala Asp Cys Gly Val Ser Arg Leu Ile
        275                 280                 285

Ala Ser Gly Ser Ala Asp Pro Glu Leu Ala Ser Ser Leu Tyr Ser Ala
    290                 295                 300

Pro Glu Cys Tyr Gln Ser Ser Arg Tyr Thr Asp Lys Ser Asp Val Tyr
305                 310                 315                 320

Ser Phe Gly Met Ile Leu Gly Val Leu Leu Thr Gly Arg Asp Pro Thr
                325                 330                 335

Asp His Phe Phe Ser Gly Glu Thr Gly Arg Gly Gly Leu Ala Arg Trp
            340                 345                 350

Leu Arg His Met Gln Gln Ser Gly Asp Ala Lys Asp Ala Leu Asp Ser
        355                 360                 365

Ser Val Leu Gly Glu Gly Glu Glu Asp Glu Met Val Met Ala Val
    370                 375                 380

Arg Val Ala Ile Ile Cys Leu Ser Asp Leu Pro Ala Asp Arg Pro Ser
385                 390                 395                 400

Ser Asp Glu Leu Val Pro Met Leu Thr Gln Leu His Ser Leu
                405                 410

<210> SEQ ID NO 88
<211> LENGTH: 433
<212> TYPE: PRT
<213> ORGANISM: Panicum hallii FIL2

<400> SEQUENCE: 88

Met Leu Val Phe Pro Ser Lys Phe Gly Ser Cys Ile Met Glu Gln Ala
1               5                   10                  15

Val Arg Met Thr Ser Lys Asn Pro Thr Lys Thr Pro Leu Leu Ala
            20                  25                  30

Thr Leu Leu Leu Leu Ala Phe Leu Ala Leu Cys Ala Pro Ala Ser
        35                  40                  45

Ser Gln Pro Leu His Ser Glu Pro Met Pro Thr Gln Ser Pro Pro Pro
    50                  55                  60

Ser Pro Thr Pro Pro Gln Ser Thr Ile Pro Arg Ala Pro Ala Gly Gly

```
                65                  70                  75                  80
Ala Ala Arg Leu Arg Arg Ile Ala Leu Gly Val Leu Phe Gly Ser Ile
                    85                  90                  95
Ser Gly Phe Leu Leu Ala Leu Ala Phe Leu Tyr Gly Ile Arg Val Ala
                100                 105                 110
Ile Leu His Ala Lys Ser Ala Pro Ala Ile Val Lys Gly Pro Val Ser
                115                 120                 125
Phe Thr Pro Gln Ile Ser Pro Lys Asn Leu Leu Ala Leu Pro Ser
                130                 135                 140
Ala Gln Pro Leu Ala His Gly Pro His Gly Lys Tyr Cys Lys Leu Ala
145                 150                 155                 160
Leu Asp Asn Asp Leu Thr Val Ala Val Lys Arg Leu Glu Ala Ala Asn
                    165                 170                 175
Arg Pro Glu Glu Ala Ser Pro Ser Met Ser Pro Ser Thr Ser Lys Ser
                180                 185                 190
Asp Met Arg Arg Val Gln Arg Gln Leu Glu Ala Leu Ala Arg Val Arg
                195                 200                 205
His Gln Asn Val Met Thr Leu Lys Ala Tyr Val Arg Glu Ala Asp Arg
210                 215                 220
Leu Ser Leu Val Tyr Asp Phe Ile Pro Gly Gly Ser Leu Glu Glu Leu
225                 230                 235                 240
Met Lys Arg Val Arg Ser Gln Gln Val Ser Leu Asn Trp Asp Ala Arg
                    245                 250                 255
Ser Arg Ile Val Val Gly Ile Ala Lys Gly Leu Arg His Leu His Phe
                260                 265                 270
Glu Tyr Ser Pro Arg Ile Leu His Cys Asn Leu Lys Pro Ser Asn Val
            275                 280                 285
Met Leu Asp Glu Gly Phe Glu Pro Ile Leu Thr Asp Cys Gly Ile Ala
            290                 295                 300
Arg Leu Ile Ala Ala Gly Ser Gly Asp Pro Glu Leu Cys Ser Gly Leu
305                 310                 315                 320
Tyr Ala Ala Pro Glu Cys Tyr Gln Ser Ser Arg Tyr Thr Asp Lys Ser
                325                 330                 335
Asp Val Tyr Ala Leu Gly Met Ile Leu Gly Val Leu Leu Thr Gly Arg
                340                 345                 350
Asp Pro Thr Asp Pro Phe Phe Ser Gly Glu Thr Gly Arg Gly Gly Leu
                355                 360                 365
Pro Arg Trp Leu Arg His Met Gln Gln Ser Ala Asp Pro Lys Glu Ala
                370                 375                 380
Leu Asp Ser Ser Ile Leu Gly Asp Glu Gly Glu Glu Glu Met Phe
385                 390                 395                 400
Met Ala Ile Arg Val Ala Ile Val Cys Leu Ser Asp Ser Pro Val Asp
                    405                 410                 415
Arg Pro Ser Ser Asp Glu Leu Val Ala Met Leu Thr Gln Leu His Ser
                420                 425                 430
Leu

<210> SEQ ID NO 89
<211> LENGTH: 433
<212> TYPE: PRT
<213> ORGANISM: Panicum hallii HAL2

<400> SEQUENCE: 89

Met Leu Val Phe Pro Ser Lys Phe Gly Ser Cys Ile Met Glu Gln Ala
```

-continued

```
1               5                   10                  15
Val Arg Met Thr Ser Lys Asn Pro Thr Lys Thr Pro Pro Phe Leu Ala
                20                  25                  30
Ile Leu Leu Leu Leu Leu Ala Phe Leu Ala Leu Cys Ala Pro Ala Ser
                35                  40                  45
Ser Gln Pro Leu His Ser Glu Pro Met Ala Thr Gln Ser Pro Pro Pro
    50                  55                  60
Ser Pro Thr Pro Pro Gln Ser Thr Ile Pro Arg Ala Gln Ala Gly Gly
65                  70                  75                  80
Ala Ala Arg Leu Arg Arg Ile Ala Leu Gly Val Leu Phe Gly Ser Ile
                85                  90                  95
Ser Gly Phe Leu Leu Ala Leu Ala Phe Leu Tyr Gly Ile Arg Val Ala
                100                 105                 110
Ile Leu His Ala Lys Ser Ala Pro Ala Ile Val Lys Gly Pro Val Ser
                115                 120                 125
Phe Thr Pro Gln Ile Ser Pro Lys Asn Leu Leu Ala Ala Leu Pro Ser
        130                 135                 140
Ala Gln Pro Leu Ala His Gly Pro His Gly Lys Tyr Cys Lys Leu Ala
145                 150                 155                 160
Leu Asp Asn Asp Leu Thr Val Ala Val Lys Arg Leu Glu Ala Ala Asn
                165                 170                 175
Arg Pro Glu Glu Ala Ser Pro Ser Met Ser Pro Ser Thr Ser Lys Ser
                180                 185                 190
Asp Met Arg Arg Val Gln Arg Gln Leu Glu Ala Leu Ala Arg Val Arg
                195                 200                 205
His Gln Asn Val Met Thr Leu Lys Ala Tyr Val Arg Glu Ala Asp Arg
        210                 215                 220
Leu Ser Leu Val Tyr Asp Phe Ile Pro Trp Gly Ser Leu Glu Asp Val
225                 230                 235                 240
Met Lys Arg Val Arg Ser Gln Gln Val Ser Leu Asn Trp Asp Ala Arg
                245                 250                 255
Ser Arg Ile Val Val Gly Ile Ala Lys Gly Leu Arg His Leu His Phe
                260                 265                 270
Glu Tyr Ser Pro Arg Ile Leu His Cys Asn Leu Lys Pro Ser Asn Val
        275                 280                 285
Met Leu Asp Glu Gly Phe Glu Pro Ile Leu Thr Asp Cys Gly Ile Ala
        290                 295                 300
Arg Leu Ile Ala Ala Gly Ser Gly Asp Pro Glu Leu Cys Ser Gly Leu
305                 310                 315                 320
Tyr Ala Ala Pro Glu Cys Tyr Gln Ser Ser Arg Tyr Thr Asp Lys Ser
                325                 330                 335
Asp Val Tyr Ala Leu Gly Met Ile Leu Gly Val Leu Leu Thr Gly Arg
                340                 345                 350
Asp Pro Thr Asp Pro Phe Phe Ser Gly Glu Thr Gly Arg Gly Ser Leu
                355                 360                 365
Pro Arg Trp Leu Arg His Met Gln Gln Ser Ala Asp Pro Lys Glu Ala
        370                 375                 380
Leu Asp Ser Ser Ile Leu Gly Asp Glu Gly Glu Glu Glu Met Phe
385                 390                 395                 400
Met Ala Ile Arg Val Ala Ile Val Cys Leu Ser Asp Ser Pro Val Asp
                405                 410                 415
Arg Pro Ser Ser Asp Glu Leu Val Ala Met Leu Thr Gln Leu His Ser
                420                 425                 430
```

Leu

<210> SEQ ID NO 90
<211> LENGTH: 417
<212> TYPE: PRT
<213> ORGANISM: Sorghum bicolor

<400> SEQUENCE: 90

Met Val Val Gly Ala Arg Met Thr Ser Arg Asn Pro Thr Lys Thr Leu
1               5                   10                  15

Pro Leu Leu Ala Thr Thr Leu Val Leu Leu Leu Ala Phe Leu Ala
            20                  25                  30

Leu Cys Ala Pro Ala Ser Ser Gln Pro Leu His Ser Glu Pro Met Ala
        35                  40                  45

Thr Gln Ser Pro Pro Arg Thr Ser Ile Pro Arg Ala Gln Val Gly
    50                  55                  60

Gly Ala Ala Arg Leu Arg Arg Ile Ala Leu Gly Val Leu Phe Gly Ser
65                  70                  75                  80

Leu Ser Gly Phe Leu Leu Ala Leu Ala Phe Leu Tyr Ala Ile Arg Leu
                85                  90                  95

Ala Ile Leu His Ala Lys Ser Thr Pro Ala Ile Ala Lys Gly Pro Val
            100                 105                 110

Ser Phe Val Pro Gln Ile Ser Ala Lys Asn Leu Leu Ala Ala Leu Pro
        115                 120                 125

Ala Ala Gln Pro Leu Ala His Gly Pro His Gly Lys Tyr Tyr Lys Leu
    130                 135                 140

Ala Leu Asp Asn Asp Leu Thr Val Ala Val Lys Arg Leu Glu Ala Ala
145                 150                 155                 160

Ser Arg Pro Glu Ala Ser Pro Ser Met Ser Pro Ser Ala Ser Lys Ser
                165                 170                 175

Asp Met Arg Arg Val Gln Arg Gln Leu Glu Val Leu Ala Arg Val Arg
            180                 185                 190

His Gln Asn Val Leu Ser Leu Lys Ala Tyr Val Arg Glu Pro Asp Arg
        195                 200                 205

Leu Ser Leu Val Tyr Asp Phe Val Pro Gly Gly Ser Leu Glu Asp Val
    210                 215                 220

Met Lys Arg Val Arg Ser Gln Gln Val Ser Leu Ser Trp Asp Ala Arg
225                 230                 235                 240

Ser Arg Ile Ala Val Gly Ile Ala Lys Gly Leu Arg His Leu His Phe
                245                 250                 255

Glu Cys Asn Pro Arg Ile Leu His Cys Asn Leu Lys Pro Ser Asn Val
            260                 265                 270

Met Leu Asp Glu Gly Phe Glu Pro Ile Leu Thr Asp Cys Gly Val Ala
        275                 280                 285

Arg Leu Ile Ala Ala Ser Ser Gly Asp Pro Glu Leu Cys Ser Gly Leu
    290                 295                 300

Tyr Ala Ala Pro Glu Cys Tyr Gln Ser Ser Arg Tyr Thr Asp Lys Ser
305                 310                 315                 320

Asp Val Tyr Ala Leu Gly Met Ile Leu Gly Val Leu Leu Thr Gly Arg
                325                 330                 335

Asp Pro Thr Asp Ser Phe Phe Ser Gly Glu Ala Gly Gln Gly Gly Leu
            340                 345                 350

Ala Arg Trp Leu Arg His Val Gln Gln Ser Ala Asp Pro Lys Glu Ala
        355                 360                 365

```
Leu Asp Ser Ser Ile Leu Gly Asp Glu Gly Glu Glu Glu Met Leu
        370             375             380

Met Ala Ile Arg Ile Ala Ile Val Cys Leu Ser Asp Ser Pro Ser Asp
385             390             395             400

Arg Pro Ser Ser Asp Glu Leu Val Ala Met Leu Met Gln Leu His Ser
            405             410             415

Leu

<210> SEQ ID NO 91
<211> LENGTH: 394
<212> TYPE: PRT
<213> ORGANISM: Brassica rapa

<400> SEQUENCE: 91

Met Glu Gln Arg Arg Arg Asn Ile Asn Thr Leu Ser Leu Leu Leu
1               5               10                  15

Leu Phe Phe Leu Ala Phe Thr Ser Thr Thr Ala Thr Thr Ser Ser Cys
                20              25              30

Arg Arg Arg Ala Val Lys His Leu Ser Thr Thr Gln Ala Thr Pro Leu
            35              40              45

Gln Ser Arg Ile Thr Pro Lys Val Ile Val Leu Ser Ile Val Ser Gly
        50              55              60

Val Leu Thr Gly Leu Leu Ser Ala Leu Ala Leu Ala Phe Leu Val Arg
65              70              75              80

Cys Ile Val Lys Tyr Met Lys Gln Thr Pro Ile Leu Lys Gly Pro Val
                85              90              95

Val Phe Ser Pro Lys Ile Thr Pro Lys Ser Leu His Ala Ala Leu Gly
                100             105             110

Asn Ser Ile His Leu Leu Gly Ser Asp Pro Asn Gly Lys Tyr His Lys
            115             120             125

Thr Val Leu Asp Asn Gly Leu Val Val Ala Val Lys Lys Leu Ser Tyr
130             135             140

Ser Ser Pro Glu Gly Gly Ala Thr Ser Lys Ser Val Lys Arg Arg Leu
145             150             155             160

Gln Lys Glu Leu Glu Leu Leu Ala Gly Leu Arg His Arg Asn Ile Met
                165             170             175

Ser Leu Arg Ala Tyr Val Arg Glu Ser Asn Glu Phe Ser Leu Val Tyr
            180             185             190

Asp Tyr Leu Pro Asn Gly Ser Leu Glu Asp Val Met Ser Lys Val Arg
        195             200             205

Gly Asn Glu Met Glu Leu Gly Trp Glu Val Arg Leu Arg Ile Ala Val
    210             215             220

Gly Ile Val Lys Gly Leu Gln Tyr Leu His Phe Gly Cys Glu Glu Gln
225             230             235             240

Gln Ile Leu His Tyr Asn Leu Lys Pro Thr Asn Val Val Leu Asp Ser
                245             250             255

Glu Phe Glu Pro Arg Leu Thr Asp Cys Gly Leu Ala Lys Ile Met Leu
            260             265             270

Ser Ser Gln Thr Ala Val Val Ser Cys Tyr Ser Ala Pro Glu Ser Ser
        275             280             285

Lys Ser Asn Arg Tyr Thr Glu Lys Ser Asp Val Phe Ser Phe Gly Met
    290             295             300

Ile Leu Gly Val Leu Leu Thr Gly Lys Asp Pro Thr Gln Pro Phe Cys
305             310             315             320
```

Val Asn Gly Ala Ser Gly Ser Leu Gly Leu Trp Leu Lys His Leu
            325                 330                 335

Gln Gln Ser Gly Glu Ser Arg Glu Ala Leu Asp Glu Ser Ile Leu Gly
            340                 345                 350

Glu Glu Val Glu Glu Asp Glu Met Leu Met Ala Leu Arg Ile Thr Ile
            355                 360                 365

Val Cys Leu Ser Asp Phe Pro Ala Asp Arg Pro Ser Ser Asp Glu Leu
            370                 375                 380

Val His Met Leu Thr Gln Leu His Ser Phe
385                 390

<210> SEQ ID NO 92
<211> LENGTH: 394
<212> TYPE: PRT
<213> ORGANISM: Brassica napus

<400> SEQUENCE: 92

Met Glu Gln Arg Arg Arg Arg Asn Ile Asn Thr Leu Ser Leu Leu Leu
1               5                   10                  15

Leu Phe Phe Leu Ala Phe Thr Ser Thr Thr Ala Thr Thr Ser Ser Cys
                20                  25                  30

Arg Arg Arg Ala Val Lys His Leu Ser Thr Thr Gln Ala Thr Pro Leu
            35                  40                  45

Gln Ser Arg Ile Thr Pro Lys Val Ile Val Leu Ser Ile Val Ser Gly
        50                  55                  60

Val Leu Thr Gly Leu Leu Ser Ala Leu Ala Leu Ala Phe Leu Val Arg
65                  70                  75                  80

Cys Ile Val Lys Tyr Met Lys Gln Thr Pro Ile Leu Lys Gly Pro Val
                85                  90                  95

Val Phe Ser Pro Lys Ile Thr Pro Lys Ser Leu His Ala Ala Leu Gly
            100                 105                 110

Asn Ser Ile His Leu Leu Gly Ser Asp Pro Asn Gly Lys Tyr His Lys
        115                 120                 125

Thr Val Leu Asp Asn Gly Leu Val Val Ala Val Lys Lys Leu Ser Tyr
130                 135                 140

Ser Ser Pro Glu Gly Gly Ala Thr Ser Lys Ser Val Lys Arg Arg Leu
145                 150                 155                 160

Gln Lys Glu Leu Glu Leu Leu Ala Gly Leu Arg His Arg Asn Ile Met
                165                 170                 175

Ser Leu Arg Ala Tyr Val Arg Glu Ser Asn Glu Phe Ser Leu Val Tyr
            180                 185                 190

Asp Tyr Leu Pro Asn Gly Ser Leu Glu Asp Val Met Ser Lys Val Arg
        195                 200                 205

Gly Asn Glu Met Glu Leu Gly Trp Glu Val Arg Leu Arg Ile Ala Val
210                 215                 220

Gly Ile Val Lys Gly Leu Gln Tyr Leu His Phe Gly Cys Glu Glu Gln
225                 230                 235                 240

Gln Ile Leu His Tyr Asn Leu Lys Pro Thr Asn Val Val Leu Asp Ser
                245                 250                 255

Glu Phe Glu Pro Arg Leu Thr Asp Cys Gly Leu Ala Lys Ile Met Leu
            260                 265                 270

Ser Ser Gln Thr Ala Val Val Ser Cys Tyr Ser Ala Pro Glu Ser Ser
        275                 280                 285

Lys Ser Asn Arg Tyr Thr Glu Lys Ser Asp Val Phe Ser Phe Gly Met

```
            290                 295                 300
Ile Leu Gly Val Leu Leu Thr Gly Lys Asp Pro Thr Gln Pro Phe Cys
305                 310                 315                 320

Val Asn Gly Ala Ser Gly Ser Leu Gly Leu Trp Leu Lys His Leu
                325                 330                 335

Gln Gln Ser Gly Glu Ser Arg Glu Ala Leu Asp Glu Ser Ile Leu Gly
                340                 345                 350

Glu Glu Val Glu Glu Asp Glu Met Leu Met Ala Leu Arg Ile Thr Ile
                355                 360                 365

Val Cys Leu Ser Asp Phe Pro Ala Asp Arg Pro Ser Ser Asp Glu Leu
370                 375                 380

Val His Met Leu Thr Gln Leu His Ser Phe
385                 390
```

<210> SEQ ID NO 93
<211> LENGTH: 398
<212> TYPE: PRT
<213> ORGANISM: Brassica napus

<400> SEQUENCE: 93

```
Met Glu Gln Arg Gly Arg Lys Arg Tyr Cys Asn Thr Val Tyr Leu Leu
1               5                   10                  15

Leu Phe Ile Phe Leu Val Phe Ser Ser Arg Thr Thr Ser Ser Ala Ser
                20                  25                  30

Cys Arg Arg Arg Ala Val Lys His Leu Ser Thr Ala Pro Pro Ser Ser
            35                  40                  45

Thr Pro Leu Glu Ser Arg Ile Thr Thr Lys Val Ile Ile Val Ser Ile
    50                  55                  60

Val Ser Gly Val Leu Thr Gly Phe Phe Ser Ala Leu Ala Leu Ala Phe
65                  70                  75                  80

Leu Val Arg Cys Thr Val Lys Tyr Leu Lys Gln Thr Pro Ile Leu Lys
                85                  90                  95

Gly Pro Val Val Phe Ser Pro Lys Ile Thr Pro Lys Ser Leu His Ala
            100                 105                 110

Ala Leu Ala Asn Gly Ile Gln Leu Leu Gly Ser Asp Pro Asn Gly Lys
        115                 120                 125

Tyr Tyr Lys Met Val Leu Asp Asn Gly Leu Val Val Ala Val Lys Arg
130                 135                 140

Leu Gly Ser Leu Glu Gly Asn Gly Gly Ser Pro Glu Ala Ala Thr Lys
145                 150                 155                 160

Ser Val Lys Arg Arg Leu Gln Lys Glu Leu Glu Leu Leu Ala Gly Leu
                165                 170                 175

Arg Asp Arg Asn Leu Met Ser Leu Arg Ala Tyr Val Arg Glu Ser Asp
            180                 185                 190

Glu Phe Ser Leu Val Tyr Asp Tyr Met Pro Asn Gly Ser Leu Asp Asp
        195                 200                 205

Val Met Thr Lys Val Arg Ala Gln Glu Leu Glu Leu Gly Trp Glu Ile
    210                 215                 220

Arg Leu Arg Val Ala Val Gly Ile Val Lys Gly Leu Gln Tyr Leu His
225                 230                 235                 240

Phe Ser Cys Glu Gln Gln Ile Leu His Tyr Asn Leu Lys Pro Thr Asn
                245                 250                 255

Val Met Leu Asp Ser Glu Phe Glu Pro Arg Leu Ala Asp Cys Gly Leu
            260                 265                 270
```

-continued

```
Ala Lys Ile Ile Pro Thr Ser His Thr Ser Val Ser Cys Tyr Ser Ala
            275                 280                 285

Pro Glu Ser Ser Gln Thr Asn Arg Tyr Thr Asp Lys Ser Asp Val Phe
        290                 295                 300

Ser Phe Gly Met Ile Leu Gly Val Leu Leu Thr Gly Arg Asp Pro Thr
305                 310                 315                 320

His Pro Phe Cys Ile Glu Gly Ala Thr Gly Gly Ser Leu Gly Gln Trp
                325                 330                 335

Leu Lys His Leu Gln Gln Thr Gly Glu Val Arg Glu Gly Leu Asp Lys
            340                 345                 350

Ser Ile Leu Gly Glu Glu Val Glu Glu Asp Glu Met Leu Met Ala Leu
        355                 360                 365

Arg Ile Thr Ile Ile Cys Leu Ser Asp Phe Pro Ala Asp Arg Pro Ser
370                 375                 380

Ser Asp Glu Leu Val His Met Leu Thr Gln Leu His Ser Phe
385                 390                 395
```

<210> SEQ ID NO 94
<211> LENGTH: 397
<212> TYPE: PRT
<213> ORGANISM: Brassica napus

<400> SEQUENCE: 94

```
Met Glu Gln Arg Arg Lys Arg Tyr Cys Asn Thr Val Tyr Leu Leu
1               5                   10                  15

Leu Phe Ile Leu Leu Val Phe Ser Ser Ile Thr Thr Ser Ser Ala Ser
            20                  25                  30

Cys Arg Arg Arg Ala Val Lys His Leu Ser Thr Ala Pro Pro Ser Ser
        35                  40                  45

Thr Pro Leu Glu Ser Lys Ile Thr Ser Lys Val Ile Ala Ile Ser Ile
50                  55                  60

Val Ser Gly Val Leu Thr Gly Leu Val Ser Ala Leu Ala Leu Ala Phe
65                  70                  75                  80

Leu Val Arg Cys Thr Val Lys Tyr Leu Lys Gln Thr Pro Ile Leu Lys
                85                  90                  95

Gly Pro Val Val Phe Ser Pro Lys Ile Thr Pro Lys Ser Leu His Ala
            100                 105                 110

Ala Leu Ala Asn Gly Ile Gln Leu Leu Gly Ser Asp Pro Asn Gly Lys
        115                 120                 125

Tyr Tyr Lys Met Val Leu Asp Asn Gly Leu Val Val Ala Val Lys Arg
130                 135                 140

Leu Gly Ser Leu Glu Gly Asn Gly Gly Ser Pro Glu Ala Thr Lys Ser
145                 150                 155                 160

Val Lys Arg Arg Leu Gln Lys Glu Leu Glu Leu Leu Ala Gly Leu Arg
                165                 170                 175

Asp Arg Asn Leu Met Ser Leu Arg Ala Tyr Val Arg Glu Ser Asp Glu
            180                 185                 190

Phe Ser Leu Val Tyr Asp Tyr Met Pro Asn Gly Ser Leu Glu Asp Val
        195                 200                 205

Met Thr Lys Val Arg Ala Glu Glu Leu Glu Leu Gly Trp Glu Ile Arg
210                 215                 220

Leu Arg Val Ala Val Gly Ile Val Lys Gly Leu Gln Tyr Leu His Phe
225                 230                 235                 240

Ser Cys Glu Gln Gln Ile Leu His Tyr Asn Leu Lys Pro Ala Asn Val
                245                 250                 255
```

```
Met Leu Asp Ser Glu Phe Glu Pro Arg Leu Ala Asp Cys Gly Leu Ala
            260                 265                 270

Lys Ile Ile Pro Ala Ser Gln Thr Ala Val Ser Cys Tyr Ser Ala Pro
        275                 280                 285

Glu Ser Ser Gln Ile Asn Arg Tyr Thr Asp Lys Ser Asp Val Phe Ser
    290                 295                 300

Phe Gly Met Ile Leu Gly Val Leu Leu Thr Gly Arg Asp Pro Thr Leu
305                 310                 315                 320

Pro Phe Ser Ile Glu Gly Ala Ser Gly Gly Ser Leu Gly Gln Trp Leu
                325                 330                 335

Lys His Leu Gln Gln Thr Gly Glu Val Arg Glu Ala Leu Asp Lys Ser
            340                 345                 350

Ile Leu Gly Glu Glu Val Glu Glu Asp Glu Met Leu Met Ala Leu Arg
        355                 360                 365

Ile Thr Ile Ile Cys Leu Ser Asp Phe Pro Ala Asp Arg Pro Ser Ser
    370                 375                 380

Asp Glu Leu Val His Met Leu Thr Gln Leu His Ser Phe
385                 390                 395

<210> SEQ ID NO 95
<211> LENGTH: 395
<212> TYPE: PRT
<213> ORGANISM: Brassica rapa

<400> SEQUENCE: 95

Met Glu Gln Arg Arg Lys Arg Tyr Cys Asn Thr Val His Leu Leu
1               5                   10                  15

Leu Phe Ile Phe Leu Val Phe Ser Ser Arg Thr Ser Ala Ser Cys Arg
            20                  25                  30

Arg Arg Ala Val Lys His Leu Ser Thr Ala Pro Pro Ser Ser Thr Pro
        35                  40                  45

Leu Glu Ser Lys Ile Thr Ser Lys Val Ile Val Ser Ile Val Ser
    50                  55                  60

Gly Val Leu Thr Gly Leu Val Ser Ala Leu Ala Leu Ala Phe Leu Val
65                  70                  75                  80

Arg Ser Thr Val Lys Tyr Leu Lys Gln Thr Pro Ile Leu Lys Gly Pro
                85                  90                  95

Val Val Phe Ser Pro Lys Ile Thr Pro Lys Ser Leu His Ala Ala Leu
            100                 105                 110

Ala Asn Gly Ile Gln Leu Leu Gly Ser Asp Pro Asn Gly Lys Tyr Tyr
        115                 120                 125

Lys Met Val Leu Asp Asn Gly Leu Val Val Ala Val Lys Arg Leu Gly
    130                 135                 140

Ser Leu Glu Gly Asn Gly Gly Ser Pro Glu Ala Thr Lys Ser Val Lys
145                 150                 155                 160

Arg Arg Leu Gln Lys Glu Leu Glu Leu Leu Ala Gly Leu Arg Asp Arg
                165                 170                 175

Asn Leu Met Ser Leu Arg Ala Tyr Val Arg Glu Ser Asp Glu Phe Ser
            180                 185                 190

Leu Val Tyr Asp Tyr Thr Pro Asn Gly Ser Leu Glu Asp Val Met Thr
        195                 200                 205

Lys Val Arg Ala Gln Glu Leu Glu Leu Gly Trp Glu Ile Arg Leu Arg
    210                 215                 220

Val Ala Val Gly Ile Val Lys Gly Leu Gln Tyr Leu His Phe Ser Cys
```

```
                225                 230                 235                 240
Glu Gln Gln Ile Leu His Tyr Asn Leu Lys Pro Thr Asn Val Met Leu
                245                 250                 255
Asp Ser Glu Phe Glu Pro Arg Leu Ala Asp Cys Gly Leu Ala Lys Ile
                260                 265                 270
Ile Pro Ala Ser His Thr Ser Val Ser Cys Tyr Ser Ala Pro Glu Ser
                275                 280                 285
Ser Gln Thr Asn Arg Tyr Thr Asp Lys Ser Asp Val Phe Ser Phe Gly
                290                 295                 300
Met Ile Leu Gly Val Leu Leu Thr Gly Arg Asp Pro Thr Leu Pro Phe
305                 310                 315                 320
Ser Ile Glu Gly Ala Ser Gly Gly Ser Leu Gly Gln Trp Leu Lys His
                325                 330                 335
Leu Gln Gln Thr Gly Glu Val Arg Glu Ala Leu Asp Lys Ser Ile Leu
                340                 345                 350
Gly Glu Glu Val Glu Glu Asp Glu Met Leu Met Ala Leu Arg Ile Thr
                355                 360                 365
Ile Ile Cys Leu Ser Asp Phe Pro Ala Asp Arg Pro Ser Ser Asp Glu
                370                 375                 380
Leu Val His Met Leu Thr Gln Leu His Ser Phe
385                 390                 395

<210> SEQ ID NO 96
<211> LENGTH: 401
<212> TYPE: PRT
<213> ORGANISM: Arabidopsis thaliana

<400> SEQUENCE: 96

Met Lys Gln Arg Arg Arg Arg Asn Gly Cys Ser Ser Ser Asn Thr Ile
1               5                   10                  15
Ser Leu Leu Leu Leu Phe Phe Leu Val Phe Phe Ser Arg Thr Ser Thr
                20                  25                  30
Ser Thr Ser Cys Arg Arg Arg Thr Val Lys His Leu Ser Thr Thr Ser
                35                  40                  45
Thr Ser Ser Thr Pro Leu Glu Ser Arg Ile Thr Ser Lys Val Ile Val
                50                  55                  60
Ile Ser Ile Val Ser Gly Ile Leu Thr Gly Leu Val Ser Ala Leu Val
65                  70                  75                  80
Leu Ala Phe Leu Val Arg Ser Ile Val Lys Phe Met Lys Gln Thr Pro
                85                  90                  95
Ile Leu Lys Gly Pro Val Val Phe Ser Pro Lys Ile Thr Pro Lys Ser
                100                 105                 110
Leu His Ala Ala Leu Ser Asn Gly Ile Gln Leu Leu Gly Ser Asp Leu
                115                 120                 125
Asn Gly Lys Tyr Tyr Lys Met Val Leu Asp Asn Gly Leu Val Val Ala
                130                 135                 140
Val Lys Arg Leu Gly Ser Leu Glu Gly Val Gly Ser Pro Glu Ser Ser
145                 150                 155                 160
Ser Ser Lys Ser Val Lys Arg Arg Leu Gln Lys Glu Leu Glu Leu Leu
                165                 170                 175
Ala Gly Leu Arg His Arg Asn Leu Met Ser Leu Arg Ala Tyr Val Arg
                180                 185                 190
Glu Ser Asp Glu Phe Ser Leu Val Tyr Asp Tyr Met Pro Asn Gly Ser
                195                 200                 205
```

```
Leu Glu Asp Val Met Asn Lys Val Arg Thr Lys Glu Val Glu Leu Gly
    210                 215                 220

Trp Glu Ile Arg Leu Arg Val Ala Val Gly Ile Val Lys Gly Leu Gln
225                 230                 235                 240

Tyr Leu His Phe Ser Cys Glu Thr Gln Ile Leu His Tyr Asn Leu Lys
                245                 250                 255

Pro Thr Asn Val Met Leu Asp Ser Glu Phe Glu Pro Arg Leu Ala Asp
                260                 265                 270

Cys Gly Leu Ala Lys Ile Met Pro Ser Ser His Thr Ala Val Ser Cys
                275                 280                 285

Tyr Ser Ala Pro Glu Ser Ser Gln Ser Asn Arg Tyr Thr Asp Lys Ser
    290                 295                 300

Asp Ile Phe Ser Phe Gly Met Ile Leu Gly Val Leu Leu Thr Gly Arg
305                 310                 315                 320

Asp Pro Thr His Pro Phe Cys Glu Glu Ser Ala Ser Gly Gly Ser Leu
                325                 330                 335

Gly Gln Trp Leu Lys His Leu Gln Ser Gly Glu Ala Arg Glu Ala
                340                 345                 350

Leu Asp Lys Thr Ile Leu Gly Glu Val Glu Glu Asp Glu Met Leu
    355                 360                 365

Met Ala Leu Arg Ile Thr Ile Ile Cys Leu Ser Asp Phe Pro Ala Asp
370                 375                 380

Arg Pro Ser Ser Asp Glu Leu Val His Met Leu Thr Gln Leu His Ser
385                 390                 395                 400

Phe

<210> SEQ ID NO 97
<211> LENGTH: 402
<212> TYPE: PRT
<213> ORGANISM: Arabidopsis lyrata

<400> SEQUENCE: 97

Met Glu Gln Arg Arg Arg Arg Arg Asn Gly Cys Ser Ser Asn Thr
1               5                   10                  15

Ile Ser Leu Leu Leu Phe Phe Phe Leu Val Phe Ser Arg Thr Ser
                20                  25                  30

Thr Ser Thr Ser Cys Arg Arg Arg Thr Val Lys His Leu Ser Thr Thr
                35                  40                  45

Ser Thr Ser Ser Thr Pro Leu Glu Ser Arg Ile Thr Ser Lys Val Ile
    50                  55                  60

Val Val Ser Ile Val Ser Gly Ile Leu Thr Gly Leu Val Ser Ala Leu
65                  70                  75                  80

Val Leu Ala Phe Leu Val Arg Ser Ile Val Lys Tyr Met Lys Gln Thr
                85                  90                  95

Pro Ile Leu Lys Gly Pro Val Val Phe Ser Pro Lys Ile Thr Pro Lys
                100                 105                 110

Ser Leu His Ala Ala Leu Gly Asn Gly Ile Gln Leu Leu Gly Ser Asp
                115                 120                 125

Pro Asn Gly Lys Tyr Tyr Lys Met Val Leu Asp Asn Gly Leu Val Val
    130                 135                 140

Ala Val Lys Arg Leu Gly Ser Leu Glu Gly Ile Gly Ser Pro Glu Thr
145                 150                 155                 160

Asn Ser Ser Lys Ser Val Lys Arg Leu Gln Lys Glu Leu Glu Leu
                165                 170                 175
```

```
Leu Ala Gly Leu Arg His Arg Asn Leu Met Ser Leu Arg Ala Tyr Val
            180                 185                 190

Arg Glu Ser Asp Glu Phe Ser Leu Val Tyr Asp Tyr Met Pro Asn Gly
        195                 200                 205

Ser Leu Glu Asp Val Met His Lys Val Arg Thr Lys Glu Val Glu Leu
    210                 215                 220

Gly Trp Glu Ile Arg Leu Arg Val Ala Val Gly Ile Val Lys Gly Leu
225                 230                 235                 240

Gln Tyr Leu His Phe Ser Cys Glu Thr Gln Ile Leu His Tyr Asn Leu
                245                 250                 255

Lys Pro Thr Asn Val Met Leu Asp Ser Glu Phe Glu Pro Arg Leu Ala
            260                 265                 270

Asp Cys Gly Leu Ala Lys Ile Met Pro Ser Ser His Thr Ala Val Phe
        275                 280                 285

Cys Tyr Ser Ala Pro Glu Ser Ser Gln Ser Asn Arg Tyr Thr Asp Lys
    290                 295                 300

Ser Asp Ile Phe Ser Phe Gly Met Ile Leu Gly Val Leu Leu Thr Gly
305                 310                 315                 320

Arg Asp Pro Thr His Pro Phe Cys Glu Glu Ser Ala Ser Gly Gly Ser
                325                 330                 335

Leu Gly Gln Trp Leu Lys His Leu Gln Gln Ser Gly Glu Ala Arg Glu
            340                 345                 350

Ala Leu Asp Lys Thr Ile Leu Gly Glu Val Glu Glu Asp Glu Met
        355                 360                 365

Leu Met Ala Leu Arg Ile Thr Ile Ile Cys Leu Ser Asp Phe Pro Ala
370                 375                 380

Asp Arg Pro Ser Ser Asp Glu Leu Val His Met Leu Thr Gln Leu His
385                 390                 395                 400

Ser Phe

<210> SEQ ID NO 98
<211> LENGTH: 394
<212> TYPE: PRT
<213> ORGANISM: Brassica napus

<400> SEQUENCE: 98

Met Glu Gln Arg Arg Arg Ser Asn Thr Ile Tyr Leu Leu Leu Leu Phe
1               5                   10                  15

Phe Phe Leu Val Phe Thr Ser Arg Thr Ser Thr Ser Ser Ser Cys Arg
            20                  25                  30

Arg Arg Thr Val Lys His Leu Ser Thr Thr Pro Pro Ser Ser Thr Pro
        35                  40                  45

Leu Glu Ser Arg Ile Thr Ser Lys Val Ile Val Phe Ser Ile Val Ser
    50                  55                  60

Gly Ile Leu Thr Gly Leu Val Ser Ala Leu Val Leu Ala Phe Leu Val
65                  70                  75                  80

Arg Ser Ile Val Lys Tyr Met Lys Gln Thr Pro Ile Leu Lys Gly Pro
                85                  90                  95

Val Val Phe Ser Pro Glu Leu Thr Pro Lys Ser Leu His Gly Ala Leu
            100                 105                 110

Gly Asn Gly Ile His Leu Leu Gly Ser Asp Pro Asn Gly Lys Tyr His
        115                 120                 125

Lys Val Val Leu Asp Asn Gly Leu Val Val Ala Val Lys Arg Leu Cys
    130                 135                 140
```

Ser Pro Glu Ala Ser Gly Ser Ser Thr Ser Arg Asn Ser Val Lys Arg
145                 150                 155                 160

Arg Leu Gln Lys Glu Leu Glu Leu Leu Ala Glu Ile Arg His Arg Asn
            165                 170                 175

Leu Met Ser Leu Arg Ala Tyr Val Arg Glu Ser Asn Glu Phe Ser Leu
        180                 185                 190

Val Tyr Asp Tyr Met Pro Asn Gly Ser Leu Glu Asp Val Met Thr Lys
    195                 200                 205

Val Arg Gly Lys Glu Leu Glu Leu Gly Trp Glu Val Arg Leu Arg Val
210                 215                 220

Ala Val Gly Ile Val Gln Gly Leu Gln Tyr Leu His Phe Ser Cys Asp
225                 230                 235                 240

His Gln Ile Leu His Tyr Asn Leu Lys Pro Thr Asn Val Met Leu Asp
            245                 250                 255

Ser Glu Phe Glu Pro Arg Leu Ala Asp Cys Gly Leu Ala Lys Ile Met
        260                 265                 270

Ala Ala Ser His Thr Gly Val Cys Tyr Ser Ala Pro Glu Ser Ser
    275                 280                 285

Gln Ser Asn Arg Tyr Thr Asp Lys Ser Asp Ile Phe Ser Phe Gly Met
290                 295                 300

Ile Leu Gly Leu Leu Leu Thr Gly Arg Asp Pro Thr Gln Pro Phe Cys
305                 310                 315                 320

Val Asp Gly Ala Ser Gly Gly Ser Leu Gly Gln Trp Leu Lys His Leu
            325                 330                 335

Gln Gln Ser Gly Glu Ala Arg Glu Ala Leu Asp Lys Ser Ile Leu Gly
        340                 345                 350

Glu Glu Val Lys Glu Asp Glu Met Leu Met Ala Leu Arg Ile Thr Ile
    355                 360                 365

Ile Cys Leu Ser Asp Phe Pro Ala Asp Arg Pro Ser Ser Asp Glu Leu
370                 375                 380

Val His Met Leu Thr Gln Leu His Ser Phe
385                 390

<210> SEQ ID NO 99
<211> LENGTH: 394
<212> TYPE: PRT
<213> ORGANISM: Brassica oleracea

<400> SEQUENCE: 99

Met Glu Gln Arg Arg Arg Ser Asn Thr Ile Tyr Leu Leu Leu Leu Phe
1               5                   10                  15

Phe Phe Leu Val Phe Thr Ser Arg Thr Asn Thr Ser Ala Ser Cys Arg
            20                  25                  30

Arg Arg Thr Val Lys His Leu Ser Thr Thr Pro Pro Ser Ser Thr Pro
        35                  40                  45

Leu Gln Ser Ser Ile Thr Ser Lys Val Met Val Phe Ser Ile Ala Ser
    50                  55                  60

Gly Ile Leu Ile Gly Leu Val Ser Ala Leu Val Leu Ala Phe Leu Val
65                  70                  75                  80

Arg Cys Ile Val Lys Tyr Met Gln Gln Thr Pro Ile Leu Lys Gly Pro
            85                  90                  95

Val Val Phe Ser Pro Glu Leu Thr Pro Lys Ser Leu Tyr Gly Ala Leu
        100                 105                 110

Gly Asn Gly Ile Gln Leu Leu Gly Ser Gly Pro Asn Gly Lys Tyr His
    115                 120                 125

Lys Val Val Leu Asp Asn Gly Leu Val Ala Val Lys Arg Leu Cys
130                 135                 140

Ser Pro Glu Ala Ser Gly Ser Ser Thr Ser Arg Asn Ser Val Lys Arg
145                 150                 155                 160

Arg Leu Gln Lys Glu Leu Glu Leu Leu Ala Ile Leu Arg His Met Asn
                165                 170                 175

Leu Met Ser Leu Arg Ala Tyr Val Leu Glu Ser Asn Glu Phe Ser Leu
            180                 185                 190

Val Tyr Asp Tyr Met Pro Asn Gly Ser Leu Glu Asp Val Met Thr Lys
        195                 200                 205

Val Arg Ala Lys Glu Leu Glu Leu Gly Trp Glu Val Arg Leu Arg Val
    210                 215                 220

Ala Val Gly Ile Val Gln Gly Leu Gln Tyr Leu His Phe Ser Cys Asp
225                 230                 235                 240

His Gln Val Leu His Tyr Asn Leu Lys Pro Thr Asn Val Met Leu Asp
                245                 250                 255

Ser Glu Phe Glu Pro Arg Leu Ala Asp Cys Gly Leu Ala Lys Ile Met
            260                 265                 270

Ala Ala Ser His Thr Gly Val Ser Cys Tyr Ser Ala Pro Glu Ser Ser
        275                 280                 285

Gln Ser Asn Arg Tyr Thr Asp Lys Ser Asp Ile Phe Ser Phe Gly Met
    290                 295                 300

Ile Leu Gly Leu Leu Thr Gly Arg Asp Pro Thr Gln Pro Phe Cys
305                 310                 315                 320

Val Asp Gly Ala Ser Gly Gly Ser Leu Gly Gln Trp Leu Lys His Leu
                325                 330                 335

Gln Gln Ser Gly Glu Ala Arg Glu Ala Leu Asp Lys Ser Ile Leu Gly
            340                 345                 350

Glu Glu Val Glu Glu Asp Glu Met Leu Met Ala Leu Arg Ile Thr Ile
        355                 360                 365

Ile Cys Leu Ser Asp Phe Pro Ala Asp Arg Pro Ser Ser Asp Glu Leu
    370                 375                 380

Val His Met Leu Thr Gln Leu His Ser Phe
385                 390

<210> SEQ ID NO 100
<211> LENGTH: 394
<212> TYPE: PRT
<213> ORGANISM: Brassica napus

<400> SEQUENCE: 100

Met Glu Gln Arg Arg Arg Ser Asn Thr Ile Tyr Leu Leu Leu Phe
1               5                   10                  15

Phe Phe Leu Val Phe Thr Ser Arg Thr Asn Thr Ser Ala Ser Cys Arg
                20                  25                  30

Arg Arg Thr Val Lys His Leu Ser Thr Thr Pro Pro Ser Ser Thr Pro
            35                  40                  45

Leu Gln Ser Ser Ile Thr Ser Lys Val Ile Val Phe Ser Ile Ala Ser
        50                  55                  60

Gly Ile Leu Ile Gly Leu Val Ser Ala Leu Val Leu Ala Phe Leu Val
65                  70                  75                  80

Arg Cys Ile Val Lys Tyr Met Gln Gln Thr Pro Ile Leu Lys Gly Pro
                85                  90                  95

Val Val Phe Ser Pro Glu Leu Thr Pro Lys Ser Leu Tyr Gly Ala Leu

```
                100                 105                 110
Gly Asn Gly Ile Gln Leu Leu Gly Ser Gly Pro Asn Gly Lys Tyr His
            115                 120                 125

Lys Val Val Leu Asp Asn Gly Leu Val Val Ala Val Lys Arg Leu Cys
130                 135                 140

Ser Pro Glu Ala Ser Gly Ser Ser Thr Ser Arg Asn Ser Val Lys Arg
145                 150                 155                 160

Arg Leu Gln Lys Glu Leu Glu Leu Leu Ala Ile Leu Arg His Met Asn
                165                 170                 175

Leu Met Ser Leu Arg Ala Tyr Val Pro Glu Ser Asn Glu Phe Ser Leu
            180                 185                 190

Val Tyr Asp Tyr Met Pro Asn Gly Ser Leu Glu Asp Val Met Thr Lys
        195                 200                 205

Val Arg Ala Lys Glu Leu Glu Leu Gly Trp Glu Val Arg Leu Arg Val
    210                 215                 220

Ala Val Gly Ile Val Gln Gly Leu Gln Tyr Leu His Phe Ser Cys Asp
225                 230                 235                 240

His Gln Val Leu His Tyr Asn Leu Lys Pro Thr Asn Val Met Leu Asp
                245                 250                 255

Ser Glu Phe Glu Pro Arg Leu Ala Asp Cys Gly Leu Ala Lys Ile Met
            260                 265                 270

Ala Ala Ser His Thr Gly Leu Ser Cys Tyr Ser Ala Pro Glu Ser Ser
        275                 280                 285

Gln Ser Asn Arg Tyr Thr Asp Lys Ser Asp Ile Phe Ser Phe Gly Met
    290                 295                 300

Ile Leu Gly Leu Leu Leu Thr Gly Arg Asp Pro Thr Gln Pro Phe Cys
305                 310                 315                 320

Val Asp Gly Ala Ser Gly Gly Ser Leu Gly Gln Trp Leu Lys His Leu
                325                 330                 335

Gln Gln Ser Gly Glu Ala Arg Glu Ala Leu Asp Lys Ser Ile Leu Gly
            340                 345                 350

Glu Glu Val Glu Glu Asp Glu Met Leu Met Ala Leu Arg Ile Thr Ile
        355                 360                 365

Ile Cys Leu Ser Asp Phe Pro Ala Asp Arg Pro Ser Ser Asp Glu Leu
    370                 375                 380

Val His Met Leu Thr Gln Ile His Ser Phe
385                 390

<210> SEQ ID NO 101
<211> LENGTH: 413
<212> TYPE: PRT
<213> ORGANISM: Trifolium pratense

<400> SEQUENCE: 101

Met Gly Leu Ile Cys Gly Cys Gly Phe Val Phe Cys Val Leu Met Phe
1               5                   10                  15

Lys Lys Arg Gln Thr Phe Phe Tyr Leu Ala Lys Glu Leu Leu Val Phe
            20                  25                  30

Gln Pro Leu Val Leu Leu Phe Leu Phe Ser Leu His His Asn Thr
        35                  40                  45

Val Gln Cys Glu Gly Arg Leu Ser Lys Asn Ile Ser Ser Glu Thr Ser
    50                  55                  60

Ser Gln Ser Asp Tyr Lys Asp Asn Pro Arg Lys Val Ile Val Ser Ile
65                  70                  75                  80
```

Val Leu Gly Ala Val Thr Gly Leu Ile Gly Ser Val Leu Phe Ala Phe
                85                  90                  95

Val Ile Arg Cys Ile Val Arg Tyr Leu Asn Arg Thr Pro Ile Leu Lys
            100                 105                 110

Gly Pro Val Ile Phe Ser Pro Lys Ile Ala Ser Lys Thr Leu Gln Leu
        115                 120                 125

Ala Leu Ser Lys Glu Asn His Leu Leu Gly Ser Ser Pro Asn Gly Lys
    130                 135                 140

Tyr Tyr Lys Thr Val Leu Glu Asn Gly Leu Thr Ile Ala Val Lys Arg
145                 150                 155                 160

Leu Thr Pro Phe Glu Ser Asn Ser Pro Glu Ser Arg Arg Lys Ser Val
                165                 170                 175

Lys Arg Gln Ile Gln Met Glu Leu Glu Leu Leu Ala Ser Leu Arg His
            180                 185                 190

Arg Asn Leu Met Ser Leu Arg Ala Tyr Val Arg Gln Asn Asp Gly Phe
        195                 200                 205

Ser Leu Val Tyr Asp Tyr Val Ser Thr Gly Ser Leu Ala Asp Val Met
    210                 215                 220

Asn Arg Val Arg Glu Asn Glu Leu Gln Ile Gly Trp Glu Val Arg Leu
225                 230                 235                 240

Arg Ile Ala Val Gly Val Val Lys Gly Leu Gln Tyr Leu His Phe Thr
                245                 250                 255

Cys Val Pro Gln Ile Leu His Phe Asn Leu Lys Pro Thr Asn Val Met
            260                 265                 270

Leu Asp Ala Glu Phe Glu Pro Arg Leu Ala Asp Tyr Gly Leu Ala Lys
        275                 280                 285

Leu Leu Pro Asn Leu Asp Arg Gly Ile Ser Leu Asn Thr Pro Pro Glu
    290                 295                 300

Cys Leu His Asn Arg Ser Arg Tyr Thr Glu Lys Ser Asp Ile Phe Gly
305                 310                 315                 320

Phe Gly Met Ile Leu Gly Val Leu Leu Thr Gly Lys Asp Ala Ala Asp
                325                 330                 335

Pro Phe Phe Gly Glu Ala Ser Arg Gly Gly Asn Leu Gly Cys Trp Leu
            340                 345                 350

Arg His Leu Lys Gln Ala Gly Glu Glu Arg Glu Ala Leu Asp Lys Ser
        355                 360                 365

Ile Leu Gly Glu Gln Gly Glu Glu Asp Glu Met Leu Met Ala Val Gly
    370                 375                 380

Ile Ala Ala Ala Cys Leu Ser Asp Met Pro Ala Asp Arg Pro Ser Ser
385                 390                 395                 400

Asp Glu Leu Val His Met Leu Thr Gln Leu Asn Ser Phe
                405                 410

<210> SEQ ID NO 102
<211> LENGTH: 413
<212> TYPE: PRT
<213> ORGANISM: Medicago truncatula

<400> SEQUENCE: 102

Met Gly Leu Ile Cys Gly Cys Gly Phe Val Phe Cys Val Phe Met Phe
1               5                   10                  15

Lys Lys Arg His Thr Pro Phe Ser Leu Ala Arg Lys Phe Leu Ser Phe
            20                  25                  30

Gln Pro Phe Val Leu Leu Leu Phe Leu Phe Ser Leu His Asp Thr
        35                  40                  45

```
Val Gln Cys Gln Gly Arg Leu Ser Lys His Met Ser Ser Glu Pro Ser
 50                  55                  60

Ser Ser Thr Ser Glu Tyr Lys Asp Asp Pro Arg Lys Ile Ile Ile Ser
 65                  70                  75                  80

Ile Val Leu Gly Ala Val Thr Gly Leu Ile Gly Ser Val Leu Phe Ala
                 85                  90                  95

Phe Val Ile Arg Cys Val Val Trp Tyr Leu Asn Arg Thr Pro Ile Leu
            100                 105                 110

Lys Gly Pro Val Ile Phe Ser Pro Lys Ile Ala Ser Lys Thr Leu Gln
            115                 120                 125

Val Ala Leu Thr Lys Glu Asn His Met Leu Gly Ser Ser Pro Asn Gly
            130                 135                 140

Lys Tyr Tyr Lys Thr Val Leu Glu Asn Gly Leu Ile Ile Ala Val Lys
145                 150                 155                 160

Arg Leu Thr Pro Phe Glu Ser Asn Ser Pro Glu Ser Arg Lys Lys Ser
                165                 170                 175

Val Lys Arg Gln Ile Gln Met Glu Leu Glu Leu Leu Ala Ser Leu Arg
            180                 185                 190

His Arg Asn Leu Met Ser Leu Arg Ala Tyr Val Arg Glu Asn Asp Gly
            195                 200                 205

Phe Ser Leu Val Tyr Asp Tyr Val Ser Thr Gly Ser Leu Ala Asp Val
210                 215                 220

Met Asn Arg Val Arg Glu Asn Glu Leu Gln Ile Gly Trp Glu Ala Arg
225                 230                 235                 240

Leu Arg Ile Ala Val Gly Val Val Lys Gly Leu Gln Tyr Leu His Phe
                245                 250                 255

Thr Cys Val Pro Gln Ile Leu His Phe Asn Leu Lys Pro Thr Asn Val
            260                 265                 270

Met Leu Asp Ala Glu Phe Glu Pro Arg Leu Ala Asp Tyr Gly Leu Ala
            275                 280                 285

Lys Leu Leu Pro Asn Leu Asp Arg Gly Ile Ser Val Asn Ile Pro Pro
            290                 295                 300

Glu Cys Ser His Asn Cys Arg Tyr Thr Glu Lys Ser Asp Ile Phe Ser
305                 310                 315                 320

Phe Gly Met Ile Leu Gly Val Leu Leu Thr Gly Lys Asp Pro Thr Asp
                325                 330                 335

Pro Phe Phe Gly Glu Ala Ser Arg Gly Gly Ser Leu Gly Cys Trp Leu
            340                 345                 350

Arg His Leu Lys Gln Ala Gly Glu Glu Arg Glu Ala Leu Asp Lys Ser
            355                 360                 365

Ile Leu Gly Glu Gln Gly Glu Glu Asp Glu Met Leu Met Ala Val Gly
            370                 375                 380

Ile Ala Ala Ala Cys Leu Ser Asp Met Pro Ala Glu Arg Pro Ser Ser
385                 390                 395                 400

Asp Glu Leu Val His Met Leu Thr Gln Leu Asn Ser Phe
                405                 410

<210> SEQ ID NO 103
<211> LENGTH: 392
<212> TYPE: PRT
<213> ORGANISM: Lupinus angustifolius

<400> SEQUENCE: 103

Met Phe Lys Arg Arg His Thr Leu Cys Ser Leu Leu Arg Glu Leu Phe
```

```
1               5                   10                  15
Leu Leu Leu Leu Phe Ser Leu His His Ser Thr Val Gln Cys Gln Gly
            20                  25                  30

Arg Leu Ser Lys His Val Ser Ser Ala Pro Tyr Ser Pro Ser Glu Tyr
            35                  40                  45

Lys Asp Asp Leu Arg Arg Ile Ile Ser Ile Val Leu Gly Gly Leu
            50                  55                  60

Thr Gly Leu Val Gly Ser Val Phe Phe Ala Phe Val Val Arg Cys Val
65                      70                  75                  80

Val Arg Tyr Leu Asn Arg Thr Pro Ile Leu Lys Gly Pro Val Ile Phe
                    85                  90                  95

Ser Pro Lys Ile Ala Pro Lys Thr Leu Glu Ser Ala Leu Ala Lys Glu
                100                 105                 110

Asn His Leu Leu Gly Ser Ser Pro Asn Gly Lys Tyr Tyr Lys Thr Val
                115                 120                 125

Leu Asp Asn Gly Leu Thr Ile Ala Val Lys Arg Leu Thr Pro Phe Glu
                130                 135                 140

Ser Asn Ser Pro Glu Met Arg Arg Lys Ser Val Lys Arg Gln Ile Gln
145                 150                 155                 160

Lys Glu Leu Glu Leu Leu Ala Ser Leu Arg His Arg Asn Leu Met Ser
                165                 170                 175

Leu Arg Ala Tyr Val Arg Glu Ala Asp Arg Phe Ser Leu Val Tyr Asp
                180                 185                 190

Tyr Val Ser Thr Gly Ser Leu Ala Asp Leu Met Asn Arg Val Arg Glu
                195                 200                 205

Asn Glu Leu Gln Leu Gly Trp Glu Val Arg Leu Arg Ile Ala Val Gly
                210                 215                 220

Ile Val Lys Gly Leu Gln Tyr Leu His Phe Thr Cys Val Pro Gln Ile
225                 230                 235                 240

Leu His Cys Asn Leu Lys Pro Thr Asn Val Met Leu Asp Ala Glu Phe
                245                 250                 255

Glu Pro Arg Leu Ala Asp Tyr Gly Leu Ser Lys Leu Leu Pro Asn Leu
                260                 265                 270

Asp Arg Gly Thr His Gly Asn Asn Pro Ser Gln Ser Leu His Asn Cys
                275                 280                 285

Ser Arg Tyr Thr Asp Lys Ser Asp Ile Phe Ser Phe Gly Met Ile Leu
                290                 295                 300

Gly Thr Leu Leu Thr Gly Lys Asp Pro Thr Asp Pro Phe Phe Gly Glu
305                 310                 315                 320

Ala Ala Ser Gly Gly Ser Leu Gly Ser Trp Leu Gln His Leu Gln Arg
                325                 330                 335

Ala Gly Glu Ala Arg Glu Ala Leu Asp Lys Ser Ile Leu Gly Glu Glu
                340                 345                 350

Gly Glu Glu Asp Glu Met Leu Met Ala Val Arg Ile Ala Ala Ala Cys
                355                 360                 365

Leu Ser Asp Ile Pro Ala Asp Arg Pro Ser Ser Asp Glu Leu Val His
                370                 375                 380

Met Leu Thr Gln Leu His Ser Phe
385                 390

<210> SEQ ID NO 104
<211> LENGTH: 406
<212> TYPE: PRT
<213> ORGANISM: Phaseolus vulgaris
```

<400> SEQUENCE: 104

```
Met Phe Arg Lys Arg His Ile Ala Ser Ser Leu Ala Arg Glu Leu Leu
1               5                   10                  15

Ala Leu Gln Pro Leu Leu Ile Leu Phe Leu Phe Ser Leu His His His
            20                  25                  30

Thr Val Gln Cys Gln Gly Arg Leu Ser Lys His Val Ser Ser Glu Pro
        35                  40                  45

Pro Ser Pro Ser Arg Thr Ser Pro Pro Ser Ser Gly Tyr Arg Asp
    50                  55                  60

Asp Pro Lys Lys Ile Ile Leu Ser Met Val Leu Gly Ala Val Thr Gly
65                  70                  75                  80

Leu Val Cys Ser Val Leu Phe Ala Leu Val Val Arg Cys Val Val Gln
                85                  90                  95

Tyr Leu Asn Arg Thr Pro Ile Leu Lys Gly Pro Val Ile Phe Ser Pro
                100                 105                 110

Lys Ile Ala Pro Lys Thr Leu Gln Leu Ala Leu Ala Lys Glu Asn His
                115                 120                 125

Leu Leu Gly Ser Ser Pro Asn Gly Lys Tyr Tyr Lys Thr Val Leu Asp
            130                 135                 140

Asn Gly Leu Thr Ile Ala Val Lys Arg Leu Thr Pro Phe Glu Ser Asn
145                 150                 155                 160

Ser Pro Glu Ala Arg Lys Asn Ser Val Lys Arg Gln Ile Gln Thr Glu
                165                 170                 175

Leu Glu Leu Leu Ala Ser Leu Arg His Arg Asn Leu Met Ser Leu Arg
            180                 185                 190

Ala Tyr Val Arg Glu Pro Asp Gly Phe Ser Leu Val Tyr Asp Tyr Val
            195                 200                 205

Ser Thr Gly Ser Leu Ala Asp Val Met Asn Lys Val Trp Glu Asn Glu
210                 215                 220

Leu Pro Phe Gly Trp Glu Val Arg Leu Arg Ile Ala Val Gly Val Val
225                 230                 235                 240

Lys Gly Leu Gln Tyr Leu His Phe Thr Cys Ala Pro Gln Ile Leu His
                245                 250                 255

Tyr Ser Leu Lys Pro Thr Asn Val Met Leu Asp Ala Asp Phe Glu Pro
                260                 265                 270

Arg Leu Ala Asp Tyr Gly Leu Ala Lys Leu Leu Pro Asn Leu Asp Arg
            275                 280                 285

Gly Thr Ser Leu Tyr Thr Pro Pro Glu Cys Phe His Asn Cys Ser Arg
290                 295                 300

Tyr Thr Asp Lys Ser Asp Ile Phe Ser Phe Gly Met Ile Leu Gly Val
305                 310                 315                 320

Leu Leu Thr Gly Lys Asp Pro Thr Asp Pro Phe Phe Gly Glu Ala Ala
                325                 330                 335

Ser Gly Gly Ser Leu Gly Cys Trp Leu Arg His Leu Gln Ala Gly
            340                 345                 350

Glu Ala Arg Asp Ala Leu Asp Lys Ser Met Leu Gly Glu Gly Glu
            355                 360                 365

Glu Asp Glu Met Leu Met Ala Val Arg Ile Ala Ala Cys Leu Ser
            370                 375                 380

Asp Met Pro Ala Asp Arg Pro Ser Ser Asp Glu Leu Val His Met Leu
385                 390                 395                 400

Thr Gln Leu His Ser Phe
```

```
            405

<210> SEQ ID NO 105
<211> LENGTH: 429
<212> TYPE: PRT
<213> ORGANISM: Vigna radiata

<400> SEQUENCE: 105

Met Ile His Ala Ser Phe Trp Ser Phe Arg Asp Trp Phe Leu Ala Leu
1               5                   10                  15

Phe Val Cys Cys Ser Leu Met Phe Arg Lys Arg Asn Ile Ala Ser Ser
            20                  25                  30

Leu Ala Arg Glu Leu Leu Ala Leu Gln Pro Leu Phe Ile Ile Phe Leu
        35                  40                  45

Phe Ser Leu His His Asn Thr Val Gln Cys Gln Gly Arg Leu Ser Lys
    50                  55                  60

His Val Ser Ser Glu Pro Pro Ser Pro Ser Arg Pro Ser Pro Pro Ser
65                  70                  75                  80

Ser Ser Gly Tyr Arg Asp Asp Pro Lys Lys Ile Ile Leu Ser Leu Val
                85                  90                  95

Leu Gly Ala Val Thr Gly Leu Val Cys Ser Val Phe Phe Ala Leu Val
            100                 105                 110

Val Arg Cys Val Val Gln Tyr Leu Asn Arg Thr Pro Ile Leu Lys Gly
        115                 120                 125

Pro Val Ile Phe Ser Pro Lys Ile Ala Pro Lys Thr Leu Gln Leu Ala
    130                 135                 140

Leu Ala Lys Glu Asn His Leu Leu Gly Ser Ser Pro Asn Gly Lys Tyr
145                 150                 155                 160

Tyr Lys Thr Val Leu Asp Asn Gly Leu Thr Ile Ala Val Lys Arg Leu
                165                 170                 175

Thr Pro Phe Gly Ser Ser Ser Pro Glu Ala Lys Lys Ser Val Lys
            180                 185                 190

Arg Gln Ile Gln Thr Glu Leu Glu Leu Leu Ala Ser Leu Arg His Arg
        195                 200                 205

Asn Leu Met Ser Leu Arg Ala Tyr Val Arg Glu Pro Asp Gly Phe Ser
    210                 215                 220

Leu Val Tyr Asp Tyr Val Ser Thr Gly Ser Leu Ala Asp Val Met Asn
225                 230                 235                 240

Arg Val Trp Glu Asn Glu Leu Ala Phe Gly Trp Glu Val Arg Leu Arg
                245                 250                 255

Ile Ala Val Gly Val Val Lys Gly Leu Gln Tyr Leu His Phe Thr Cys
            260                 265                 270

Ala Pro Gln Ile Leu Leu His Tyr Asn Leu Lys Pro Thr Asn Val Met
        275                 280                 285

Leu Asp Gly Asp Phe Glu Pro Arg Leu Ala Asp Tyr Gly Leu Ala Lys
    290                 295                 300

Leu Leu Pro Asn Leu Asp Arg Gly Thr Ser Leu Tyr Thr Pro Pro Glu
305                 310                 315                 320

Cys Phe His Asn Cys Ser Arg Tyr Thr Asp Lys Ser Asp Ile Phe Ser
                325                 330                 335

Phe Gly Met Ile Leu Gly Val Leu Thr Gly Lys Asp Pro Thr Asp
            340                 345                 350

Pro Phe Phe Gly Glu Ala Ala Ser Gly Gly Ser Leu Gly Gly Trp Leu
        355                 360                 365
```

-continued

```
Arg His Leu Gln Gln Ala Gly Asp Ala Arg Asp Ala Leu Asp Lys Ser
    370                 375                 380

Met Leu Gly Glu Glu Gly Glu Asp Glu Met Leu Met Ala Val Arg
385                 390                 395                 400

Ile Ala Ala Ala Cys Leu Ser Asp Met Pro Ala Asp Arg Pro Ser Ser
                    405                 410                 415

Asp Glu Leu Val His Met Leu Thr Gln Leu His Ser Phe
                420                 425
```

<210> SEQ ID NO 106
<211> LENGTH: 408
<212> TYPE: PRT
<213> ORGANISM: Glycine max

<400> SEQUENCE: 106

```
Met Phe Arg Lys Arg His Ile Leu Ser Ser Leu Ala Arg Glu Leu Leu
1               5                   10                  15

Ala Leu Gln Pro Leu Phe Leu Leu Phe Leu Phe Ser Leu His His Asn
                20                  25                  30

Thr Val Gln Cys Gln Gly Arg Leu Ser Lys His Val Ser Ser Glu Pro
                35                  40                  45

Pro Ser Pro Ser Arg Pro Ser Ser Ala Ala Pro Ser Ser Ser Gly Tyr
        50                  55                  60

Lys Asp Asp Pro Arg Lys Ile Ile Leu Ser Met Val Leu Gly Ala Val
65                  70                  75                  80

Thr Gly Leu Val Cys Ser Val Leu Phe Ala Leu Val Val Arg Cys Val
                85                  90                  95

Val Gln Tyr Leu Asn Arg Thr Pro Ile Leu Lys Gly Pro Val Ile Phe
                100                 105                 110

Ser Pro Lys Ile Ala Ser Lys Thr Leu Gln Ser Ala Leu Ala Lys Glu
            115                 120                 125

Asn His Leu Leu Gly Ser Ser Pro Asn Gly Lys Tyr Tyr Lys Thr Met
        130                 135                 140

Leu Asp Asn Gly Leu Thr Ile Ala Val Lys Arg Leu Thr Pro Phe Glu
145                 150                 155                 160

Ser Asn Ser Pro Glu Ala Lys Arg Lys Ser Val Lys Arg Gln Ile Gln
                165                 170                 175

Thr Glu Leu Glu Leu Leu Ala Ser Leu Arg Asn Arg Asn Leu Met Ser
                180                 185                 190

Leu Arg Ala Tyr Val Arg Glu Pro Asp Gly Phe Ser Leu Val Tyr Asp
            195                 200                 205

Tyr Ala Ser Thr Gly Ser Leu Ala Asp Val Leu Asn Arg Val Arg Glu
        210                 215                 220

Asn Glu Leu Pro Phe Gly Trp Glu Val Arg Leu Arg Ile Ala Val Gly
225                 230                 235                 240

Val Val Lys Gly Leu Gln Tyr Leu His Phe Thr Cys Val Pro Gln Ile
                245                 250                 255

Leu His Tyr Asn Leu Lys Pro Thr Asn Val Met Leu Asp Ala Glu Phe
                260                 265                 270

Glu Pro Arg Leu Ala Asp Tyr Gly Leu Ala Lys Leu Leu Pro Asn Leu
            275                 280                 285

Asp Arg Gly Ser Ser Leu Tyr Thr Pro Pro Glu Cys Phe His Asn Cys
        290                 295                 300

Ser Arg Tyr Thr Asp Lys Ser Asp Ile Phe Ser Phe Gly Ile Ile Leu
305                 310                 315                 320
```

```
Gly Val Leu Leu Thr Ser Lys Asp Pro Thr Asp Pro Phe Phe Gly Glu
            325                 330                 335

Ala Ala Ser Gly Gly Ser Leu Gly Cys Trp Leu Arg His Leu Gln Gln
            340                 345                 350

Ala Gly Glu Ser Arg Glu Ala Leu Asp Lys Ser Met Leu Gly Glu Glu
            355                 360                 365

Gly Glu Glu Asp Glu Met Leu Met Ala Val Arg Ile Ala Ala Ala Cys
370                 375                 380

Leu Ser Asp Met Pro Ala Asp Arg Pro Ser Ser Asp Glu Leu Val His
385                 390                 395                 400

Met Leu Thr Gln Leu His Ser Phe
            405

<210> SEQ ID NO 107
<211> LENGTH: 408
<212> TYPE: PRT
<213> ORGANISM: Glycine max

<400> SEQUENCE: 107

Met Phe Arg Lys Arg His Thr Leu Ser Ser Leu Ala Arg Glu Leu Leu
1               5                   10                  15

Ala Phe Gln Pro Leu Phe Leu Leu Phe Leu Phe Ser Leu His His Asn
            20                  25                  30

Thr Met Gln Cys Gln Gly Arg Leu Ser Lys His Val Ser Ser Glu Pro
        35                  40                  45

Pro Ser Pro Ser Arg Ser Thr Pro Ser Pro Ser Ser Ser Gly Tyr
    50                  55                  60

Lys Asp Asp Pro Arg Lys Ile Ile Leu Ser Met Val Leu Gly Ala Val
65                  70                  75                  80

Thr Gly Leu Val Ser Ser Ala Leu Phe Ala Leu Val Val Arg Cys Val
                85                  90                  95

Val Gln Tyr Leu Asn Arg Thr Pro Ile Leu Lys Gly Pro Val Ile Phe
            100                 105                 110

Ser Pro Lys Ile Ala Pro Met Thr Leu Gln Ser Ala Leu Ala Lys Glu
        115                 120                 125

Asn His Leu Leu Gly Ser Ser Pro Asn Gly Lys Tyr Tyr Lys Thr Val
    130                 135                 140

Leu Asp Asn Gly Leu Thr Ile Ala Val Lys Arg Leu Thr Pro Phe Glu
145                 150                 155                 160

Ser Asn Ser Pro Glu Ala Lys Arg Lys Ser Val Lys Arg Gln Ile Gln
                165                 170                 175

Thr Glu Leu Glu Leu Leu Ala Ser Leu Arg His Arg Asn Leu Met Ser
            180                 185                 190

Leu Arg Ala Tyr Val Arg Glu Pro Asp Gly Phe Ser Leu Val Tyr Asp
        195                 200                 205

Tyr Val Ser Thr Gly Ser Leu Ala Asp Val Leu Ser Lys Val Arg Glu
    210                 215                 220

Asn Glu Leu Pro Phe Gly Trp Glu Val Arg Leu Arg Ile Ala Val Gly
225                 230                 235                 240

Val Val Lys Gly Leu Gln Tyr Leu His Phe Thr Cys Val Pro Gln Ile
                245                 250                 255

Leu His Tyr Asn Leu Lys Pro Thr Asn Val Met Leu Asp Ala Glu Phe
            260                 265                 270

Glu Pro Arg Leu Ala Asp Tyr Gly Leu Ala Lys Leu Leu Pro Asn Leu
```

```
                275                 280                 285
Asp Gly Gly Ser Ser Leu Tyr Thr Pro Pro Glu Cys Phe His Asn Cys
290                 295                 300

Ser Arg Tyr Thr Asp Lys Ser Asp Ile Phe Ser Phe Gly Met Ile Leu
305                 310                 315                 320

Gly Val Leu Leu Thr Gly Lys Asp Pro Thr Asp Pro Phe Phe Gly Glu
                325                 330                 335

Ala Ala Ser Gly Gly Ser Leu Gly Cys Trp Leu Arg His Leu Gln Gln
                340                 345                 350

Ala Gly Glu Ala His Glu Ala Leu Asp Lys Ser Met Leu Gly Glu Glu
                355                 360                 365

Gly Glu Glu Asp Glu Met Leu Met Ala Val Arg Ile Ala Ala Ala Cys
370                 375                 380

Leu Ser Asp Met Pro Ala Asp Arg Pro Ser Ser Asp Glu Leu Val His
385                 390                 395                 400

Met Leu Thr Gln Leu His Ser Phe
                405

<210> SEQ ID NO 108
<211> LENGTH: 399
<212> TYPE: PRT
<213> ORGANISM: Actinidia chinensis

<400> SEQUENCE: 108

Met Leu Arg Phe Val Val Ser Met Glu Lys Thr Ser Cys Val Asn Leu
1               5                   10                  15

Glu Leu Val Leu Leu Ile Ile Cys Leu Cys Asn Thr Ser Val Gln
                20                  25                  30

Cys Gln Thr Arg Pro Ile Asn His Ile Ser Ala Glu Pro Pro Ser Pro
                35                  40                  45

Ser Arg Ala Pro Glu Leu Lys Asn Lys Phe Gln Lys Ile Ile Leu Ser
50                  55                  60

Ile Leu Phe Gly Ile Val Thr Gly Leu Ile Cys Ser Phe Leu Phe Ala
65                  70                  75                  80

Phe Thr Val Arg Cys Phe Val Arg Tyr Ile Ser Arg Thr Pro Ile Leu
                85                  90                  95

Lys Gly Pro Val Ile Phe Ser Pro Lys Ile Asp Pro Lys Thr Leu Gln
                100                 105                 110

Leu Ala Leu Ala Asn Glu Asn Gln Leu Leu Gly Ser Ser Pro Asn Gly
                115                 120                 125

Lys Tyr Tyr Lys Thr Val Leu Asp Asn Gly Leu Thr Ile Ala Val Lys
                130                 135                 140

Arg Leu Glu Pro Phe Glu Asn Gly Ser Pro Gln Ala Gln Ile Lys Ser
145                 150                 155                 160

Val Lys Arg Arg Met Gln Gln Glu Leu Glu Met Leu Ala Ser Leu Arg
                165                 170                 175

His Arg Asn Leu Met Ser Leu Arg Ala Phe Val Arg Glu Ser Asp Gly
                180                 185                 190

Leu Cys Leu Val Tyr Asp Tyr Met His Ile Gly Ser Leu Glu Asp Ala
                195                 200                 205

Met Lys Arg Val Arg Glu Asn Gln Leu Glu Leu Arg Trp Glu Pro Arg
                210                 215                 220

Leu Arg Ile Ala Val Gly Ile Val Lys Gly Leu Gln Phe Leu His Phe
225                 230                 235                 240
```

-continued

Ser Cys Asn Pro Ser Arg Val Leu His Tyr Asn Leu Lys Pro Ser Asn
                245                 250                 255

Val Met Leu Asp Ala Glu Phe Glu Pro Arg Leu Ala Asp Cys Gly Leu
            260                 265                 270

Ala Lys Met Val Met Pro Asn Leu Asp Arg Ala Pro Ser Gly Tyr Asp
        275                 280                 285

Ala Pro Glu Cys Phe Gln Ser Cys Arg Tyr Thr Asp Lys Ser Asp Val
    290                 295                 300

Phe Ser Phe Gly Val Ile Leu Gly Val Leu Leu Thr Gly Arg Asp Pro
305                 310                 315                 320

Met Asp Pro Phe Phe Glu Glu Ser Ala Ser Gly Gly Ser Leu Gly Arg
                325                 330                 335

Trp Leu Arg His Leu Gln His Ala Gly Glu Ala Arg Glu Ala Leu Asp
            340                 345                 350

Lys Ser Ile Ile Gly Glu Glu Val Glu Glu Asp Glu Met Leu Met Ala
        355                 360                 365

Val Arg Ile Ser Val Val Cys Gln Ser Asp Leu Pro Ala Asp Arg Pro
    370                 375                 380

Ser Ser Asp Glu Leu Val Ser Met Leu Thr Gln Leu Asn Ser Phe
385                 390                 395

<210> SEQ ID NO 109
<211> LENGTH: 399
<212> TYPE: PRT
<213> ORGANISM: Actinidia chinensis

<400> SEQUENCE: 109

Met Leu Arg Val Val Ala Ser Met Glu Lys Thr Asn Cys Val Thr Leu
1               5                   10                  15

Glu Leu Val Leu Leu Leu Ile Phe Cys Leu Cys Asn Thr Ser Val Gln
            20                  25                  30

Cys Gln Thr Arg Pro Ile Asn His Ile Ser Ala Glu Pro Pro Ser Pro
        35                  40                  45

Ser Arg Ala Pro Glu Leu Lys Asn Lys Phe Gln Lys Ile Ile Leu Ser
    50                  55                  60

Ile Leu Leu Gly Ile Val Thr Gly Leu Ile Cys Ser Ile Leu Phe Ala
65                  70                  75                  80

Phe Thr Val Arg Cys Phe Ile Arg Tyr Ile Ser Arg Thr Pro Ile Leu
                85                  90                  95

Lys Gly Pro Val Ile Phe Ser Pro Lys Ile Asp Pro Lys Thr Leu Gln
            100                 105                 110

Leu Ala Leu Ala Asn Glu Asn Gln Leu Leu Gly Ser Ser Pro Asn Gly
        115                 120                 125

Lys Tyr Tyr Lys Thr Met Leu Asp Asn Gly Leu Thr Ile Ala Val Lys
    130                 135                 140

Arg Leu Glu Pro Phe Glu Asn Gly Ser Pro Gln Ala Gln Ser Lys Ser
145                 150                 155                 160

Val Lys Arg Arg Met Gln Gln Glu Leu Glu Met Leu Ala Ser Leu Arg
                165                 170                 175

His Arg Asn Leu Met Ser Leu Arg Ala Phe Val Arg Glu Ser Asp Arg
            180                 185                 190

Leu Cys Leu Val Tyr Asp Tyr Met His Ile Gly Ser Leu Glu Asp Val
        195                 200                 205

Met Lys Arg Val Arg Glu Asn Gln Leu Glu Leu Arg Trp Glu Leu Arg
    210                 215                 220

```
Leu Arg Ile Ala Val Gly Ile Val Lys Gly Leu Gln Phe Leu His Phe
225                 230                 235                 240

Ser Cys Asn Pro Thr Arg Phe Leu His Tyr Asn Leu Lys Pro Ser Asn
            245                 250                 255

Val Met Leu Asp Ala Glu Phe Glu Pro Arg Leu Ala Asp Cys Gly Leu
        260                 265                 270

Ala Lys Leu Val Met Pro Asn Leu Asp Arg Ala Pro Ser Gly Tyr Asp
    275                 280                 285

Ala Pro Glu Cys Phe Gln Asn Cys Arg Tyr Thr Asp Lys Ser Asp Val
290                 295                 300

Phe Ser Phe Gly Val Ile Leu Gly Val Leu Leu Met Gly Arg Asp Pro
305                 310                 315                 320

Met Asp Pro Phe Phe Glu Glu Ser Ala Ser Gly Gly Ser Phe Gly Arg
            325                 330                 335

Trp Leu Arg His Leu Gln His Ala Gly Glu Ala Arg Glu Ala Leu Asp
        340                 345                 350

Lys Arg Ile Ile Gly Glu Glu Val Glu Glu Asp Glu Met Leu Met Ala
    355                 360                 365

Val Arg Ile Ser Val Val Cys Gln Ser Asp Leu Pro Ala Asp Arg Pro
370                 375                 380

Ser Ser Asp Glu Leu Val Ser Met Leu Thr Gln Leu Asn Ser Phe
385                 390                 395

<210> SEQ ID NO 110
<211> LENGTH: 390
<212> TYPE: PRT
<213> ORGANISM: Prunus persica

<400> SEQUENCE: 110

Met Asp Arg Arg Arg Ser Thr Ser Lys Phe Asn Ser Arg Leu Thr Arg
1               5                   10                  15

Leu Leu Leu Leu Leu Phe Ile Phe Cys Phe Arg Gln Glu Thr Val Gln
            20                  25                  30

Cys Gln Glu Thr Glu Pro Pro Ser Ser Ser Lys Gln Pro His Phe Lys
        35                  40                  45

Asn Gln Leu Gln Arg Ile Ile Leu Ser Ile Val Leu Gly Val Val Thr
    50                  55                  60

Gly Leu Ile Cys Ala Leu Leu Thr Ala Leu Leu Val Arg Cys Phe Leu
65                  70                  75                  80

Arg Tyr Ile Ser Arg Thr Pro Ile Leu Lys Gly Pro Val Ile Phe Ser
                85                  90                  95

Pro Lys Ile Asp Pro Lys Thr Leu Gln Leu Ala Leu Thr Asn Glu Asn
            100                 105                 110

Gln Leu Leu Gly Ser Ser Pro Asn Gly Lys Tyr Tyr Arg Thr Val Leu
        115                 120                 125

Asp Asn Gly Leu Ile Ile Ala Val Lys Gln Leu Gly Pro Phe Ser Glu
    130                 135                 140

Cys Ser Ser Pro Glu Ser Gln Ser Lys Ser Val Lys Arg Arg Ile Gln
145                 150                 155                 160

Gln Glu Leu Glu Val Leu Ala Gly Leu Arg His Arg His Leu Met Ser
                165                 170                 175

Leu Arg Ala Tyr Val Arg Glu His Asp Arg Phe Ser Leu Val Tyr Asp
            180                 185                 190

Phe Val Pro Asn Gly Ser Leu Glu Asp Ala Met Asn Arg Val Arg Ala
```

```
            195                 200                 205
Asn Gln Leu Gln Leu Gly Trp Glu Val Arg Leu Arg Val Ala Val Gly
210                 215                 220

Val Ile Lys Gly Leu Gln Tyr Leu His Ser Tyr Val Pro Gln Ile Met
225                 230                 235                 240

His Tyr Asn Leu Lys Pro Thr Asn Val Met Leu Asp Ser Glu Phe Glu
            245                 250                 255

Pro Arg Leu Gly Asp Tyr Gly Leu Ala Lys Leu Thr Pro Tyr Leu Asp
            260                 265                 270

Gly Ala Thr Ser Gly Tyr Ser Ala Pro Glu Cys Phe Gln Asn Gly Arg
            275                 280                 285

Tyr Ser Asp Lys Ser Asp Ile Phe Ser Phe Gly Met Ile Leu Gly Val
            290                 295                 300

Leu Leu Thr Gly Arg Asp Pro Thr Asp Ala Phe Phe Gly Glu Ala Ala
305                 310                 315                 320

Ser Gly Gly Ser Leu Gly Arg Trp Leu Arg His Leu Gln Gln Ala Gly
                325                 330                 335

Glu Ala Arg Glu Ala Leu Asp Lys Ser Ile Ile Gly Glu Glu Gly Glu
                340                 345                 350

Glu Asp Glu Met Leu Met Ala Val Arg Ile Ala Val Val Cys Leu Ser
                355                 360                 365

Asp Leu Pro Ala Glu Arg Pro Ser Ser Asp Gly Leu Val His Met Leu
370                 375                 380

Thr Gln Leu His Ser Phe
385                 390

<210> SEQ ID NO 111
<211> LENGTH: 390
<212> TYPE: PRT
<213> ORGANISM: Vitis vinifera

<400> SEQUENCE: 111

Met Glu Lys Thr Ser Arg Glu Ala Ile Ser Leu Leu Phe Leu Leu Ile
1               5                   10                  15

Phe Ile His Phe Tyr Asn Val Lys Cys Gln Glu Asn Ile Ile Asn Arg
                20                  25                  30

Val Ser Thr Asp Ser Ser Pro Ser Pro Ser Arg Glu Ala Glu Phe Lys
            35                  40                  45

Ser Gly Leu Lys Lys Ile Ile Leu Ser Ile Val Phe Gly Val Leu Thr
50                  55                  60

Gly Leu Leu Ser Ala Ala Leu Cys Ala Gly Ile Val His Cys Val Val
65                  70                  75                  80

Arg Tyr Met Asn Arg Thr Pro Ile Leu Lys Gly Pro Val Val Phe Ser
                85                  90                  95

Pro Lys Ile Ala Pro Lys Thr Val Gln Ser Ala Leu Asp Ser Glu Asn
            100                 105                 110

Gln Leu Leu Gly Ser Ser Pro Asn Gly Lys Tyr Tyr Lys Thr Ala Leu
        115                 120                 125

Asp Asn Gly Leu Ile Ile Ala Val Lys Arg Leu Glu Pro Phe Glu Thr
130                 135                 140

Gly Ser Pro Glu Thr Gln Ser Lys Ser Val Lys Arg Ile Gln Gln
145                 150                 155                 160

Glu Leu Glu Met Leu Ala Asn Leu Arg His Arg Asn Leu Met Ser Leu
                165                 170                 175
```

```
Arg Ala Tyr Val Arg Asp Ser Asp Arg Phe Ser Leu Val Tyr Asp Tyr
            180                 185                 190

Val Pro Thr Gly Ser Leu Glu Asp Ala Met Asn Arg Val Arg Glu Asn
        195                 200                 205

Gln Leu Gln Leu Ser Trp Glu Val Arg Leu Arg Ile Ala Val Gly Val
    210                 215                 220

Ile Lys Gly Leu Gln Tyr Leu His Phe Ser Cys Val Pro Arg Ile Leu
225                 230                 235                 240

His Tyr Asn Leu Lys Pro Thr Asn Val Met Leu Asp Ala Glu Phe Glu
                245                 250                 255

Pro Arg Leu Ala Asp Cys Gly Leu Ala Lys Leu Met Pro Asn Leu Asp
            260                 265                 270

Arg Ala Ala Ser Gly Tyr Ser Ala Pro Glu Cys Phe Gln Asn Cys Arg
        275                 280                 285

Tyr Thr Glu Lys Ser Asp Val Phe Ser Phe Gly Val Ile Leu Gly Val
    290                 295                 300

Leu Leu Thr Gly Arg Asp Pro Met Asp Pro Phe Phe Ser Glu Ala Ala
305                 310                 315                 320

Gly Gly Gly Ser Leu Gly Arg Trp Leu Arg His Leu Gln Gln Ala Gly
                325                 330                 335

Glu Ala Arg Glu Ala Leu Asp Lys Ser Ile Leu Gly Glu Glu Val Glu
            340                 345                 350

Glu Asp Glu Met Leu Met Ala Val Arg Ile Ala Val Cys Leu Ser
        355                 360                 365

Asp Leu Pro Ala Asp Arg Pro Ser Ser Asp Glu Leu Val Pro Met Leu
    370                 375                 380

Thr Gln Leu His Ser Phe
385                 390

<210> SEQ ID NO 112
<211> LENGTH: 392
<212> TYPE: PRT
<213> ORGANISM: Gossypium raimondii

<400> SEQUENCE: 112

Met Ala Lys Met Ser Gly Cys Ile Val Thr Val Ala Leu Leu Leu Leu
1               5                   10                  15

Leu Leu Leu Cys Leu His Gln Thr Pro Val Glu Cys Lys Glu Arg Leu
                20                  25                  30

Ile Arg Gln Leu Ser Ser Gln Pro Ser Ser Ala Thr Lys Pro Gln Glu
            35                  40                  45

Phe Lys Ile Gly Phe Lys Arg Val Ile Leu Ser Ile Val Leu Gly Ile
50                  55                  60

Leu Thr Gly Leu Ile Gly Ala Ile Leu Phe Ala Leu Leu Ile Lys Ile
65                  70                  75                  80

Ala Val Gln Tyr Ile Asn Gln Thr Pro Phe Leu Lys Gly Pro Val Ile
                85                  90                  95

Phe Ser Pro Lys Ile Ser Ser Lys Thr Leu Gln Ser Ala Leu Ala Asn
            100                 105                 110

Glu Asn Gln Leu Leu Gly Ser Ser Asn Gly Lys Tyr Tyr Lys Thr
        115                 120                 125

Val Leu Asp Asn Gly Leu Thr Val Ala Val Lys Val Leu Glu Pro Phe
    130                 135                 140

Asp Ser Gly Ser Pro Glu Met Gln Ser Lys Ser Val Lys Arg Arg Ile
145                 150                 155                 160
```

```
Gln Gln Glu Leu Glu Val Leu Ala Ser Leu Arg His Arg His Leu Arg
            165                 170                 175

Ser Leu Arg Ala Tyr Val Arg Glu Ser Asp Arg Phe Ser Leu Val Tyr
        180                 185                 190

Asp Tyr Met Pro Met Gly Ser Leu Glu Asp Ala Met Asn Gly Val Arg
            195                 200                 205

Glu Asn His Leu Glu Leu Arg Trp Asp Val Arg Leu Arg Ile Ala Val
        210                 215                 220

Gly Val Ile Lys Gly Leu Gln Tyr Leu His Phe Thr Cys Val Pro Gln
225                 230                 235                 240

Ile Leu His Tyr Asn Leu Lys Pro Thr Asn Val Met Leu Asp Ala Glu
            245                 250                 255

Phe Glu Pro Arg Leu Ala Asp Cys Gly Leu Ala Lys Leu Met Pro Asn
        260                 265                 270

Ile Asp Arg Ala Thr Ser Gly Tyr Cys Ala Pro Glu Cys Leu Gln Asn
            275                 280                 285

Cys Arg Tyr Thr Asp Lys Ser Asp Ile Phe Ser Phe Gly Met Ile Leu
        290                 295                 300

Gly Val Leu Leu Thr Gly Arg Tyr Pro Thr Asp Ser Phe Phe Arg Glu
305                 310                 315                 320

Ala Val Ser Gly Gly Ser Leu Gly Gln Trp Leu Arg His Leu Gln Gln
            325                 330                 335

Ala Gly Glu Ala His Glu Ala Leu Asp Lys Ser Ile Leu Gly Glu Glu
        340                 345                 350

Val Glu Glu Asp Glu Met Leu Met Ala Val Arg Ile Ala Val Val Cys
            355                 360                 365

Leu Ser Asp Ser Pro Asp Asp Arg Pro Ser Ser Asp Glu Leu Val Thr
        370                 375                 380

Met Leu Thr Gln Leu His Ser Phe
385                 390

<210> SEQ ID NO 113
<211> LENGTH: 390
<212> TYPE: PRT
<213> ORGANISM: Corchorus capsularis

<400> SEQUENCE: 113

Met Gly Lys Gly Arg Arg Cys Thr Leu Ser Leu Leu Phe Leu Leu Leu
1               5                   10                  15

Leu Cys Phe His Gln Thr Thr Val His Cys Lys Glu Arg Leu Ile Arg
            20                  25                  30

His Leu Ser Ser Gln Pro Pro Ser Pro Ser Lys Pro Gln Glu Phe Lys
        35                  40                  45

Ile Gly Leu Lys Arg Ile Ile Leu Ser Ile Val Leu Gly Ile Leu Thr
    50                  55                  60

Gly Leu Ala Gly Ala Leu Val Val Ala Leu Phe Ile Lys Phe Ala Val
65                  70                  75                  80

Gln Tyr Met Asn Gln Thr Pro Ile Leu Lys Gly Pro Val Ile Phe Ser
            85                  90                  95

Pro Lys Ile Ser Ala Lys Thr Leu Gln Ser Ala Leu Ala Asn Glu Asn
        100                 105                 110

Gln Leu Leu Gly Ser Ser Asn Gly Lys Tyr Tyr Lys Thr Val Leu
        115                 120                 125

Asp Asn Gly Leu Thr Val Ala Val Lys Val Leu Glu Pro Phe Asp Asn
```

```
            130                 135                 140
Gly Ser Pro Glu Arg Gln Ser Lys Ser Val Lys Arg Ile Gln Gln
145                 150                 155                 160

Glu Leu Glu Val Leu Ala Ser Leu Arg His Arg His Leu Met Ser Leu
                165                 170                 175

Arg Ala Tyr Val Arg Glu Ser Asp Arg Phe Ser Leu Val Tyr Asp Tyr
            180                 185                 190

Met Pro Thr Gly Ser Leu Glu Asp Ala Met Asn Arg Val Arg Gly Asn
                195                 200                 205

Gln Leu Gln Leu Gly Trp Asp Val Arg Leu Arg Ile Ala Val Gly Val
            210                 215                 220

Ile Lys Gly Leu Gln Tyr Leu His Phe Thr Cys Ile Pro Gln Ile Leu
225                 230                 235                 240

His Tyr Asn Leu Lys Pro Thr Asn Ile Met Leu Asp Ala Glu Phe Glu
                245                 250                 255

Pro Arg Leu Ala Asp Cys Gly Leu Ala Lys Leu Met Pro Asn Ile Asp
            260                 265                 270

Arg Ala Thr Ser Gly Tyr Ser Ala Pro Glu Cys Phe Gln Asn Cys Arg
                275                 280                 285

Tyr Thr Asp Lys Ser Asp Ile Phe Ser Phe Gly Met Ile Leu Gly Val
            290                 295                 300

Leu Leu Thr Gly Arg Asp Pro Ala Asp Pro Phe Phe Gly Glu Ala Ala
305                 310                 315                 320

Ser Gly Gly Ser Leu Gly Gln Trp Leu Arg His Leu Gln Gln Ala Gly
                325                 330                 335

Glu Ala Arg Glu Ala Leu Asp Lys Ser Ile Leu Gly Glu Glu Val Glu
            340                 345                 350

Glu Asp Glu Met Leu Met Ala Val Arg Ile Ala Val Val Cys Leu Ser
                355                 360                 365

Asp Leu Pro Ala Asp Arg Pro Ser Ser Asp Glu Leu Val Pro Met Leu
            370                 375                 380

Thr Gln Leu His Ser Phe
385                 390

<210> SEQ ID NO 114
<211> LENGTH: 400
<212> TYPE: PRT
<213> ORGANISM: Theobroma cacao Matina 1-6

<400> SEQUENCE: 114

Met Phe Val Cys Gly Phe Val Ala Ser Met Glu Lys Arg Ser Cys Thr
1               5                   10                  15

Leu Ser Leu Leu Leu Leu Leu Leu Leu Leu Cys Phe His Leu Thr
                20                  25                  30

Thr Val Gln Cys Glu Gly Arg Leu Ile Arg Tyr Leu Ser Ser Gln Pro
            35                  40                  45

Pro Ser Pro Ser Thr Pro Gln Glu Phe Lys Ile Gly Phe Lys Arg Ile
        50                  55                  60

Val Leu Ser Ile Ala Leu Gly Ile Leu Thr Gly Leu Ile Gly Ala Ile
65                  70                  75                  80

Leu Phe Ala Leu Leu Ile Lys Phe Ala Val Gln Tyr Met Asn Gln Thr
                85                  90                  95

Pro Ile Leu Lys Gly Pro Val Ile Phe Ser Pro Lys Ile Ser Ala Lys
            100                 105                 110
```

-continued

```
Thr Leu Gln Ser Ala Leu Ser Thr Glu Asn Gln Leu Gly Ser Ser
            115                 120                 125

Ser Asn Gly Lys Tyr Tyr Lys Thr Val Leu Asp Asn Gly Leu Thr Val
130                 135                 140

Ala Val Lys Val Leu Glu Pro Phe Asp Asn Gly Ser Pro Glu Arg His
145                 150                 155                 160

Ser Lys Ser Val Lys Arg Ile Gln Gln Glu Leu Glu Ile Leu Ala
            165                 170                 175

Ser Leu Arg His Arg His Leu Met Ser Leu Arg Ala Tyr Val Arg Glu
            180                 185                 190

Ser Asp Arg Phe Ser Leu Val Tyr Asp Tyr Met Pro Thr Gly Ser Leu
            195                 200                 205

Glu Asp Ala Met Asn Arg Val Arg Gly Asn Gln Leu Gln Leu Gly Trp
            210                 215                 220

Asp Val Arg Leu Arg Ile Ala Val Gly Val Ile Lys Gly Leu Gln Tyr
225                 230                 235                 240

Leu His Phe Thr Cys Ile Pro Gln Ile Leu His Tyr Asn Leu Lys Pro
                245                 250                 255

Thr Asn Val Met Leu Asp Ala Glu Leu Glu Pro Arg Val Ala Asp Cys
            260                 265                 270

Gly Leu Ala Lys Leu Met Pro Asn Ile Asp Arg Ala Thr Ser Gly Tyr
            275                 280                 285

Gly Ala Pro Glu Cys Phe Glu Asn Cys Arg Tyr Thr Asp Lys Ser Asp
            290                 295                 300

Ile Phe Ser Phe Gly Met Ile Leu Gly Val Leu Leu Thr Gly Arg Asp
305                 310                 315                 320

Pro Thr Asp Pro Phe Phe Gly Glu Ala Ser Ser Gly Ser Leu Arg
                325                 330                 335

Gln Trp Leu Arg His Leu Gln Gln Ala Gly Glu Ala Arg Glu Ala Leu
            340                 345                 350

Asp Lys Ser Ile Leu Gly Glu Glu Val Glu Glu Asp Glu Met Leu Met
            355                 360                 365

Ala Val Arg Ile Ala Val Val Cys Leu Ser Asp Leu Pro Ala Asp Arg
370                 375                 380

Pro Ser Ser Asp Glu Leu Val Pro Met Leu Thr Gln Leu His Ser Phe
385                 390                 395                 400

<210> SEQ ID NO 115
<211> LENGTH: 398
<212> TYPE: PRT
<213> ORGANISM: Manihot esculenta

<400> SEQUENCE: 115

Met Glu Lys Arg Arg Tyr Ser Ser Gln Leu Thr Ser Lys Val Thr Ala
1               5                   10                  15

Leu Leu Leu Leu Leu Ser Phe Cys Phe His Pro Ile Val Val Gln Cys
            20                  25                  30

Gln Glu Ser Asn Ile Lys Met Thr Arg His Leu Ser Ser Glu Thr Pro
            35                  40                  45

Pro Ser Arg Ser Pro Gln Phe His Thr Gly Leu Lys Arg Ile Leu Leu
        50                  55                  60

Ser Ile Gly Leu Gly Val Leu Thr Gly Leu Thr Gly Ala Val Leu Cys
65                  70                  75                  80

Ala Cys Val Val Arg Phe Phe Val Arg Tyr Met Asn Arg Thr Pro Ile
                85                  90                  95
```

Leu Lys Gly Pro Val Thr Phe Ser Pro Asn Ile Ala Pro Lys Thr Leu
              100                 105                 110

Gln Ser Ala Leu Ala Ser Glu Asn Gln Leu Leu Gly Ser Ser Ser Asn
            115                 120                 125

Gly Lys Tyr Tyr Arg Lys Val Leu Asp Asn Asp Leu Thr Val Ala Val
        130                 135                 140

Lys Arg Leu Glu Pro Phe Glu Asn Gly Ser Pro Glu Arg Gln Ser Lys
145                 150                 155                 160

Ala Val Lys Arg Arg Ile Gln Gln Glu Leu Glu Arg Leu Ala Ser Leu
                165                 170                 175

Arg His Arg Asn Leu Met Ser Leu Arg Ala Tyr Val Arg Glu Ser Asp
            180                 185                 190

Arg Phe Ser Leu Val Tyr Asp Tyr Val Pro Thr Gly Ser Leu Glu Asp
        195                 200                 205

Ala Met Asn Arg Val Arg Asp Asn Gln Leu Gln Leu Gly Trp Glu Val
    210                 215                 220

Arg Leu Arg Ile Ala Val Gly Val Val Lys Gly Leu Arg Tyr Leu His
225                 230                 235                 240

Phe Glu Cys Val Pro Gln Ile Leu His Tyr Asn Leu Lys Pro Thr Asn
                245                 250                 255

Val Met Leu Asp Ala Glu Phe Glu Pro Arg Leu Ala Asp Ser Gly Leu
            260                 265                 270

Ala Lys Leu Met Pro Asn Leu Asp Arg Thr Thr Ser Gly Tyr Ser Ala
        275                 280                 285

Pro Glu Cys Phe Gln Asn Cys Arg Tyr Thr Glu Lys Ser Asp Ile Phe
    290                 295                 300

Ser Phe Gly Met Ile Leu Gly Val Leu Leu Thr Gly Arg Asp Pro Thr
305                 310                 315                 320

Asp Pro Phe Phe Gly Glu Ala Ala Ser Gly Gly Ser Leu Gly His Trp
                325                 330                 335

Leu Arg His Leu Gln His Ala Gly Glu Ala Arg Glu Ala Leu Asp Lys
            340                 345                 350

Ser Ile Leu Gly Glu Gly Glu Glu Asp Glu Met Leu Met Ala Val
        355                 360                 365

Arg Ile Ala Val Val Cys Leu Ser Asp Leu Pro Ala Asp Arg Pro Ser
    370                 375                 380

Ser Asp Glu Leu Val Leu Met Leu Ser Gln Leu His Ser Phe
385                 390                 395

<210> SEQ ID NO 116
<211> LENGTH: 394
<212> TYPE: PRT
<213> ORGANISM: Populus trichocarpa

<400> SEQUENCE: 116

Met Gly Lys Arg Arg Tyr Ser Thr Gln Ile Ser Asn Asn Lys Asp Thr
1               5                   10                  15

Ser Ser Leu Leu Phe Leu Phe Ile Leu Cys Leu Tyr Tyr Thr Thr Val
            20                  25                  30

Gln Cys Gln Glu Ser Ser Lys Val Thr Pro Pro Phe Pro Ser Thr Pro
        35                  40                  45

Thr His Ser Lys Asn Gly Leu Lys Arg Ile Leu Val Ser Ile Phe Leu
    50                  55                  60

Gly Val Leu Thr Gly Leu Thr Gly Ala Val Val Phe Ala Phe Val Val

```
              65                  70                  75                  80
Arg Phe Leu Val Arg Tyr Met Lys Arg Thr Pro Ile Leu Lys Gly Pro
                    85                  90                  95

Val Ile Phe Ser Pro Lys Ile Thr Pro Lys Ser Leu Gln Ser Ala Leu
            100                 105                 110

Glu Asn Glu Asn Gln Leu Leu Gly Ser Ser Asn Gly Lys Tyr Tyr
        115                 120                 125

Arg Thr Val Leu Asp Asn Gly Leu Thr Ile Ala Val Lys Arg Phe Glu
    130                 135                 140

Pro Phe Glu Ile Gly Ser Pro Glu Arg Gln Ser Lys Ser Val Lys Arg
145                 150                 155                 160

Arg Ile Gln Gln Glu Leu Glu Met Leu Ala Ser Leu Arg His Arg Asn
                    165                 170                 175

Leu Met Ser Leu Arg Ala Tyr Val Arg Glu Pro Asp Arg Phe Ser Leu
            180                 185                 190

Val Tyr Asp Cys Val Pro Thr Gly Ser Leu Glu Asp Ala Met Asn Arg
        195                 200                 205

Val Arg Glu Asn Glu Leu Gln Leu Gly Trp Glu Val Arg Leu Arg Ile
    210                 215                 220

Ala Val Gly Val Ile Lys Gly Leu Arg Tyr Leu His Phe Asp Cys Val
225                 230                 235                 240

Pro Gln Ile Leu His Tyr Asn Leu Lys Pro Arg Asn Val Ile Leu Asp
                    245                 250                 255

Ala Glu Phe Glu Pro Arg Leu Ala Asp Phe Gly Leu Ala Lys Leu Thr
            260                 265                 270

Pro Asn Leu Asp Arg Ala Thr Ser Gly Tyr Ser Ala Pro Glu Cys Phe
        275                 280                 285

Gln Asn Cys Arg Tyr Thr Asp Lys Ser Asp Val Phe Ser Phe Gly Met
    290                 295                 300

Ile Leu Gly Val Leu Leu Thr Gly Arg Asp Pro Thr Asp Pro Phe Phe
305                 310                 315                 320

Arg Glu Thr Ala Ser Gly Gly Ser Leu Gly Pro Trp Leu Arg His Leu
                    325                 330                 335

Gln Gln Ala Gly Glu Ala Arg Glu Ala Leu Asp Lys Ser Ile Leu Gly
            340                 345                 350

Glu Glu Val Glu Glu Asp Glu Met Leu Met Ala Val Arg Ile Ala Val
        355                 360                 365

Val Cys Leu Ser Asp Met Pro Ala Asp Arg Pro Ser Ser Asp Glu Leu
    370                 375                 380

Val Pro Met Leu Ser Gln Leu His Ser Phe
385                 390

<210> SEQ ID NO 117
<211> LENGTH: 394
<212> TYPE: PRT
<213> ORGANISM: Populus trichocarpa

<400> SEQUENCE: 117

Met Glu Lys Arg Arg Tyr Ser Leu Arg Val Ser Asn Ser Lys Val Thr
1                   5                   10                  15

Ala Ser Leu Leu Phe Leu Phe Val Leu Cys Leu Tyr Tyr Ala Ser Val
                    20                  25                  30

Gln Cys Gln Glu Ser Ser Lys Val Thr Pro Pro Ser Pro Ser Thr Pro
            35                  40                  45
```

```
Thr Gln Ser Lys Asn Gly Leu Lys Arg Ile Leu Val Ser Ile Phe Leu
    50                  55                  60

Gly Val Leu Thr Gly Leu Ile Gly Ala Val Val Phe Ala Phe Val Val
65                  70                  75                  80

Arg Phe Leu Val Arg Tyr Met Lys Arg Thr Pro Ile Leu Lys Gly Pro
                85                  90                  95

Val Ile Phe Ser Pro Lys Ile Thr Pro Lys Ser Leu Gln Ser Ala Leu
            100                 105                 110

Glu Asn Glu Asn Gln Leu Leu Gly Ser Ser Asn Gly Lys Tyr Tyr
        115                 120                 125

Arg Thr Ala Leu Asp Asn Gly Leu Thr Ile Ala Val Lys Arg Phe Glu
    130                 135                 140

Pro Phe Glu Ile Gly Ser Pro Glu Arg Gln Ser Lys Ser Val Lys Arg
145                 150                 155                 160

Arg Ile Gln Gln Glu Leu Glu Met Leu Ala Ser Leu Arg His Arg Asn
                165                 170                 175

Leu Met Ser Leu Arg Ala Tyr Val Arg Glu Pro Asp Arg Phe Ser Leu
            180                 185                 190

Val Tyr Asp Tyr Val Pro Thr Gly Ser Leu Glu Asp Ala Met Asn Arg
        195                 200                 205

Val Arg Glu Asn Glu Leu Gln Leu Gly Trp Glu Val Arg Leu Arg Ile
    210                 215                 220

Ala Val Gly Val Ile Lys Gly Leu Arg Tyr Leu His Phe Glu Cys Ala
225                 230                 235                 240

Pro Gln Ile Leu His Tyr Asn Leu Lys Pro Arg Asn Val Ile Leu Asp
                245                 250                 255

Ala Glu Phe Glu Pro Arg Leu Ala Asp Phe Gly Leu Ala Lys Leu Thr
            260                 265                 270

Pro Asn Leu Asp Arg Ala Thr Ser Gly Tyr Ser Ala Pro Glu Cys Phe
        275                 280                 285

Gln Asp Cys Arg Tyr Ser Asp Lys Ser Asp Val Phe Ser Phe Gly Met
    290                 295                 300

Ile Leu Gly Val Leu Leu Thr Gly Arg Asp Pro Thr Asp Pro Phe Phe
305                 310                 315                 320

Gly Glu Thr Ala Ser Gly Gly Ser Leu Gly Arg Trp Leu Arg His Leu
                325                 330                 335

Gln Gln Ala Gly Glu Ala Arg Glu Ala Leu Asp Lys Ser Leu Leu Gly
            340                 345                 350

Glu Glu Val Glu Glu Asp Glu Met Leu Met Ala Val Arg Ile Ala Val
        355                 360                 365

Val Cys Gln Ser Glu Met Pro Ala Asp Arg Pro Ser Ser Asp Glu Leu
    370                 375                 380

Val Pro Met Leu Ser Gln Leu His Ser Phe
385                 390

<210> SEQ ID NO 118
<211> LENGTH: 414
<212> TYPE: PRT
<213> ORGANISM: Zea mays

<400> SEQUENCE: 118

Met Thr Ser Arg Asn Pro Thr Lys Thr Leu Ser Val Leu Thr Thr Leu
1               5                   10                  15

Leu Leu Leu Leu Glu Phe Leu Ala Leu Cys Ala Pro Ala Ser Ala Gln
                20                  25                  30
```

-continued

```
Pro Leu His Ser Glu Pro Met Ala Thr Gln Ser Pro Pro Pro Leu
         35                  40                  45
Pro Pro Gly Ser Thr Ile Pro Arg Ala Gln Ala Gly Gly Ala Ala Arg
 50                  55                  60
Leu Arg Arg Ile Ala Leu Gly Val Leu Phe Gly Ser Leu Ser Gly Phe
 65                  70                  75                  80
Leu Leu Ala Leu Ala Phe Leu Tyr Ala Ile Arg Leu Ala Ile Leu His
                 85                  90                  95
Ala Lys Ser Thr Pro Ala Ile Ala Lys Gly Pro Val Ser Phe Ala Pro
                100                 105                 110
Gln Ile Ser Ala Lys Asn Leu Leu Ala Ala Leu Pro Ala Ala Gln Pro
                115                 120                 125
Leu Ala His Gly Pro His Gly Lys Tyr Tyr Lys Leu Ala Leu Asp Asn
         130                 135                 140
Asp Leu Thr Val Ala Val Lys Arg Leu Glu Ala Ala Ser Arg Pro Glu
145                 150                 155                 160
Ala Ser Pro Ser Met Ser Pro Ser Ala Ser Lys Ser Asp Met Arg Arg
                165                 170                 175
Val Gln Arg Gln Leu Glu Ala Leu Ala Arg Val Arg His Gln Asn Val
                180                 185                 190
Leu Ser Leu Lys Ala Tyr Val Arg Glu Ala Asp Arg Leu Ser Leu Val
         195                 200                 205
Tyr Asp Phe Val His Gly Gly Ser Leu Glu Asp Leu Met Lys Arg Val
         210                 215                 220
Arg Ser Gln Gln Val Ser Leu Gly Trp Asp Ala Arg Ser Arg Ile Ala
225                 230                 235                 240
Val Gly Ile Ala Lys Gly Leu Arg His Leu His Phe Glu Cys Asn Pro
                245                 250                 255
Arg Ile Val His Cys Asn Leu Lys Pro Ser Asn Val Met Leu Asp Glu
                260                 265                 270
Gly Leu Glu Pro Leu Leu Ala Asp Cys Gly Val Ala Arg Leu Ile Ala
         275                 280                 285
Ala Gly Ser Gly Asp Pro Glu Leu Cys Thr Gly Leu Tyr Ala Ala Pro
         290                 295                 300
Glu Cys Tyr Gln Ser Ser Arg Tyr Thr Asp Lys Ser Asp Val Tyr Ala
305                 310                 315                 320
Leu Gly Met Ile Leu Gly Val Leu Leu Thr Gly Arg Asp Pro Thr Asp
                325                 330                 335
Ser Phe Phe Ser Gly Glu Ser Thr Gly Gln Gly Gly Leu Pro Arg Trp
                340                 345                 350
Leu Arg His Thr Gln Gln Ser Ala Asp Pro Lys Glu Thr Leu Asp Ser
         355                 360                 365
Ser Ile Leu Gly Asp Glu Gly Glu Glu Glu Met Leu Met Ala Ile
         370                 375                 380
Arg Val Ala Ile Val Cys Leu Ser Asp Ser Pro Thr Asp Arg Pro Ser
385                 390                 395                 400
Ser Asp Glu Leu Val Ala Met Leu Thr Gln Leu His Ser Leu
                405                 410
```

<210> SEQ ID NO 119
<211> LENGTH: 44
<212> TYPE: PRT
<213> ORGANISM: Zea mays

```
<400> SEQUENCE: 119

Leu Ala Leu Cys Ala Pro Ala Ser Ala Gln Pro Leu His Ser Glu Pro
1               5                   10                  15

Met Ala Thr Gln Ser Pro Pro Pro Leu Pro Pro Gly Ser Thr Ile
            20                  25                  30

Pro Arg Ala Gln Ala Gly Gly Ala Ala Arg Leu Arg
        35                  40

<210> SEQ ID NO 120
<211> LENGTH: 64
<212> TYPE: PRT
<213> ORGANISM: Zea mays

<400> SEQUENCE: 120

Leu Thr Thr Leu Leu Leu Leu Glu Phe Leu Ala Leu Cys Ala Pro
1               5                   10                  15

Ala Ser Ala Gln Pro Leu His Ser Glu Pro Met Ala Thr Gln Ser Pro
            20                  25                  30

Pro Pro Pro Leu Pro Pro Gly Ser Thr Ile Pro Arg Ala Gln Ala Gly
        35                  40                  45

Gly Ala Ala Arg Leu Arg Arg Ile Ala Leu Gly Val Leu Phe Gly Ser
    50                  55                  60

<210> SEQ ID NO 121
<211> LENGTH: 84
<212> TYPE: PRT
<213> ORGANISM: Zea mays

<400> SEQUENCE: 121

Ser Arg Asn Pro Thr Lys Thr Leu Ser Val Leu Thr Thr Leu Leu Leu
1               5                   10                  15

Leu Leu Glu Phe Leu Ala Leu Cys Ala Pro Ala Ser Ala Gln Pro Leu
            20                  25                  30

His Ser Glu Pro Met Ala Thr Gln Ser Pro Pro Pro Leu Pro Pro
        35                  40                  45

Gly Ser Thr Ile Pro Arg Ala Gln Ala Gly Gly Ala Ala Arg Leu Arg
    50                  55                  60

Arg Ile Ala Leu Gly Val Leu Phe Gly Ser Leu Ser Gly Phe Leu Leu
65                  70                  75                  80

Ala Leu Ala Phe

<210> SEQ ID NO 122
<211> LENGTH: 4433
<212> TYPE: DNA
<213> ORGANISM: Zea mays

<400> SEQUENCE: 122
gcgcgcgcgc cggggagcgg ggacggggcg gaggagaatg tttggctggt ccgggtccgg    60
tcgcacggca tggtggtgga cgcgagccgc ctgcgagggc cgaggggaga gggatgcgtc   120
aagaaagctc tcggcttttta gcttgctttg ggcgcccaca ccaatgccac actgctctgc   180
tctccgagta acttattgcg agcagcgccc caggtgaccg agcgagcggg ccggcgaggg   240
ctcagctttg gataattctt gctccctctt gtcctttcgg tttgaagctt tctggaggga   300
gaagggagca cgcagctcgg cgccagtgag agagaggatt agaggagcga gaggaaaggg   360
ggagatcatg cttgcagagc gtgctccgtg atgcggtgag cgccgctaac ctcggttgat   420
ttcttggtgg gaggcgacaa acgcgtgcgt gagccgccgc ttgcttggga ggtggtggtg   480
```

```
agaccaggcg tgctccttcg cacttgtctc tgtttgagtt cgttgtcgtc aggtactcct      540
cacgagctcc acgccgcgcg cgccttgggc gactgccttt tcgattcgtc ttctttgatg      600
catattttct ctttctgtag gtaaatatca cgagcaccat gctcgagttc ttgtagctcc      660
gcagcttcct cgcttcttgc atcctttgca acttgtctcc tgttgttttc ctctgatttc      720
catggaggaa agatgctggg tgtgccagtg atgtgggcgt ggagcaggca acaattggct      780
cgtcctggac attgatcgat tctcccctat tctcgtccaa ggaattttat tcgtttctcc      840
tagcaagtcg tgtatgcttg tttcgtggag gtaggagcta ggatgacgag caggaaccct      900
accaaaaccc tgtcggtcct gaccactctc ctgctgctgc ttgagttcct cgcgctgtgc      960
gcgcccgcct ccgcccagcc gctccactcg agcccatggc tacgcagtc cccgccgccg      1020
ccgctgccgc cggggtccac gattcccgg gcgcaggccg cgcggcgccgc acgcctccgc      1080
cgcattgcgc tcggggtcct cttcggctcc ctctccggtt tcctcctcgc gctcgccttc      1140
ctctacgcca tccgcctcgc catcctccac gccaagagca cgcccgcgat cgccaagggc      1200
cccgtctcct tcgccccgca aatctccgcc aagaacctcc tggccgcgct ccccgccgcg      1260
cagccgctcg cccatgggcc ccatggcaag tactacaagc tggcactcga caacgacctc      1320
accgtcgccg tcaagcgcct cgaggcggcc agccgccccg aggcctcgcc gtccatgtcc      1380
ccgagcgcgt ccaagtcgga catgaggagg gtgcagaggc agcttgaggc acttgctcgg      1440
gtcaggcacc agaatgtgtt gtcgttgaag gcatacgttc gcgaggcgga ccgcctctcg      1500
ctcgtgtacg acttcgtcca tgggggcagc ctcgaggatc tgatgaagag ggtaaggtcg      1560
cagcaagtca gcctcggttg ggatgcgagg agcaggattg ctgttgggat tgccaaggga      1620
ctgaggcact tgcattttga gtgcaatccg aggatagtcc actgcaacct caagccgtcc      1680
aatgtgatgc tagacgaagg tttggagcca ttattggcag attgtggtgt tgcaaggctg      1740
attgcagcag gttcaggtga tccagaattg tgcactggcc tctacgctgc tccagaatgc      1800
tatcaaagca gcaggtaaca tcaacgtgct agcattttca gttctttttt ctgaatttaa      1860
agaattagct aaaattcctga aaatctcagc attctggtaa ccctgtggga taggatggaa      1920
tttacaggaa acaatccaat tcttgcatga gtattgaaaa aaacacattc taagggctct      1980
tggcttattg ttttgatact tgatcgtata aatgaaacct tcagatctac caatgtattt      2040
ctcatgattg tcactcttga agtgaagaag ggaatctaaa tctagtttgg gtcagaattt      2100
tctagtatta aattatatca actaaatgtt acttatatga cattcttgat gaatggtgat      2160
catatatcat tcccgctcgg tgaaaggata cccaatgaca agaagatatg tcgtagactt      2220
tgtttgagtt ccttgctatg catgtatata atctttagaa acagatggct ggtgcgtata      2280
tgttcgcatt tttggatatc aaatctcaac tgttctaata aaattctcgg accatggaaa      2340
tcccaaaggt gtttcgtgca ttatagaagc atggagatat aagaaaggaa ttgtagaaat      2400
ctatgacgta tatagaggtt cctttaatta ttttcgtttt gctttgtcta gcttgttgac      2460
attgtggaca aactatatgt tgtagtgact ttacccgatc attctctgta tttgacttct      2520
gcctgggttc ggagtgatgc cacaagcatc tgagtattgt tttagaataa ctagtggaag      2580
tttgatatgt ctctggtttg gcaaaacaga aattaagctt aagacttcca ctttacatag      2640
gatgggggtt tagctcaatt gattgtgtgg gagactaaga ggttttagt catgcacacc      2700
caaccatgtt ggttaaagcc ctcttcagct tgagtttgag tgttttttccc ctcttaatga      2760
ttaatgatca tgaaaacttt tattcaaaaa aaaatcatca aaactgccta cccctcctag      2820
```

```
tttggtatct tttttgaact tccattatat atattttat taaaaaaatt cttaacccac    2880
cagataccag tggtttaaag gcgccgcccg ctcctaggcg tccaagagct caagcaatct    2940
gaggcgcctt aagaaccatt gtagatagta tacatccatt gacttgtgga tgctaccatc    3000 cagttttttcc aagttactac tagctagtgg tcttctttgt cattaaactt gccacaagag    3060
taactgagaa ggcataaagc ataaaaatga tgatcatccc tagggcttag tgaaagtatc    3120
taacttttcc ttttggcgac atgagaatct ttactttgct agaggacctc aattttgcgc    3180
gcctttgatg ctcccgcttt tcataaattc ctggcgtgag ccgtgagggc atgcagaata    3240
ccggcccgct ccctttttat gtccaaaaat gctattgcta cctttttttc attcaggcgg    3300
accttccata tgccccccat caaagaataa atcctttgag gattggcatt ctgattccat    3360
cgttcatatt tctcctggca aacccagcta tgctatgtca gtagattttt agagggtttg    3420
cttcagtcat tgtagtggtg ggttttagt ttacttgcac agttgcaccc cttgagagga    3480
agaagaagta tactgattgt ttcgaacaaa acggatcttc tttctgtac aagtactgta    3540 gttgatctat ccatgtaatt ctttctttga tgatttgaga ctcaactgtt tggtggtacg    3600
tacaggtaca cggataagag tgatgtgtac gcccttggca tgatcctggg cgtgctgctc    3660
actgggagag acccgacaga ctctttcttc tcgggagaga gtaccgggca gggcggcctc    3720
ccaagatggc tccggcacac gcagcagtcc gcggacccga agaaacgct ggatagcagc    3780 atcctggggg acgagggaga agaggaggag atgctgatgg ccattcgggt tgccattgtc    3840
tgcctctcgg actcgccaac cgaccggcca tccagcgacg agctcgtcgc catgctaacg    3900
cagctccaca gcttatgatt aatcaccata tatcgcaaat ttcttgagcg gctgccgctg    3960
cgcatggcct taaaaccatg gggggcgat catgttggat cagtgcttcc tgtttcacag    4020
ctagcacggg ggagtgtgca gcagatctca ttgtgtggtg cttgtgagtc acaagcgctg    4080
aaatggtcga caagggaact gacagttcaa ggccatatag gacaggcgca gtcgctgtgt    4140
tccctgtacg attcatcagt gatgtagtag ctaggtacaa tacaagatgg tggttgagct    4200
tcctgggttg ttttgcgcgt gggctgtgaa tatgtcttgg tagaaaaaaa gctctgtgcc    4260
gtggatctga tctgttggtg ttagctgtag cctgtgtata gcctgtagaa agacgtgctt    4320
gtgctgtgca ctgagaccca tcatgtacac ccccccggct ccactccaat ttgcctgaga    4380
gcagagagac tatgatgccg agtatttaac aggctgctgg ggccaacggt ttc            4433
```

<210> SEQ ID NO 123
<211> LENGTH: 133
<212> TYPE: DNA
<213> ORGANISM: Zea mays
<400> SEQUENCE: 123

```
tcgcgctgtg cgcgcccgcc tccgcccagc cgctccactc ggagcccatg gctacgcagt    60
ccccgccgcc gccgctgccg ccggggtcca cgattccccg ggcgcaggcc ggcggcgccg    120
cacgcctccg ccg                                                       133
```

<210> SEQ ID NO 124
<211> LENGTH: 93
<212> TYPE: DNA
<213> ORGANISM: Zea mays
<400> SEQUENCE: 124

```
tccgcccagc cgctccactc ggagcccatg gctacgcagt ccccgccgcc gccgctgccg    60
ccggggtcca cgattccccg ggcgcaggcc ggc                                  93
```

<210> SEQ ID NO 125
<211> LENGTH: 78
<212> TYPE: DNA
<213> ORGANISM: Zea mays

<400> SEQUENCE: 125
cagccgctcc actcggagcc catggctacg cagtccccgc cgccgccgct gccgccgggg    60
tccacgattc cccgggcg                                                 78

<210> SEQ ID NO 126
<211> LENGTH: 27
<212> TYPE: DNA
<213> ORGANISM: Artificial sequences
<220> FEATURE:
<223> OTHER INFORMATION: Synthetic oligonucleotide

<400> SEQUENCE: 126
ttcctcgcgc tgtgcgcgcc cgcctcc                                       27

<210> SEQ ID NO 127
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 127
tccgcccagc cgctccactc ggagccc                                       27

<210> SEQ ID NO 128
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 128
tccactcgga gcccatggct acgcagt                                       27

<210> SEQ ID NO 129
<211> LENGTH: 27
<212> TYPE: DNA
<213> ORGANISM: Artificial sequence
<220> FEATURE:
<223> OTHER INFORMATION: Artificial sequence

<400> SEQUENCE: 129
tccccgccgc cgccgctgcc gccgggg                                       27

<210> SEQ ID NO 130
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 130
tccacgattc cccgggcgca ggccggc                                       27

<210> SEQ ID NO 131
<211> LENGTH: 66
<212> TYPE: PRT
<213> ORGANISM: Arabidopsis thaliana

```
<400> SEQUENCE: 131

Met Lys Gln Arg Arg Arg Arg Asn Gly Cys Ser Ser Ser Asn Thr Ile
1               5                   10                  15

Ser Leu Leu Leu Leu Phe Phe Leu Val Phe Phe Ser Arg Thr Ser Thr
                20                  25                  30

Ser Thr Ser Cys Arg Arg Arg Thr Val Lys His Leu Ser Thr Thr Ser
                35                  40                  45

Thr Ser Ser Thr Pro Leu Glu Ser Arg Ile Thr Ser Lys Val Ile Val
        50                  55                  60

Ile Ser
65

<210> SEQ ID NO 132
<211> LENGTH: 71
<212> TYPE: PRT
<213> ORGANISM: Zea mays

<400> SEQUENCE: 132

Met Thr Ser Arg Asn Pro Thr Lys Thr Leu Ser Val Leu Thr Thr Leu
1               5                   10                  15

Leu Leu Leu Leu Glu Phe Leu Ala Leu Cys Pro Ala Ser Ala Gln
                20                  25                  30

Pro Leu His Ser Glu Pro Met Ala Thr Gln Ser Pro Pro Pro Leu
                35                  40                  45

Pro Pro Gly Ser Thr Ile Pro Arg Ala Gln Ala Gly Ala Ala Arg
        50                  55                  60

Leu Arg Arg Ile Ala Leu Gly
65                  70

<210> SEQ ID NO 133
<211> LENGTH: 79
<212> TYPE: PRT
<213> ORGANISM: Triticum aestivum

<400> SEQUENCE: 133

Met Ala Pro Gly Ala Gly Thr Ala Ala Ala Thr Lys Asn Pro Thr Lys
1               5                   10                  15

Thr Leu Ala Ala Ile Leu Leu Val Leu Leu Ala Asp Leu Pro
                20                  25                  30

Leu Cys Ala Ser Gln Pro Pro Leu His Ser Gln Pro Leu Pro Ala Thr
                35                  40                  45

Gln Ser Pro Ala Ala Pro Leu Pro Pro Gln Pro Ser Ala Pro His
        50                  55                  60

Ala Arg Ala Gly Gly Ala Ala Arg Leu Arg Arg Ile Ala Leu Gly
65                  70                  75

<210> SEQ ID NO 134
<211> LENGTH: 79
<212> TYPE: PRT
<213> ORGANISM: Triticum dicoccoides

<400> SEQUENCE: 134

Met Ala Pro Gly Ala Gly Thr Ala Ala Ala Thr Lys Asn Pro Thr Lys
1               5                   10                  15

Thr Leu Ala Ala Ile Leu Leu Val Leu Leu Ala Asp Leu Pro
                20                  25                  30

Leu Cys Ala Ser Gln Pro Pro Leu His Ser Gln Pro Leu Pro Ala Thr
                35                  40                  45
```

-continued

Gln Ser Pro Ala Ala Pro Leu Pro Pro Pro Gln Pro Ser Ala Pro His
    50                  55                  60

Ala Arg Ala Gly Gly Ala Arg Leu Arg Arg Ile Ala Leu Gly
65                  70                  75

<210> SEQ ID NO 135
<211> LENGTH: 79
<212> TYPE: PRT
<213> ORGANISM: Triticum aestivum

<400> SEQUENCE: 135

Met Ala Pro Gly Ala Gly Thr Ala Ala Ala Thr Lys Asn Pro Thr Lys
1               5                   10                  15

Thr Leu Ala Ala Thr Leu Leu Leu Val Leu Leu Ala Asp Leu Pro
            20                  25                  30

Leu Cys Ala Ser Gln Pro Pro Leu His Ser Gln Pro Leu Pro Ala Thr
            35                  40                  45

Gln Ser Pro Ala Ala Pro Leu Pro Pro Pro Gln Pro Arg Ala Pro His
    50                  55                  60

Ala Arg Ala Gly Gly Ala Ala Arg Leu Arg Arg Ile Ala Leu Gly
65                  70                  75

<210> SEQ ID NO 136
<211> LENGTH: 79
<212> TYPE: PRT
<213> ORGANISM: Aegilops tauschii

<400> SEQUENCE: 136

Met Ala Pro Gly Ala Gly Thr Ala Ala Ala Thr Lys Asn Pro Thr Lys
1               5                   10                  15

Thr Leu Ala Ala Thr Leu Leu Leu Val Leu Leu Ala Asp Leu Pro
            20                  25                  30

Leu Cys Ala Ser Gln Pro Pro Leu His Ser Gln Pro Leu Pro Ala Thr
            35                  40                  45

Gln Ser Pro Ala Ala Pro Leu Pro Pro Pro Gln Pro Arg Ala Pro His
    50                  55                  60

Ala Arg Ala Gly Gly Ala Arg Leu Arg Arg Ile Ala Leu Gly
65                  70                  75

<210> SEQ ID NO 137
<211> LENGTH: 79
<212> TYPE: PRT
<213> ORGANISM: Triticum aestivum

<400> SEQUENCE: 137

Ala Thr Gly Ala Gly Thr Ala Ala Ala Ala Lys Asn Pro Thr Lys
1               5                   10                  15

Thr Leu Ala Thr Leu Leu Leu Val Leu Leu Ala Asp Leu Pro
            20                  25                  30

Leu Cys Ala Ser Gln Pro Pro Leu His Ser Gln Pro Leu Pro Ala Thr
            35                  40                  45

Gln Ser Pro Ala Ala Pro Leu Pro Pro Pro Gln Pro Arg Gly Pro Arg
    50                  55                  60

Ala Gln Ala Gly Gly Ala Ala Arg Leu Arg Arg Ile Ala Leu Gly
65                  70                  75

<210> SEQ ID NO 138
<211> LENGTH: 79

```
<212> TYPE: PRT
<213> ORGANISM: Triticum dicoccoides

<400> SEQUENCE: 138

Ala Pro Gly Ala Gly Thr Ala Ala Ala Ala Lys Asn Pro Thr Lys
1               5                   10                  15

Thr Leu Ala Thr Leu Leu Leu Val Leu Leu Leu Ala Asp Leu Pro
                20                  25                  30

Leu Cys Ala Ser Gln Pro Leu His Ser Gln Pro Leu Ser Ala Thr
                35                  40                  45

Gln Ser Pro Ala Ala Pro Leu Pro Pro Gln Pro Arg Pro Arg
        50                  55                  60

Ala Gln Ala Gly Gly Ala Ala His Leu Arg Arg Ile Ala Leu Gly
65                  70                  75

<210> SEQ ID NO 139
<211> LENGTH: 78
<212> TYPE: PRT
<213> ORGANISM: Brachypodium distachyon

<400> SEQUENCE: 139

Met Ala Arg Gly Gly Val Val Gly Lys Lys Asn Pro Thr Lys
1               5                   10                  15

Thr Leu Ala Ala Ile Leu Leu Leu Leu Leu Ala Val Phe Pro
                20                  25                  30

Arg Pro Ala Ala Ser Gln Pro Leu His Ser Glu Pro Met Ser Thr Gln
                35                  40                  45

Gln Ser Pro Pro Pro Pro Gln Gln Gln Ser Lys Ile Pro His Ala Gln
        50                  55                  60

Pro Gly Gly Gly Ala Ala Arg Leu Arg Arg Ile Ala Leu Gly
65                  70                  75

<210> SEQ ID NO 140
<211> LENGTH: 80
<212> TYPE: PRT
<213> ORGANISM: Oryza brachyantha

<400> SEQUENCE: 140

Met Glu Glu Gly Gly Gly Met Met Ala Ser Lys Asn Pro Thr Lys Thr
1               5                   10                  15

Leu Ala Ile Leu Leu Leu Val Leu Val Phe Phe Leu Leu Ser Leu Cys
                20                  25                  30

Ser Leu Ala Ala Ser Gln Pro Leu His Ser Glu Pro Met Ser Thr Ala
                35                  40                  45

Glu Tyr Ser Pro Pro Pro Ser Pro Pro Pro Gln Ser Lys Ile Pro
        50                  55                  60

His Ala Gln Ala Gly Gly Ala Ala Arg Leu Arg Arg Ile Val Leu Gly
65                  70                  75                  80

<210> SEQ ID NO 141
<211> LENGTH: 69
<212> TYPE: PRT
<213> ORGANISM: Oryza punctata

<400> SEQUENCE: 141

Met Glu Met Met Ala Ser Lys Asn Pro Thr Lys Thr Leu Ala Val His
1               5                   10                  15

Leu Leu Leu Leu Leu Val Phe Phe Leu Ser Leu Ala Ser Ser Gln Pro
                20                  25                  30
```

Leu His Ser Glu Pro Met Ser Thr Thr Thr Gln Ser Pro Pro Pro
                35                  40                  45

Gln Ser Lys Ile Pro His Ala Gln Ala Gly Gly Ala Ala Arg Leu Arg
 50                  55                  60

Arg Ile Val Leu Gly
 65

<210> SEQ ID NO 142
<211> LENGTH: 72
<212> TYPE: PRT
<213> ORGANISM: Oryza meridionalis

<400> SEQUENCE: 142

Met Glu Met Met Ala Ser Lys Asn Pro Thr Lys Thr Leu Leu Leu Leu
 1               5                  10                  15

Leu Leu Leu Val Phe Phe Leu Ser Leu Ala Cys Ser Gln Pro Leu His
                20                  25                  30

Ser Glu Pro Met Ser Thr Thr Ala Thr Thr Gln Ser Ala Pro Pro Pro
                35                  40                  45

Pro Pro Pro Gln Ser Lys Ile Pro His Ala Glu Ala Gly Gly Ala Ala
 50                  55                  60

Arg Leu Arg Arg Ile Val Leu Gly
 65                  70

<210> SEQ ID NO 143
<211> LENGTH: 69
<212> TYPE: PRT
<213> ORGANISM: Oryza sativa Indica Group

<400> SEQUENCE: 143

Met Ala Ser Lys Asn Pro Thr Lys Thr Leu Leu Leu Leu Leu Leu Val
 1               5                  10                  15

Phe Phe Leu Ser Leu Ala Cys Ser Gln Pro Leu His Ser Glu Pro Met
                20                  25                  30

Ser Thr Thr Thr Thr Ala Thr Gln Pro Ala Pro Pro Pro Pro Pro Pro
                35                  40                  45

Gln Ser Lys Ile Pro His Ala Glu Ala Gly Gly Ala Ala Arg Leu Arg
 50                  55                  60

Arg Ile Val Leu Gly
 65

<210> SEQ ID NO 144
<211> LENGTH: 73
<212> TYPE: PRT
<213> ORGANISM: Oryza nivara

<400> SEQUENCE: 144

Met Glu Met Met Ala Ser Lys Asn Pro Thr Lys Thr Leu Leu Leu Leu
 1               5                  10                  15

Leu Leu Leu Val Phe Phe Leu Ser Leu Ala Cys Ser Gln Pro Leu His
                20                  25                  30

Ser Glu Pro Met Ser Thr Thr Thr Thr Ala Thr Gln Pro Ala Pro Pro
                35                  40                  45

Pro Pro Pro Pro Gln Ser Lys Ile Pro His Ala Glu Ala Gly Gly Ala
 50                  55                  60

Ala Arg Leu Arg Arg Ile Val Leu Gly
 65                  70

<210> SEQ ID NO 145
<211> LENGTH: 85
<212> TYPE: PRT
<213> ORGANISM: Oryza rufipogon

<400> SEQUENCE: 145

Leu Cys Ser Pro Arg Ala Ile Ala Ser Pro Leu Ser Met Glu Met
1               5                   10                  15

Ala Ser Lys Asn Pro Thr Lys Thr Leu Leu Leu Leu Leu Leu Val
            20                  25                  30

Phe Phe Leu Ser Leu Ala Cys Ser Gln Pro Leu His Ser Glu Pro Met
            35                  40                  45

Ser Thr Thr Thr Thr Ala Thr Gln Pro Ala Pro Pro Pro Pro Pro
    50                  55                  60

Gln Ser Lys Ile Pro His Ala Glu Ala Gly Gly Ala Ala Arg Leu Arg
65                  70                  75                  80

Arg Ile Val Leu Gly
                85

<210> SEQ ID NO 146
<211> LENGTH: 75
<212> TYPE: PRT
<213> ORGANISM: Oryza barthii

<400> SEQUENCE: 146

Met Glu Met Met Ala Ser Lys Asn Pro Thr Lys Thr His Leu Leu
1               5                   10                  15

Leu Leu Leu Leu Val Phe Phe Leu Ser Leu Ala Cys Ser Gln Pro Leu
            20                  25                  30

His Ser Glu Pro Met Ser Thr Thr Thr Thr Thr Ala Thr Gln Pro Thr
            35                  40                  45

Pro Pro Pro Pro Pro Pro Gln Ser Lys Ile Pro His Ala Glu Ala Gly
        50                  55                  60

Gly Ala Ala Arg Leu Arg Arg Ile Val Leu Gly
65                  70                  75

<210> SEQ ID NO 147
<211> LENGTH: 73
<212> TYPE: PRT
<213> ORGANISM: Oryza sativa Japonica Group

<400> SEQUENCE: 147

Met Glu Met Met Ala Ser Lys Asn Pro Thr Lys Thr Leu Leu Leu
1               5                   10                  15

Leu Leu Leu Val Phe Phe Leu Ser Leu Ala Cys Ser Gln Pro Leu His
            20                  25                  30

Ser Glu Pro Met Ser Thr Thr Thr Thr Ala Thr Gln Pro Ala Pro Pro
            35                  40                  45

Pro Pro Pro Pro Gln Ser Lys Ile Pro His Ala Glu Ala Gly Gly Ala
        50                  55                  60

Ala Arg Leu Arg Arg Ile Val Leu Gly
65                  70

<210> SEQ ID NO 148
<211> LENGTH: 73
<212> TYPE: PRT
<213> ORGANISM: Oryza glumipatula

<400> SEQUENCE: 148

Met Glu Met Met Ala Ser Lys Asn Pro Thr Lys Thr Leu Leu Leu
1               5                   10                  15

Leu Leu Leu Val Phe Phe Leu Ser Leu Ala Cys Ser Gln Pro Leu His
            20                  25                  30

Ser Glu Pro Met Ser Thr Thr Thr Ala Thr Gln Pro Ala Pro Pro
            35                  40                  45

Pro Pro Pro Pro Gln Ser Lys Ile Pro His Ala Glu Ala Gly Gly Ala
        50                  55                  60

Ala Arg Leu Arg Arg Ile Val Leu Gly
65                  70

<210> SEQ ID NO 149
<211> LENGTH: 72
<212> TYPE: PRT
<213> ORGANISM: Setaria italica

<400> SEQUENCE: 149

Met Thr Ser Lys Asn Pro Thr Lys Thr Pro Pro Leu Leu Ala Thr Leu
1               5                   10                  15

Leu Leu Leu Leu Ala Phe Leu Ala Leu Cys Ala Pro Ala Ala Ser Gln
            20                  25                  30

Pro Leu His Ser Glu Pro Met Ala Thr Gln Ser Pro Pro Pro Ser Pro
            35                  40                  45

Ala Pro Pro Gln Ser Arg Ile Pro Arg Ala Gln Val Gly Gly Ala Ala
        50                  55                  60

Arg Leu Arg Arg Ile Ala Leu Gly
65                  70

<210> SEQ ID NO 150
<211> LENGTH: 79
<212> TYPE: PRT
<213> ORGANISM: Panicum hallii FIL2

<400> SEQUENCE: 150

Ile Met Glu Gln Ala Val Arg Met Thr Ser Lys Asn Pro Thr Lys Thr
1               5                   10                  15

Pro Pro Leu Leu Ala Thr Leu Leu Leu Leu Ala Phe Leu Ala Leu
            20                  25                  30

Cys Ala Pro Ala Ser Ser Gln Pro Leu His Ser Glu Pro Met Pro Thr
            35                  40                  45

Gln Ser Pro Pro Pro Ser Pro Thr Pro Gln Ser Thr Ile Pro Arg
        50                  55                  60

Ala Pro Ala Gly Gly Ala Ala Arg Leu Arg Arg Ile Ala Leu Gly
65                  70                  75

<210> SEQ ID NO 151
<211> LENGTH: 79
<212> TYPE: PRT
<213> ORGANISM: Panicum hallii HAL2

<400> SEQUENCE: 151

Ile Met Glu Gln Ala Val Arg Met Thr Ser Lys Asn Pro Thr Lys Thr
1               5                   10                  15

Pro Pro Phe Leu Ala Ile Leu Leu Leu Leu Ala Phe Leu Ala Leu
            20                  25                  30

Cys Ala Pro Ala Ser Ser Gln Pro Leu His Ser Glu Pro Met Ala Thr
            35                  40                  45

```
Gln Ser Pro Pro Pro Ser Pro Thr Pro Pro Gln Ser Thr Ile Pro Arg
    50                  55                  60

Ala Gln Ala Gly Gly Ala Ala Arg Leu Arg Arg Ile Ala Leu Gly
 65                  70                  75
```

<210> SEQ ID NO 152
<211> LENGTH: 75
<212> TYPE: PRT
<213> ORGANISM: Sorghum bicolor

<400> SEQUENCE: 152

```
Met Val Val Gly Ala Arg Met Thr Ser Arg Asn Pro Thr Lys Thr Leu
 1               5                  10                  15

Pro Leu Leu Ala Thr Thr Leu Val Leu Leu Leu Ala Phe Leu Ala
            20                  25                  30

Leu Cys Ala Pro Ala Ser Ser Gln Pro Leu His Ser Glu Pro Met Ala
            35                  40                  45

Thr Gln Ser Pro Pro Pro Arg Thr Ser Ile Pro Arg Ala Gln Val Gly
    50                  55                  60

Gly Ala Ala Arg Leu Arg Ile Ala Leu Gly
 65                  70                  75
```

<210> SEQ ID NO 153
<211> LENGTH: 60
<212> TYPE: PRT
<213> ORGANISM: Brassica rapa

<400> SEQUENCE: 153

```
Met Glu Gln Arg Arg Arg Arg Asn Ile Asn Thr Leu Ser Leu Leu Leu
 1               5                  10                  15

Leu Phe Phe Leu Ala Phe Thr Ser Thr Thr Ala Thr Thr Ser Ser Cys
            20                  25                  30

Arg Arg Arg Ala Val Lys His Leu Ser Thr Thr Gln Ala Thr Pro Leu
            35                  40                  45

Gln Ser Arg Ile Thr Pro Lys Val Ile Val Leu Ser
    50                  55                  60
```

<210> SEQ ID NO 154
<211> LENGTH: 60
<212> TYPE: PRT
<213> ORGANISM: Brassica napus

<400> SEQUENCE: 154

```
Met Glu Gln Arg Arg Arg Arg Asn Ile Asn Thr Leu Ser Leu Leu Leu
 1               5                  10                  15

Leu Phe Phe Leu Ala Phe Thr Ser Thr Thr Ala Thr Thr Ser Ser Cys
            20                  25                  30

Arg Arg Arg Ala Val Lys His Leu Ser Thr Thr Gln Ala Thr Pro Leu
            35                  40                  45

Gln Ser Arg Ile Thr Pro Lys Val Ile Val Leu Ser
    50                  55                  60
```

<210> SEQ ID NO 155
<211> LENGTH: 63
<212> TYPE: PRT
<213> ORGANISM: Brassica napus

<400> SEQUENCE: 155

```
Met Glu Gln Arg Gly Arg Lys Arg Tyr Cys Asn Thr Val Tyr Leu Leu
 1               5                  10                  15
```

```
Leu Phe Ile Phe Leu Val Phe Ser Ser Arg Thr Ser Ser Ala Ser
                20                  25                  30

Cys Arg Arg Arg Ala Val Lys His Leu Ser Thr Ala Pro Pro Ser Ser
         35                  40                  45

Thr Pro Leu Glu Ser Arg Ile Thr Thr Lys Val Ile Ile Val Ser
     50                  55                  60
```

<210> SEQ ID NO 156
<211> LENGTH: 63
<212> TYPE: PRT
<213> ORGANISM: Brassica napus

<400> SEQUENCE: 156

```
Met Glu Gln Arg Arg Lys Arg Tyr Cys Asn Thr Val Tyr Leu Leu
1                5                  10                  15

Leu Phe Ile Leu Leu Val Phe Ser Ser Ile Thr Thr Ser Ser Ala Ser
                20                  25                  30

Cys Arg Arg Arg Ala Val Lys His Leu Ser Thr Ala Pro Pro Ser Ser
         35                  40                  45

Thr Pro Leu Glu Ser Lys Ile Thr Ser Lys Val Ile Ala Ile Ser
     50                  55                  60
```

<210> SEQ ID NO 157
<211> LENGTH: 61
<212> TYPE: PRT
<213> ORGANISM: Brassica rapa

<400> SEQUENCE: 157

```
Met Glu Gln Arg Arg Arg Lys Arg Tyr Cys Asn Thr Val His Leu Leu
1                5                  10                  15

Leu Phe Ile Phe Leu Val Phe Ser Ser Arg Thr Ser Ala Ser Cys Arg
                20                  25                  30

Arg Arg Ala Val Lys His Leu Ser Thr Ala Pro Pro Ser Ser Thr Pro
         35                  40                  45

Leu Glu Ser Lys Ile Thr Ser Lys Val Ile Val Val Ser
     50                  55                  60
```

<210> SEQ ID NO 158
<211> LENGTH: 67
<212> TYPE: PRT
<213> ORGANISM: Arabidopsis thaliana

<400> SEQUENCE: 158

```
Met Glu Gln Arg Arg Arg Arg Arg Asn Gly Cys Ser Ser Asn Thr
1                5                  10                  15

Ile Ser Leu Leu Leu Phe Phe Phe Leu Val Phe Phe Ser Arg Thr Ser
                20                  25                  30

Thr Ser Thr Ser Cys Arg Arg Arg Thr Val Lys His Leu Ser Thr Thr
         35                  40                  45

Ser Thr Ser Ser Thr Pro Leu Glu Ser Arg Ile Thr Ser Lys Val Ile
     50                  55                  60

Val Val Ser
65
```

<210> SEQ ID NO 159
<211> LENGTH: 61
<212> TYPE: PRT
<213> ORGANISM: Arabidopsis lyrata

```
<400> SEQUENCE: 159

Met Glu Gln Arg Arg Ser Asn Thr Ile Tyr Leu Leu Leu Leu Phe
1               5                   10                  15

Phe Phe Leu Val Phe Thr Ser Arg Thr Ser Thr Ser Ser Cys Arg
                20                  25                  30

Arg Arg Thr Val Lys His Leu Ser Thr Thr Pro Pro Ser Ser Thr Pro
            35                  40                  45

Leu Glu Ser Arg Ile Thr Ser Lys Val Ile Val Phe Ser
    50                  55                  60

<210> SEQ ID NO 160
<211> LENGTH: 61
<212> TYPE: PRT
<213> ORGANISM: Brassica napus

<400> SEQUENCE: 160

Met Glu Gln Arg Arg Ser Asn Thr Ile Tyr Leu Leu Leu Leu Phe
1               5                   10                  15

Phe Phe Leu Val Phe Thr Ser Arg Thr Asn Thr Ser Ala Ser Cys Arg
                20                  25                  30

Arg Arg Thr Val Lys His Leu Ser Thr Thr Pro Pro Ser Ser Thr Pro
            35                  40                  45

Leu Gln Ser Ser Ile Thr Ser Lys Val Met Val Phe Ser
    50                  55                  60

<210> SEQ ID NO 161
<211> LENGTH: 61
<212> TYPE: PRT
<213> ORGANISM: Brassica oleracea

<400> SEQUENCE: 161

Met Glu Gln Arg Arg Ser Asn Thr Ile Tyr Leu Leu Leu Leu Phe
1               5                   10                  15

Phe Phe Leu Val Phe Thr Ser Arg Thr Asn Thr Ser Ala Ser Cys Arg
                20                  25                  30

Arg Arg Thr Val Lys His Leu Ser Thr Thr Pro Pro Ser Ser Thr Pro
            35                  40                  45

Leu Gln Ser Ser Ile Thr Ser Lys Val Ile Val Phe Ser
    50                  55                  60

<210> SEQ ID NO 162
<211> LENGTH: 74
<212> TYPE: PRT
<213> ORGANISM: Trifolium pratense

<400> SEQUENCE: 162

Gly Cys Gly Phe Val Phe Cys Val Leu Met Phe Lys Lys Arg Gln Thr
1               5                   10                  15

Phe Phe Tyr Leu Ala Lys Glu Leu Leu Val Phe Gln Pro Leu Val Leu
                20                  25                  30

Leu Leu Phe Leu Phe Ser Leu His His Asn Thr Val Gln Cys Glu Gly
            35                  40                  45

Arg Leu Ser Lys Asn Ile Ser Glu Thr Ser Ser Gln Ser Asp Tyr
    50                  55                  60

Lys Asp Asn Pro Arg Lys Val Ile Val Ser
65                  70

<210> SEQ ID NO 163
```

-continued

```
<211> LENGTH: 75
<212> TYPE: PRT
<213> ORGANISM: Medicago truncatula

<400> SEQUENCE: 163

Gly Cys Gly Phe Val Phe Cys Val Phe Met Phe Lys Lys Arg His Thr
1               5                   10                  15

Pro Phe Ser Leu Ala Arg Lys Phe Leu Ser Phe Gln Pro Phe Val Leu
            20                  25                  30

Leu Leu Phe Leu Phe Ser Leu His Asp Thr Val Gln Cys Gln Gly
        35                  40                  45

Arg Leu Ser Lys His Met Ser Ser Glu Pro Ser Ser Ser Thr Ser Glu
    50                  55                  60

Tyr Lys Asp Asp Pro Arg Lys Ile Ile Ile Ser
65                  70                  75

<210> SEQ ID NO 164
<211> LENGTH: 58
<212> TYPE: PRT
<213> ORGANISM: Lupinus angustifolius

<400> SEQUENCE: 164

Met Phe Lys Arg Arg His Thr Leu Cys Ser Leu Leu Arg Glu Leu Phe
1               5                   10                  15

Leu Leu Leu Leu Phe Ser Leu His His Ser Thr Val Gln Cys Gln Gly
            20                  25                  30

Arg Leu Ser Lys His Val Ser Ser Ala Pro Tyr Ser Pro Ser Glu Tyr
        35                  40                  45

Lys Asp Asp Leu Arg Arg Ile Ile Ile Ser
    50                  55

<210> SEQ ID NO 165
<211> LENGTH: 72
<212> TYPE: PRT
<213> ORGANISM: Phaseolus vulgaris

<400> SEQUENCE: 165

Met Phe Arg Lys Arg His Ile Ala Ser Ser Leu Ala Arg Glu Leu Leu
1               5                   10                  15

Ala Leu Gln Pro Leu Leu Ile Leu Phe Leu Phe Ser Leu His His His
            20                  25                  30

Thr Val Gln Cys Gln Gly Arg Leu Ser Lys His Val Ser Ser Glu Pro
        35                  40                  45

Pro Ser Pro Ser Arg Thr Ser Pro Pro Ser Ser Ser Gly Tyr Arg Asp
    50                  55                  60

Asp Pro Lys Lys Ile Ile Leu Ser
65                  70

<210> SEQ ID NO 166
<211> LENGTH: 81
<212> TYPE: PRT
<213> ORGANISM: Vigna radiata

<400> SEQUENCE: 166

Leu Ala Leu Phe Val Cys Cys Ser Leu Met Phe Arg Lys Arg Asn Ile
1               5                   10                  15

Ala Ser Ser Leu Ala Arg Glu Leu Leu Ala Leu Gln Pro Leu Phe Ile
            20                  25                  30

Ile Phe Leu Phe Ser Leu His His Asn Thr Val Gln Cys Gln Gly Arg
```

```
                35                  40                  45
Leu Ser Lys His Val Ser Ser Glu Pro Pro Ser Pro Ser Arg Pro Ser
        50                  55                  60

Pro Pro Ser Ser Ser Gly Tyr Arg Asp Asp Pro Lys Lys Ile Ile Leu
65                  70                  75                  80

Ser

<210> SEQ ID NO 167
<211> LENGTH: 74
<212> TYPE: PRT
<213> ORGANISM: Glycine max

<400> SEQUENCE: 167

Met Phe Arg Lys Arg His Ile Leu Ser Ser Leu Ala Arg Glu Leu Leu
1               5                   10                  15

Ala Leu Gln Pro Leu Phe Leu Leu Phe Leu Phe Ser Leu His His Asn
                20                  25                  30

Thr Val Gln Cys Gln Gly Arg Leu Ser Lys His Val Ser Ser Glu Pro
            35                  40                  45

Pro Ser Pro Ser Arg Pro Ser Ser Ala Ala Pro Ser Ser Ser Gly Tyr
        50                  55                  60

Lys Asp Asp Pro Arg Lys Ile Ile Leu Ser
65                  70

<210> SEQ ID NO 168
<211> LENGTH: 74
<212> TYPE: PRT
<213> ORGANISM: Glycine max

<400> SEQUENCE: 168

Met Phe Arg Lys Arg His Thr Leu Ser Ser Leu Ala Arg Glu Leu Leu
1               5                   10                  15

Ala Phe Gln Pro Leu Phe Leu Leu Phe Leu Phe Ser Leu His His Asn
                20                  25                  30

Thr Met Gln Cys Gln Gly Arg Leu Ser Lys His Val Ser Ser Glu Pro
            35                  40                  45

Pro Ser Pro Ser Arg Ser Thr Pro Ser Pro Ser Ser Ser Gly Tyr
        50                  55                  60

Lys Asp Asp Pro Arg Lys Ile Ile Leu Ser
65                  70

<210> SEQ ID NO 169
<211> LENGTH: 64
<212> TYPE: PRT
<213> ORGANISM: Actinidia chinensis

<400> SEQUENCE: 169

Met Leu Arg Phe Val Val Ser Met Glu Lys Thr Ser Cys Val Asn Leu
1               5                   10                  15

Glu Leu Val Leu Leu Ile Ile Cys Leu Cys Asn Thr Ser Val Gln
                20                  25                  30

Cys Gln Thr Arg Pro Ile Asn His Ile Ser Ala Glu Pro Pro Ser Pro
            35                  40                  45

Ser Arg Ala Pro Glu Leu Lys Asn Lys Phe Gln Lys Ile Ile Leu Ser
        50                  55                  60

<210> SEQ ID NO 170
<211> LENGTH: 64
```

```
<212> TYPE: PRT
<213> ORGANISM: Actinidia chinensis

<400> SEQUENCE: 170

Met Leu Arg Val Val Ala Ser Met Glu Lys Thr Asn Cys Val Thr Leu
1               5                   10                  15

Glu Leu Val Leu Leu Ile Phe Cys Leu Cys Asn Thr Ser Val Gln
                20                  25                  30

Cys Gln Thr Arg Pro Ile Asn His Ile Ser Ala Glu Pro Pro Ser Pro
                35                  40                  45

Ser Arg Ala Pro Glu Leu Lys Asn Lys Phe Gln Lys Ile Ile Leu Ser
            50                  55                  60

<210> SEQ ID NO 171
<211> LENGTH: 57
<212> TYPE: PRT
<213> ORGANISM: Prunus persica

<400> SEQUENCE: 171

Met Asp Arg Arg Arg Ser Thr Ser Lys Phe Asn Ser Arg Leu Thr Arg
1               5                   10                  15

Leu Leu Leu Leu Leu Phe Ile Phe Cys Phe Arg Gln Glu Thr Val Gln
                20                  25                  30

Cys Gln Glu Thr Glu Pro Pro Ser Ser Ser Lys Gln Pro His Phe Lys
                35                  40                  45

Asn Gln Leu Gln Arg Ile Ile Leu Ser
            50                  55

<210> SEQ ID NO 172
<211> LENGTH: 57
<212> TYPE: PRT
<213> ORGANISM: Vitis vinifera

<400> SEQUENCE: 172

Met Glu Lys Thr Ser Arg Glu Ala Ile Ser Leu Leu Phe Leu Leu Ile
1               5                   10                  15

Phe Ile His Phe Tyr Asn Val Lys Cys Gln Glu Asn Ile Ile Asn Arg
                20                  25                  30

Val Ser Thr Asp Ser Ser Pro Ser Pro Ser Arg Glu Ala Glu Phe Lys
                35                  40                  45

Ser Gly Leu Lys Lys Ile Ile Leu Ser
            50                  55

<210> SEQ ID NO 173
<211> LENGTH: 59
<212> TYPE: PRT
<213> ORGANISM: Gossypium raimondii

<400> SEQUENCE: 173

Met Ala Lys Met Ser Gly Cys Ile Val Thr Val Ala Leu Leu Leu Leu
1               5                   10                  15

Leu Leu Leu Cys Leu His Gln Thr Pro Val Glu Cys Lys Glu Arg Leu
                20                  25                  30

Ile Arg Gln Leu Ser Ser Gln Pro Ser Ser Ala Thr Lys Pro Gln Glu
                35                  40                  45

Phe Lys Ile Gly Phe Lys Arg Val Ile Leu Ser
            50                  55

<210> SEQ ID NO 174
```

-continued

```
<211> LENGTH: 57
<212> TYPE: PRT
<213> ORGANISM: Gorchorus capsularis

<400> SEQUENCE: 174

Met Gly Lys Gly Arg Arg Cys Thr Leu Ser Leu Leu Phe Leu Leu Leu
1               5                   10                  15

Leu Cys Phe His Gln Thr Thr Val His Cys Lys Glu Arg Leu Ile Arg
            20                  25                  30

His Leu Ser Ser Gln Pro Pro Ser Lys Pro Gln Glu Phe Lys
        35                  40                  45

Ile Gly Leu Lys Arg Ile Ile Leu Ser
    50                  55

<210> SEQ ID NO 175
<211> LENGTH: 67
<212> TYPE: PRT
<213> ORGANISM: Theobroma cacao Matina 16

<400> SEQUENCE: 175

Met Phe Val Cys Gly Phe Val Ala Ser Met Glu Lys Arg Ser Cys Thr
1               5                   10                  15

Leu Ser Leu Leu Leu Leu Leu Leu Leu Cys Phe His Leu Thr
            20                  25                  30

Thr Val Gln Cys Glu Gly Arg Leu Ile Arg Tyr Leu Ser Ser Gln Pro
        35                  40                  45

Pro Ser Pro Ser Thr Pro Gln Glu Phe Lys Ile Gly Phe Lys Arg Ile
    50                  55                  60

Val Leu Ser
65

<210> SEQ ID NO 176
<211> LENGTH: 65
<212> TYPE: PRT
<213> ORGANISM: Manihot esculenta

<400> SEQUENCE: 176

Met Glu Lys Arg Arg Tyr Ser Ser Gln Leu Thr Ser Lys Val Thr Ala
1               5                   10                  15

Leu Leu Leu Leu Leu Ser Phe Cys Phe His Pro Ile Val Val Gln Cys
            20                  25                  30

Gln Glu Ser Asn Ile Lys Met Thr Arg His Leu Ser Ser Glu Thr Pro
        35                  40                  45

Pro Ser Arg Ser Pro Gln Phe His Thr Gly Leu Lys Arg Ile Leu Leu
    50                  55                  60

Ser
65

<210> SEQ ID NO 177
<211> LENGTH: 61
<212> TYPE: PRT
<213> ORGANISM: Populus trichocarpa

<400> SEQUENCE: 177

Met Gly Lys Arg Arg Tyr Ser Thr Gln Ile Ser Asn Asn Lys Asp Thr
1               5                   10                  15

Ser Ser Leu Leu Phe Leu Phe Ile Leu Cys Leu Tyr Tyr Thr Thr Val
            20                  25                  30

Gln Cys Gln Glu Ser Ser Lys Val Thr Pro Pro Phe Pro Ser Thr Pro
```

```
                35                  40                  45
Thr His Ser Lys Asn Gly Leu Lys Arg Ile Leu Val Ser
            50                  55                  60

<210> SEQ ID NO 178
<211> LENGTH: 61
<212> TYPE: PRT
<213> ORGANISM: Populus trichocarpa

<400> SEQUENCE: 178

Met Glu Lys Arg Arg Tyr Ser Leu Arg Val Ser Asn Ser Lys Val Thr
1               5                   10                  15

Ala Ser Leu Leu Phe Leu Phe Val Leu Cys Leu Tyr Tyr Ala Ser Val
            20                  25                  30

Gln Cys Gln Glu Ser Ser Lys Val Thr Pro Pro Ser Pro Ser Thr Pro
        35                  40                  45

Thr Gln Ser Lys Asn Gly Leu Lys Arg Ile Leu Val Ser
    50                  55                  60

<210> SEQ ID NO 179
<211> LENGTH: 200
<212> TYPE: DNA
<213> ORGANISM: Zea mays

<400> SEQUENCE: 179
accaaaaccc tgtcggtcct gaccactctc ctgctgctgc ttgagttcct cgcgctgtgc      60
gcgcccgcct ccgcccagcc gctccactcg gagcccatgg ctacgcagtc cccgccgccg     120
ccgctgccgc cggggtccac gattccccgg gcgcaggccg gcggcgccgc acgcctccgc     180
cgcattgcgc tcggggtcct                                                 200

<210> SEQ ID NO 180
<211> LENGTH: 197
<212> TYPE: DNA
<213> ORGANISM: Artificial sequence
<220> FEATURE:
<223> OTHER INFORMATION: Synthetic polynucleotide

<400> SEQUENCE: 180
accaaaaccc tgtcggtcct gaccactctc ctgctgctgc ttgagttcct cgcgctgtgc      60
gcgccctccg cccagccgct ccactcggag cccatggcta cgcagtcccc gccgccgccg     120
ctgccgccgg ggtccacgat tccccgggcg caggccggcg cgccgcacg cctccgccgc     180 attgcgctcg gggtcct                                                    197

<210> SEQ ID NO 181
<211> LENGTH: 194
<212> TYPE: DNA
<213> ORGANISM: Artificial sequence
<220> FEATURE:
<223> OTHER INFORMATION: Synthetic polynucleotide

<400> SEQUENCE: 181
accaaaaccc tgtcggtcct gaccactctc ctgctgctgc ttgagttcct cgcgctgtgc      60
gcgcccgcct ccgcccagcc gctccactcg gagcccatg agtccccgcc gccgccgctg     120
ccgccggggt ccacgattcc ccgggcgcag gccggcggcg ccgcacgcct ccgccgcatt     180
gcgctcgggg tcct                                                       194

<210> SEQ ID NO 182
```

```
<211> LENGTH: 194
<212> TYPE: DNA
<213> ORGANISM: Artificial sequence
<220> FEATURE:
<223> OTHER INFORMATION: Synthetic polynucleotide

<400> SEQUENCE: 182
accaaaaccc tgtcggtcct gaccactctc ctgctgctgc ttgagttcct cgcgctgtgc      60
gcgcccgccc agccgctcca ctcggagccc atggctacgc agtccccgcc gccgccgctg     120
ccgccggggt ccacgattcc ccgggcgcag gccggcggcg ccgcacgcct ccgccgcatt     180
gcgctcgggg tcct                                                      194

<210> SEQ ID NO 183
<211> LENGTH: 194
<212> TYPE: DNA
<213> ORGANISM: Artificial sequence
<220> FEATURE:
<223> OTHER INFORMATION: Synthetic polynucleotide

<400> SEQUENCE: 183
accaaaaccc tgtcggtcct gaccactctc ctgctgctgc ttgagttcct cgcgctgtgc      60
gcgcccgcct ccgcccagcc gctccacccc atgctacgc agtccccgcc gccgccgctg     120
ccgccggggt ccacgattcc ccgggcgcag gccggcggcg ccgcacgcct ccgccgcatt     180
gcgctcgggg tcct                                                      194

<210> SEQ ID NO 184
<211> LENGTH: 191
<212> TYPE: DNA
<213> ORGANISM: Artificial sequence
<220> FEATURE:
<223> OTHER INFORMATION: Synthetic polynucleotide

<400> SEQUENCE: 184
accaaaaccc tgtcggtcct gaccactctc ctgctgctgc ttgagttcct cgcgctgtgc      60
gcgcccgcct ccgcccagcc gctccactcg gagcccatgt ccccgccgcc gccgctgccg     120
ccggggtcca cgattccccg ggcgcaggcc ggcggcgccg cacgcctccg ccgcattgcg     180
ctcggggtcc t                                                         191

<210> SEQ ID NO 185
<211> LENGTH: 191
<212> TYPE: DNA
<213> ORGANISM: Artificial sequence
<220> FEATURE:
<223> OTHER INFORMATION: Synthetic polynucleotide

<400> SEQUENCE: 185
accaaaaccc tgtcggtcct gaccactctc ctgctgctgc ttgagttcct cgcgctgtgc      60
gcgcccgcct ccgcccagcc gctccactcg gagcccatgg ctacgcagtc cccgccgccg     120
ccgcggtcca cgattccccg ggcgcaggcc ggcggcgccg cacgcctccg ccgcattgcg     180
ctcggggtcc t                                                         191

<210> SEQ ID NO 186
<211> LENGTH: 191
<212> TYPE: DNA
<213> ORGANISM: Artificial sequence
<220> FEATURE:
<223> OTHER INFORMATION: Synthetic polynucleotide

<400> SEQUENCE: 186
```

```
accaaaaccc tgtcggtcct gaccactctc ctgctgctgc ttgagttcct cgcgctgtgc    60
gcgcccgcct ccgcccagcc gctccactcg agcccatgt cccgccgcc gccgctgccg     120 ccggggtcca cgattccccg ggcgcaggcc ggcggcgccg cacgcctccg ccgcattgcg    180
ctcggggtcc t                                                         191
```

<210> SEQ ID NO 187
<211> LENGTH: 188
<212> TYPE: DNA
<213> ORGANISM: Artificial sequence
<220> FEATURE:
<223> OTHER INFORMATION: Synthetic polynucleotide

<400> SEQUENCE: 187

```
accaaaaccc tgtcggtcct gaccactctc ctgctgctgc ttgagttcct cgcgctgtgc    60
gcgcccgcct ccgcccagcc gctccactcg agcccatgg ctacgcagtc cccgccgccg    120
ccgctgccgc cggggtccac gattccccgg ggcgccgcac gcctccgccg cattgcgctc    180
ggggtcct                                                             188
```

<210> SEQ ID NO 188
<211> LENGTH: 188
<212> TYPE: DNA
<213> ORGANISM: Artificial sequence
<220> FEATURE:
<223> OTHER INFORMATION: Synthetic polynucleotide

<400> SEQUENCE: 188

```
accaaaaccc tgtcggtcct gaccactctc ctgctgctgc ttgagttcct cgcgctgtgc    60
gcgcccgccc agccgctcca ctcggagccc atggtgtccc cgccgccgcc gctgccgccg    120
gggtccacga ttccccgggc gcaggccggc ggcgccgcac gcctccgccg cattgcgctc    180
ggggtcct                                                             188
```

<210> SEQ ID NO 189
<211> LENGTH: 185
<212> TYPE: DNA
<213> ORGANISM: Artificial sequence
<220> FEATURE:
<223> OTHER INFORMATION: Synthetic polynucleotide

<400> SEQUENCE: 189

```
accaaaaccc tgtcggtcct gaccactctc ctgctgctgc ttgagttcct cgcgctgtgc    60
gcgcccgcct ccgcccagcc gctccactcg agcccatgg ctatgccgct gccgccgggg    120
tccacgattc cccgggcgca ggccggcggc gccgcacgcc tccgccgcat tgcgctcggg    180
gtcct                                                                185
```

<210> SEQ ID NO 190
<211> LENGTH: 158
<212> TYPE: DNA
<213> ORGANISM: Artificial sequence
<220> FEATURE:
<223> OTHER INFORMATION: Synthetic polynucleotide

<400> SEQUENCE: 190

```
accaaaaccc tgtcggtcct gaccactctc ctgctgctgc ttgagttcct cgcgctgtgc    60
gcgcccgcct ccgcccagcc gctgccgccg ggtccacga ttccccgggc gcaggccggc    120
ggcgccgcac gcctccgccg cattgcgctc ggggtcct                            158
```

```
<210> SEQ ID NO 191
<211> LENGTH: 155
<212> TYPE: DNA
<213> ORGANISM: Artificial sequence
<220> FEATURE:
<223> OTHER INFORMATION: Synthetic polynucleotide

<400> SEQUENCE: 191
accaaaaccc tgtcggtcct gaccactctc cagccgctcc actcggagcc catggctacg      60
cagtccccgc cgccgccgct gccgccgggg tccacgattc cccgggcgca ggccggcggc     120
gccgcacgcc tccgccgcat tgcgctcggg gtcct                                155
```

METHODS FOR CONTROLLING MERISTEM SIZE FOR CROP IMPROVEMENT

STATEMENT REGARDING ELECTRONIC FILING OF A SEQUENCE LISTING

A Sequence Listing in ASCII text format, submitted under 37 C.F.R. § 1.821, entitled 1499.29_ST25.txt, 596,676 bytes in size, generated on Jun. 1, 2021 and filed via EFS-Web, is provided in lieu of a paper copy. This Sequence Listing is hereby incorporated herein by reference into the specification for its disclosures.

STATEMENT OF PRIORITY

This application claims the benefit, under 35 U.S.C. § 119 (e), of U.S. Provisional Application No. 63/033,273 filed on Jun. 2, 2020, the entire contents of which is incorporated by reference herein.

FIELD OF THE INVENTION

This invention relates to compositions and methods for modifying CORYNE (CRN) genes in plants, optionally to increase kernel row number. The invention further relates to plants having a modified CRN gene and, for example, increased kernel row number produced using the methods and compositions of the invention.

BACKGROUND OF THE INVENTION

New plant organs are initiated at the growing tip of the plant called the meristem. In the meristem a population of undifferentiated stem cells is maintained. During growth, the meristem allocates stem-cells to newly formed organs, including seeds, while at the same time reserving some stem-cells to continually maintain the meristem. Several conserved molecular mechanisms have been described that control the size of the stem cell population to ensure organized growth and proper meristem size.

As a result of the modular nature of maize ear development, larger meristems tend to initiate more flowers, and thus, meristem size has a direct effect on kernel row number and yield. The number of flowers initiated during the development of the maize ear directly limits grain yield. An increased number of flowers initiated around the circumference of the ear (kernel row number or KRN) was a major trait selected during maize domestication. Significant advancements through breeding have resulted in dramatic increases in kernel row number, from 2 in teosinte, the ancestor of maize, to ~8-20 rows in modern elite maize varieties. In diverse maize lines kernel row number can get as high as 36.

In the canonical regulatory pathway described in the model plant *Arabidopsis*, CLAVATA3 (CLV3) peptide is secreted from cells in the meristem apex and moves through the apoplast into the central stem-cell domain where it interacts with several Leucine Rich Receptors (LRRs) including CLAVATA1 (CLV1) and CLAVATA2 (CLV2). This receptor-ligand interaction stimulates signaling that ultimately acts to reduce WUS expression and restrict the expansion of the stem cell population. One of the targets of WUS is the CLV3 gene itself, and in this way WUS acts to limit its own expression and maintain stem cell homeostasis (Fletcher, J. C., *Plants* 7:87 (2018)).

Loss of function mutations in CLV1, CLV2, or CLV3 result in an expansion of the WUS domain and increased meristem size (Schoof et al., *Cell* 100:635-644 (2000)). Often this increase in meristem size results in aberrant plant growth because the meristem expands uncontrollably and becomes disorganized, a phenomenon called fasciation (Je et al., *Nat Genet* 48: ng.3567 (2016a)). Importantly, a larger meristem does not just make larger organs, but rather an increased number of organs around a larger area. Because of this relationship between meristem size and organ number, mutations in maize CLV-WUS signaling genes can lead to increased flower number and yield. CLV-WUS signaling is transduced downstream via CRN. While strong loss-of-function mutations in the maize CLV2 ortholog FACIATED EAR2 (FEA2) result in enlarged meristems and an increase in KRN, the ear is disordered and as a result there is no yield increase (Taguchi-Shiobara et al., *Gene Dev* 15:2755-2766 (2001)).

Improved strategies for modulating meristem size are needed to improve crop performance.

SUMMARY OF THE INVENTION

One aspect of the invention provides a plant or plant part thereof comprising at least one non-natural mutation in a short extracellular (EC) domain of an endogenous CORYNE (CRN) gene that encodes a CRN protein.

A second aspect of the invention provides a plant cell, comprising an editing system comprising: (a) a CRISPR-Cas effector protein; and (b) a guide nucleic acid (gRNA, gDNA, crRNA, crDNA, sgRNA, sgDNA) comprising a spacer sequence with complementarity to an endogenous target gene encoding an CRN protein.

A third aspect of the invention provides a corn plant cell comprising at least one non-naturally occurring mutation within a CRN gene, wherein the mutation is a substitution, insertion or a deletion that is introduced using an editing system that comprises a nucleic acid binding domain that binds to a target site in the CRN gene.

A fourth aspect of the invention provides a method of producing/breeding a transgene-free edited corn plant, comprising: crossing the corn plant of the invention with a transgene free corn plant, thereby introducing the at least one non-natural mutation into the corn plant that is transgene-free; and selecting a progeny corn plant that comprises the at least one non-natural mutation and is transgene-free, thereby producing a transgene free edited corn plant.

A fifth aspect of the invention provides a method of providing a plurality of corn plants having increased kernel number, the method comprising planting two or more plants of the invention in a growing area, thereby providing a plurality of corn plants having increased kernel number as compared to a plurality of control corn plants not comprising the mutation.

A sixth aspect of the invention provides a method of generating variation in a region of a corn CRN protein, comprising: introducing an editing system into a corn plant cell, wherein the editing system is targeted to a region of a corn CRN gene that encodes the region of the corn CRN protein, wherein the region comprises a sequence having at least 70% sequence identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) to any one of the amino acid sequences of SEQ ID NO:119-121 or the region is encoded by a sequence having at least 70% identity to the nucleotide sequence of SEQ ID NOs: 123-125; and contacting the region of the CRN gene with the editing system, thereby introducing into the plant cell a mutation into the region of the CRN protein; and generating variation in the region of the CRN protein.

A seventh aspect of the invention provides a method for editing a specific site in the genome of a plant cell, the method comprising: cleaving, in a site specific manner, a target site within an endogenous CRN gene in the plant cell, the endogenous CRN gene comprising a sequence having at least 70% sequence identity to the nucleotide sequence of SEQ ID NO:122, or encoding a sequence having at least 70% sequence identity to the amino acid sequence of SEQ ID NO:118, thereby generating an edit in the endogenous CRN gene of the plant cell and producing a plant cell comprising the edit in the endogenous CRN gene.

An eighth aspect provides a method for making a corn plant, comprising: (a) contacting a population of corn plant cells comprising a wild-type endogenous CRN gene with a nuclease linked to a nucleic acid binding domain (e.g., DNA binding domain, e.g., editing system) that binds to a sequence having at least 70% sequence identity to the nucleotide sequence of SEQ ID NO: 122, to a sequence having at least 70% identity to the nucleotide sequence of SEQ ID NOs: 123-125, optionally SEQ ID NO:125, to a sequence encoding an amino acid sequence having at least 70% sequence identity to SEQ ID NO:118; or to a sequence encoding an amino acid sequence having at least 70% sequence identity to any one of the amino acid sequences of SEQ ID NOs: 112-114; (b) selecting a corn plant cell from the population in which at least one wild-type endogenous CRN gene has been mutated; and (c) growing the selected plant cell into a corn plant.

A ninth aspect provides a method for increasing kernel number in a corn plant, comprising (a) contacting a corn plant cell comprising an endogenous CRN gene with a nuclease targeting the endogenous CRN gene, wherein the nuclease is linked to a nucleic acid binding domain (e.g., DNA binding domain, e.g., editing system) that binds to a target site in the endogenous CRN gene, wherein the endogenous CRN gene: (i) encodes a sequence having at least 70% sequence identity to the amino acid sequence of SEQ ID NO:118; (ii) comprises a sequence having at least 70% sequence identity to the nucleotide sequence of SEQ ID NO:122; (iii) comprises a region having a sequence with at least 70% sequence identity to the nucleotide sequence of SEQ ID NOs: 123-125, optionally SEQ ID NO: 125; and/or (iv) comprises a region encoding a sequence having at least 70% sequence identity to any one of the amino acid sequences of SEQ ID NOs: 119-121 to produce a corn plant cell comprising a mutation in the endogenous CRN gene, thereby producing the corn plant comprising at least one cell having a mutation in the endogenous CRN gene; and (b) growing the corn plant cell into a corn plant comprising the mutation in the endogenous CRN gene, thereby producing a corn plant have a mutated endogenous CRN gene and an increased kernel number.

A tenth aspect provides method for producing a corn plant or part thereof comprising at least one cell having a mutated endogenous CRN gene, the method comprising contacting a target site in an endogenous CRN gene in the corn plant or plant part with a nuclease comprising a cleavage domain and a nucleic acid binding domain, wherein the nucleic acid binding domain binds to a target site in the endogenous CRN gene, wherein the endogenous CRN gene (a) encodes a sequence having at least 70% sequence identity to the amino acid sequence of SEQ ID NO: 118; (b) comprises a sequence having at least 70% sequence identity to the nucleotide sequence of SEQ ID NO:122; (c) comprises a region having a sequence with at least 70% sequence identity to the nucleotide sequence of SEQ ID NOs: 123-125, optionally SEQ ID NO: 125; and/or (d) comprises a region encoding a sequence having at least 70% sequence identity to the amino acid sequence of SEQ ID NOs: 119-121, to produce a plant cell comprising a mutation in the endogenous CRN gene, thereby producing the corn plant or part thereof comprising at least one cell having a mutation in the endogenous CRN gene.

An eleventh aspect of the invention provides a method for producing a corn plant or part thereof comprising a mutated endogenous CRN gene and exhibiting increased kernel number, the method comprising contacting a target site in an endogenous CRN gene in the corn plant or plant part with a nuclease comprising a cleavage domain and a nucleic acid binding domain, wherein the nucleic acid binding domain binds to a target site in the endogenous CRN gene, wherein the endogenous CRN gene: (a) encodes a sequence having at least 70% sequence identity to the amino acid sequence of SEQ ID NO: 118; (b) comprises a sequence having at least 70% sequence identity to the nucleotide sequence of SEQ ID NO: 122; (c) comprises a region having a sequence with at least 70% sequence identity to the nucleotide sequence of SEQ ID NOs: 123-125, optionally SEQ ID NO:125; and/or (d) comprises a region encoding a sequence having at least 70% sequence identity to any one of the amino acid sequence of SEQ ID NOs: 119-121, thereby producing the corn plant or part thereof comprising an endogenous CRN gene having a mutation and exhibiting increased kernel number.

A twelfth aspect provides a guide nucleic acid that binds to a target site in a CRN gene, the target site comprising a sequence having at least 70% sequence identity to the nucleotide sequence of SEQ ID NO:122, at least 70% sequence identity to the nucleotide sequence of SEQ ID NO: 123-125, optionally SEQ ID NO:125; encoding a sequence having at least 70% sequence identity to the amino acid sequence of SEQ ID NO:118, or encoding a sequence having at least 70% sequence identity to any one of the amino acid sequences of SEQ ID NO: 119-121.

In a thirteenth aspect, a system is provided comprising a guide nucleic acid of the invention and a CRISPR-Cas effector protein that associates with the guide nucleic acid.

A fourteenth aspect provides a gene editing system comprising a CRISPR-Cas effector protein in association with a guide nucleic acid, wherein the guide nucleic acid comprises a spacer sequence that binds to an endogenous CRN gene.

In a fifteenth aspect, a complex comprising a CRISPR-Cas effector protein comprising a cleavage domain and a guide nucleic acid, wherein the guide nucleic acid binds to a target site in an endogenous CRN gene, wherein the endogenous CRN gene, wherein the endogenous CRN gene: (a) encodes a sequence having at least 70% sequence identity to the amino acid sequence of SEQ ID NO:118; (b) comprises a sequence having at least 70% sequence identity to the nucleotide sequence of SEQ ID NO:122; (c) comprises a region having a sequence with at least 70% sequence identity to the nucleotide sequence of any one of SEQ ID NO: 123-125, optionally SEQ ID NO:125; and/or (d) comprises a region encoding a sequence having at least 70% sequence identity to any one of the amino acid sequences of SEQ ID NOs: 119-121, wherein the cleavage domain cleaves a target strand in the CRN gene.

In sixteenth aspect, an expression cassette is provided, the expression cassette comprising (a) a polynucleotide encoding CRISPR-Cas effector protein comprising a cleavage domain and (b) a guide nucleic acid that binds to a target site in an endogenous CRN gene, wherein the guide nucleic acid comprises a spacer sequence that is complementary to and binds to (i) a portion of a nucleic acid encoding an amino acid sequence having at least 70% sequence identity the amino acid sequence of SEQ ID NO:118; (ii) a portion of a sequence having at least 70% sequence identity to the nucleotide sequence of SEQ ID NO: 122; (iii) a portion of a sequence having at least 70% sequence identity to any one of the nucleotide sequences of SEQ ID NO: 123-125, optionally SEQ ID NO:125; and/or (iv) a portion of sequence having at least 70% sequence identity to a sequence encoding any one of the amino acid sequences of SEQ ID NO: 119-121.

In an additional aspect, a method of creating a mutation in an endogenous CRN gene in a plant provided, comprising: (a) targeting a gene editing system to a portion of the CRN gene, the portion comprising (i) a sequence having at least 70% sequence identity to any one of the nucleotide sequences of SEQ ID NOs: 123-125, optionally SEQ ID NO:125; and/or (ii) a sequence having at least 70% sequence identity to a sequence encoding any one of the amino acid sequences of SEQ ID NO:118-121, and (b) selecting a plant that comprises a substitution of an amino acid residue in the EC domain of the CRN gene, optionally an alternative amino acid in amino acid residue at position 477.

A further aspect of the invention provides a nucleic acid encoding a dominant negative mutation, a semi-dominant mutation, a hypomorphic mutation, or a weak loss-of-function mutation of a corn CRN protein.

In an additional aspect, a corn plant or part thereof is provided comprising a nucleic acid of the invention. In a further aspect, a corn plant or part thereof is provided that exhibits increased kernel number. In some aspects a corn plant is provided that also exhibits increased yield, and improved disease resistance as well as exhibits larger meristems and root meristems that are maintained. Further provided are plants comprising in their genome one or more mutated CORYNE (CRN) genes produced by the methods of the invention as well as polypeptides, polynucleotides, nucleic acid constructs, expression cassettes and vectors for making a plant of this invention.

These and other aspects of the invention are set forth in more detail in the description of the invention below.

BRIEF DESCRIPTION OF THE SEQUENCES

SEQ ID NOs: 1-17 are exemplary Cas12a amino acid sequences useful with this invention.

SEQ ID NOs: 18-20 are exemplary Cas12a nucleotide sequences useful with this invention.

SEQ ID NO:21-22 are exemplary regulatory sequences encoding a promoter and intron.

SEQ ID NOs: 23-29 are exemplary cytosine deaminase sequences useful with this invention.

SEQ ID NOs: 30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs: 42-44 provides an example of a protospacer adjacent motif position for a Type V CRISPR-Cas12a nuclease.

SEQ ID NOs: 45-47 provide example peptide tags and affinity polypeptides useful with this invention.

SEQ ID NOs: 48-58 provide example RNA recruiting motifs and corresponding affinity polypeptides useful with this invention.

SEQ ID NOs: 59-60 are exemplary Cas9 polypeptide sequences useful with this invention.

SEQ ID NOs: 61-71 are exemplary Cas9 polynucleotide sequences useful with this invention.

SEQ ID NOs: 72-118 are example CRN polypeptide sequences.

SEQ ID NO:119 is an example EC domain amino acid sequence from a maize CRN polypeptide.

SEQ ID NO:120 and SEQ ID NO:121 are example target regions of a CRN polypeptide.

SEQ ID NO:122 is an example CRN genomic sequence.

SEQ ID NOs: 123-125 are example target regions in the CRN genomic sequence.

SEQ ID NOs: 126-130 are example spacer sequences for nucleic acid guides useful with this invention.

SEQ ID NOs: 131-178 are the sequences shown in FIG. 1 from top to bottom.

SEQ ID NO:179 is a portion of the wildtype CRN sequence as shown in FIG. 2, top line.

SEQ ID NOs: 180-191 show example edits of a CRN nucleotide sequence as shown in FIG. 2, second line to bottom line.

BRIEF DESCRIPTION OF THE DRAWINGS

Figure 1:
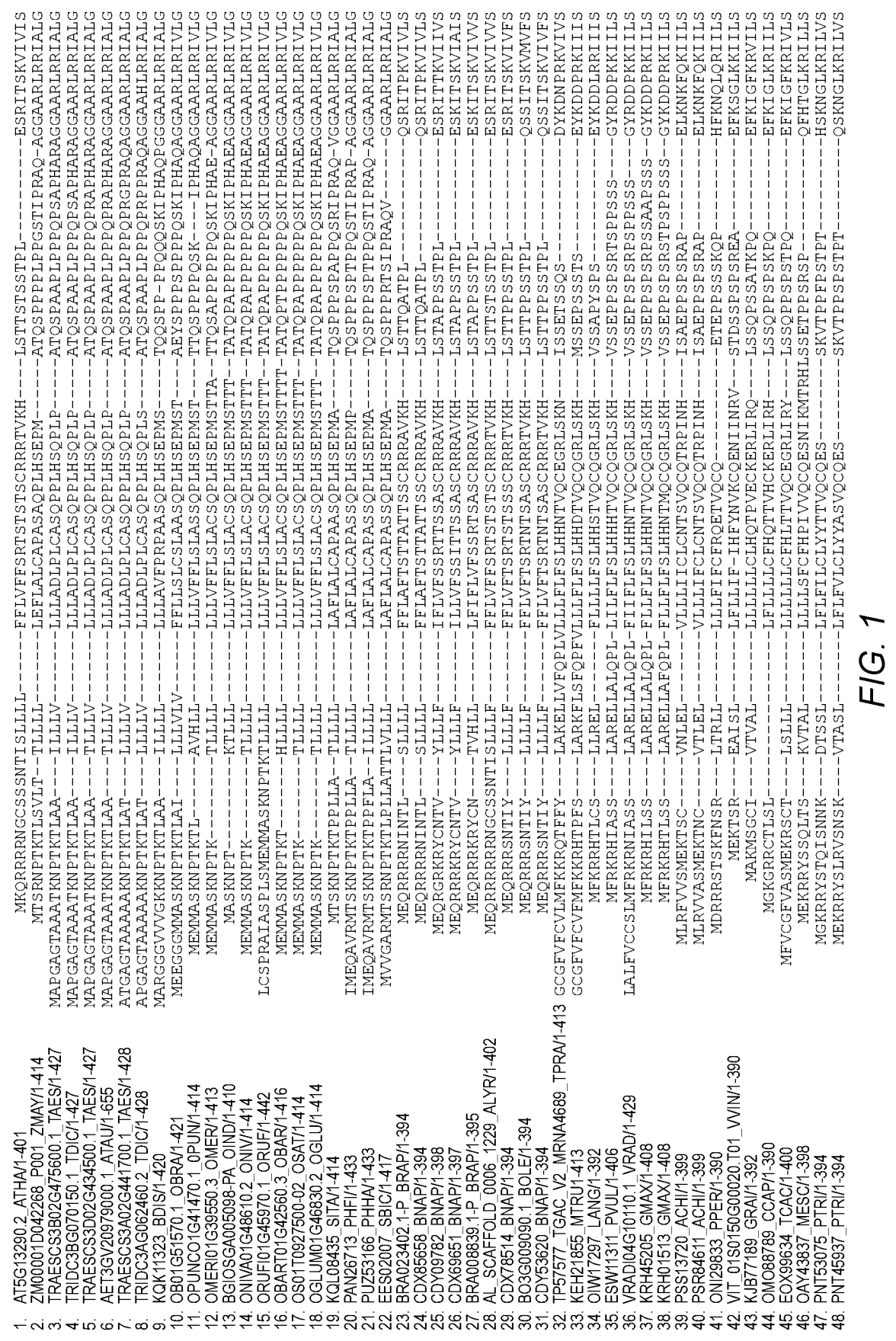

FIG. 1 provides an alignment of various CRN polypeptides showing the EC domain (from top to bottom: SEQ ID NOs: 131-178).

DETAILED DESCRIPTION

Figure 2:
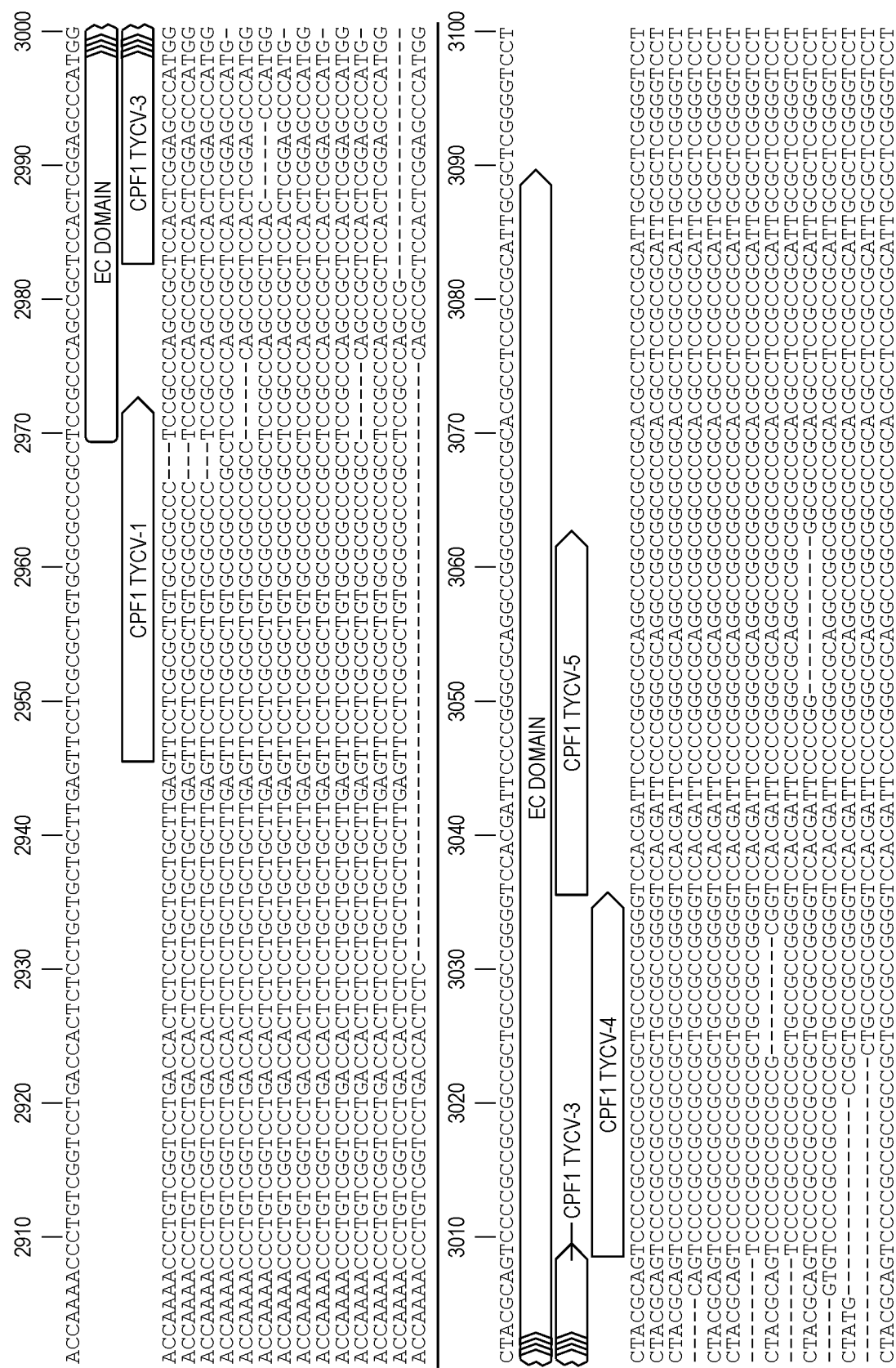
FIG. 2 provides an alignment of mutated sequences with the wild type CRN sequence (from top to bottom: SEQ ID NO:179-191).

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even±0.1% of the specified value as well as the specified value. For example, "about X" where X is the measurable value, is meant to include X as well as variations of ±10%, ±5%, ±1%, ±0.5%, or even±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500% or more as compared to a control. For example, a plant comprising a mutation in a CRN gene as described herein can exhibit increased kernel row number (e.g., producing ears having increased kernel row number) that is at least about 5% or greater than that of a control plant not comprising the same mutation, optionally wherein the length of the ears comprising increased kernel row number is not substantially decreased (e.g., a decrease in length of less than 30% as compared to an ear of a plant not comprising the same FEA2 mutation). A control plant is typically the same plant as the edited plant but the control plant has not been similarly edited and therefore does not comprise the mutation. A control plant may be an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients and the like).

A "control" plant may be an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients and the like).

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence. A "heterologous" nucleotide/polypeptide may originate from a foreign species, or, if from the same species, is substantially modified from its native form in composition and/or genomic locus by deliberate human intervention.

A "native" or "wild type" nucleic acid, nucleotide sequence, polypeptide or amino acid sequence refers to a naturally occurring or endogenous nucleic acid, nucleotide sequence, polypeptide or amino acid sequence. In some contexts, a "wild type" nucleic acid is a nucleic acid that is not edited as described herein and can differ from an "endogenous" gene that may be edited as described herein (e.g., a mutated endogenous gene). In some contexts, a "wild type" nucleic acid (e.g., unedited) may be heterologous to the organism in which the wild type nucleic acid is found (e.g., a transgenic organism). As an example, a "wild type endogenous CORYNE (CRN) gene" is an CRN gene that is naturally occurring in or endogenous to the reference organism, e.g., a plant, e.g., a maize plant, and may be subject to modification as described herein, after which, such a modified endogenous gene is no longer wild type.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is nonfunctional.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in Techniques et Utilisations des Marqueurs Moleculaires Les Colloques, Vol. 72, pp. 45-56 (1995); and Openshaw et al., *Marker-assisted Selection in Backcross Breeding*, in Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterologous" refers to a nucleotide/polypeptide that originates from a foreign species, or, if from the same species, is substantially modified from its native form in composition and/or genomic locus by deliberate human intervention.

A plant in which at least one orthologous IPA1 gene encoding an SPL transcription factor is modified as described herein (e.g., comprises a modification as described herein) may have improved yield traits as compared to a plant that does not comprise the modification in the at least one orthologous IPA1 gene. As used herein, "improved yield traits" refers to any plant trait associated with growth, for example, biomass, yield, nitrogen use efficiency (NUE), inflorescence size/weight, fruit yield, fruit quality, fruit size, seed size, seed number, foliar tissue weight, nodulation number, nodulation mass, nodulation activity, number of seed heads, number of tillers, number of branches, number of flowers, number of tubers, tuber mass, bulb mass, number of seeds, total seed mass, rate of leaf emergence, rate of tiller/branch emergence, rate of seedling emergence, length of roots, number of roots, size and/or weight of root mass, or any combination thereof. Thus, in some aspects, "improved yield traits" may include, but is not limited to, increased inflorescence production, increased fruit production (e.g., increased number, weight and/or size of fruit; e.g., increase number, weight, and/or size of ears for, e.g., maize), increased fruit quality, increased number, size and/or weight of roots, increased meristem size, increased seed size, increased biomass, increased leaf size, increased nitrogen use efficiency, increased height, increased internode number and/or increased internode length as compared to a control plant or part thereof (e.g., a plant that does not comprise a mutated endogenous IPA1 nucleic acid (e.g., a mutated IPA1 gene)). Improved yield traits can also result from increased planting density of plants of the invention. Thus, in some aspects, a plant of the invention is capable of being planted at an increased density (as a consequence of altered plant architecture resulting from the endogenous mutation), which results in improved yield traits as compared to a control plant that is planted at the same density. In some aspects, improved yield traits can be expressed as quantity of grain produced per area of land (e.g., bushels per acre of land).

As used herein a "control plant" means a plant that does not contain an edited IPA1 gene or genes as described herein that imparts an enhanced/improved trait (e.g., yield trait) or altered phenotype. A control plant is used to identify and select a plant edited as described herein and that has an enhanced trait or altered phenotype as compared to the control plant. A suitable control plant can be a plant of the parental line used to generate a plant comprising a mutated IPA1 gene(s), for example, a wild type plant devoid of an edit in an endogenous IPA1 gene as described herein. A suitable control plant can also be a plant that contains recombinant nucleic acids that impart other traits, for example, a transgenic plant having enhanced herbicide tolerance. A suitable control plant can in some cases be a progeny of a heterozygous or hemizygous transgenic plant line that is devoid of the mutated IPA1 gene as described herein, known as a negative segregant, or a negative isogenic line.

An enhanced trait may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and increased water use efficiency as compared to a control plant. An altered phenotype may be, for example, plant height, biomass, canopy area, anthocyanin content, chlorophyll content, water applied, water content, and water use efficiency.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. However, any technique can be used to measure the amount of, the comparative level of, or the difference in any selected chemical compound or macromolecule in the transgenic plants.

As used herein an "enhanced trait" means a characteristic of a plant resulting from mutations in an IPA1 gene(s) as described herein. Such traits include, but are not limited to, an enhanced agronomic trait characterized by enhanced plant morphology, physiology, growth and development, yield, nutritional enhancement, disease or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a mutation in an endogenous IPA1 gene encoding an SPL transcription factor as described herein relative to a plant not comprising the mutation, such as a wild-type plant, or a negative segregant. In some cases, the trait modification can be evaluated quantitatively. For example, the trait modification can entail an increase or decrease in an observed trait characteristics or phenotype as compared to a control plant. It is known that there can be natural variations in a modified trait. Therefore, the trait modification observed entails a change of the normal distribution and magnitude of the trait characteristics or phenotype in the plants as compared to a control plant.

The present disclosure relates to a plant with improved economically important characteristics, more specifically increased yield. More specifically the present disclosure relates to a plant comprising a mutation(s) in an IPA1 gene(s) as described herein, wherein the plant has increased yield as compared to a control plant devoid of said mutation(s). In some embodiments, plants produced as described herein exhibit increased yield or improved yield trait components as compared to a control plant. In some embodiments, a plant of the present disclosure exhibits an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination.

"Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers ("florets") per panicle/plant; increased seed fill rate; an increased number of filled seeds; increased seed size (length, width, area, perimeter), which can also influence the composition of seeds; and/or increased seed volume, which can also influence the composition of seeds. In one embodiment, increased yield can be increased seed yield, for example, increased seed weight; increased number of filled seeds; and increased harvest index.

Increased yield can also result in modified architecture, or can occur because of modified plant architecture.

Increased yield can also manifest as increased harvest index, which is expressed as a ratio of the yield of harvestable parts, such as seeds, over the total biomass The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 20, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, or 900 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a "portion" of a wild type CRISPR-Cas repeat sequence (e.g., a wild Type CRISR-Cas repeat, e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a fragment or a portion of a CRN nucleic acid may comprise, consist essentially of or consist of about 10, 20, 30, 40, 50, 60, 70, 80, 90, 100, 120, 130, 140, 150, 160, 170, 180, 190, 200, 220, 240, 260, 280, 300, 320, 340, 360, 380, 400, 420, 440, 460, 480, 500, 520, 540, 550, 560, 565, 570, 575, 580, 585, 590, 595, 600, 605, 610, 615, 620, 625, 630, 635, 640, 645, 650, 655, 660, 665, 670, 680, 690, 700, 720, 740, 760, 780, 800, 820, 840, 860, 880, 900, 920, 940, 960, 980, 1000, 1020, 1040, 1060, 1080, 1100, 1120, 1140, 1160, 1180, 1100, 1120, 1140, 1160, 1180, 1200, 1220, 1240, 1260, or 1280 consecutive nucleotides or any range or value therein of a nucleic acid encoding a CRN polypeptide, optionally a fragment or a portion of a CRN gene may be about 10, 20, 30, 40, 50, 90, 100 to about 200, 300, 400, 500, 600, 700, 800, 900, 1000, 1100, 1200, or about 1280 consecutive nucleotides in length, about 100 to about 1150 consecutive nucleotides in length, about 400 to about 800 consecutive nucleotides in length, about 500 to about 700 consecutive nucleotides in length, about 550 to about 600 consecutive nucleotides in length, about 300 to about 400 consecutive nucleotides in length, about 200 to about 300 consecutive nucleotides in length, about 100 to about 200 consecutive nucleotides in length, about 100 to about 150 consecutive nucleotides in length, about 50 to about 100 consecutive nucleotides in length, about 10 to about 50 consecutive nucleotides in length, or any range or value therein.

In some embodiments, a "sequence-specific nucleic acid binding domain" (e.g., sequence-specific DNA binding domain, sequence-specific RNA binding domain) may bind to one or more fragments or portions of nucleotide sequences encoding CRN polypeptides as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, 290, or more consecutive amino acids of a reference polypeptide. In some embodiments, a fragment or portion of a CRN polypeptide may comprise, consist essentially of or consist of about 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 195, 196, 197, 198, 199, 200, 201, 202, 203, 204, 205, 206, 207, 208, 209, 210, 211, 212, 213, 214, 215, 216, 217, 218, 219, 220, 221, 22, 223, 224, 225, 226, 227, 228, 229, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, or 420 consecutive amino acid residues, or any range or value therein, (e.g., a fragment or a portion of any one of SEQ ID NOs: 66-111 (e.g., SEQ ID NOs: 112-114)).

As used herein with respect to nucleic acids, the term "functional fragment" refers to nucleic acid that encodes a functional fragment of a polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene. Frameshift mutations in a gene can result in the production of a polypeptide that is longer, shorter or the same length as the wild type polypeptide depending on when the first stop codon occurs following the mutated region of the gene.

In some embodiments, a deletion useful with this invention may result in an in-frame mutation. In some embodiments, such a deletion may be a dominant negative mutation, a semi-dominant mutation, a hypomorphic mutation, a weak loss-of-function mutation or a null allele, which when comprised in a plant can result in the plant exhibiting increased kernel number as compared to a plant not comprising said deletion. In some embodiments, a deletion may be a deletion of 1 base pair to about 160 base pairs (e.g., about 3 base pairs to about 10 base pairs, about 3 base pairs to about 20 base pairs, about 3 base pairs to about 30 base pairs, about 3 base pairs to about 35 base pairs, about 3 base pairs to about 40 base pairs, about 3 base pairs to about 45 base pairs, about 3 base pairs to about 50 base pairs, about 3 base pairs to about 80 base pairs, about 3 base pairs to about 100 base pairs, about 3 base pairs to about 160 base pairs, about 10 base pairs to about 160 base pairs, about 15 base pairs to about 160 base pairs, about 20 base pairs to about 160 base pairs, about 30 base pairs to about 160 base pairs, about 50 base pairs to about 160 base pairs, about 75 base pairs to about 160 base pairs, or about 96 base pairs to about 160 base pairs; e.g., about 1, 2, 3, 4, 5, 6, 7, 8, 9, 10, 11, 12, 13, 14 or 15 base pairs to about 30, 35, 40, 45, 50, 55, 60, 65, 70, 75, 80, 85, 90, 95, 100, 110, 120, 130, 140, 150, or 160 base pairs). An CRN gene may be edited in more than one location, thereby providing a CRN gene comprising more than one mutation. In some embodiments, such a plant may also exhibit larger meristems, maintenance of root meristems and increased yield and increased disease resistance. Additional advantages of the present invention include, but are not limited to regulating growth, regulating meristem size, regulating vascular development, controlling organ number, facilitating increased plant regeneration from tissue culture, increasing fruit size and or controlling plant secondary growth.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide.

As used herein, the phrase "substantially identical," or "substantial identity" in the context of two nucleic acid molecules, nucleotide sequences, or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, about 100, 200, 300, 400 consecutive nucleotides to about 500, 600, 700, 800, 1000, 1100, 1200 consecutive nucleotides or more, or any range therein, up to the full length of the sequence. In some embodiments, nucleotide sequences can be substantially identical over at least about 20 consecutive nucleotides (e.g., about 20, 21, 22, 23, 24, 25, 26, 27, 28, 29, 30, 31, 32, 33, 34, 35, 36, 37, 38, 39, 40, 50, 60, 70, or 80 or more consecutive nucleotides).

In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 300, 350 or more amino acids in length or more consecutive amino acid residues). In some embodiments, two or more CRN polypeptides may be identical or substantially identical (e.g., at least 70% to 99.9% identical, e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% identical or any range or value therein).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron may be referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a nucleic acid binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid, or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g. extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) Proc. Natl. Acad. Sci USA 84:5745-5749), Adh promoter (Walker et al. (1987) *Proc. Natl. Acad. Sci. USA* 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79:87-94), maize (Christensen et al., 1989. *Plant Molec. Biol.* 12:619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231:150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP U.S. Pat. No. 255,378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9 (5): 297-306 (2015)), ZmSTK2_USP from maize (Wang et al. *Genome* 60 (6): 485-495 (2017)), LAT52 and LAT59 from tomato (Twell et al. *Development* 109 (3): 705-713 (1990)), Zm13 (U.S. Pat. No. 10,421,972), $PLA_2$-δ promoter from *Arabidopsis* (U.S. Pat. No. 7,141, 424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37 (8): 1108-1115), corn light harvesting complex promoter (Bansal et al. (1992) Proc. Natl. Acad. Sci. USA 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) Mol. Gen. Genet. 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) Mol. Gen. Genet. 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) Science 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain (e.g., a sequence-specific DNA binding domain), a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one (e.g., one or more) of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific nucleic acid binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific nucleic acid binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g., expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally, included are shuttle vectors by which is meant a DNA vehicle capable, naturally or by design, of replication in two different host organisms, which may be selected from actinomycetes and related species, bacteria and eukaryotic (e.g., higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific nucleic acid binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific nucleic acid binding protein, the reverse transcriptase and/or the deaminase are expressed and the sequence-specific nucleic acid binding protein binds to the target nucleic acid, and the reverse transcriptase and/or deaminase may be fused to either the sequence-specific nucleic acid binding protein or recruited to the sequence-specific nucleic acid binding protein (via, for example, a peptide tag fused to the sequence-specific nucleic acid binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromosomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

The present invention provides methods and compositions for reducing the influence of genes that normally act to restrict meristem size to generate plants with larger meristems, to maintain the root meristem, to increase kernel row number (optionally without substantially decreasing ear length (e.g., without decreasing ear length more than 30% as compared to an ear of a plant not comprising the same CRN mutation)) and/or to improve one or more yield traits, as well as to improve disease resistance.

Figure 4:
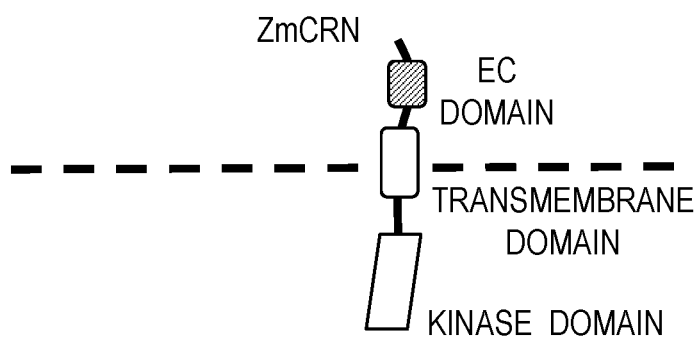
FIG. 4 provides a cartoon exemplifying a maize CRN polypeptide functioning in planta.

The CLV1, CLV2, and CLV3 genes are part of several overlapping signaling pathways that utilize a similar mechanism to regulate meristem size. Plants express many CLV3-like (CLE) peptides which are sensed by many leucine-rich repeat (LRR) domains, and the downstream signaling regulates a myriad of growth processes in the plant (Fletcher, J. C., Plants 7:87 (2018)). The role of CRN in conveying downstream signaling appears to be conserved between Arabidopsis and Maize (Nimchuk et al., Plant Cell 23:851-854 (2011); Guo et al., Plant J. 63:889-900 (2010); Zhu et al., Plant J. 61:223-233 (2009); Müller et al., The Plant Cell Online 20:934-946 (2008); Miwa et al., Plant Cell Physiol. 49:1752-1757 (2008); Je et al., Nat. Genet. 48: ng.3567 (2018)). Both Arabidopsis and Maize CRN are predicted to encode inactive psuedokinases suggesting CRN may act as a protein scaffold for complex formation (Nimchuk et al., Plant Cell 23:851-854 (2011)). Indeed, the current model for CRN function in Arabidopsis hypothesizes that CRN/CLV2 dimerization facilitates transit of both proteins from the endoplasmic reticulum (ER) to the plasma membrane (PM) where CLE-mediated signaling takes place. When CLV2 and CRN are separated as monomers, charged amino acids prevent PM transiting and the proteins are held in the ER. When CRN and CLV2 pair, these charged amino acids are masked and export of both proteins from the ER to PM takes place, a phenomenon called charge masking (Bleckmann et al. Plant Phys. 152:166-176 (2010)). The short extracellular domain (EC) of CRN is required for membrane transiting but is not required for dimerization with CLV2, suggesting the EC domain may perform a charge masking function. See, e.g., FIG. 4.

As is understood in the art, different amino acids can carry a negative, positive, or neutral charge. The combined action of a sequence of amino acids determines the charge of a region of a particular protein. In the present invention, by changing the amino acid composition along the CRN EC domain, the charge of the protein region that is involved in charge masking FEA2 can be changed and in-turn the transiting of the FEA2/CRN protein complex to the membrane can be modified. Without intending to be bound by any particular theory, it is believed that the positive charge in CRN masks the negative charge of FEA2, which is required for transiting. Thus, as an example, deletions of a CRN polypeptide may provide a reduction in positive charge, and thus, less charge masking of FEA2 and greater complex retention in the ER. Increased ER retention in this model would antagonize signaling mediated by the CRN/FEA2 complex resulting in increased meristem size, increased kernel row number and improved yield.

Accordingly, as described herein, editing technology is used to target CRN genes in plants to generate plants with larger meristems, having increased kernel number (optionally without substantially reducing ear length, e.g., exhibits a decrease in ear length of no more than 30% as compared to an ear of a plant not comprising the same CRN mutation), increased yield, and improved disease resistance as well as to generate plants that maintain their root meristem. Mutations that may be useful for production of plants exhibiting increased kernel number include, for example, substitutions, deletions and insertions. In some aspects, a mutation generated by the editing technology can be a point mutation, an in-frame deletion, a mutation that generates a premature stop codon, a null mutation, a dominant negative mutation, a semi-dominant mutation, hypomorphic mutation, or a weak loss-of-function mutation.

In some embodiments, the invention provides a plant or plant part thereof, the plant or plant part comprising at least one non-natural mutation (e.g., 1, 2, 3, 4, 5, or more mutations) in an endogenous CORYNE (CRN) gene that encodes a CRN protein. In some embodiments, the at least one non-natural mutation results in a null mutation, a dominant negative mutation, a semi-dominant mutation, a hypomorphic mutation, and/or a weak loss-of-function mutation.

In some embodiments, a plant cell is provided, the plant cell comprising an editing system comprising: (a) a CRISPR-Cas effector protein; and (b) a guide nucleic acid (gRNA, gDNA, crRNA, crDNA, sgRNA, sgDNA) comprising a spacer sequence with complementarity to an endogenous target gene encoding a CRN protein. The editing system may be used to generate a mutation in the endogenous target gene encoding a CRN protein. In some embodiments, the mutation is a non-natural mutation. In some embodiments, a guide nucleic acid of an editing system may comprise the nucleotide sequence (a spacer sequence; guide) of any one of SEQ ID NOs: 126-130.

The mutation in a CRN gene of the plant, plant part thereof or the plant cell may be any type of mutation, including a base substitution, a base deletion and/or a base insertion. In some embodiments, a non-natural mutation may comprise a base substitution to an A, a T, a G, or a C. In some embodiments, the at least one non-natural mutation may be a base substitution from a C to a T (C>T), a G to an A (G>A), an A to a G (A>G) or a T to a C (T>C). In some embodiments, a non-natural mutation may be a deletion of at least one base pair (e.g., 1 base pair to about 200 base pairs) or an insertion of at least one base pair (e.g., 1 base pair to about 50 base pairs). In some embodiments, a deletion may comprise 1 base pair to about 10 consecutive base pairs (e.g., 1, 2 bp to about 3, 4, 5, 6, 7, 8, 9, or 10 bp; e.g., 1, 2, 3, 4, 5, 6, 7, 8, 9, 10 consecutive base pairs), 1 base pair to about 20 consecutive base pairs (e.g., 1, 2, 3, 4, 56, 7, 8, 9, 101, 12, 13, 14, 15, 16, 17, 18, 19, or 20 consecutive base pairs; e.g., 1, 2 3, 4, 5, 6 bp to about 7, 8, 9, 10, 11, 12, 13, 14, 15, 16, 17, 18, 19, or 20 consecutive base pairs), 1 base pair to about 30 consecutive base pairs, 1 base pair to about 40 consecutive base pairs, 1 base pair to about 50 consecutive base pairs (e.g., 1, 2, 4, 5, 6, 7, 8, 9, 10, 11, 12, 13, 14, 15, 16, 17, 18, 19, 20, 21, 22, 23, 24, 25 consecutive base pairs to about 26, 27, 28, 29, 30, 31, 32, 33, 34, 35, 36, 37, 38, 39, 40, 41, 42, 43, 44, 45, 46, 47, 48, 49, 50 consecutive base pairs), or about 30, 31, 32, 33, 34, 35, 36, 37, 38, 39, 40, 41, 42, 43, 44, 45, 46, 47, 48, 49, 50 consecutive base pairs to about 60, 70, 80, 90, 100, 110, 120, 130, 131, 132, 133, 134, 135, 136, 137, 138, 139, 140, 145, 150, 155, or 160 consecutive base pairs or any value or range therein of a CRN gene. In some embodiments, a deletion may be a deletion that includes the entire EC region in a CRN gene (e.g., SEQ ID NO: 119 in maize). In some embodiments, a deletion is an in-frame deletion. In some embodiments, a deletion provides a premature stop codon and a truncated CRN gene and/or protein.

In some embodiments, a non-natural mutation useful with this invention may results in at least one (e.g., one or more) amino acid substitution in the EC region of a CRN gene. In some embodiments, a non-natural mutation resulting in one or more substituted amino acid residues in a CRN gene may be located: (a) at position 23 to position 66 with reference amino acid position numbering of SEQ ID NO:118, (b) at position 29 to position 75 with reference amino acid position numbering of SEQ ID NOs: 72-77; (c) at position 29 to position 74 with reference amino acid position numbering of SEQ ID NO:78; (d) at position 29 to position 76 with reference amino acid position numbering of SEQ ID NO:79; (e) at position 22 to position 65 with reference amino acid position numbering of SEQ ID NO:80; (f) at position 22 to position 68 with reference amino acid position numbering of SEQ ID NO:81; (g) at position 16 to position 65 with reference amino acid position numbering of SEQ ID NO:82; (h) at position 20 to position 69 with reference amino acid position numbering of SEQ ID NOs: 83, 86, or 87; (i) at position 48 to position 97 with reference amino acid position numbering of SEQ ID NO:84; (j) at position 21 to position 71 with reference amino acid position numbering of SEQ ID NO: 85; (k) at position 41 to position 86 with reference amino acid position numbering of SEQ ID NO: 88 or SEQ ID NO:89; (l) at position 31 to position 71 with reference amino acid position numbering of SEQ ID NO:90; (m) at position 21 to position 56 with reference amino acid position numbering of SEQ ID NO:91; (n) at position 22 to position 56 with reference amino acid position numbering of SEQ ID NO:92; (o) at position 22 to position 59 with reference amino acid position numbering of SEQ ID NO:93 or SEQ ID NO:94; (p) at position 20 to position 57 with reference amino acid position numbering of SEQ ID NOs: 95, 98, 99 or 100; (q) at position 25 to position 62 with reference amino acid position numbering of SEQ ID NO: 96; (r) at position 26 to position 63 with reference amino acid position numbering of SEQ ID NO: 97; (s) at position 40 to position 75 with reference amino acid position numbering of SEQ ID NO:101; (t) at position 40 to position 76 with reference amino acid position numbering of SEQ ID NO: 102; (u) at position 19 to position 54 with reference amino acid position numbering of SEQ ID NO:103; (v) at position 25 to position 68 with reference amino acid position numbering of SEQ ID NO: 104; (w) at position 47 to position 90 with reference amino acid position numbering of SEQ ID NO:105; (x) at position 25 to position 70 with reference amino acid position numbering of SEQ ID NO:106 or SEQ ID NO:107; (y) at position 22 to position 60 with reference amino acid position numbering of SEQ ID NO: 108 or SEQ ID NO: 109; (z) at position 23 to position 53 with reference amino acid position numbering of SEQ ID NO: 110; (aa) at position 15 to position 53 with reference amino acid position numbering of SEQ ID NO:111 or SEQ ID NO:113; (bb) at position 17 to position 55 with reference amino acid position numbering of SEQ ID NO: 112; (cc) at position 25 to position 63 with reference amino acid position numbering of SEQ ID NO:114; (dd) at position 21 to position 61 with reference amino acid position numbering of SEQ ID NO: 115; or (ee) at position 23 to position 57 with reference amino acid position numbering of SEQ ID NO:116 or SEQ ID NO:117. In some embodiments, the mutation results in one or more substituted amino acid residues located at position 23 to position 66 with reference amino acid position numbering of SEQ ID NO:118

An endogenous CRN gene useful with this invention may (a) encode a sequence having at least 95% sequence identity to any one of the amino acid sequences of SEQ ID NO: 72-118, optionally SEQ ID NO:118; (b) comprise a region having a sequence with at least 90% sequence identity to the nucleotide sequence of SEQ ID NO:122-125; and/or (c) encode a sequence having at least 90% sequence identity to any one of the amino acid sequences of SEQ ID NOs: 119-121. In some embodiments, a mutated CRN gene comprises at least about 90% sequence identity to any one of the nucleic acid sequences of SEQ ID NOs: 180-191.

In some embodiments, a plant comprising at least one mutation (e.g., one or more mutations) in an endogenous CRN gene exhibits increased maintenance of meristems and/or increased kernel number as compared to a plant without the at least one non-natural mutation. In some embodiments, the plant comprising at least one mutation in an endogenous CRN gene is a corn plant which exhibits increased kernel number. In some embodiments, the plant comprising at least one mutation in an endogenous CRN gene is a corn plant which exhibits increased yield and/or increased disease resistance. In some embodiments, a plant (e.g., a corn plant) may be regenerated from a plant part and/or plant cell of the invention, wherein the regenerated plant (e.g., regenerated corn plant) comprises the mutation in the endogenous (RN gene and a phenotype of increased kernel number as compared to a plant (e.g., a corn plant) not comprising the mutation.

In some embodiments, a corn plant cell is provided, the corn plant cell comprising at least one non-natural mutation within a CRN gene, wherein the mutation is a substitution, insertion or a deletion that is introduced using an editing system that comprises a nucleic acid binding domain that binds to a target site in the CRN gene. In some embodiments, the substitution, insertion or a deletion results in a null allele, a dominant negative allele, a semi-dominant allele, hypomorphic mutation, or a weak loss-of-function allele. In some embodiments, a deletion results in an in-frame deletion allele. In some embodiments, the target site is within a region of the CRN gene, the region comprising a sequence having at least 90% sequence identity (e.g., about 90, 91, 92, 93, 94, 95, 96, 97, 98, 99, 99.5, 99.6, 99.7, 99.8, 99.9, or 100% sequence identity) to the nucleotide sequence of any one of SEQ ID NOs: 123-125 and/or encoding a sequence having at least 95% sequence identity (e.g., about 95, 96, 97, 98, 99, 99.5, 99.5, 99.6, 99.7, 99.8, 99.9, or 100% sequence identity) to any one of the amino acid sequences of SEQ ID NO: 119-121.

In some embodiments, a method of producing/breeding a transgene-free edited corn plant is provided, the method comprising: crossing a corn plant of the present invention (e.g., a corn plant comprising a mutation in a CRN gene and having increased kernel number) with a transgene free corn plant, thereby introducing the at least one non-natural mutation (e.g., one or more non-natural mutations) into the corn plant that is transgene-free; and selecting a progeny corn plant that comprises the at least one non-natural mutation and is transgene-free, thereby producing a transgene free edited corn plant.

Also provided herein is a method of providing a plurality of corn plants having increased kernel number, the method comprising planting two or more corn plants of the invention (e.g., 2, 3, 4, 5, 6, 7, 8, 9, 10 or more corn plants comprising a mutation in a CRN polypeptide and having increased kernel number) in a growing area (e.g., a field (e.g., a cultivated field, an agricultural field), a growth chamber, a greenhouse, a recreational area, a lawn, and/or a roadside and the like), thereby providing a plurality of corn plants having increased kernel number as compared to a plurality of control corn plants not comprising the mutation. In some embodiments, the plurality of plants may also exhibit larger meristems, increased yield, increased disease resistance and maintenance of their root meristems. The invention further provides a method of generating variation in a region of a CRN protein, comprising: introducing an editing system into a corn plant cell, wherein the editing system is targeted to a region of a CRN gene that encodes the region of the CRN protein, wherein the region comprises a sequence having at least 70% sequence identity to any one of the amino acid sequences of SEQ ID NO: 119-121 or the region is encoded by a sequence having at least 70% identity to the nucleotide sequence of SEQ ID NOs: 123-125; and contacting the region of the CRN gene with the editing system, thereby introducing into the plant cell a mutation into the region of the CRN protein; and generating variation in the region of the CRN protein.

Figure 3:
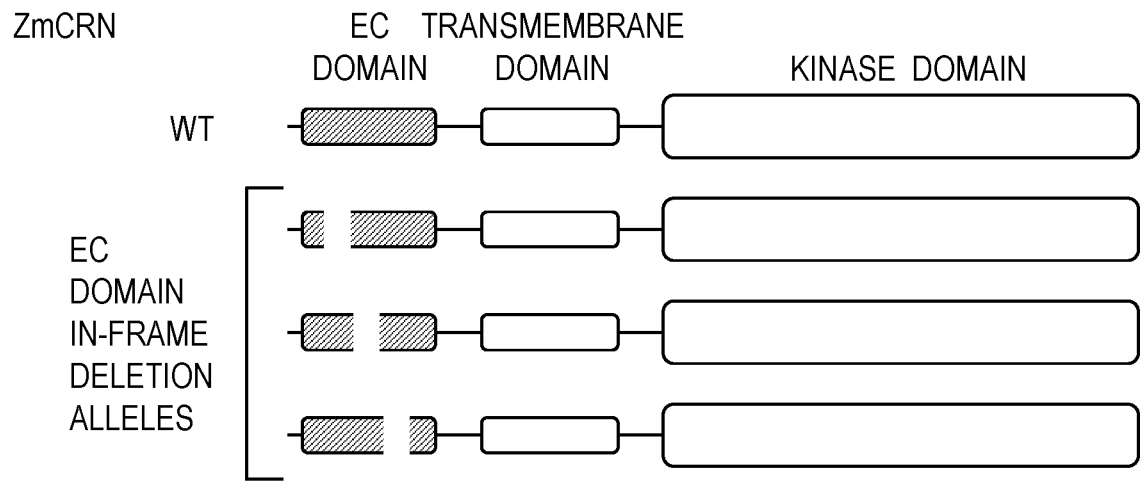
FIG. 3 provides a cartoon exemplifying a structure of wild type (WT) maize CRN protein and edited maize CRN proteins showing in-frame deletions.

In some embodiments, a method for editing a specific site in the genome of a corn plant cell, the method comprising: cleaving, in a site specific manner, a target site within an endogenous CRN gene in the plant cell, the endogenous CRN gene comprising a sequence having at least 70% sequence identity to the nucleotide sequence of SEQ ID NO:122, or encoding a sequence having at least 70% sequence identity to the amino acid sequence of SEQ ID NO: 118, thereby generating an edit in the endogenous CRN gene of the plant cell and producing a plant cell comprising the edit in the endogenous CRN gene. The endogenous CRN gene encodes a CRN protein and the edit results in variation of amino acids in the coding region of the CRN protein. In some embodiments, the edit results in a non-naturally occurring mutation, including but not limited to a deletion, substitution, or insertion, wherein the edit may result in a null mutation, a dominant negative mutation, a semi-dominant mutation, a hypomorphic mutation, or a weak loss-of-function mutation. In some embodiments, the non-naturally occurring mutation is a deletion, optionally wherein the deletion is in the EC domain of a CRN gene (See, FIG. 3—representation of various deletions within the EC domain). In some embodiments, the entire EC domain of the CRN gene may be deleted. In some embodiments, the deletion may result in an edited CRN nucleic acid having at least 90% sequence identity to any one of SEQ ID NOs: 180-191. In some embodiments, a deletion results in an in-frame deletion. In some embodiments, a deletion results in the generation of a premature stop codon. In some embodiments, a non-natural mutation produces variability in a region (e.g., EC domain) of a CRN polypeptide (e.g., amino acid residues located at position 23 to position 66 with reference amino acid position numbering of SEQ ID NO:118 and/or in the EC region of any one of the amino acid sequences of SEQ ID NOs: 72-117 as described herein). In some embodiments, a method of editing may further comprise regenerating a corn plant from the corn plant cell comprising the edit in the endogenous CRN gene, thereby producing a corn plant comprising the edit in its endogenous CRN gene and having a phenotype of increased kernel number when compared to a control corn plant (e.g., an isogenic corn plant) that does not comprise the edit.

In some embodiments, a method for making a corn plant, comprising: (a) contacting a population of corn plant cells comprising a wild-type endogenous CRN gene with a nuclease linked to a nucleic acid binding domain (e.g., DNA binding domain; e.g., editing system) that binds to a sequence having at least 70% sequence identity to the nucleotide sequence of SEQ ID NO: 122, to a sequence having at least 70% identity to the nucleotide sequence of any one of SEQ ID NOs: 123-125, to a sequence encoding an amino acid sequence having at least 70% sequence identity to SEQ ID NO:118; or to a sequence encoding an amino acid sequence having at least 70% sequence identity to any one of SEQ ID NOs: 119-121; (b) selecting a corn plant cell from the population in which at least one endogenous CRN gene has been mutated; and (c) growing the selected plant cell into a corn plant.

In some embodiments, a method increasing kernel number in a corn plant, comprising (a) contacting a corn plant cell comprising an endogenous CRN gene with a nuclease targeting the endogenous CRN gene, wherein the nuclease is linked to a nucleic acid binding domain (e.g., editing system) that binds to a target site in the endogenous CRN gene, wherein the endogenous CRN gene: (i) encodes a sequence having at least 70% sequence identity to the amino acid sequence of SEQ ID NO:118; (ii) comprises a sequence having at least 70% sequence identity to the nucleotide sequence of SEQ ID NO:122; (iii) comprises a region having a sequence with at least 70% sequence identity to the nucleotide sequence of any one of SEQ ID NOs: 123-125; and/or (iv) comprises a region encoding a sequence having at least 70% sequence identity to the amino acid sequence of SEQ ID NOs: 119-121 to produce a corn plant cell comprising a mutation in the endogenous CRN gene, thereby producing the corn plant comprising at least one cell (e.g., one or more cells) having a mutation in the endogenous CRN gene; and (b) growing the corn plant cell into a corn plant comprising the mutation in the endogenous CRN gene, thereby producing a corn plant have a mutated endogenous CRN gene and an increased kernel number.

In some embodiments, a method for producing a corn plant or part thereof comprising at least one cell (e.g., one or more cells) having a mutated endogenous CRN gene, the method comprising contacting a target site in an endogenous CRN gene in the corn plant or plant part with a nuclease comprising a cleavage domain and a nucleic acid binding domain, wherein the nucleic acid binding domain binds to a target site in the endogenous CRN gene, wherein the endogenous CRN gene (a) encodes a sequence having at least 70% sequence identity to the amino acid sequence of SEQ ID NO:118; (b) comprises a sequence having at least 70% sequence identity to the nucleotide sequence of SEQ ID NO:122; (c) comprises a region having a sequence with at least 70% sequence identity to the nucleotide sequence of any one of SEQ ID NOs: 123-125; and/or (d) comprises a region encoding a sequence having at least 70% sequence identity to the amino acid sequence of SEQ ID NOs: 119-121, to produce a plant cell comprising a mutation in the endogenous CRN gene, thereby producing the corn plant or part thereof comprising at least one cell having a mutation in the endogenous CRN gene.

Also provided herein is a method for producing a corn plant or part thereof comprising a mutated endogenous CRN gene and exhibiting increased kernel number, the method comprising contacting a target site in an endogenous CRN gene in the corn plant or plant part with a nuclease comprising a cleavage domain and a nucleic acid binding domain, wherein the nucleic acid binding domain binds to a target site in the endogenous CRN gene, wherein the endogenous CRN gene: (a) encodes a sequence having at least 70% sequence identity to the amino acid sequence of SEQ ID NO:118; (b) comprises a sequence having at least 70% sequence identity to the nucleotide sequence of SEQ ID NO: 122; (c) comprises a region having a sequence with at least 70% sequence identity to the nucleotide sequence of any one of SEQ ID NOs: 123-125; and/or (d) comprises a region encoding a sequence having at least 70% sequence identity to the amino acid sequence of SEQ ID NOs: 119-121, thereby producing the corn plant or part thereof comprising an endogenous CRN gene having a mutation and exhibiting increased kernel number.

In some embodiments, a corn plant or part thereof comprising at least one cell (e.g., one or more cells) having a mutation in the endogenous CRN gene as described herein, comprises a sequence having at least 90% identity to any one of the sequences of SEQ ID NOs: 180-191.

In some embodiments, a nuclease may cleave an endogenous CRN gene, thereby introducing the mutation into the endogenous CRN gene. A nuclease useful with the invention may be any nuclease that can be utilized to edit/modify a target nucleic acid. Such nucleases include, but are not limited to a zinc finger nuclease, transcription activator-like effector nucleases (TALEN), endonuclease (e.g., Fok1) and/or a CRISPR-Cas effector protein. Likewise, a nucleic acid binding domain useful with the invention may be any nucleic acid binding domain (e.g., DNA binding domain) that can be utilized to edit/modify a target nucleic acid. Such nucleic acid binding domains include, but are not limited to, a zinc finger, transcription activator-like DNA binding domain (TAL), an argonaute and/or a CRISPR-Cas effector DNA binding domain.

In some embodiments, a method of editing an endogenous CRN gene in a corn plant or plant part is provided, the method comprising contacting a target site in an CRN gene in the corn plant or plant part with a cytosine base editing system comprising a cytosine deaminase and a nucleic acid binding domain that binds to a target site in the CRN gene, the CRN gene (a) encoding a sequence having at least 70% sequence identity to the amino acid sequence of SEQ ID NO: 118; (b) comprising a sequence having at least 70% sequence identity to the nucleotide sequence of SEQ ID NO: 122; (c) comprising a region having a sequence with at least 70% sequence identity to the nucleotide sequence of any one of SEQ ID NOs: 123-125; and/or (d) comprising a region encoding a sequence having at least 70% sequence identity to the amino acid sequence of SEQ ID NOs: 119-121, thereby editing the endogenous CRN gene in the corn plant or part thereof and producing a corn plant or part thereof comprising at least one cell (e.g., one or more cells) having a mutation in the endogenous CRN gene.

In some embodiments, a method of editing an endogenous CRN gene in a corn plant or plant part is provided, the method comprising contacting a target site in an CRN gene in the corn plant or plant part with an adenosine base editing system comprising an adenosine deaminase and a nucleic acid binding domain that binds to a target site in the CRN gene, the CRN gene (a) encoding a sequence having at least 70% sequence identity to the amino acid sequence of SEQ ID NO: 118; (b) comprising a sequence having at least 70% sequence identity to the nucleotide sequence of SEQ ID NO: 122; (c) comprising a region having a sequence with at least 70% sequence identity to the nucleotide sequence of any one of SEQ ID NOs: 123-125; and/or (d) comprising a region encoding a sequence having at least 70% sequence identity to the amino acid sequence of SEQ ID NOs: 119-121, thereby editing the endogenous CRN gene in the corn plant or part thereof and producing a plant or part thereof comprising at least one cell having a mutation in the endogenous CRN gene.

In some embodiments, a mutation in an edited endogenous CRN gene as described herein produces a sequence having at least 90% identity to any one of the sequences of SEQ ID NOs: 180-191.

In some embodiments, a method of detecting a mutant CRN gene (a mutation in an endogenous CRN gene) is provide, the method comprising detecting in the genome of a plant a deletion in a nucleic acid encoding the amino acid sequence of SEQ ID NO:118, wherein the amino acid sequence of SEQ ID NO:118 comprises a mutation in one or more amino acid residue(s) located from position 23 to position 66 with reference amino acid position numbering of SEQ ID NO:118. In some embodiments, the mutation is the result of a nucleotide substitution of C>T, G>A, A>G or T>C.

In some embodiments, the present invention provides a method of detecting a mutation in an endogenous CRN gene, comprising detecting in the genome of a plant a mutated CRN gene. In some embodiments, the mutated CRN gene comprises a sequence having at least 90% sequence identity to the nucleotide sequence of any one of SEQ ID NOs: 180-191.

In some embodiments, the present invention provides a method of producing a plant comprising a mutation in an endogenous CRN gene and at least one polynucleotide of interest (e.g., one or more polynucleotides of interest), the method comprising crossing a plant of the invention comprising at least one mutation in an endogenous CRN gene (a first plant) with a second plant that comprises the at least one polynucleotide of interest to produce progeny plants; and selecting progeny plants comprising at least one mutation in the CRN gene and the at least one polynucleotide of interest, thereby producing the plant comprising a mutation in an endogenous CRN gene and at least one polynucleotide of interest.

The present invention further provides a method of producing a plant comprising a mutation in an endogenous CRN gene and at least one polynucleotide of interest, the method comprising introducing at least one polynucleotide of interest into a plant of the present invention comprising at least one mutation in a CRN gene, thereby producing a plant comprising at least one mutation in a CRN gene and at least one polynucleotide of interest. In some embodiments, the plant is a corn plant.

In some embodiments, the present invention provides a method of producing a plant comprising a mutation in an endogenous CRN gene and at least one polynucleotide of interest, the method comprising introducing at least one polynucleotide of interest into a plant of the invention comprising at least one mutation in an endogenous CRN gene, thereby producing a plant comprising at least one mutation in a CRN gene and at least one polynucleotide of interest. In some embodiments, the plant is a corn plant.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, disease resistance, increased yield, increased nutrient use efficiency or abiotic stress resistance.

A CORYNE (CRN) gene useful with this invention includes any CRN gene in which a mutation as described herein can confer increased kernel number in a plant or part thereof comprising the mutation (e.g., SEQ ID NOs: 72-118). In some embodiments, a CRN polypeptide comprises an amino acid sequence having at least 70% identity (e.g., about 70, 71, 72, 73, 74, 75, 80, 81, 82, 83, 84, 85, 86, 87, 88, 89, 90, 91, 92, 93, 94, 95, 96, 97, 98, 99, 99.5, 100% sequence identity) to SEQ ID NO: 118 or comprising any one of the amino acid sequences of SEQ ID NOs: 119-121 (e.g., the CRN polypeptide comprises an EC domain comprising the amino acid sequence of, for example, SEQ ID NO:119, SEQ ID NO:120, or SEQ ID NO:121) within the CRN polypeptide). In some embodiments, a CRN polypeptide comprises an amino acid sequence having at least 70% identity (e.g., about 70, 71, 72, 73, 74, 75, 80, 81, 82, 83, 84, 85, 86, 87, 88, 89, 90, 91, 92, 93, 94, 95, 96, 97, 98, 99, 99.5, 100% sequence identity) to SEQ ID NO:72-118. In some embodiments, a CNR gene may comprise a sequence having at least about 70% sequence identity (e.g., about 70, 71, 72, 73, 74, 75, 80, 81, 82, 83, 84, 85, 86, 87, 88, 89, 90, 91, 92, 93, 94, 95, 96, 97, 98, 99, 99.5, 100% sequence identity) to the nucleotide sequence of SEQ ID NO:122, or the CRN gene comprises within it a sequence having at least 70% identity to any one of the nucleotide sequences of any one of SEQ ID NOs: 123-125.

In some embodiments, the at least one non-natural mutation (e.g., one or more non-natural mutations) in an endogenous CRN gene in a corn plant may be a substitution, a deletion and/or an insertion. In some embodiments, the at least one non-natural mutation in an endogenous CRN gene in a corn plant may be a substitution, a deletion and/or an insertion that results in a null mutation, a dominant negative mutation, a semi-dominant mutation, hypomorphic mutation, or a weak loss-of-function mutation and a plant having the phenotype of increased kernel number as compared to a control corn plant (e.g., isogenic plant) not comprising the edit/mutation. For example, the mutation may be a substitution, a deletion and/or an insertion of one or more amino acid residues (e.g., 1, 2, 3, 4, 5, 6, 7, 8, 9, 10 or more amino acids of the CRN polypeptide) or the mutation may be a substitution, a deletion and/or an insertion of at least 1 nucleotide to about 160 consecutive nucleotides (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides, or any range or value therein) (e.g., a base substitution, deletion and/or insertion) from the gene encoding the CRN polypeptide. In some embodiments, the non-natural mutation may be a deletion. In some embodiments, the mutation may be a deletion of at least about 18 consecutive base pairs to about 160 consecutive base pairs (e.g., about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 consecutive base pairs to about 60, 70, 80, 90, 100, 110, 120, 130, 131, 132, 133, 134, 135, 136, 137, 138, 139, 140, 145, 150, 155, or 160 consecutive base pairs or any value or range therein of a CRN gene. In some embodiments, a deletion results in an in-frame deletion allele. In some embodiments, the at least one non-natural mutation may be a base substitution to an A, a T, a G, or a C. In some embodiments, the at least one non-natural mutation may be a base substitution to from a C to a T (C>T), a G to an A (G>A), an A to a G (A>G) or a T to a C (T>C). In some embodiments, the non-natural mutation is in the EC region of a CRN.

In some embodiments, a mutation in an endogenous CRN gene may be made following cleavage by an editing system that comprises a nuclease and a nucleic acid binding domain that binds to a target site within a target nucleic acid (e.g., a CRN gene), the target nucleic acid (e.g., CRN gene) (a) encoding a sequence having at least 70% sequence identity to the amino acid sequence of SEQ ID NO:118; (b) comprising a sequence having at least 70% sequence identity to the nucleotide sequence of SEQ ID NO: 122; (c) comprising a region having a sequence with at least 70% sequence identity to the nucleotide sequence of any one of SEQ ID NOs: 123-125; and/or (d) comprising a region encoding a sequence having at least 70% sequence identity to the amino acid sequence of SEQ ID NOs: 119-121. In some embodiments, the nuclease cleaves the endogenous CRN gene, and a mutation is introduced into the endogenous CRN gene. In some embodiments, the cleavage results in a mutation in an endogenous CRN gene comprising a sequence having at least 90% identity to any one of the sequences of SEQ ID NOs: 180-191.

Further provided herein are guide nucleic acids (e.g., gRNA, gDNA, crRNA, crDNA) that bind to a target site in a CRN gene, wherein the endogenous CRN gene comprises: a sequence having at least 70% sequence identity to the nucleotide sequence of SEQ ID NO:122 or any one of the nucleotide sequences of any one of SEQ ID NOs: 123-125; encodes a sequence having at least 70% sequence identity to the amino acid sequence of SEQ ID NO:118, or any one of the amino acid sequences of SEQ ID NO:119-121. In some embodiments, a guide nucleic acid comprises a spacer having the nucleotide sequence of any one of SEQ ID NOs: 126-130.

In some embodiments, a guide nucleic acid is provided that binds to a target nucleic acid in a CORYNE (CRN) gene in a corn plant, the CRN gene having the gene identification number (gene ID) of Zm00001d042268.

With regard to corn (Zea mays), markers of the present invention are described herein with respect to the positions of marker loci in the B73 corn genome, version 4, "B73 RefGen_v4" (assembly aka B73 RefGen_v4, AGPv4) at the MaizeGDB internet resource (maizegdb.org/assembly).

In some embodiments, a system is provided comprising a guide nucleic acid comprising a spacer having the nucleotide sequence of any one of SEQ ID NOs: 126-130 and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

The invention further provides a gene editing system comprising a CRISPR-Cas effector protein in association with a guide nucleic acid and the guide nucleic acid comprises a spacer sequence that binds to a CRN gene, the CRN gene (a) encoding a sequence having at least 70% sequence identity to the amino acid sequence of SEQ ID NO:118; (b) comprising a sequence having at least 70% sequence identity to the nucleotide sequence of SEQ ID NO: 122; (c) comprising a region having a sequence with at least 70% sequence identity to the nucleotide sequence of any one of SEQ ID NOs: 123-125; and/or (d) comprising a region encoding a sequence having at least 70% sequence identity to the amino acid sequence of SEQ ID NOs: 119-121. In some embodiments, a spacer sequence of the guide nucleic acid may comprise the nucleotide sequence of any one of SEQ ID NOs: 126-130. In some embodiments, the gene editing system may further comprise a tracr nucleic acid that associates with the guide nucleic acid and a CRISPR-Cas effector protein, optionally wherein the tracr nucleic acid and the guide nucleic acid are covalently linked. As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site in a gene.

The present invention further provides a complex comprising a CRISPR-Cas effector protein comprising a cleavage domain and a guide nucleic acid, wherein the guide nucleic acid binds to a target site in an endogenous CRN gene, wherein the endogenous CRN gene, wherein the endogenous CRN gene: (a) encodes a sequence having at least 70% sequence identity to the amino acid sequence of SEQ ID NO:118; (b) comprises a sequence having at least 70% sequence identity to the nucleotide sequence of SEQ ID NO: 122; (c) comprises a region having a sequence with at least 70% sequence identity to the nucleotide sequence of any one of SEQ ID NOs: 123-125; and/or (d) comprises a region encoding a sequence having at least 70% sequence identity to the amino acid sequence of SEQ ID NOs: 119-121, wherein the cleavage domain cleaves a target strand in the CRN gene. In some embodiments, the cleavage domain cleaves a target strand in the CRN gene such that it results in a mutation in an endogenous CRN gene, the mutated CRN gene comprising a sequence having at least 90% identity to any one of the sequences of SEQ ID NOs: 180-191.

In some embodiments, expression cassettes are provided that comprise (a) a polynucleotide encoding CRISPR-Cas effector protein comprising a cleavage domain and (b) a guide nucleic acid that binds to a target site in an endogenous CRN gene, wherein the guide nucleic acid comprises a spacer sequence that is complementary to and binds to (i) a portion of a nucleic acid encoding an amino acid sequence having at least 70% sequence identity the amino acid sequence of SEQ ID NO:118; (ii) a portion of a sequence having at least 70% sequence identity to the nucleotide sequence of SEQ ID NO: 122; (iii) a portion of a sequence having at least 70% sequence identity to the nucleotide sequence of any one of SEQ ID NOs: 123-125; and/or (iv) a portion of sequence having at least 70% sequence identity to a sequence encoding the amino acid sequence of SEQ ID NO: 119-121.

Also provided herein are nucleic acids encoding a mutated CRN gene that when present in a corn plant or plant part results in the corn plant comprising a phenotype of increased kernel number as compared to a corn plant or plant part not comprising the CRN mutation. In some embodiments, a mutated CRN gene may comprise a sequence having at least 90% sequence identity to the nucleotide sequence of any one of SEQ ID NOs: 180-191.

Nucleic acid constructs of the invention (e.g., a construct comprising a sequence specific nucleic acid binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids (e.g., endogenous CRN genes) and/or their expression.

Any corn plant comprising an endogenous CRN gene that is capable of conferring increased kernel number when modified as described herein may be modified (e.g., mutated, e.g., base edited, cleaved, nicked, etc.) as described herein (e.g., using the polypeptides, polynucleotides, RNPs, nucleic acid constructs, expression cassettes, and/or vectors of the invention) to increase kernel number in the corn plant.

A plant exhibiting increased kernel number (e.g., a corn plant) may have an increase in kernel number by about 5% to about 100% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% or more or any range or value therein; e.g., about 5% to about 10%, about 5% to about 15%, about 5% to about 20%, about 10% to about 50%, about 10% to about 80%, about 10% to about 90%, about 10% to about 100%, about 20% to about 50%, about 20% to about 80%, about 20% to about 90%, about 20% to about 100%, about 30% to about 50%, about 30% to about 80%, about 30% to about 90%, about 30% to about 100%, about 50% to about 100%, about 75% to about 100% or more, and any range or value therein) as compared to a plant or part thereof that does not comprise the mutated endogenous CRN gene.

In some embodiments, plants exhibiting increased kernel row number as described herein (e.g., a plant that produces ears having increased kernel row number) produce ears that are also not substantially decreased in length. As used herein, an ear of a plant comprising a mutation as described herein that is "not substantially decreased in length" has a length that is reduced by less than 30% (e.g., reduced by 0% or reduced by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30%) as compared to a plant that does not comprise the same CRN mutation.

In some embodiments, a corn plant or plant part thereof is provided comprising at least one non-natural mutation in at least one endogenous CORYNE (CRN) gene having the gene identification number (gene ID) of Zm00001d042268.

The term "plant part," as used herein, includes but is not limited to reproductive tissues (e.g., petals, sepals, stamens, pistils, receptacles, anthers, pollen, flowers, fruits, flower bud, ovules, seeds, and embryos); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

An editing system useful with this invention can be any site-specific (sequence-specific) genome editing system now known or later developed, which system can introduce mutations in target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (e.g., DNA binding domain), a nuclease, and/or other polypeptide, and/or a polynucleotide.

In some embodiments, an editing system can comprise one or more sequence-specific nucleic acid binding domains (e.g., DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing an CRN gene may comprise contacting a target nucleic acid (e.g., a nucleic acid encoding an CRN protein) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid.

In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific nucleic acid binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing an CRN gene may comprise contacting a target nucleic acid (e.g., a nucleic acid encoding a CRN) with a sequence-specific nucleic acid binding fusion protein (e.g., a sequence-specific DNA binding protein (e.g., a CRISPR-Cas effector protein or domain)) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific nucleic acid binding fusion protein to the target nucleic acid and the sequence-specific nucleic acid binding fusion protein is capable of recruiting the deaminase fusion protein to the target nucleic acid via the peptide tag-affinity polypeptide interaction, thereby editing a locus within the target nucleic acid. In some embodiments, the sequence-specific nucleic acid binding fusion protein may be fused to the affinity polypeptide that binds the peptide tag and the deaminase may be fuse to the peptide tag, thereby recruiting the deaminase to the sequence-specific nucleic acid binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific nucleic acid binding fusion proteins, deaminase fusion proteins and guides may be provided as ribonucleoproteins (RNPs).

In some embodiments, methods such as prime editing may be used to generate a mutation in an endogenous CRN gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantageous of the various methods of recruiting proteins for use in the editing to the target site, such methods including both non-covalent and covalent interactions between the proteins and nucleic acids used in the selected process of genome editing.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a sequence-specific nucleic acid binding domain may be a CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Casl, CaslB, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g, Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes*, *S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. Example Cas9 sequences include, but are not limited to, the amino acid sequences of SEQ ID NO: 59 and SEQ ID NO:60 or the nucleotide sequences of SEQ ID NOs: 61-71.

In some embodiments, the CRISPR-Cas effector protein may be a Cas9 polypeptide derived from *Streptococcus pyogenes* and recognizes the PAM sequence motif NGG, NAG, NGA (Mali et al, Science 2013; 339 (6121): 823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al, Science, 2010; 327 (5962): 167-170, and Deveau et al, J Bacteriol 2008; 190 (4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190 (4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from *Leptotrichia shahii*, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease see, e.g., SEQ ID NOs: 1-20). Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, target array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally-occurring cytosine deaminase, including but not limited to a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO:28 or SEQ ID NO: 29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO: 24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO: 25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:30. In some embodiments, a mutated/evolved *E. coli* TadA* comprises the amino acid sequence of SEQ ID NOs: 31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific DNA binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt function; and/or generation of point mutations in genomic DNA to disrupt splice junctions.

The nucleic acid constructs of the invention encoding a base editor comprising a sequence-specific DNA binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Casl, CaslB, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Casl, CaslB, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. Nucleic Acids Res. 35 (Web Server issue): W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g., protospacer) (e.g., consecutive nucleotides of a sequence (a) encoding an amino acid sequence having at least 70% sequence identity to SEQ ID NO: 118; (b) having at least 70% sequence identity to the nucleotide sequence of SEQ ID NO: 122; (c) comprising a region having at least 70% sequence identity to the nucleotide sequence of any one of SEQ ID NOs: 123-125; and/or (d) comprising a region encoding an amino acid sequence having at least 70% sequence identity to any one of SEQ ID NOs: 119-121). In some embodiments, a spacer sequence may include, but is not limited to, the nucleotide sequences of any one of SEQ ID NOs: 126-130. The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
5'-NNNNNNNNNNNNNNNNNNNNNN-3'  RNA Spacer (SEQ ID NO: 42)
   ||||||||||||||||||||
3'AAANNNNNNNNNNNNNNNNNNNNNN-5'  Target strand (SEQ ID NO: 43)
   ||||
5'TTTNNNNNNNNNNNNNNNNNNNNNN-3'  Non-target strand (SEQ ID NO: 44)
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains, CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26 (5): 910-924 (2017)); Gilbreth (*Curr Opin Struc Biol* 22 (4): 413-420 (2013)), U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs: 45-47.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs: 48-58.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-

RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs, e.g., at least 10 to about 25 motifs, e.g., about 10, 11, 12, 13, 14, 15, 16, 17, 18, 19, 20, 21, 22, 23, 24, or 25 motifs), optionally wherein when two or more RNA recruiting motifs are present they may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide Pumilio/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together, e.g., dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The nucleic acid constructs of the invention (e.g., a construct comprising a sequence specific nucleic acid binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

Accordingly, plants or plant cultivars which are to be treated with preference in accordance with the invention include all plants which, through genetic modification, received genetic material, which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the CryIA, CryIAb, CryIAc, CryIIA, CryIIIA, CryIIIB2, Cry9c Cry2Ab, Cry3Bb and CryIF proteins or toxic fragments thereof and also hybrids or combinations thereof, especially the CryIF protein or hybrids derived from a CryIF protein (e.g. hybrid CryIA-CryIF proteins or toxic fragments thereof), the CryIA-type proteins or toxic fragments thereof, preferably the CryIAc protein or hybrids derived from the CryIAc protein (e.g. hybrid CryIAb-CryIAc proteins) or the CryIAb or Bt2 protein or toxic fragments thereof, the Cry2Ae, Cry2Af or Cry2Ag proteins or toxic fragments thereof, the CryIA. 105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci US A. 28; 93 (11): 5389-94, the Cry proteins as described in WO2001/47952, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g. WO2007/024782), a mutated *Arabidopsis* ALS/AHAS gene (e.g. U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480);); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control-herbicide tolerance, deposited as ATCC PTA 11384, described in US-A 2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait-herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS1 1 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control-herbicide tolerance, not deposited, described in US-A 2005-039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession N° PTA-11041) optionally stacked with event EE-GM1/LL27 or event EE-GM2/LL55 (WO2011/063413A2), event DAS-68416-4 (soybean, herbicide tolerance, ATCC Accession N° PTA-10442, WO2011/066360A1), event DAS-68416-4 (soybean, herbicide tolerance, ATCC Accession N° PTA-10442, WO2011/066384A1), event DP-040416-8 (corn, insect control, ATCC Accession N° PTA-11508, WO2011/075593A1), event DP-043A47-3 (corn, insect control, ATCC Accession N° PTA-11509, WO2011/075595A1), event DP-004114-3 (corn, insect control, ATCC Accession N° PTA-11506, WO2011/084621A1), event DP-032316-8 (corn, insect control, ATCC Accession N° PTA-11507, WO2011/084632A1), event MON-88302-9 (oilseed rape, herbicide tolerance, ATCC Accession N° PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession N°. PTA-10296, WO2012/051199A2), event DAS-44406-6 (soybean, stacked herbicide tolerance, ATCC Accession N°. PTA-11336, WO2012/075426A1), event DAS-14536-7 (soybean, stacked herbicide tolerance, ATCC Accession N°. PTA-11335, WO2012/075429A1), event SYN-000H2-5 (soybean, herbicide tolerance, ATCC Accession N°. PTA-11226, WO2012/082548A2), event DP-061061-7 (oilseed rape, herbicide tolerance, no deposit N° available, WO2012071039A1), event DP-073496-4 (oilseed rape, herbicide tolerance, no deposit N° available, US2012131692), event 8264.44.06.1 (soybean, stacked herbicide tolerance, Accession N° PTA-11336, WO2012075426A2), event 8291.45.36.2 (soybean, stacked herbicide tolerance, Accession N°. PTA-11335, WO2012075429A2), event SYHT0H2 (soybean, ATCC Accession N°. PTA-11226, WO2012/082548A2), event MON88701 (cotton, ATCC Accession N° PTA-11754, WO2012/134808A1), event KK179-2 (alfalfa, ATCC Accession N° PTA-11833, WO2013/003558A1), event pDAB8264.42.32.1 (soybean, stacked herbicide tolerance, ATCC Accession N° PTA-11993, WO2013/010094A1), event MZDT09Y (corn, ATCC Accession N° PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1

Gene editing tools are used to create alleles of the CRN gene that reduce signaling and increase kernel row number (KRN) without compromising ear organization (e.g., without substantially reducing ear length). The CRN gene encodes an inactive pseudo-kinase with a short extracellular (EC) domain. See FIG. 1. The EC of CRN is required for plasma membrane transiting but is not required for dimerization with CLV2, suggesting that the EC domain may perform a charge masking function. To alter the charge masking of FEA2, CRN genes are modified to produce CRN polypeptide mutations that may provide a reduction in positive charge, and thus, less charge masking of FEA2 and greater complex retention in the ER.

Example 2. Design of the Editing Constructs for Fea2 Editing

The genomic sequence of the CRN gene was identified in a proprietary maize line. From this reference sequence, spacer sequences (SEQ ID NOs: 126-130) were designed for use in editing constructs. The editing constructs contained a CRISPR-Cas effector and a spacer sequence designed to target the EC domain of the CRN protein encoded by the CRN gene. Spacers were deployed with either a Cas-effector cutting enzyme or a Cas-effector base editing complex.

Example 3. Transformation and Selection of Edited E0 Plants

A vector encoding a selected spacer as well as the chosen CRISPR-Cas effector were introduced into dried excised maize embryos using *Agrobacterium*. Transformed tissue was maintained in vitro with antibiotic selection to regenerate positive transformants. Healthy non-chimeric plants (E0) were selected and plugged in growth trays. Tissue was collected from regenerating plants (E0 generation) for DNA extraction and subsequent molecular screening was employed to identify edits in the CRN gene. FIG. 2 shows some of the edits obtained and their position within the EC domain of the CRN gene. Plants identified to be (1) healthy, non-chimeric and fertile, with (2) low transgene copy and (3) a deletion in the EC domain were advanced to the next generation. E0 plants that satisfied all the above criteria were selfed to produce the E1 generation. Selected Els were selfed to generate the E2 generation. We identified several families with deletions in and around the EC domain.

Example 4. Phenotypic Assessment of Trait Activity

Seeds for E1 and E2 material were sown in flats and later transferred to pots after seedlings were established. All materials were cultivated under standard greenhouse conditions and grown to reproductive maturity. Following standard practices, emerging ears were covered with small paper bags prior to the emergence of silk and tassels were covered during anthesis for the capture of pollen on a plant-by-plant basis. All ears were removed from the plants after dry-down.

After ear harvest and dry-down, kernel row number was manually counted for all ears. Data represent the average of three row counts per ear taken from the mid-section of the ear where row lineages were most defined. In order to prevent double counting of rows, a marker (e.g., paper clip) was inserted in between the rows where the counts initiated and to designate where row counting should cease. Unedited germplasm, and lines transformed with a Gus plasmid were used as wild-type controls for phenotyping. Table 1 shows kernel row number (KRN) for E1 and E2 families derived from selfed E0 and selfed E1 ears, respectively. BCF1 ears are a cross of edited E1 plants with a WT inbred different than the original WT transformation line.

In Table 1, the edit is provided with reference to the CRN gene represented by SEQ ID NO: 122. Thus, the full-length sequence for each edited gene can be determined by locating within SEQ ID NO:122 the named base pair position under column labeled "allele" and delete the number of base pairs (nucleotides) provided (e.g., 964:9D is a 9 base pair deletion starting at position 964 of SEQ ID NO:122).

TABLE 1

CRN gene edits

| Generation | Spacer SEQ ID | Allele (Coordinates with respect to SEQ ID NO. 122) | Allele Description | KRN Average | Sample Size |
|---|---|---|---|---|---|
| WT Control | NA | WT | WT Transformation line | 15.6 | 10 |
| WT Control | NA | WT | WT Inbred used for hybrid cross | 12.6 | 7 |
| E1 | 126 | 964:9D, 960:17D compound het | 3AA in-frame deletion, premature stop compound het | 18 | 1 |
| E1 | 126 | 964:3D, 964:9D compound het | 1AA, 3AA in-frame deletion compound het | 16 | 1 |
| E1 | 126 | 959:27D, 964:9D compound het | 9AA, 3AA in-frame deletion compound het | 16 | 1 |
| E1 | 126 | 959:27D, 964:3D compound het | 9AA, 1AA in-frame deletion compound het | 18 | 1 |
| E1 | 127 | 983:11D het | premature stop het | 17.8 | 9 |
| E1 | 127 | 983:11D homo | premature stop homo | 18.2 | 3 |
| E1 | 127 | 987:6D homo | 2AA in-frame deletion homo | 18 | 2 |
| E1 | 128 | 977:42D homo | 14AA in-frame deletion homo | 17.4 | 12 |
| E1 | 128 | 964:6D homo | 2AA in-frame deletion homo | 16.4 | 5 |
| E1 | 128 | 998:9D het | 3AA in-frame deletion het | 16 | 4 |
| E1 | 128 | 964:6D-964:6D, 1000:6D compound het | 2x 2AA in-frame deletion with >V compound het | 17 | 4 |
| E1 | 128 | 998:9D homo | 3AA in-frame deletion homo | 16 | 2 |
| E1 | 128 | 964:6D,1000:6D homo | 2x 2AA in-frame deletion with >V homo | 17 | 1 |
| E1 | 128 | 964:6D het | 2AA in-frame deletion het | 16 | 1 |
| WT Control | NA | WT | WT Transformation line | 16 | 1 |
| WT Control | NA | WT | WT Inbred used for hybrid cross | 14 | 1 |
| E2 | 126 | 964:9D homo | 3AA in-frame deletion homo | 20 | 1 |
| E2 | 126 | 964:3D homo | 1AA in-frame deletion homo | 16 | 1 |
| E2 | 126 | 960:17D homo | premature stop homo | 18 | 1 |
| E2 | 126 | 959:27D homo | 9AA in-frame deletion homo | 18 | 1 |
| E2 | 127 | 987:6D homo | 2AA in-frame deletion homo | 16 | 1 |

TABLE 1-continued

CRN gene edits

| Generation | Spacer SEQ ID | Allele (Coordinates with respect to SEQ ID NO. 122) | Allele Description | KRN Average | Sample Size |
|---|---|---|---|---|---|
| E2 | 127 | 983:11D homo | premature stop homo | 26 | 1 |
| E2 | 128 | 964:6D, 1000:6D homo | 2x 2AA in-frame deletion with >V homo | 22 | 1 |
| E2 | 128 | 964:6D homo | 2AA in-frame deletion homo | 20 | 1 |
| BCF1 Hybrid | 127 | 983:11D hybrid het | premature stop F1 hybrid het | 18 | 1 |
| BCF1 Hybrid | 128 | 977:42D hybrid het | 14AA in-frame deletion F1 hybrid het | 16 | 1 |

WT = wild-type
Homo = homozygous;
Het = heterozygous (one WT copy, one edited copy);
Compound het = one copy has one edit, the other copy has the other edit The foregoing is illustrative of the present invention and is not to be construed as limiting thereof. The invention is defined by the following claims, with equivalents of the claims to be included therein.

That which is claimed is:

1. A corn plant or plant part thereof comprising at least one non-natural mutation in an endogenous CORYNE (CRN) gene that encodes a wild type CRN protein, wherein the wild type CRN protein comprises a sequence having at least 95% identity to SEQ ID NO:118 and the mutation is an in-frame deletion of one or more codons that results in the deletion of one or more amino acid residues located from position 23 to position 66 with reference to amino acid position numbering of SEQ ID NO:118, or is an out-of-frame deletion that results in a premature stop codon and a truncated CRN protein, wherein the out-of-frame deletion is located in a region of the endogenous CRN gene that encodes position 23 to position 66 with reference to amino acid position numbering of SEQ ID NO:118, wherein the corn plant exhibits increased kernel row number without fasciation compared to a control corn plant devoid of the at least one non-natural mutation.

2. The corn plant or part thereof of claim 1, wherein the at least one non-natural mutation is a base deletion of at least 1 base pair to 132 base pairs.

3. The corn plant or part thereof of claim 1, wherein the at least one non-natural mutation is located in a nucleic acid sequence having at least 95% sequence identity to any one of SEQ ID NOs: 123-125.

4. The corn plant or part thereof of claim 1, wherein the endogenous CRN gene comprises a sequence having at least 95% sequence identity to SEQ ID NO: 122.

5. The corn plant or part thereof of claim 1, wherein the at least one non-natural mutation results in a mutated CRN protein that is encoded by a nucleotide sequence having at least 95% sequence identity to any one of SEQ ID NOs: 180-191.

6. The corn plant or part thereof of claim 1, wherein the mutated CRN gene comprises a sequence having at least 90% sequence identity to the nucleotide sequence of any one of SEQ ID NOs: 180-191.

7. A method for editing a specific site in the genome of a corn plant cell, the method comprising: cleaving, in a site specific manner, a target site within an endogenous CORYNE (CRN) gene in the corn plant cell, wherein the endogenous CRN gene encodes a wild type CRN protein having at least 95% sequence identity to the amino acid sequence of SEQ ID NO:118, thereby generating an edit in the endogenous CRN gene of the corn plant cell and producing a corn plant cell comprising the edit in the endogenous CRN gene, wherein the edit is an in-frame deletion of one or more codons that results in the deletion of one or more amino acid residues located from position 23 to position 66 with reference amino acid position numbering of SEQ ID NO: 118, or is an out-of-frame deletion that results in a premature stop codon and a truncated CRN protein, wherein the out-of-frame deletion is located in a region of the endogenous CRN gene that encodes position 23 to position 66 with reference to amino acid position numbering of SEQ ID NO:118.

8. The method of claim 7, further comprising regenerating a corn plant from the corn plant cell comprising the edit in the endogenous CRN gene to produce a corn plant comprising the edit in its endogenous CRN gene, wherein the corn plant exhibits increased kernel row number without fasciation compared to a control corn plant devoid of the edit.

* * * * *

UNITED STATES PATENT AND TRADEMARK OFFICE
CERTIFICATE OF CORRECTION

PATENT NO. : 12,410,438 B2  
APPLICATION NO. : 17/335264  
DATED : September 9, 2025  
INVENTOR(S) : O'Connor et al.

Page 1 of 1

It is certified that error appears in the above-identified patent and that said Letters Patent is hereby corrected as shown below:

In the Specification

Column 7, Line 26: Please correct "even±0.1%" to read --even ± 0.1%--

Column 7, Line 29: Please correct "even+0.1%" to read --even ± 0.1%--

Column 17, Line 48: Please correct "20, 20," to read --20, 30,--

Column 18, Line 12: Please correct "1100, 1120, 1140, 1160, 1180, 1100, 1120, 1140, 1160, 1180," to read --1100, 1120, 1140, 1160, 1180,--

Column 18, Line 57: Please correct "221, 22," to read --221, 222,--

Column 34, Line 44: Please correct "56," to read --5, 6,--

Column 34, Line 45: Please correct "9, 101," to read --9, 10,--

Column 34, Line 46: Please correct "2 3," to read --2, 3,--

Column 36, Line 20: Please correct "(RN" to read --CRN--

Column 48, Line 30: Please correct "Hou et ah," to read --Hou et al,--

Column 52, Line 8: Please correct "15, 6," to read --15, 16,--

Signed and Sealed this  
Thirteenth Day of January, 2026

John A. Squires  
*Director of the United States Patent and Trademark Office*